US011160858B2

(12) United States Patent
Escriou et al.

(10) Patent No.: US 11,160,858 B2
(45) Date of Patent: Nov. 2, 2021

(54) LIVE RECOMBINANT MEASLES-M2 VIRUS—ITS USE IN ELICITING IMMUNITY AGAINST INFLUENZA VIRUSES

(71) Applicants: INSTITUT PASTEUR, Paris (FR); CENTRE NATIONAL DE LA RECHERCHE SCIENTIFIQUE, Paris (FR)

(72) Inventors: Nicolas Robert Xavier Escriou, Paris (FR); Frederic Tangy, Les Lilas (FR); Ho Hong Hai Vo, Ivry sur Seine (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 431 days.

(21) Appl. No.: 15/580,764

(22) PCT Filed: Jun. 10, 2016

(86) PCT No.: PCT/EP2016/063359
§ 371 (c)(1),
(2) Date: Jul. 9, 2018

(87) PCT Pub. No.: WO2016/198642
PCT Pub. Date: Dec. 15, 2016

(65) Prior Publication Data
US 2018/0228888 A1    Aug. 16, 2018

(30) Foreign Application Priority Data
Jun. 12, 2015   (EP) ..................................... 15305918

(51) Int. Cl.
*A61K 39/145* (2006.01)
*A61K 39/12* (2006.01)
*A61K 39/00* (2006.01)

(52) U.S. Cl.
CPC ............ *A61K 39/145* (2013.01); *A61K 39/12* (2013.01); *A61K 2039/5256* (2013.01); *A61K 2039/5258* (2013.01); *A61K 2039/55* (2013.01); *A61K 2039/70* (2013.01); *C12N 2760/16122* (2013.01); *C12N 2760/16123* (2013.01); *C12N 2760/16134* (2013.01); *C12N 2760/18434* (2013.01); *C12N 2760/18441* (2013.01)

(58) Field of Classification Search
None
See application file for complete search history.

(56) References Cited

U.S. PATENT DOCUMENTS

| 6,562,350 B1 * | 5/2003 | Wang | ....................... C12N 7/00 424/202.1 |
| 2004/0204581 A1 * | 10/2004 | Skiadopoulos | ......... A61P 31/14 536/23.72 |
| 2006/0013826 A1 * | 1/2006 | Tangy | .................... A61K 39/21 424/199.1 |
| 2011/0091501 A1 * | 4/2011 | Kalnin | ................. A61K 39/145 424/227.1 |
| 2018/0228888 A1 * | 8/2018 | Escriou | ................ A61K 39/145 |

FOREIGN PATENT DOCUMENTS

| WO | WO 99/07839 | * | 2/1999 |
| WO | 03/022204 A2 |   | 3/2003 |
| WO | 2004/001051 A1 |   | 12/2003 |
| WO | WO 2007/066334 | * | 6/2007 |
| WO | WO 2015/071009 | * | 5/2015 |

OTHER PUBLICATIONS

Sequence alignment of SEQ ID No. 21 with Geneseq db access No. AAY01234 by Neirynck et al. (WO9907839).*
Sequence alignment of SEQ ID No. 40 with Geneseq db access No. AGD21015 by Amon et al in WO2007066334.*
Lum et al. (Vaccine. 2010; 28: 1566-1574).*
Sequence alignment of SEQ ID No. 19 with Geneseq db access No. AEE68472 by Luke et al in WO2005116270.*
Sequence alignment of SEQ ID No. 32 with Geneseq db access No. AZF52579 by Kaminaka et al in WO2011024748.*
Sequence alignment of SEQ ID No. 4 with Geneseq db access No. AZU49962 by Mourez et al in WO2012038832.*
Lie Deng, et al., "M2e-Based Universal Influenza A Vaccines," Vaccines, 2015, 3, 105-136.
International Search Report, PCT/EP2016/063359, dated Nov. 2, 2016.

* cited by examiner

Primary Examiner — Shanon A. Foley
(74) Attorney, Agent, or Firm — Arrigo, Lee, Guttman & Mouta-Bellum LLP

(57) ABSTRACT

The invention relates to an active ingredient which is a live attenuated recombinant measles virus expressing influenza A virus antigen(s) and to its use in the elicitation of immunity, in particular protective immunity and advantageously broad-spectrum protective immunity against influenza A virus. In particular, the influenza A virus is selected among epidemic seasonal viruses and/or endemic viruses circulating in the human population and advantageously encompasses a pandemic virus such as H1N1v.

16 Claims, 18 Drawing Sheets
Specification includes a Sequence Listing.

Figure 1:
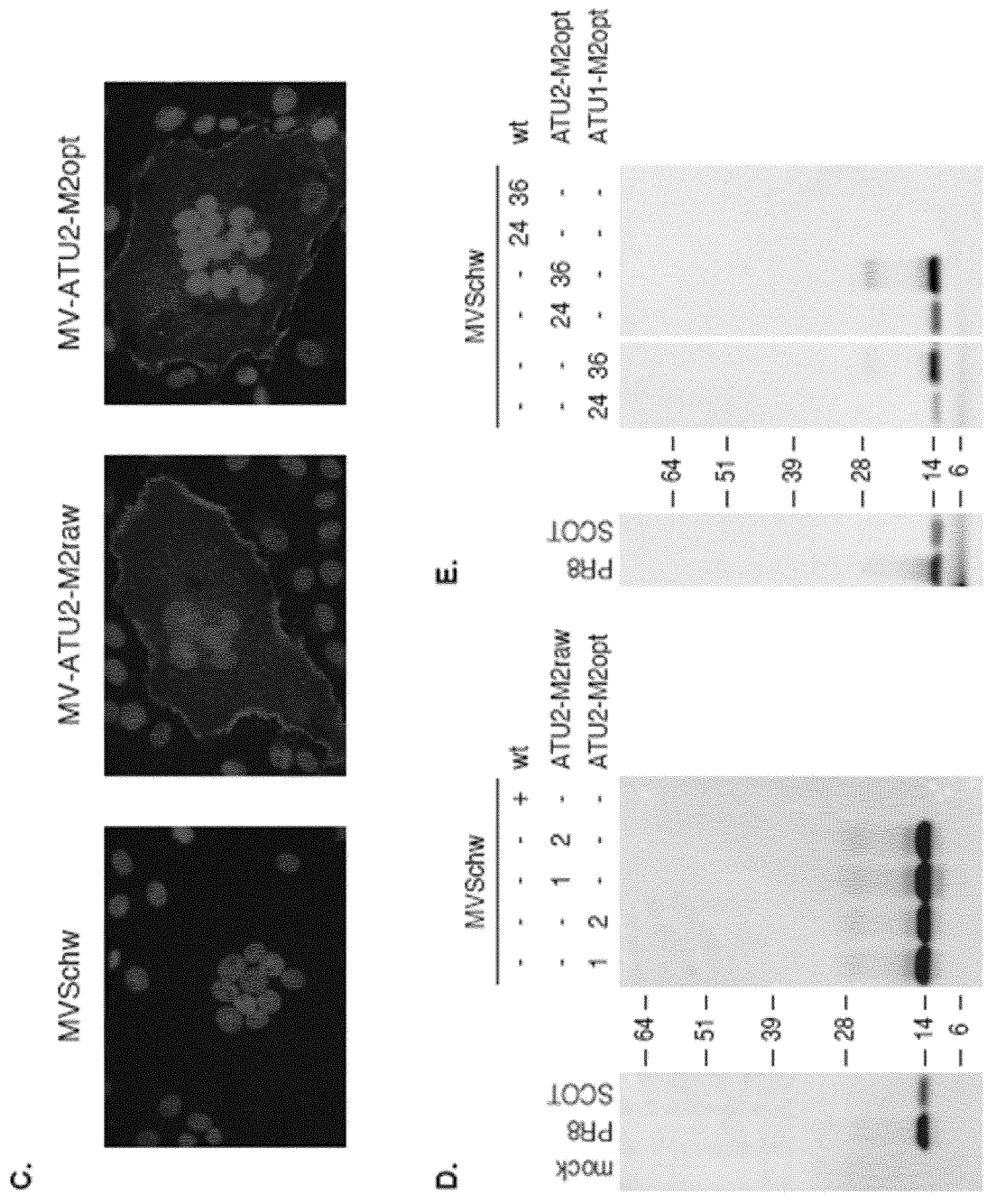

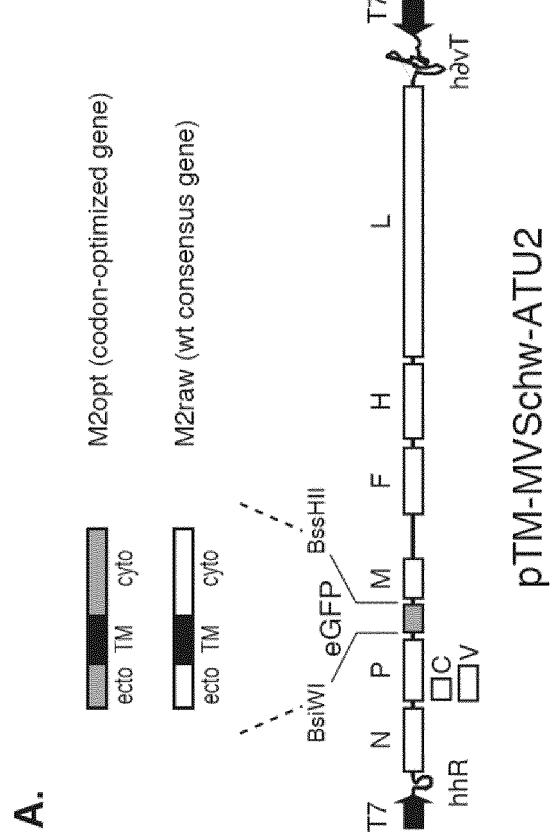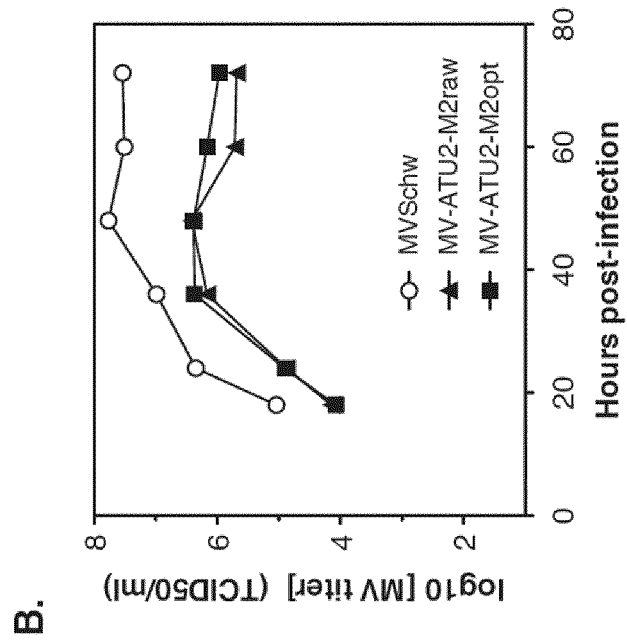
Figure 1

Figure 2:
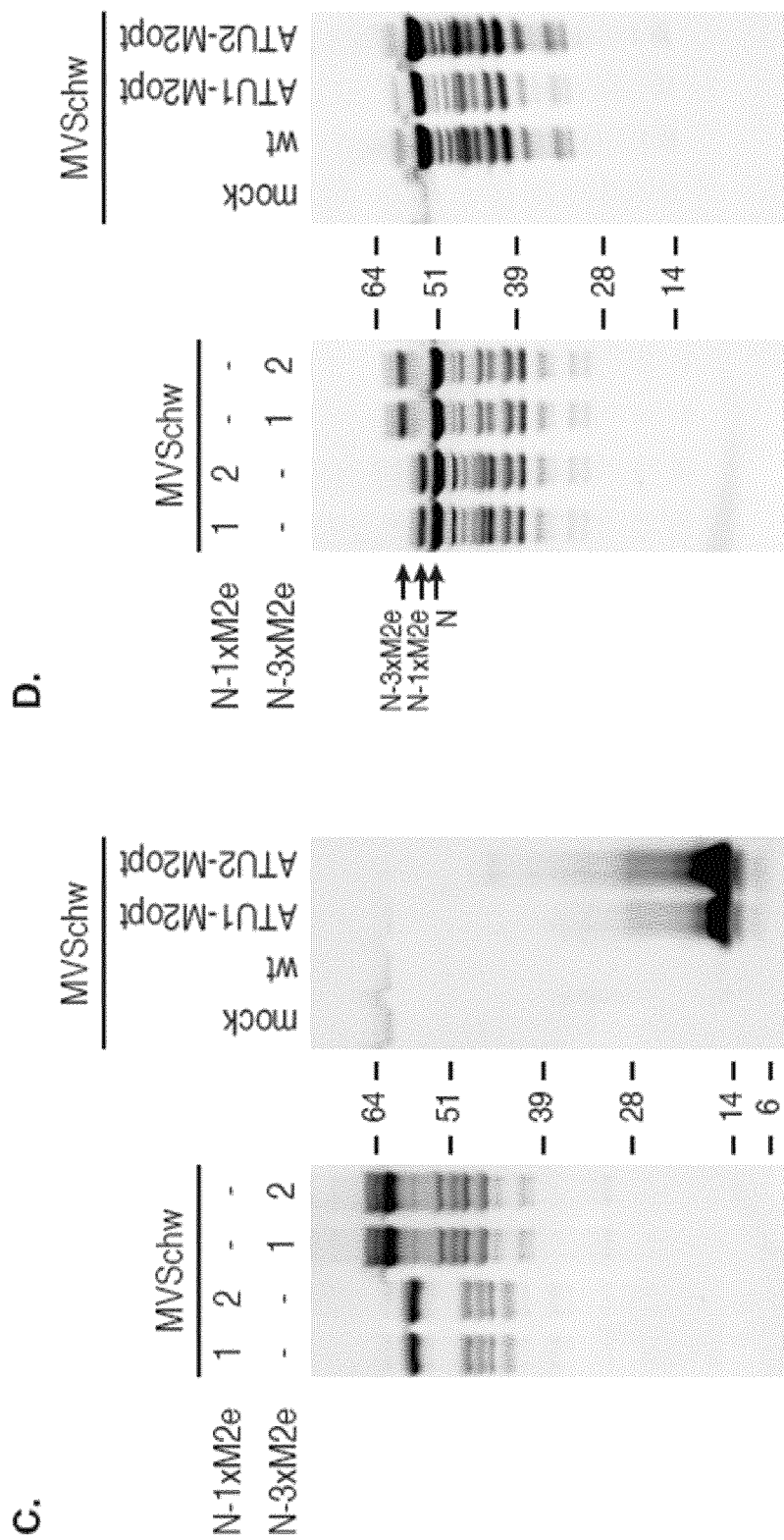

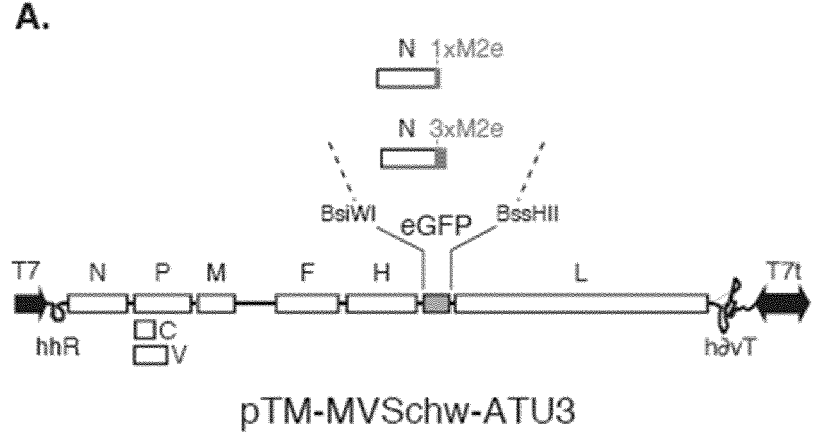
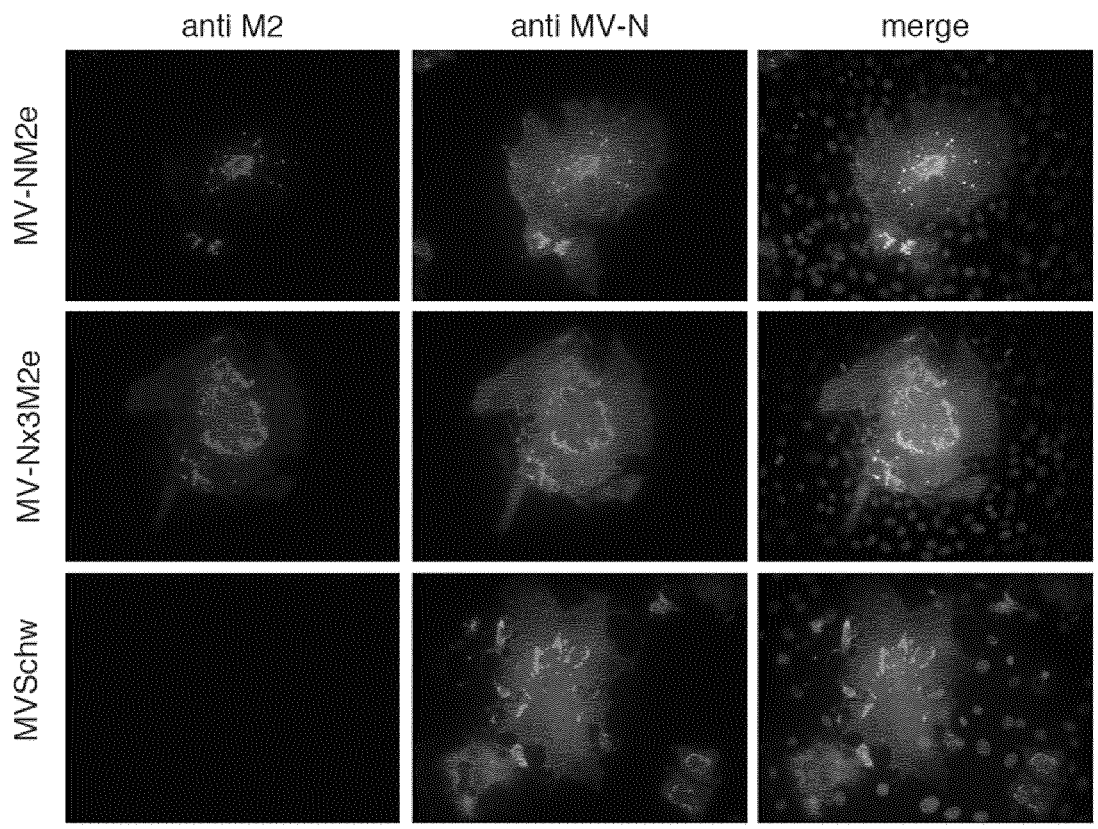
Figure 2

Figure 4

Figure 7

A SEQ ID No.18 M2opt_synthetic_gene

```
  1 GCTAGCGGAT CCCGTACGAC CATGAGCCTG CTGACCGAGG TGGAAACCCC CATCAGAAAC
 61 GAGTGGGGCT GCCGGTGCAA CGACAGCAGC GATCCCCTGG TGGTGGCCGC CAGCATCATC
121 GGCATCCTGC ACCTGATCCT GTGGATTCTG GACCGGCTGT TCTTCAAGTG CATCTACAGA
181 CTGTTCAAGC ACGGCCTGAA GAGAGGCCCC AGCACAGAAG GCGTGCCCGA GAGCATGCGG
241 GAAGAGTACC GGAAAGAACA GCAAAGACGC GTGGACGCCG ACGACAGCCA CTTCGTGTCC
301 ATCGAGCTGG AATGATAAGC GCGCCTCGAG GAATTC
```

B SEQ ID NO.19 M2_consensus_protein

```
  1 MSLLTEVETP IRNEWGCRCN DSSDPLVVAA SIIGILHLIL WILDRLFFKC IYRLFKHGLK
 61 RGPSTEGVPE SMREEYRKEQ QNAVDADDSH FVSIELE
```

C SEQ ID No.21 M2e_consensus_polypeptide

```
  1 SLLTEVETPI RNEWGCRCND SSD
```

D SEQ ID No.22 M1opt_synthetic_gene

```
  1 GCTAGCGGAT CCCGTACGAC CCGGCCCTCT GAAGGCCGAG CATGAGCCTG CTGACCGAGG TGGAAACCTA CGTGCTGAGC
 61 ATCATCCCCA GCGGCCCTCT GAAGGCCGAG ATCGCTCAGC GGCTGGAAGA CGTGTTCGCC TGTGTTCGCC
121 GGCAAGAACA CCGACCTGGA AGCCCTGATG AATGGCTGAA AACCCGGCCC CCGTGCCCTC CATCCTGAGC
181 CCCCTGACCA AGGGCATCCT GGGCTTCGTG TTCACCCTGA CTGAACGGCA ACGGCGACCC TGAGAGAGGC
241 CTGCAGCGGA GAAGATTCGT GCAGAACGCC CTGGCCAGCT GCATGGGCCT GATCTACAAC CGGCGCCAAA
301 GACCGGGCCG TGAAGCTGTA CCGGAAGCTG TGCTGGGCCC AGATGGTGCA GGCCATGAGG GTCAGCCTCT GATCTACAAC
361 GAGATCGCCC TGAGCTACTC CCAGATGGCC CAGGGCTCTT GCATGGGCCT GATCTACAAC ATGCGAGCAG
421 CGGATGGGCG CCGTGACAAG AGAGGTGGCC TTTGGCCTG TGTGCCCAC ATGCGAGCAG CCCCCTGATC
481 ATCGCCGACA GCCAGCACCG GTCCCACAGA CAGAGTGTCA CCACCACCAA AGCCCATGAA ACAGATGGCC
541 CGGCACGAGA ACAGAATGGT GCTGGCCCTC GAAGTGGCCT CTCAGGCCCG GCAGATGGTG
601 GGCCAGCTCT GAGCAGCCGC CGAAGCTATG CAGCCCACCCC AGCAGCAGCA CCGGCCTGAA GGACGACCTG
661 CAGGCCATGA GAGCCATCGG CACCCACCCT CCAGAAAAGA ATGGGGCGTGC AGATGCAGCG GTTTAAGTAA
721 CTGGAAAATC TGCAAGCTTA CCAGAAAAGA ATGGGGCGTGC AGATGCAGCG GTTTAAGTAA
781 TGACGAGCGC GCCTCGAGGA ATTC
```

E SEQ ID No.23 M1_consensus_protein

```
  1 MSLLTEVETY VLSIIPSGPL KAEIAQRLED VFAGKNTDLE ALMEWLKTRP ILSPLTKGIL
 61 GFVFTLTVPS ERGLQRRRFV QNALNGNGDP NNMDRAVKLY RKLKREITFH GAKEIALSYS
121 AGALASCMGL IYNRMGAVTT EVAFGLVCAT CEQIADSQHR SHRQMVTTTN PLIRHENRMV
181 LASTTAKAME QMAGSSEQAA EAMEVASQAR QMVQAMRAIG THPSSSTGLK DDLLENLQAY
241 QKRMGVQMQR FK
```

```
   1 CGTACGGCCA CCATGGCCTC TCAGGGCACC AAGAGAAGCT ACGAGCAGAT GGAAACCGAC
  61 GGCGAGCGGC AGAACGCCAC CGAGATTAGA GCCAGCGTGG GCAGAATGAT CGGCCGGCATC
 121 GGCCGGTTCT ACATCCAGAT GTGCACCGAG CTGAAGCTGA GCGACTACGA GGGCCGGCTG
 181 ATCCAGAACA GCCTGACCAT CGAGCGGATG GTGCTGAGCG CCTTCGACGA GCGGCGGAAC
 241 AAGTACCTGG AAGAACACCC CAGCGCCGGC AAGGACCCCA AGAAAACAGG CGGCCCTATC
 301 TACAGACGGG TGGACGGCAA GAGCTGGTGC GAGCTGGTGC TGTACGACAA AGAGGAAATC
 361 CGGCGGATCT GGCGGCAGGC CAACAATGGC GAAGATGCCA CAGCCGGCCT GACCCACATC
 421 ATGATCTGGC ACAGCAACCT GAACGACGCC ACCTACCAGC GGACCAGAGC ACTCGTGCGG
 481 ACAGGCATGG ACCCCAGAAT GTGCAGCCTG ATGCAGGGCA GCACCCTGCC CAGAAGATCT
 541 GGCGCTGCTG GCGCAGTCGT GAAGGGCGTG GGAACCATGG TCATGGAACT GATCAGGATG
 601 ATCAAGCGGG GAATCAACGA CCGGAACTTT TGGAGAGGCG AGAACGGCAG AAAGACCCGC
 661 AGCCCTACG AGAGGATGTG CAATATCCTG AAGGGCAAGT TCCAGACAGC CGCCCAGCGG
 721 GCCATGATGG ATCAAGTGCG CGAGAGCAGA AACCCCGGCA ACGCCGAGAT CGAGGACCTG
 781 ATCTTCCTGG CCAGAAGCGC CCTGATCCTG AGGGGCTCTG TGGCCCACAA ACTTCGAGAA
 841 CCTGCCTGCG TGTACGGACC TGCCGTGGCC AGCGGCTACG ACTTCGAGAA GAGAGGCTAC
 901 AGCCTCGTGG GCATCGACCC ATTCAAGCTG CTGCAGAACT CCCAGGTGTA CAGCCTGATC
 961 CGGCCCAACG AGAACCCCGC CCACAAGTCT CAGCTCGTGT GGATGGCCTG TCACAGCGCC
1021 GCCTTCGAGG ATCTGAGAGT GTCCAGCTTC ATCCGGGGCA CAAAGGTGTC CCCCAGAGGC
1081 AAGCTGAGCA CCAGAGGCGT GCAGATCGCC AGCAACGAGA ATATGGACAA CATGGGCAGC
1141 TCCACCCTGG AACTGCGGAG CCGGTATTGG GCCATCAGAA CCAGAAGCGG CGGCAACACC
1201 AACCAGCAGA GAGCCTCTGC CGGACAGATC AGCGTGCAGC CCACCTTTAG CGTGCAGAGA
1261 AACCTGCCCT TCGAGAAGGC CACAATCATG GCCGCCTTCA CCGGCAATAC CGAGGGCAGA
1321 ACCAGCGACA TGCGGACCGA GATCATCAGA ATGATGGAAA GCGCCAAGCC CGAGGAAGTG
1381 TCATTCCAGG GCAGGGGCGT GTTCGAGCTG TCCGACGAGA AGCCACCAA CCCCATCGTG
1441 CCCAGCTTCG ACATGAGCAA CGAGGGCAGC TACTTCTTCG GCGACAACGC CGAAGAGTAC
1501 GACAACTCCG GAGGATCTGG CGGCTCTCTG CTGACCGAGG TGAAACCCC CATCAGAAAC
1561 GAGTGGGGCT GCCGGTGCAA CGACAGCTCT GATGGCGGCG GAAGCCTGCT GACAGAAGTG
1621 GAAACACCTA TTCGGAATGA GTGGGaTGC AGATGCAATG ACTCCAGCGA CGGCGGAGGC
1681 AGTCTGCTGA CTGAAGTGGA AACCCCAATT CGCAACGAAT GGGGATGTCG CTGTAACGAT
1741 AGCAGCGACT GATAACGAGC GCGC

SEQ ID No. 24
NPflu-3xM2e_fusion_gene
```

Figure 7

G

```
  1 MASQGTKRSY EQMETDGERQ NATEIRASVG RMIGGIGRFY IQMCTELKLS DYEGRLIQNS
 61 LTIERMVLSA FDERRNKYLE EHPSAGKDPK KTGGPIYRRV DGKWMRELVL YDKEEIRRIW
121 RQANNGEDAT AGLTHIMIWH SNLNDATYQR TRALVRTGMD PRMCSLMQGS TLPRRSGAAG
181 AAVKGVGTMV MELIRMIKRG INDRNFWRGE NGRKTRSAYE RMCNILKGKF QTAAQRAMMD
241 QVRESRNPGN AEIEDLIFLA RSALILRGSV AHKSCLPACV YGPAVASGYD FEKEGYSLVG
301 IDPFKLLQNS QVYSLIRPNE NPAHKSQLVW MACHSAAFED LRVSSFIRGT KVSPRGKLST
361 RGVQIASNEN MDNMGSSTLE LRSRYWAIRT RSGGNTNQQR ASAGQISVQP TFSVQRNLPF
421 EKATIMAAFT GNTEGRTSDM RAEIIRMMES AKPEEVSFQG RGVFELSDEK ATNPIVPSFD
481 MSNEGSYFFG DNAEEYDNSG GSGGSLLTEV ETPIRNEWGC RCNDSSDGGG SLLTEVETPI
541 RNEWGCRCND SSDGGGSLLT EVETPIRNEW GCRCNDSSD
```

SEQ ID No. 25
NPflu-3xM2e_fusion_protein

H

```
  1 MATLLRSLAL FKRNKDKPPI TSGSGGAIRG IKHIIIVPIP GDSSITTRSR LLDRLVRLIG
 61 NPDVSGPKLT GALIGILSLF VESPGQLIQR ITDDPDVSIR LLEVVQSDQS QSGLTFASRG
121 TNMEDEADQY FSHDDPISSD QSRFGWFGNK EISDIEVQDP EGFNMILGTI LAQIWVLLAK
181 AVTAPDTAAD SELRRWIKYT QQRRVVGEFR LERKWLDVVR NRIAEDLSLR RFMVALILDI
241 KRTPGNKPRI AEMICDIDTY IVEAGLASFI LTIKFGIETM YPALGLHEFA GELSTLESLM
301 NLYQQMGETA PYMVILENSI QNKFSAGSYP LLWSYAMGVG VELENSMGGL NFGRSYFDPA
361 YFRLGQEMVR RSAGKVSSTL ASELGITAED ARLVSEIAMH TTEDKISRAV GPRQAQVSFL
421 HGDQSENELP RLGGKEDRRV KQSRGEARES YRETGPSRAS DARAAHLPTG TPLDIDTATE
481 SSQDPQDSRR SADALLRLQA MAGISEEQGS DTDTPIVYND RNLLDSGGSG GSLLTEVETP
541 IRNEWGCRCN DSSDGGGSLL TEVETPIRNE WGCRCNDSSD GGGSLLTEVE TPIRNEWGCR
601 CNDSSD
```

SEQ ID No. 29

N-3xM2e_fusion_protein

Figure 9

Figure 11

LIVE RECOMBINANT MEASLES-M2 VIRUS—ITS USE IN ELICITING IMMUNITY AGAINST INFLUENZA VIRUSES

The invention relates to the field of immunity against influenza A virus. In this respect, the invention provides vectorized antigens derived from influenza viruses that trigger an immune response against influenza A viruses. The invention accordingly relates to an active ingredient which is a live attenuated recombinant measles virus expressing influenza A virus antigen(s) and to its use in the elicitation of immunity, in particular protective immunity and advantageously broad-spectrum protective immunity against influenza A virus.

Influenza is caused by Influenza virus which typically infects people around the world during seasonal epidemics resulting in severe illness or death for a large number of the infected human hosts. In addition to seasonal epidemics, influenza viruses may emerge as novel strains that may cause pandemics.

Influenza virus classifies as influenza A, influenza B and influenza C types and influenza A strains are considered to be the primary pathogens responsible for seasonal illness and also pandemic influenza outbreak. The influenza A virus is classified by reference to surface antigens which are the hemagglutinin antigen (HA) of which 18 subtypes have been identified and the neuraminidase antigen (NA) which defines 11 subtypes. A virus strain thus qualifies as A/HxNy wherein "x" qualifies the subtype of HA and "y" qualifies the subtype of NA antigens. These surface antigens are known to constitute targets of the immune response. Among the various subtypes, A/H1N1 and A/H3N2 are virus subtypes that have been circulating in the human population since 1918 and 1968 respectively; they are thus considered to derive antigens suitable for the design of seasonal vaccine and their HA and NA antigens are accordingly encompassed within vaccine compositions against seasonal flu. However, as the HA and NA antigens continuously evolve in the virus strains under the selective pressure of the immune system of their hosts, vaccines that make use of these antigens have to be redesigned every year and updated. HA and NA undergo two types of antigenic evolution. The first type is antigenic drift, which corresponds to accumulation of point mutations overtime and results in viruses that are antigenically different. The second type is antigenic shift, an abrupt and major change in the influenza A viruses infecting humans resulting in new hemagglutinin and/or new hemagglutinin and neuraminidase proteins. Shift results from the introduction in the human population of a new influenza A subtype or a virus with a hemagglutinin or a hemagglutinin/neuraminidase combination that is so different from the same subtype in humans that most people do not have immunity to the new virus. Such a "shift" occurred in 2009 when a new H1N1 strain (called H1N1pdm or H1N1v) emerged and quickly spread, causing a pandemic and ultimately replacing the seasonal H1N1.

It remains accordingly necessary to propose alternative vaccine candidates that would escape the drawbacks associated with the high variation of the antigens of influenza A viruses and, in addition, would be capable of providing protection against a broad range of influenza A strains, especially epidemic influenza A strains and advantageously pandemic influenza A strains. Difficulties however have been encountered in the developed and disclosed strategies even when such strategies aimed at targeting the conserved influenza antigenic motifs among different strains of influenza virus, in particular conserved motifs in nucleoprotein (NP), matrix (M1 and M2) proteins or HA glycoprotein.

M2-based influenza vaccines have been proposed as a promising target for the elicitation of an immune response against influenza virus, because of its conserved amino acid sequence. In particular various vaccine candidates have been disclosed using the extracellular domain of the protein (M2e). However the various attempts using the M2 or the M2e antigens have not proved to elicit antibodies or T-cell response that would be strong enough and long lasting to efficiently and broadly protect human against influenza virus, be it against a seasonal virus or a pandemic one and these results have been correlated with poor immunity observed with this antigen during infection (Deng L. et al 2015).

The M2e ectodomain of the M2 protein has also been subject of various studies attempting to determine its interest in the design of a vaccine as M2e appears to be highly conserved among human epidemic virus strains whatever the subtype, and does not appear to take part in the drift/shift phenomena impacting the immunity competition (that is seen for example with the HA antigen) thus making this M2e antigen an attractive antigen for the elicitation of a protective response against infection with influenza virus when defining a broad-spectrum influenza A vaccine enabling elicitation of a long-lasting response. However this domain is also only minimally immunogenic during infection and conventional vaccination, possibly due to low abundance of M2 in virions. It has nevertheless been observed that the B cell repertoire is capable of generating a specific anti-M2e antibody response when a mammalian host primed with a first virus infection is then boosted by re-infection with an influenza virus including a heterosubtypic one (Deng L. et al 2015).

The inventors have thus assumed that the interest of the M2 antigen, and in particular of portions of the M2 antigen that contain the M2e domain, needed further thoughts to improve their potential and possibly required the development of an appropriate vector molecule or system.

With the aim of developing a vaccine against seasonal or emerging or pandemic influenza viruses that could be used in children (in particular in young children or babies) or in adult population, the inventors designed a strategy based on the expression of the M2 influenza antigen (or a suitable portion thereof) by a measles virus vector, wherein in particular the measles virus is selected among live attenuated measles viruses such as vaccine measles viruses.

The invention accordingly proposes a new approach to vectorize influenza antigens including M2 derived antigens wherein this approach takes benefits from the carrier properties and possibly of the immune properties of the vector and show improved immunogenicity. They hence provide a recombinant live attenuated measles virus capable of eliciting an immune response in human individuals that would be effective and long lasting against illness resulting from influenza A virus infection.

The invention relates to the use of the measles virus as a vector to express influenza A virus immunogens or epitopes wherein said immunogens or epitopes encompass polypeptides derived from an M2 protein (including the M2 protein), in particular the ectodomain of an M2 protein, wherein the M2 protein is advantageously a protein expressed from a consensus amino acid sequence derived from the amino acid sequences from multiple M2 proteins of influenza A virus strains.

Accordingly, the invention relates to a recombinant measles virus (MV) expressing at least a first antigen comprising or consisting in (i) a M2 antigen whose amino acid sequence is a consensus amino acid sequence representative of the M2 sequences of a selection of various subtypes of Influenza A viruses including circulating seasonal human viruses and optionally one or many pandemic human virus(es) and/or of a selection of various subtypes of Influenza A viruses including animal viruses, in particular endemic animal viruses and optionally animal virus(es) reported to have infected human subjects and considered to pose a pandemic risk, (ii) a portion comprising the ectodomain of said M2 antigen of (i) or consisting in said ectodomain.

The recombinant measles virus prepared according to the invention is derived from a measles virus which is advantageously a live attenuated measles virus, such as a virus authorized as a vaccine strain. The vaccine strain of measles virus can be distinguished from wild-type viruses by determination of the genotype from clinical samples or virus isolates. (See Specimens for Detection of Measles RNA by RT-PCR or Virus Isolation Lab Tools—Center of disease Control and Prevention.)

A measles virus suitable to carry out the invention may thus be a Schwarz strain known to be a live-attenuated vaccine strain (Rouvax® by Aventis Pasteur-France or Priorix® from GalxoSmithkline Pharma GmbH-Austria) or a Moraten strain that was shown to have the same nucleotide sequence as the Schwarz strain, or an AIK-C strain, a Zagreb strain (vaccine strains of the Edmonston lineage), or a TD97 strain, a CAM70 strain, a Leningrad-16 strain, a Shanghai-191 strain, a Changchun-47 strain (derived from different wild-type isolates) (Bankamp B. et al 2011). In a particular embodiment, the Schwarz strain or the Moraten strain is used.

In a particular embodiment of the invention, the recombinant measles virus is obtained starting from a cDNA corresponding to the full-length antigenomic RNA of the virus strain and cloned from virus particles of the live attenuated MV strain, in particular of the Schwarz or Moraten strain according to a process which is fully disclosed in WO 04/000876 (incorporated by reference) and the recombinant virus is rescued according to the process disclosed in WO04/000876 application for the rescue of measles virus particles starting from the preparation of a cDNA encoding the full length antigenomic (+)RNA of the virus. Regarding MV cDNA preparation and rescue of a cloned Schwarz strain of MV reference is made also to Combredet C et al (2003). The same rescue process may be used for other strains among the above cited ones using a molecular clone of the virus RNA. The recombinant Measles virus according to the invention may be grown on Vero cells. The recombinant MV may be presented for use in a liquid formulation. The Examples section provides also relevant indications in this regard for the preparation of the recombinant measles virus particles.

A "consensus sequence" according to the invention, in particular a consensus amino acid sequence is a sequence, respectively an amino acid sequence, which is the result of one of the following conception or selection methods:

a) it is derived from (i.e., defined) the alignment of multiple sequences of a determined protein identified for selected virus strains (especially influenza A strains) and in which each residue, in particular each amino acid residue, is the one which is the most frequent at the aligned positions in the different selected sequences occurring in known or in particular published virus strains that have been isolated. Accordingly, the residues which are shared at a given site among all selected sequences are present in the consensus sequence at said site and when a residue is variable at a given position among the selected sequences the most frequently found residue is retained in the consensus sequence at this position. When a considered residue is different in all the sequences selected for the definition of the consensus, the identity of this residue may be chosen to correspond to the residue in the sequence of the most predominant virus either in a relevant period of time or in terms of impact on health or b) it is a sequence of (i) a particular influenza virus, especially influenza A virus, which is selected for its capability to elicit an immune response which is sufficiently broad to protect against other viruses, including viruses from a different subtype or lineage or (ii) it is a sequence of a particular virus cluster which cluster does not show sequence diversity and against which an immune response is sought, such cluster being illustrated by pandemic viruses.

Accordingly, a consensus sequence according to the invention is a representative sequence as a result of steps carried out to conceive it or based on existing viral sequences; in particular but not necessarily it is a theoretical representative sequence of a group of determined actual sequences. Alternatively a consensus sequence is a sequence of an actual virus which is however essentially shared by a sufficient number of viruses within at least one lineage or subtype or cluster and accordingly does not show divergence (i.e., the comparison of the considered sequence within the group of interest shows less than 10% differences) in the sequence of amino acid residues of at least the protein(s)/antigens of interest (such a M2 or M2e or NP or M1 polypeptides of influenza A viruses) to present relevancy for the definition of an immunogenic product with a view to design a vaccine. A consensus sequence is used according to the invention to express a molecule which is a nucleic acid molecule or a polypeptide.

When reference is made to a consensus sequence in the present disclosure, each of these alternatives may be contemplated except where specified differently or technically inappropriate according to the understanding of the person skilled in the art. In a particular embodiment of the invention, the consensus sequence is the sequence as obtained under a).

The "M2 antigen" according to the invention is a structural tetrameric type III transmembrane protein of influenza A virus and is highly conserved among human influenza A subtypes. M2 protein is abundantly expressed on the surface of virus-infected cells. Antibodies against M2 are found in the serum of convalescent individuals after they have been infected with influenza A virus. The M2 protein contains 97 amino acids and is expressed from spliced mRNA derived from influenza gene segment 7 which also encodes the matrix M1. M2 mainly acts as a viroporin having a ion-channel activity. According to the invention, the amino acid sequence of the M2 antigen is a native viral sequence or is a consensus sequence derived from various viruses as disclosed herein.

The "ectodomain" of the M2 antigen (designated M2e) according to the invention is the external domain of the M2-protein in influenza A virus located on the N-terminal portion of the M2 protein (starting with residue 2 of the M2 protein). This domain is 23 amino acids in length (among which 9 residues are also present in the M1 protein and are the most conserved residues).

In a particular embodiment of the invention, the consensus sequence for the M2 protein is used to define the M2e antigen. In an embodiment, the consensus sequence of the M2 antigen (especially suitable for the design of the M2e antigen) encompasses alignment of the sequences of these polypeptides from the seasonal A/H1N1 and A/H3N2 virus subtypes and optionally A/H9N2. In another embodiment, the consensus sequence is obtained by alignment of the sequences of this antigen from these strains together with the corresponding sequence from the pandemic strain pdmH1N1 (also designated H1N1v) found in 2009. In another embodiment, the consensus sequence of the M2 antigen (especially suitable for the design of the M2e antigen) also encompasses alignment of the sequences of these polypeptides from the avian A/H5N1, A/H9N2 and A/H7N9 virus subtypes. In another embodiment, the consensus sequence of the M2 antigen (especially suitable for the design of the M2e antigen) also encompasses alignment of the sequences of these polypeptides from the avian A/H5N1, A/H9N2 and A/H7N9 virus subtypes and further encompasses the alignement of the sequences of these polypeptides from the H5N6 and H10N8 virus subtypes detected in human. In another embodiment, the consensus sequence is obtained by alignment of the sequences of this antigen from these strains (according in particular to the various above groups) together with the corresponding sequence from the pandemic strain pdmH1N1 (also designated H1N1v) In another embodiment, the alignment may further encompass the corresponding sequence of the influenza A strain newly emerged as an epidemic strain or as a pandemic strain, or of an influenza animal strains reported to have infected human subjects and considered to pose a pandemic threat. In a particular embodiment the M2 or M2e consensus amino acid sequence is a human-type or an avian-type consensus sequence.

A "portion" of an antigen according to the invention is a molecule that consists in a fragment of the antigen wherein the amino acid sequence of this fragment is accordingly shorter than the amino acid sequence of the antigen and contains a segment of contiguous residues of the full-length sequence of the antigen. An amino acid sequence of such portion has at least 6 contiguous amino acid residues of the sequence of the antigen and advantageously consists or comprises one or a plurality of epitopes of the antigen, B and/or T cell epitopes. It may be less or equal to 25 amino acid residues long.

In an embodiment of the invention, the influenza A viruses referred to for the design of the consensus sequence of the M2 antigen encompass seasonal viruses that originate from distinct virus lineages or from distinct virus subtypes or from distinct virus clusters. Optionally, these viruses further encompass pandemic strains or animal strains reported to have infected human subjects and considered to pose a pandemic threat. In one virus lineage, one or many viruses may be used as reference. Among influenza A virus lineages, the following are especially considered: the human H1N1 lineage since its reemergence in 1977, the human H3N2 lineage since its emergence in 1968, the human H1N1v lineage since its recent emergence in 2009, and lineages of avian H5N1, H9N2 or H7N9 viruses which may emerge in the human population and pose a pandemic threat (WHO). Other animal virus subtypes including avian H2 and H9 viruses and swine H1 and H3 viruses may also pose a pandemic threat and are especially considered. The sequences of the influenza viruses and of their polypeptides are available in database such as NCBI where they are updated as soon as new viruses or isolates are characterized. The selection of the viruses for the design of the consensus sequence for the M2 antigen or the M2e portion thereof may take into account the diversity of strains in a lineage over time, or the overall diversity of strains within a given subtype. If alignment is performed to achieve the consensus sequence, before alignment is performed between the amino acid sequences of an antigen of various subtypes or various lineages or various clusters, a step of alignment may be carried out within each subtype or lineage (within a cluster no significant divergence is observed, in particular less than 3% or not more than 2% differences) to design a consensus sequence reflecting the diversity of strains for each subtype or lineage of virus. Illustration of the steps carried out to design a consensus sequence is provided in the Examples section and the method proposed may be applied similarly to other selections of virus lineages than those characterizing the spectrum of H1N1, H3N2 and pandemic H1N1v.

The inventors have observed that the recombinant measles virus of the invention expressing the influenza M2 antigen or M2e-based antigen elicits an antibody response against the influenza antigen in mice susceptible to infection by measles virus which response is stronger than the response observed after natural infection with the homotypic influenza strain. In addition, the inventors have shown that the response may be increased by a boost administration of the recombinant measles virus expressing the influenza M2 antigen or M2e-based antigen.

Surprisingly, the inventors have shown in addition that mice (restricted for CMH H2b) immunized with the recombinant measles virus of the invention developed an immune response against the M2e or the M2 antigen of influenza A virus although these mice were known to have a restricted haplotype that would hardly elicit a response as seen in the past using a composition comprising DNA encoding the M2 antigen or a composition comprising synthetic peptides derived from the M2e sequence that was intended for the induction of an immune response against the M2 antigen (Misplon et al., 2010; Wolf et al., 2011). The recombinant measles virus takes part in the observed phenomenon by its capacity to help overcoming the failure of the immunized host to possibly recognize the epitope of the influenza A virus antigen in the proper CMH context, by supplying a T helper response against the MV that proves to be appropriate in helping the elicitation of the response of the host against said influenza A virus antigen.

In an embodiment, the invention relates to a recombinant measles virus as disclosed herein wherein the M2 antigen has a consensus amino acid sequence derived from the M2 sequences of viruses comprising A/H1N1 and A/H3N2 seasonal strains and A/H1N1 pandemic variant strain. In another embodiment, the recombinant measles virus as disclosed herein is such that the M2 antigen has a consensus amino acid sequence derived from the M2 sequences of viruses comprising A/H5N1, A/H9N2 and A/H7N9 avian strains and optionally A/H1N1 pandemic variant strain. Using as a first antigen the M2 antigen or a portion thereof comprising the ectodomain of M2 originating from many seasonal viruses and a pandemic variant strain may provide a broad-spectrum vaccine of the type of universal vaccine sought against influenza A.

In an embodiment of the invention, the recombinant measles virus expresses the M2 ectodomain (M2e) the amino acid sequence of which is SEQ ID No. 21.

In another embodiment, the recombinant measles virus expresses an M2e-based antigen that comprises the above sequence. In particular, this M2e-based antigen is the M2 antigen that has the sequence of SEQ ID No.19.

The thus defined sequence of the ectodomain of M2 is a consensus sequence. After being defined as a consensus the M2e domain may be comprised within a M2e-based antigen which is an antigen modified with respect to the M2e domain. Such modification may result by the addition of terminal amino acid residues, in particular 1, 2, 3, 4 or 5 additional amino acid residues which are or are not amino acids encompassed within an actual M2 protein such as residues naturally framing the M2e domain in the consensus sequence or in an actual sequence, i.e., the sequence of the antigen of an identified virus or virus strain. The M2 antigen may alternatively or further be modified to give rise to a M2e-based antigen by the addition of a linker sequence such as a glycin-rich sequence e.g. an SGGSGG sequence (SEQ ID No.38) which provides flexibility or by the addition of a spacer sequence such as a glycine-rich sequence of the GGG type or an alanine-rich sequence with 2 to 6 consecutive alanine residues. An M2e-based antigen may also encompass an antigen consisting of or comprising multiple copies of M2e domain(s) or multiple copies of such M2e domain(s) comprising the above disclosed specific modifications consisting in addition of terminal amino acid residues and/or linker or spacer sequences. The M2e-based antigen may accordingly be a chimeric antigen through the combination of multiple M2E domains.

According to these embodiments of the invention, the recombinant measles virus comprises, inserted in its genome, a polynucleotide encoding the M2 consensus antigen of the influenza A virus or encoding the M2e consensus domain. Preferably, the polynucleotide is inserted in an additional transcription unit (ATU) cloned into an intergenic region of the cDNA corresponding to the full-length antigenomic RNA of the measles virus. Nucleic acid constructs suitable for the expression of the M2 antigen or the M2e-based antigen are in particular illustrated in the Examples section. In particular the transgene encoding one or multiple polypeptides characteristic of the influenza virus as disclosed herein, may be introduced in the ATU1, ATU2 or ATU3 as provided in the plasmids designated pTM-MVSchw-ATU1 having the sequence of SEQ ID No.14, or pTM-MVSchw-ATU2 having the sequence of SEQ ID No.15 or pTM-MVSchw-ATU3 having the sequence of SEQ ID No.16, wherein they would replace the sequence encoding the eGFP. In a particular embodiment, the transgene is inserted in ATU2 (between the P and M genes of the measles genome) or even upstream such as in ATU1 in order to increase the expression of influenza polypeptide based on the expression gradient of the measles genome. According to a preferred embodiment an M2e-based antigen, in particular an antigen encompassing multiple copies of M2e as disclosed herein or a fusion of such an M2e-based antigen (such as N-M2e wherein N is the measles antigen) is inserted in said ATU3 or in said ATU2. When double recombinant measles virus is prepared such as a measles virus recombined with the M2e-based antigen as disclosed above and with an additional antigen of the influenza virus (such as M1 or NP), the nucleotide sequence of the latter may be inserted in ATU2 and the sequence of the M2e-based antigen may be inserted in another ATU, in particular in ATU3 or in ATU1.

In an embodiment of the invention, the genome of the recombinant measles virus of the invention comprises multiple copies of polynucleotide(s) encoding the ectodomain of the M2 antigen.

The feature "multiple copies of polynucleotide(s) encoding the M2e domain" means that more than one copy of a polynucleotide encoding this domain is present in the MV vector genome, therefore enabling the expression of "multiple copies encoding the M2e domain" in a thus formed chimeric M2e-based antigen. In particular 2, 3, 4, or 5 or more copies of an identical M2e domain or of distinct M2e domains are encompassed within a chimeric antigen. Domains are considered distinct when they have sequences that have diverging amino acid residues at one or more than one site when compared to the determined consensus sequence of M2 or of M2e. Domains may be distinct but nevertheless similar when the diverging positions do not exceed 10% (90% identity) or preferably do not exceed 5% (95% identity) of the number of amino acid residues in the compared sequences (the diverging sequence compared to the consensus sequence and the consensus sequence determining the number of amino acid residues). Distinct M2e domains may be those of different consensus sequences or may originate from different clusters, different lineages or different subtypes. The multiple copies of the M2e domain may be directly fused to the adjacent copy(ies) or separated from the adjacent copy(ies) by a linker (a particular linker is illustrated in the constructs provided as examples and as SEQ ID No.38). Multiple copies of the M2e antigen may be connected by linker or spacer sequences as disclosed herein. The expression by the recombinant measles virus of the invention, of multiple copies of the M2 antigen or the M2e-based antigen may favor the elicitation of a stronger and broader immune response resulting from an increased abundance of the influenza antigen and/or more favorable exposure to the immune system of the host. Examples of multiple copies of M2e domain that may advantageously be expressed by the live recombinant measles virus of the invention consist of chimeric polypeptides comprising or consisting of the consensus sequence of M2e for the A/H1N1 and the A/H3N2 lineages (SEQ ID No.21) and the consensus sequence of M2e for the A/H1N1v pandemic strain (SEQ ID No.32). These sequences of various M2e show 4 amino acid residues of difference (17%). As an alternative combination of sequences for a M2e domain, the consensus sequence for the A/H1N1 and the A/H3N2 lineages may be associated with the sequence of the M2e domain of A/H5N1 (SLLTEVETPT RNEWECRCSD SSD SEQ ID No.40). These sequences are different at 3 amino acid residue positions (13%). Multiple copies of M2e domain constitute a M2e containing antigen (or M2e-based antigen) according to the invention.

In a particular embodiment of the invention, the M2 antigen or the M2e containing antigen (M2e-based antigen) when expressed by the recombinant measles virus is borne by a carrier molecule, in particular fused to an extremity (N- or C-terminal) of a carrier protein. Such a carrier molecule may be chosen for its ability to help presenting the M2 or M2e-containing antigen by the recombinant measles virus when it is produced and replicates in the immunized host. It may additionally or alternatively consist in an immunogenic molecule involved in the elicitation of an immune response against influenza A virus, including the NP protein of the influenza virus or a consensus sequence of said protein such as NPflu protein having the sequence of SEQ ID No. 31.

The invention thus relates in particular to a recombinant measles virus wherein in its genome, the polynucleotide encoding the ectodomain(s) of the M2 antigen or one of the polynucleotides encoding the multiple ectodomain(s) of the M2 antigen (including when such ectodomain(s) is (are) encompassed in an M2e-based antigen) is genetically fused with a polynucleotide encoding a carrier protein, optionally an immunogenic carrier protein. The genetic fusion is advantageously carried out at the extremity of the DNA encoding the carrier protein. Accordingly when a feature is disclosed herein by reference to the M2e domain the feature applies either to the M2e domain in the strict sense of it or to the M2e encompassed in more complex sequence such as those disclosed herein for the M2e-based antigen.

In a particular embodiment of the invention, the carrier molecule is a protein of the measles virus, in particular a structural protein of the virus. In an advantageous embodiment, the protein is the Nucleoprotein (N) of a measles virus, especially a N protein of the strain used to rescue recombinant measles virus particles of the invention, such as the Schwarz strain. In another advantageous embodiment, the protein is the Nucleoprotein (NP) of one of influenza virus strains cited herein, including the NP protein of an influenza virus or a consensus sequence of said protein such as NPflu protein having the sequence of SEQ ID No. 31. It may be alternatively a variant thereof such as a portion, in particular an immunogenic portion of this protein, in particular an immunogenic portion of the protein the amino acid sequence of which is SEQ ID No. 31. Preferably, the polynucleotide encoding the M2 or the M2e-based antigen of the influenza virus and, when present, the polynucleotides encoding the carrier protein globally fulfill the "rule of six" or are adapted to fulfill said rule. Examples of M2e-based antigen borne by a carrier according to the invention are NPflu-M2e, or NPflu-3xM2e having the sequence of SEQ ID No. 25.

In a particular embodiment of the invention, the recombinant measles virus expresses a fusion of the measles N protein with one or multiple copies of the M2e domain. As an example a fusion of N with 3 copies of the M2e domain fused at the C- or N-terminal part of the N is expressed.

In a particular embodiment the M2 antigen or the M2e-based antigen is fused to the C-terminal end of the N protein or to the C-terminal end of a portion of the N protein that comprises the Ncore domain. Examples of the fusion protein between the MV N protein and the M2 antigen or the M2e-based antigen are illustrated as SEQ ID No. 28 ($N_{MV}$-M2e fusion protein) and SEQ ID No. 29 ($N_{MV}$-3xM2e fusion protein). In these particular embodiments, the $N_{MV}$ and the M2e antigens are separated by a linker and when multiple M2e peptides are included in the fusion protein they are also separated by linker sequences.

Preferably the fusion protein leads to the expression of additional N proteins of MV rather than to the substitution of the native N protein by the fusion protein. Hence, the fusion protein comprising the MV N protein is expressed in addition to the native N protein.

In a particular embodiment, in order to express the chimeric antigen consisting of the carrier-M2e or the carrier-nxM2e fusion (wherein "n" represents the number of M2e copies) a polynucleotide encoding said fusion is inserted in the cDNA of the MV vector in an ATU (an additional transcription unit which is a multiple-cloning-site cassette) provided in the vector at a position located in the intergenic region between the P and the M genes of MV or at position located between the H and the L genes. This enables the recombinant virus to express both the native and the fused chimeric N-M2e or N-nxM2e proteins. Accordingly, in the RNPs (Ribonucleoproteins) which are produced by the recombinant measles virus, the chimeric N-M2e or N-nxM2e proteins are displayed on the RNPs. Constructs encompassing the ATU in the vector backbone are illustrated in the Examples section. In particular the transfer vector used to derive a construct of the invention suitable to express a live recombinant measles virus may be one of the following plasmids: pTM-MVSchw-ATU1 having the sequence of SEQ ID No.14, or pTM-MVSchw-ATU2 having the sequence of SEQ ID No.15 or pTM-MVSchw-ATU3 having the sequence of SEQ ID No.16. All these plasmids contain the sequence encoding the eGFP marker that may be deleted.

In another embodiment of the invention, alternatively to a protein of measles virus, wherein the carrier protein is an antigen of Influenza A virus, in particular is the nucleoprotein NP or an immunogenic portion thereof.

As examples of such carrier originating from an influenza virus or from a consensus sequence of a protein of an influenza virus, the nucleoprotein (NP protein) is suitable to provide a T epitope of influenza virus, which epitope can be boosted in a host who would become infected by an influenza A virus after receiving the recombinant measles virus of the invention and the presence of which would thus elicit or improve the immune reaction.

The carrier may be an immunogenic portion of a protein rather than the whole protein if the immunogenicity of the carrier is sought. The skilled person would be able to determine an immunogenic portion of a protein by simple tests carried out on fragments of the protein determining whether the fragment elicit an antibody response or a cellular response. An immunogenic portion of a protein may in particular consist of a truncated protein or a deletion variant of the protein such as a fragment consisting of more than 50% of the native protein or in particular 90% or more or 95% or more in length of the whole protein.

The NP protein of an influenza A virus may be the expression product of a consensus sequence wherein the consensus is designed in the same way as the consensus for the M2 antigen. It may alternatively be an actual (i.e., native) sequence of a particular viral strain. The NP protein of influenza A virus is the nucleocapsid protein having 498 amino acid residues. According to the invention the NP protein is the full-length protein or a portion suitable to act as a carrier and optionally as an immunogen. An example of the NP protein suitable for use according to the invention corresponds to the sequence of SEQ ID No.31 encoded by the polynucleotide of sequence SEQ ID No. 30. In a particular embodiment, the NP protein is used in a fusion protein with 3 copies of the M2e domain such as illustrated by the protein whose sequence is SEQ ID No.25. encoded by the transgene consisting of SEQ ID No.24.

As stated above, the recombinant measles virus expresses at least a first antigen of influenza A virus. Accordingly, in further embodiments of the invention, wherein such embodiments may also encompass any of the features recited above or their combinations, the recombinant measles virus may express additional antigens (wherein the term antigen is used interchangeably with protein or polypeptide and encompasses immunogenic portions of native proteins), including additional influenza A antigen(s) (e.g. NP or M1 antigens) that may be expressed by consensus amino acid sequences or sequences of actual strains or isolates. Alternatively or in addition, the recombinant measles virus may express antigens of other viruses, including of other influenza types or subtypes than those used in the design of the consensus sequence of the M2 antigen, such as antigens, in particular M2 antigen, of influenza B virus type. Such distinct antigen may be designated as a second or a further antigen when more than one additional antigen is present. According to the invention, when reference is made to the M2 antigen or to an antigen comprising the M2e domain (M2e-based antigen), reference is primarily made to the antigen with a consensus amino acid sequence. Similarly, said further antigens of influenza A virus may optionally be a consensus sequence built using analogous steps to those defined herein and illustrated in the Example section.

Independently of the carrier molecule, as stated above, the recombinant measles virus may express further antigen(s) of the influenza A virus. Such further antigens may be selected for their ability to elicit, in particular to prime or to boost an immune response in a host or to take part in the response elicited by other antigens. They may be expressed as a consensus antigen having a consensus sequence defined as explained herein for the consensus of the M2 protein, in particular using the alignment of the sequences of the antigens of the same influenza viruses as those involved in the design of the consensus sequence of the M2 protein.

Accordingly, the invention is directed to a live recombinant measles virus which also expresses one or multiple further antigen(s) of an influenza A virus or one or multiple further antigen(s) the amino sequence of which is a consensus sequence representative of the sequence of a determined antigen of viruses from a selection of various subtypes of Influenza A viruses wherein the selection includes circulating seasonal human virus(es) and optionally pandemic human virus(es) and/or animal virus(es) reported to have infected people and considered to pose a pandemic threat.

Among suitable proteins of influenza A virus for the constitution of the further antigen(s) M1 (matrix protein), NP and/or NA (Neuraminidase) proteins or immunogenic portions thereof are preferred. In particular, both M1 and NP proteins may be suitable as they are highly conserved and are the target of cellular responses in individuals infected by influenza virus. The M1 protein may also promote the budding of influenza VLPs from cells. The NA protein may also be suitable as it is a known immunogen and because it may enhance the budding for the release of viral particles or of influenza VLPs from cells. The NA protein is also less susceptible to antigenic drift than the hemagglutinin protein (HA). It may therefore interestingly complete the M2 protein or the M2e-based protein for the induction of a broad immune response. Accordingly, a recombinant measles virus expressing the M2 antigen or the M2e-based antigen and the NA antigen of a particular subtype may provide a semi-universal vaccine able to induce wide coverage against influenza A of the corresponding subtype(s).

In a particular embodiment of the invention, the recombinant measles virus expresses a further antigen which is the M1 protein having the sequence of SEQ ID No.23 which is a consensus sequence encoded by the polynucleotide whose sequence is SEQ ID NO.22 and/or the NP protein having the sequence of SEQ ID No.31.

In an embodiment of the invention, the influenza A antigens expressed by the recombinant measles virus are M1 and M2 or M1 and M2e-based proteins either as a M1-M2 fusion protein, as a M2-M1 fusion protein or as M1-M2e-based fusion protein, as a M2e-based-M1 fusion protein. These fusion proteins may be designed using the polynucleotides disclosed as SEQ ID No. 17, SEQ ID No.18 (for M2) or SEQ ID No.20 (for M2e) and SEQ ID No. 22 for M1. In order to be expressed by the genome of the recombinant MV, the polynucleotide encoding said fusion protein is advantageously inserted in the ATU2 at position between the P and the M genes of MV. In another embodiment, the antigens of influenza A virus (for example M2 (or M2e-based antigen) and M1 or, M2 (or M2e-based antigen) and NP, or even the three antigens M1, M2 (or M2e-based antigen) and NP) expressed by the recombinant MV are inserted in different ATUs. For example if influenza A M2 (or M2e-based antigen) NP and M1 are used one is expressed from a polynucleotide inserted in an ATU located before the N gene of MV, one is expressed from a polynucleotide inserted in an ATU located between the P and the M genes and the third one is expressed from a polynucleotide inserted in an ATU located between the H and the L genes of MV. Alternatively, the M1 and NP proteins of influenza may be expressed as a fusion protein. The use of multiple influenza A virus antigens may enable to improve protection with the induction of both humoral and cellular responses.

In another aspect, the invention relates to nucleic acid constructs required for the rescue of a recombinant measles virus as defined herein. These constructs encompass a nucleic acid construct which comprises or consist in a cDNA whose nucleotide sequence comprises (i) a nucleotide sequence that encodes the sequence of a full-length antigenomic RNA of MV (i.e., corresponds to the RNA except for the change of the U nucleotides into T) and wherein one or multiple Additional Transcription Unit(s) (ATU) has (have) been inserted upstream of the N gene (ATU1) and/or in the intergenic region(s) between the P and M genes (ATU2) and/or between the H and L genes (ATU3) of MV and, (ii) operably linked into said ATU or ATUs (in frame), a heterologous nucleotide sequence encompassing an open reading frame that encodes one or multiple antigen(s) of influenza A virus as defined herein and in particular in the Examples and by reference to the sequences of the sequence listing. In order to be cloned into the ATU, the polynucleotide encoding the amino acid sequence of the influenza A antigen(s) (and if present of the carrier) may be flanked by added restriction sites.

In a particular embodiment, if necessary or suitable, the nucleic acid molecule is such that the polynucleotide encoding the consensus sequence of the influenza A virus may encompass modifications such as editing modifications to remove MV editing ($A_5G_3$)- and core gene end ($A_4CKT$)-like sequences on both strands of the nucleic acid. Additional modifications may concern cis-acting sequence motifs such as internal TATA-boxes, chi-sites, ribosomal entry sites, ARE, INS and CRS sequence elements, or repetitive sequences, RNA secondary structures and splice donor and acceptor sites.

In an embodiment, the nucleic acid construct may be codon optimized to improve expression in mammalian cells, in particular in human cells. Codon optimization may be carried out on the sequence encoding the influenza A virus antigens or may be carried out both on the sequence encoding the influenza A antigens and if appropriate their carrier protein. Codon optimization is known from the skilled person and is illustrated in the Examples provided herein.

The polynucleotides encoding the influenza A antigen(s) possibly linked with a carrier may be prepared according to techniques available to the person skilled in the art such as by chemical synthesis.

The nucleic acid of the invention encompassing the cDNA encoding the full-length antigenomic (+)RNA of the measles virus and the other antigens in particular the influenza A virus antigen(s), including the optional sequence of the carrier, may advantageously fulfill the "rule of six" which is known to take place in the sequence of natural MV genomes and to enable recovery of high yield of live recombinant measles virus. Accordingly this nucleic acid should have a number of nucleotides on each strand which is a multiple of six. Alternatively, the rule of six is not fulfilled by the construct of the recombinant viral genome and the yield of recombinant virus in the rescue is altered, possibly after repair of the error relating to the compliance with the rule of six.

Among the nucleic acid constructs, the invention concerns in particular vectors (transfer vectors) suitable for the rescue of the recombinant measles virus of the invention. Vectors are said to be suitable for the rescue when they provide functional polynucleotides encoding the full-length measles virus antigenomic (+)RNA together with the nucleic acid constructs encoding the influenza A antigen(s) and are thus able to provide the genome of viral particles and their proteins when they are used for transformation of a cell, in particular a mammalian cell, especially a human cell, chosen for the rescue wherein said cell expresses measles virus proteins necessary for transcomplementation in particular when the cell is transcomplemented with vector(s) providing sequences of the P, N and L proteins of the MV. Such constructs have been amply disclosed in Combredet C. et al (2003) and in WO 04/000876.

Accordingly, the invention concerns a transfer vector, in particular a plasmid vector, suitable for the rescue of a recombinant measles virus as defined herein which comprises as an insert operably linked in the vector backbone, cloned into the cDNA encoding the full-length antigenomic RNA of the measles virus, a polynucleotide encoding one or many antigens as defined herein.

A particular transfer vector suitable for the expression of the recombinant measles virus according to the invention is a recombinant plasmid carrying a cDNA whose nucleotide sequence comprises (i) a nucleotide sequence that encodes the sequence of the full-length antigenomic RNA of MV wherein one or multiple Additional Transcription Unit (ATU) has (have) been inserted upstream of the N gene and/or in intergenic regions and, (ii) inserted in said ATU or ATUs a heterologous polynucleotide the sequence of which encompasses an open reading frame that encodes one or many antigen(s) as defined herein. These vectors are advantageously derived from the plasmids designated pTM-MVSchw-ATU1 having the sequence of SEQ ID No.14, or pTM-MVSchw-ATU2 having the sequence of SEQ ID No.15 or pTM-MVSchw-ATU3 having the sequence of SEQ ID No.16, wherein the sequence encoding the eGFP would be replaced by inserts encoding the influenza virus protein(s) and optionally carrier protein(s) of different origin.

In a particular aspect, the transfer vector is a pTM plasmid derived from a pBluescript plasmid is selected from the group of:
  pTM-MVSchw-ATU1 or pTM-MVSchw-ATU2 or pTM-MVSchw-ATU3 wherein the sequence encoding an M2 antigen is inserted in ATU1 or ATU2 or in ATU3,
  pTM-MVSchw-ATU3 wherein the sequence encoding the fusion of the C-terminal end of the Nucleoprotein of the MV virus and the sequence encoding one or multiple ectodomain(s) of an M2 protein (M2e) is inserted in ATU3;
  pTM-MV-ATU1-M2raw having the sequence of SEQ ID No.1, pTM-MV-ATU2-M2raw having the sequence of SEQ ID No.3, pTM-MV-ATU1-M2opt having the sequence of SEQ ID No.2, pTM-MV-ATU2-M2opt having the sequence of SEQ ID No.4, pTM-MV-ATU3-M2opt having the sequence of SEQ ID No.8
  pTM-MV-ATU3-N-1xM2e having the sequence of SEQ ID No.5, pTM-MV-ATU3-N-3xM2e having the sequence of SEQ ID No.6 (N is the measles virus N protein)
  pTM-MV-M1&M2 having the sequence of SEQ ID No.9
  pTM-MV-NPflu&M2 having the sequence of SEQ ID No.10 and pTM-MV-ATU2-NPflu having the sequence of SEQ ID No.11 which is the parental construct for pTM-MV-NPflu&M2,
  pTM-MV-ATU2-NPflu-3xM2e having the sequence of SEQ ID No.13
  pTM-MV-ATU2-M1opt having the sequence of SEQ ID No.7.
  pTM-MV-ATU2-N-3xM2e having the sequence of SEQ ID No.12, where N is the measles protein.

The invention also concerns the polynucleotides consisting in the inserts included in the measles virus genome of said plasmids as they are indicated in the provided sequences. In particular, the invention relates to the polynucleotides whose sequences are the following:
  SEQ ID No.17 for M2raw synthetic gene wherein the sequence encoding M2 is a sequence encoding a consensus protein, SEQ ID No.18 for M2opt synthetic gene wherein the sequence is optimized, in particular codon optimized with respect to the raw sequence,
  SEQ ID No.20 for sequence encoding the consensus M2e polypeptide, which sequence is optimized,
  SEQ ID No.22 for the optimized sequence encoding the M1 consensus protein,
  SEQ ID No.24 for the fusion polynucleotide encoding NPflu-3xM2e fusion protein,
  SEQ ID No.26 for the fusion polynucleotide encoding N-1xM2e fusion protein where N is from the measles virus and wherein a linker links the N and the M2e sequences,
  SEQ ID No.27 for the fusion polynucleotide encoding N-3xM2e fusion protein wherein a linker links the N and the M2e sequences and links the multiple M2e sequences
  SEQ ID No. 30 for the synthetic gene encoding the consensus NPflu protein.
  a polynucleotide encoding any of the polypeptide the sequence of which consists of a sequence selected in the following group: SEQ ID No.19, SEQ ID No.21, SEQ ID No. 23, SEQ ID No.25, SEQ ID No.28, SEQ ID No.29, SEQ ID No.31, SEQ ID No.32 and SEQ ID No.40.

The invention also relates to the use of a transfer vector as described herein for the preparation of a recombinant measles virus as defined in the present invention.

The invention thus also concerns a rescue system for the assembly of infectious recombinant measles virus particles and optionally influenza A VLPs, comprising a cell, preferably a mammalian cell or cell line, transformed, in particular transfected, with vectors, in particular plasmid vectors, suitable for the expression of a polymerase such as a T7 polymerase, and for the expression of the N, P and L proteins of a measles virus, wherein said cell is further transfected with a vector according to the invention.

In particular the cells used for the rescue are selected among a 293-T7-NP cell line deposited on Jun. 14, 2006 with the CNCM (Paris, France) under number 1-3618 or a 293-Tnls7-NP deposited on Aug. 4, 2006 with the CNCM (Paris, France) under number 1-3662.

For the preparation of the recombinant measles virus of the invention, the cDNA cloned as the insert into the transfer vector may be obtained after a step of purifying the genomic RNA of measles virus from particles of the virus, in particular from particles of a live-attenuated strain or a vaccine strain such as the Schwarz strain.

The invention also concerns an immunogenic composition comprising a recombinant measles virus of the invention as defined herein according to any of the embodiments disclosed, a pharmaceutical vehicle suitable for administration to a host and optionally an adjuvant of the immune response.

In addition to the recombinant measles virus of the invention, the immunogenic composition may comprise influenza virus-like particles (VLPs) that form during the rescue and production of the recombinant measles virus. The invention also concerns said influenza virus-like particles (VLPs) and their use as active ingredient for the elicitation of the immune response against influenza A virus or improvement of the response elicited by the live recombinant measles virus of the invention. The immunogenic composition may be, may comprise or may be derived from a supernatant or a lysate of cells producing the recombinant measles virus of the invention.

An immunogenic composition according to the invention may be formulated using additional substances such as salts, preservation substances, buffers, texture agents . . . .

The immune response may be an antibody response and/or a cellular response including a T cell response. The response thus elicited is protective, advantageously confers a broad and long lasting protection.

The invention also concerns a recombinant measles virus as defined herein, for use as active ingredient in the elicitation of an immune response for prophylactic protection against a condition or a disease resulting from the infection by an influenza virus A in a human host.

In particular, the invention relates to a recombinant measles virus as defined herein, for use as active ingredient in the elicitation of an immune response for prophylactic protection against a condition resulting from the infection by an influenza virus A, wherein the influenza A virus is one of the A/H1N1, A/H3N2, A/H5N1 or A/H7N9 or A/H9N2 or H1N1v virus.

The invention also relates to a recombinant measles virus as defined herein, for use as active ingredient in the elicitation of an immune response for prophylactic protection against flu in a human host, in particular in children.

In a particular embodiment, the invention relates to a recombinant measles virus as defined herein, optionally in combination with Influenza VLPs for the elicitation of antibodies against the influenza A virus and/or for the elicitation of a cellular response against the infection by the influenza A virus in a human host.

In an embodiment of the invention, the recombinant measles virus optionally in combination with Influenza VLPs, is used for protection, in particular for prophylactic protection, against a condition or a disease resulting from the infection by an influenza virus A in a human host.

The invention also concerns a method to prevent the onset of flu or the onset of a condition resulting from infection by an influenza A virus in a human host, comprising administering to said human host, in particular in a child, one or multiple doses of a composition comprising a recombinant measles virus as defined herein, optionally in a prime-boost administration regimen.

According to a particular aspect of the invention, the immunogenic composition is formulated for administration to children.

The administration of the immunogenic composition of the invention may be performed by known administration routes including systemic or peripheral administration.

The invention also relates to the use of a recombinant measles virus according to any one of the herein described embodiments, optionally in combination of Influenza VLPs in the preparation of active ingredients for the prevention of the infection by an influenza A virus or the prevention of the outcome of the infection by an influenza A virus, in a multivalent vaccine for a human host, such as a combined measles, mumps, rubella and influenza multivalent vaccine or a measles, mumps, rubella, varicella and influenza multivalent vaccine.

According to a particular embodiment of such preparation of active ingredients, the recombinant measles virus of the invention is also used as active ingredient for the prevention of an infection by measles virus or for the prevention of the outcome of an infection by the measles virus.

The invention also concerns a cell transformed, in particular transfected with the vectors, especially the plasmid vectors, suitable to carry out the rescue of recombinant measles virus according to the invention and comprising nucleotide sequences expressing a polymerase such as a T7 polymerase, and nucleotide sequences expressing the N, P and L proteins of a measles virus, wherein said cell is further transfected with a transfer vector as defined herein in conditions enabling production of recombinant measles virus.

The invention also relates to the products recovered from the thus defined cell used to rescue or from cells used to amplify the rescued virus such as Vero cells. The invention thus concerns in particular the supernatant of such cells or the lysate prepared from such cells expressing the rescued recombinant measles virus of the invention.

These products, in particular the supernatant or lysate of cells used for the production of the recombinant measles virus of the invention, may be used in the preparation of active ingredients for an immunogenic composition of the invention.

Additional features may be derived from the examples which follow and from the figures.

FIGURE LEGENDS

FIG. 1: Characterization of MV-M2 Recombinant Viruses Expressing the Full-Length Transmembrane M2 Protein.

A. Schematic representation of the pTM-MVSchw-ATU2 vector containing the Schwarz MV cDNA with a green fluorescent protein (eGFP) gene as an additional transcription unit (ATU) between the P and the M genes (ATU2). Wild-type (M2raw) and codon-optimized (M2opt) synthetic genes coding for the full-length M2 consensus protein were inserted into pTM-MVSchw-ATU2 between the BsiWI and BssHII sites of the ATU, in place of the eGFP gene. Both M2raw and M2opt genes were also inserted into pTM-MVSchw-ATU1 as an additional ATU upstream of the N gene (not shown).

MV genes are indicated: N (nucleoprotein), P (phosphoprotein) and V/C (accessory proteins), M (matrix), F (fusion), H (hemaglutinin), L (polymerase). T7: T7 RNA polymerase promoter. hhR: hammerhead ribozyme. T7t: T7 RNA polymerase terminator. h∂vR: hepatitis delta virus (HDV) ribozyme.

B. Growth kinetics of recombinant MV-M2 viruses. Vero NK cells were infected with parental MVSchw or recombinant MV-ATU2-M2raw or MV-ATU2-M2opt viruses at an MOI of 0.1. The cells were collected at the indicated time points, and the cell-associated virus titers were determined as described in Materials and Methods.

C. Immunofluorescence staining of M2 polypeptides in syncytia of MV-M2-infected Vero NK cells. Cells were fixed 30-36 hours after infection with the indicated viruses and stained with mouse monoclonal anti-M2 antibody (14C2) and AF555-conjugated anti-mouse IgG antibodies. Magnification: ×40.

D. and E. Western blot analysis of M2 polypeptides expression. M2 was detected in lysates of Vero-NK cells infected with the indicated MV-M2 or parental MVSchw viruses using mouse monoclonal anti-M2 antibody (14C2). Lysates of MV-infected cells were diluted 1 in 4 (D) or 1 in 10 (E) before being assayed. Lysates prepared from MDCK cells infected with A/Scotland/20/74 (SCOT) or A/PuertoRico/8/34 (PR8) influenza viruses at a MOI of 5 were used as positive controls. The positions of molecular weight markers (size in kDa) are indicated. D. Two viral clones (1, 2) of MV-M2raw and MV-M2opt were assayed as indicated. E. Lysates were harvested 24 or 36 hours post-infection as indicated.

FIG. 2: Characterization of MV-NM2e Recombinant Viruses Expressing N-M2e Fusion Proteins.

A. Schematic representation of the pTM-MVSchw-ATU3 vector containing the Schwarz MV cDNA with a green fluorescent protein (eGFP) gene as an ATU between the H and the L genes (ATU3). Genes encoding the MV N protein fused to a single copy of M2 ectodomain consensus sequence (N-1xM2e) or to three tandem copies of M2e (N-3xM2e) were inserted into pTM-MVSchw-ATU3 between the BsiWI and BssHII sites of the ATU, in place of the eGFP gene.

MV genes are indicated as in FIG. 1.

B. Immunofluorescence staining in syncytia of MV-NM2e-infected Vero NK cells. Cells were fixed 30-36 hours after infection with the indicated viruses and stained with mouse monoclonal anti-M2 antibody (14C2) and AF555-conjugated anti-mouse IgG antibodies, and with rabbit polyclonal anti-MV-N and AF488-conjugated anti-rabbit IgG antibodies. Single-color and merged images are shown. Magnification: ×20.

C. and D. Western blot analysis of N-M2e fusion polypeptides expression. N-M2e fusion proteins were detected in lysates of Vero-NK cells infected with the indicated MV-NM2e or parental MVSchw viruses using mouse monoclonal anti-M2 antibody (14C2, panel C) or rabbit polyclonal anti-MV-N(panel D). Two viral clones (1, 2) of MV-N-1xM2e and MV-N-3xM2e were assayed as indicated. Lysates prepared from Vero NK cells infected with MV-ATU1-M2opt or MV-ATU2-M2opt were used as positive controls. The positions of MV N protein and N-M2e fusion proteins as well as molecular weight markers (size in kDa) are indicated.

FIG. 3: Antibody Response in CD46-IFNAR Mice Immunized with MV-M2 Recombinant Viruses.

Groups of 6 or 12 CD46-IFNAR mice were injected twice intraperitoneally at four-week interval with $10^5$ $TCID_{50}$ of the indicated recombinant MV-M2 measles viruses or with parental MVSchw, as control. Another group of mice was immunized with two intranasal administration of 0.1 LD50 of mouse-adapted A/Scotland/20/74 (SCOT) influenza virus. Sera were collected 3 weeks after each injection (IS1 and IS2, respectively). M2e-specific (A, C) or MV-specific (B, D) IgG antibody titers were determined by indirect ELISA, as described in Material and Methods. A-D. Each symbol represents an individual mouse, and the short horizontal line indicates the mean value of the group. Detection limits of the assays are indicated by dotted lines.

D-E. Survival curves for 5-6 mice per group were recorded for 22 days after intranasal challenge with 10 LD50 of mouse-adapted A/Scotland/20/74 (H3N2) or A/Paris/2590/09 (H1N1v) influenza viruses.

FIG. 4: Antibody Response in CD46-IFNAR Mice Immunized with MV-NM2e Recombinant Viruses.

Groups of CD46-IFNAR mice were injected twice intraperitoneally at four-week interval with $10^5$ $TCID_{50}$ of the indicated recombinant MV-NM2e measles viruses or with parental MVSchw, as control. Another group of mice was immunized with MV-ATU2-M2opt. Sera were collected 3 weeks after each injection (IS1 and IS2, respectively). M2e-specific (A) or MV-specific (B) IgG antibody titers were determined by indirect ELISA.

C. M2e-specific, IgG1 (filled circles) and IgG2a (open circles) isotype titers were determined for IS2 sera by indirect ELISA.

D. Specific antibodies against the native form of the M2 protein were measured using a cell-based ELISA, as described in Material and Methods.

A-D. Each symbol represents an individual mouse, and the short horizontal line indicates the mean value of the group. Detection limits of the assays are indicated by dotted lines.

E. Survival curves were recorded for 21 days after intranasal challenge with 10 LD50 of mouse-adapted A/Scotland/20/74 (H3N2) influenza virus.

FIG. 5: Contribution of Humoral Response to Protection

Survival of C57BL/6 mice (6 mice/group) lethally challenged with 10 LD50 of mouse-adapted A/Scotland/20/74 (H3N2) influenza virus after passive transfer of pooled sera from CD46-IFNAR mice immunized with MV-ATU1-M2opt or MV-ATU2-M2opt recombinant virus. Control mice received sera from CD46-IFNAR mice immunized with empty parental MVSchw.

FIG. 6: Characterization of Double Recombinant Measles Viruses Expressing Both M1 and M2 Proteins.

A. Schematic representation of the pTM-MV-ATU2-M1 vector containing the Schwarz MV cDNA with the M1 codon-optimized consensus gene as an ATU between the P and the M genes (ATU2), of the pTM-MV-ATU3-M2 vector with the M2 codon-optimized consensus gene as an ATU between the H and the L genes (ATU3), and of the double recombinant pTM-MV-M1&M2 vector.

MV genes are indicated as in FIG. 1.

B. and C. Western blot analysis of M1 and M2 polypeptide expression. M1 and M2 were detected in lysates of Vero-NK cells infected with the indicated recombinant or parental measles viruses using mouse monoclonal anti-M1 (GA2B, panel B) or anti-M2 antibody (14C2, panel C). Three viral clones (1, 2, 3) of each viral construct were assayed as indicated. Lysates prepared from MDCK cells infected with A/Scotland/20/74 (SCOT) influenza virus were used as positive controls. The positions of M1 and M2 proteins as well as molecular weight markers (size in kDa) are indicated.

FIG. 7: Examples of Sequences of Polynucleotides or Proteins Used in the Invention FIG. 8: Antibody Response in CD46-IFNAR Mice Immunized with Dual Recombinant Measles Viruses Expressing Both M1 and M2 Proteins.

Groups of 12 CD46-IFNAR mice were injected twice intraperitoneally at four-week interval with $10^5$ TCID50 of the indicated single recombinant MV-ATU3-M2opt and MV-ATU2-M1opt viruses, with the dual recombinant MV-M1&M2 virus or with parental MVSchw, as control. Another group of mice was immunized with the former MV-ATU2-M2opt. Sera were collected 3 weeks after each injection (IS1 and IS2, respectively). M2e-specific (A) or MV-specific (B) IgG antibody titers were determined by indirect ELISA, as described in Materials and Methods. A-B. Each symbol represents an individual mouse, and the short horizontal line indicates the mean value of the group. Detection limits of the assays are indicated by dotted lines.

C. Survival curves were recorded for 21 days after intranasal challenge with 10 LD50 of mouse-adapted A/Scotland/20/74 (H3N2) influenza virus.

D. Weight curves of infected mice were recorded. Values represent the mean weight of surviving mice, expressed as the percentage of initial weight at day of infection. SD are represented by one-sided vertical bars. For clarity, filled symbols indicate that all mice of the group were alive on the day of monitoring, half-filled symbols that at least one mouse died previously and open symbols that a single mouse remained alive in the group.

FIG. 9: Characterization of Dual Recombinant Measles Viruses Expressing Both NP and M2 Full-Length Influenza Proteins, or a Fusion Protein Between the NP Protein and 3 Copies of the M2e Ectodomain.

A. Schematic representation of the pTM-MV-ATU2-NP-flu vector containing the Schwarz MV cDNA with the NP codon-optimized consensus gene as an ATU between the P and the M genes (ATU2), of the pTM-MV-ATU3-M2 vector with the M2 codon-optimized consensus gene as an ATU between the H and the L genes (ATU3), and of the dual recombinant pTM-MV-NPflu&M2 vector. MV genes are indicated as in FIG. 1.

B. Schematic representation of the pTM-MVSchw-ATU2 vector as described in FIG. 1. The gene encoding the consensus influenza type A nucleoprotein (NPflu) fused to three tandem copies of M2e (NPflu-3xM2e) was inserted into pTM-MVSchw-ATU2 between the BsiWI and BssHII sites of the ATU, in place of the eGFP gene.

C. and D. Western blot analysis of NP and M2 polypeptide expression. NP and M2 (or M2e) were detected in lysates of Vero-NK cells infected with the indicated recombinant or parental measles viruses using rabbit polyclonal anti-influenza virion antibodies (panel C) or mouse monoclonal anti-M2 antibody (14C2, panel D). Three or four viral clones (1, 2, 3, 4) of each viral construct were assayed as indicated. Lysates prepared from MDCK cells infected with A/Scotland/20/74 (SCOT) influenza virus were used as positive controls. The positions of NPflu, M2 and NPflu-3xM2e proteins as well as molecular weight markers (size in kDa) are indicated.

FIG. 10: Antibody and Cellular Responses in CD46-IFNAR Mice Immunized with Dual Recombinant Measles Viruses Expressing Both NP and M2 Proteins.

Groups of CD46-IFNAR mice were injected twice intraperitoneally at four-week interval with $10^5$ TCID50 of the indicated single recombinant MV-ATU2-NPflu and MV-ATU3-M2opt viruses, with the dual recombinant MV-NPflu&M2 virus or with parental MVSchw, as control. Sera were collected 3 weeks after each injection (IS1 and IS2, respectively). M2e-specific (A) or MV-specific (B) IgG antibody titers were determined by indirect ELISA.

C. Frequency of influenza-specific IFN-γ-producing T cells in the spleens of immunized mice was quantified by ELISPOT 7 to 10 days after a single injection of the indicated recombinant measles viruses. ELISPOT was performed as described in Materials and Methods, in response to the NP366 (H3N2) consensus peptide (class I), the NP366 (SCOT) peptide of the A/Scotland/20/74 challenge virus (class I) and the NP260-273 conserved peptide (class II).

A-C. Each symbol represents an individual mouse, and the short horizontal line indicates the mean value of the group. Detection limits of the assays are indicated by dotted lines.

D. Survival curves were recorded for 21 days after intranasal challenge with 10 LD50 of mouse-adapted A/Scotland/20/74 (H3N2) influenza virus.

E. Weight curves of infected mice were recorded. Values represent the mean weight of surviving mice, expressed as the percentage of initial weight at day of infection. SD are represented by one-sided vertical bars. For clarity, filled symbols indicate that all mice of the group were alive on the day of monitoring and half-filled symbols that at least one mouse died previously.

FIG. 11: Characterization of a MV-N-3xM2e Recombinant Virus Expressing a N-M2e Fusion Protein from ATU2.

A. Schematic representation of the pTM-MVSchw-ATU2 vector containing the Schwarz MV cDNA with a green fluorescent protein (eGFP) gene as an ATU between the P and the M genes (ATU2). The gene encoding the MV N protein fused to three tandem copies of M2e (N-3xM2e) was inserted into pTM-MVSchw-ATU2 between the BsiWI and BssHII sites of the ATU, in place of the eGFP gene.

MV genes are indicated as in FIG. 1.

B. and C. Western blot analysis of N-M2e fusion polypeptide expression. N-3xM2e fusion protein was detected in lysates of Vero-NK cells infected with the indicated virus using mouse monoclonal anti-M2 antibody (14C2, panel B) or rabbit polyclonal anti-MV-N (panel C). Two viral clones (1, 2) of MV-ATU2-N-3xM2e were assayed as indicated. Lysates prepared from Vero NK cells infected with MV-ATU3-N-3xM2e or MVSchw were used as positive controls. The positions of MV N protein and N-3xM2e fusion protein as well as molecular weight markers (size in kDa) are indicated.

EXAMPLES

Materials and Methods

Cell Lines and Viruses

Vero-NK (African Green Monkey Kidney) cells were grown at 37° C. under 5% $CO_2$ in complete DMEM (Dulbecco's modified Eagle medium with 4.5 mg/ml L-glucose, 100 U/ml penicillin and 100 μg/ml streptomycin), supplemented with 5% heat-inactivated fetal bovine serum (FBS). Helper 293-T7-MV cells stably expressing T7 RNA polymerase and N and P genes from Schwarz MV were grown in complete DMEM supplemented with 10% FBS.

MDCK (Madin-Darby canine kidney) cells were grown at 37° C. under 5% $CO_2$ in MEM (Minimum Essential Media), supplemented with penicillin, streptomycin and 10% FBS (MEM-10). MDCK-M2 cells that constitutively express the full-length M2 consensus sequence were generated by repeated transduction with a lentiviral TRIP-M2opt vector. Cells expressing high-levels of M2 on the cell surface were selected by fluorescence-activated cell sorting and stably maintained in culture in MEM-10 supplemented with 20 μg/ml of rimantadine, an M2 proton channel inhibitor (Sigma-Aldrich).

The mouse-adapted influenza A/Scotland/20/74 (H3N2) virus was previously described (Ramisse et al., 1998). Working stocks were prepared from lung homogenates by two successive amplifications in MDCK cells at a multiplicity of infection (MOI) of $10^{-3}$ for 3 days at 35° C. in completed MEM supplemented with 1 μg/ml TPCK-treated trypsin. Virus titers were determined on MDCK cells by a standard plaque assay under Avicel® overlays and are expressed as plaque forming unit per ml (pfu/ml).

The A/Paris/2590/09 virus (Jonges M. et al 2010) was isolated by the National Influenza Center (Northern-France) at the Institut Pasteur in Paris (France) from nasal swab collected in Paris during the 2009 pandemic, and passaged twice in MDCK cells. The eight genomic segments were cloned from viral RNA into a bidirectional transcription plasmid derived from pHW2000 (Hoffmann et al., 2002) to generate recombinant viruses. The rescued virus was adapted to mice by serial passage of pulmonary homogenates of infected to naive mice, and further amplified in MDCK cells as described above to constitute working stocks.

Plasmid Constructs The MVSchw recombinant plasmid constructs were derived from the previously described pTM-MVSchw-ATU1, -ATU2 and -ATU3 plasmid vectors (Combredet et al., 2003). These vectors were cloned from a commercial batch of the licensed vaccine Rouvax (kindly provided by Sanofi Pasteur MSD, Marcy l'Etoile, France). They carry an infectious cDNA corresponding to the anti-genome of the Schwarz MV vaccine strain and an additional transcription unit containing unique BsiWI and BssHII restriction sites for the insertion of foreign open reading frames upstream from the N gene (ATU1), between the P and M genes (ATU2) and between the H and L genes (ATU3).

A full-length M2 consensus sequence, reflecting circulating human influenza lineages (seasonal A/H3N2 and A/H1N1 strains, as well as the 2009 pandemic A/H1N1 variants i.e., H1N1v), was generated from complete M2 coding sequences available at the NCBI Influenza Virus Sequence Database, accessed in October 2011 (Bao et al., 2008). Briefly, a total of 1148 complete M2 coding sequences, representing the spectrum of H3N2 (540 sequences), H1N1 (386 sequences) and H1N1v (222 sequences) influenza A diversity in humans from 1918 to 2011, were selected and downloaded. From these data, sequence alignments and consensus sequences were computed for each of the three subtypes on the CLC Main Workbench platform (version 6.1.1) using the default settings. Next, a global consensus was generated by giving the same weight to each of H3N2, H1N1 and H1N1v M2 consensus and following the majority rule whenever applicable. When the three consensus differed at a given position, the H3N2 value was chosen to reflect the predominance of this subtype during the 2011-2012 flu season in the northern hemisphere at the time of design. The global consensus sequence was further edited to remove MV editing $(A_5G_3)$- and core gene end $(A_4CKT)$-like sequences on both strands. This consensus sequence was named M2raw and has the sequence of SEQ ID No. 17.

The full-length M2raw consensus sequence was chemically synthesized by Geneart (Life Technologies) with additional BsiWI and BssHII restriction sites at the 5' and 3' ends, respectively. The sequence respects the "rule of six", which stipulates that the number of nucleotides of the MV genome must be a multiple of 6 (Calain and Roux, 1993; Schneider et al., 1997). A human codon-optimized version of the consensus (M2opt) was also synthesized and has the sequence of SEQ ID No. 18. In addition to codon bias optimization for high expression in mammalian cells, MV editing $(A_5G_3)$- and core gene end $(A_4CKT)$-like sequences, and regions of very high (>80%) or low (<30%) GC content were avoided whenever possible. Furthermore, cis-acting sequence motifs such as internal TATA-boxes, chi-sites, ribosomal entry sites, ARE, INS, and CRS sequence elements, as well as repetitive sequences, RNA secondary structures and splice donor and acceptor sites, were avoided. Both M2raw and M2opt cDNAs were inserted into BsiWI/BssHII-digested pTM-MVSchw-ATU1(eGFP) vector, resulting in pTM-MV-ATU1-M2raw and pTM-MV-ATU1-M2opt plasmids. Similarly, pTM-MV-ATU2-M2raw and pTM-MV-ATU2-M2opt were generated by inserting both cDNAs into pTM-MVSchw-ATU2(eGFP).

A construct encoding the MV N protein fused to a single copy of M2 ectodomain (M2e) derived from the consensus sequence was chemically synthesized by Geneart. This construct encompassed the 5' extremity of the MV rescue plasmid from the T7 and hammerhead ribozyme sequence up to nt 2042 of MV antigenome. It contains unique BspE1 and BstB1 restriction enzyme sites in order to permit subsequent exchange of the M2e ectodomain sequence. In this synthetic gene, the M2e peptide (SLLTEVETPI RNEWGCRCND SSD SEQ ID No.21) is connected to the C-terminus of MV nucleoprotein through a flexible SGGSGG linker (N-1xM2e fusion protein). A second construct was obtained by exchange of the BspE1-BstB1 fragment with a synthetic and codon-optimized sequence encoding three tandem copies of M2e consensus connected by GGG spacers. A restriction enzyme site was also included after the third copy of M2e sequence for further subcloning. Next, the construct encoding the N-3xM2e fusion protein was used as a template for PCR amplification using the forward primer 5'-AGT CGTACGGAGATGGCCACACTTTTAAGG-3' (SEQ ID No.33) containing BsiWI restriction site (underlined) and the reverse primer 5'-GGCCTTGAGAGCCCGGATG-3' (SEQ ID No.34). The N-1xM2e coding sequence was amplified by PCR using the same forward primer and the reverse primer 5'-GTT GCGCGCTCGTTATCAATCAGAGCTGTCGTTGCAC-3' (SEQ ID No.35) containing BssHII restriction site. After digestion with BsiWI and BssHII restriction enzymes, the resulting DNA fragments were inserted into the corresponding sites of pTM-MVSchw-ATU3(eGFP) plasmid and both pTM-MV-ATU3-N-1xM2e and pTM-MV-ATU3-N-3xM2e constructs were checked by sequencing of the insert.

Rescue of Recombinant MV-M2 and MV-NM2e Viruses

The pTM recombinant plasmids were used to rescue recombinant viruses using a helper-cell-based system as previously described (Combredet et al., 2003). Single viral clones were amplified on Vero-NK cells. All viral stocks were produced after infection at a MOI of 0.1, stored at −80° C. and titrated by an endpoint limiting dilution assay on Vero-NK cell monolayers. Infectious titers were determined as 50% tissue culture infectious doses ($TCID_{50}$) according to the Reed and Muench method (Reed and Muench, 1938). Growth curves of recombinant and parental viruses were determined on Vero-NK cells infected at a MOI of 0.1, as described (Combredet et al., 2003).

Immunofluorescence Assays

Monolayers of Vero-NK cells plated on 20 mm glass coverslips in a 12-well plate were infected with the recombinant or parental MVSchw viruses at a MOI of 0.01. When syncytia were clearly visible but not yet confluent (30-36 hours post-infection), cells were washed in Dulbecco's PBS and fixed with PBS-4% paraformaldehyde for 20 minutes. In order to analyze the expression of N-M2e fusion proteins, cells were further permeabilized with PBS-0.2% triton X-100 for 10 minutes at 4° C. Coverslips were then incubated with 0.5 µg/ml of 14C2 mouse anti-M2e monoclonal antibody (Santa Cruz Biotechnology) or with rabbit polyclonal anti-MV-N(Covalab) diluted 1/1500 in PBS-1% donkey serum (DKS). After subsequent incubation with Alexa Fluor-labeled donkey anti-mouse or anti-rabbit IgG conjugates (Life Technologies, 1/500 dilution), the coverslips were mounted on slides with DAPI-containing Prolong Gold Antifade Reagent (Life Technologies) and analyzed under a DM IRB fluorescence microscope (Leica) using a 20× objective or 40× oil immersion objective. Pictures were acquired with a QICAM Fast 1394 camera (QImaging) and processed with the Qcapture Pro software (version 6.0.0.412, QImaging).

Western Blots

Monolayers of Vero-NK cells were infected at a MOI of 0.05 with the recombinant MV-M2, MV-NM2e or parental MVSchw viruses. 24 or 36 h post-infection, cell extracts were harvested in Laemmli sample buffer and denatured by heating at 95° C. for 10 min. Proteins were separated by 4-12% SDS Bis-Tris polyacrylamide gels (Life Technologies) and transferred onto a PVDF membrane prior to immunoblotting with 14C2 anti-M2e antibody (Santa Cruz Biotechnology, 0.2 µg/ml) or with anti-MV-N antibody (Covalab, 1/10000 dilution). Following incubation with Alexa Fluor 680-labeled donkey anti-mouse or anti-rabbit IgG conjugates (Life Technologies, 1/40000 dilution), fluorescence was captured with an Odyssey Infrared Imaging system (Li-Cor Biosciences).

Mice Experiments and Characterization of Humoral Immune Responses

All experiments were approved and conducted in accordance to the Pasteur Institute guidelines in compliance with European animal welfare regulations (http://ec.europa.eu/environment/chemicals/lab _animals/home_en.htm). The protocol was approved by the Institut Pasteur animal care and use committee. All experiments were conducted under enhanced biosafety level 2 conditions. To obtain $CD46^{+/-}$ $IFN\alpha/\beta R^{-/-}$ mice permissive for measles vaccine (Mrkic et al., 1998), FVB mice heterozygous for the measles vaccine CD46 receptor transgene were backcrossed to 129/Sv mice lacking the type IFN (Combredet et al., 2003). After more than 10 generations of backcrossing in our breeding colony, the resulting CD46-IFNAR line acquired a uniform 129/Sv background.

Six- to nine-week-old CD46-IFNAR mice were used to assess the immune response induced by recombinant MV-M2 and MV-NM2e viruses. Unless otherwise stated, groups of 6 mice were injected intraperitoneally (i.p.) with $10^5$ $TCID_{50}$ of recombinant or parental MVSchw or with PBS as a control. Booster injections were administered four weeks thereafter. Serum samples were collected three weeks after each injection (IS1 and IS2 sera, respectively).

Antibody response to the M2 protein in immunized mice was measured by indirect ELISA. Briefly, biotinylated M2e peptide corresponding to the consensus M2e sequence (SLLTEVETPIRNEWGCRCNDSSDK-biotin—SEQ ID No. 39, Eurogentec) was immobilized on streptavidine-coupled microtiter plates (Nunc) at a concentration of 1 µg/ml in 50 µl PBS. The M2e-coupled plates were subsequently incubated with serial dilutions of the test sera. Bound antibodies were revealed with mouse-specific anti-IgG secondary antibody conjugated to horseradish peroxidase (Southern Biotech, 1/8000) and TMB (3,3'-5,5'-tetramethylbenzidine, KPL). The isotype determination of the antibody responses was performed using isotype-specific (IgG1 and IgG2a) secondary antibodies coupled to horseradish peroxidase (Southern Biotech). The reaction was stopped by addition of an equal volume of $H_3PO_4$ (1 M) and absorbance of each well was read at 450 nm/620 nm. The M2e-specific antibody titers were calculated as the reciprocal of the highest dilution of individual serum, giving an absorbance of 0.5 over blank value. MV-specific antibodies were similarly measured using ELISA plates (Maxisorp, Nunc) coated with 50 ng/well of purified measles antigens (Jena Bioscience, Germany).

Specific antibodies against the native form of the M2 protein were measured using a cell-based ELISA. Briefly, monolayers of MDCK and MDCK-M2 cells in 96-well microtiter plates were incubated with serial dilutions of the test sera. Bound antibodies were revealed with anti-mouse IgG secondary antibody and TMB substrate as described above. Readings from wells seeded with MDCK cells were subtracted from wells with MDCK-M2 cells and the M2-specific IgG titers were calculated as the reciprocal of the highest dilution of individual serum, giving an absorbance of 0.2.

Challenge Infection of Animals with Influenza Virus

Four weeks after the second immunization, animals were lightly anesthetized with ketamine/xylazine solution (50 mg/kg and 10 mg/kg respectively) and, unless otherwise stated, inoculated intranasally with 10 Lethal Dose 50 (LD50) of virus in 30 µl PBS. Mice were weighed every other day and monitored daily for signs of morbidity and mortality over 21 days. Animals that lost more than 30% of their initial weight were euthanized by cervical dislocation.

Passive Immunization and Virus Challenge

Immune sera were prepared from CD46-IFNAR mice previously immunized with MV-M2 recombinant viruses and control MVSchw virus. Blood was collected 3 and 4 weeks after the second administration of virus, and serum was prepared by clotting the blood at room temperature for 2 to 4 hours, followed by 2 hours incubation at 4° C. and centrifugation Sera were pooled per immunization group, filter-sterilized and kept at −20° C.

Eight-week-old C57BL/6 mice (Charles River) were injected by the i.p. route with 400 µl of pooled immune serum, diluted in PBS up to 500 µl, or with 500 µl PBS alone as a control. The day after, the passively immunized mice were challenged with 10 LD50 of the mouse-adapted A/Scotland/20/74 (H3N2) strain and monitored, as described above.

Supplementary Materials and Methods for the Construction and Characterization of Recombinant MV-M1 and MV-M1&M2 Viruses A full-length M1 consensus sequence, reflecting circulating human influenza lineages (seasonal A/H3N2 and A/H1N1 strains, as well as the 2009 pandemic A/H1N1 variants), was generated from complete M1 protein sequences available at the NCBI Influenza Virus Sequence Database, accessed in January 2013. Briefly, a total of 4686 complete M1 protein sequences, representing the spectrum of H3N2 (1480 sequences from the period of 2007-2012), H1N1 (1740 sequences from the period of 1977-2012) and H1N1v (1466 sequences) influenza A diversity in humans from 1977 or 2007 to 2012, were selected and downloaded. From these data, sequence alignments and consensus sequences were computed for each of the three subtypes on the CLC Main Workbench platform (version 6.7.1) using the default settings. Next, a global consensus was generated by giving the same weight to each of H3N2, H1N1 and H1N1v M1 consensus and following the majority rule whenever applicable. When the three consensus differed on a given position, the H3N2 value was chosen to reflect the overall predominance of this subtype during the 2011-2012 and 2012-2013 flu seasons in the northern hemisphere preceeding the time of design. The amino acid sequence of the M1 global consensus was then processed to generate a codon-optimized nucleotide sequence for high expression in mammalian cells. This coding sequence was further edited to inhibit alternative splicing and prevent synthesis of truncated M2-like polypeptide, and to avoid MV editing ($A_5G_3$)- and core gene end ($A_4CKT$)-like sequences, and regions of very high (>80%) or low (<30%) GC content whenever possible. Furthermore, cis-acting sequence motifs such as internal TATA-boxes, chi-sites, ribosomal entry sites, ARE, INS, and CRS sequence elements, as well as repetitive sequences, RNA secondary structures and other cryptic splice donor and acceptor sites, were avoided. The optimized nucleotide sequence of the M1 global consensus (M1opt) was chemically synthesized (Geneart, Life Technologies) with additional BsiWI and BssHII restriction sites at the 5' and 3' ends, respectively. The sequence respects the "rule of six", which stipulates that the number of nucleotides of the MV genome must be a multiple of 6.

Insertion of M1opt and M2opt cDNAs in BsiWI/BssHII-digested pTM-MVSchw-ATU2(eGFP) and pTM-MVSchw-ATU3(eGFP) vectors resulted in pTM-MV-ATU2-M1 and pTM-MV-ATU3-M2 plasmids, respectively. These two plasmids were then digested with SalI restriction enzyme and ligated to produce the double recombinant pTM-MV-M1&M2 plasmid.

Rescue and characterization of MV-ATU2-M1, MV-ATU3-M2 and MV-M1&M2 recombinant viruses were performed as described above. The GA2B anti-M1 mAb (Thermo Scientific, 0.2 µg/ml) was used for immunofluorescence and western blot assays of M1 expression.

Supplementary Materials and Methods for the Design of a Consensus Nucleoprotein (NP) Gene and of a Construct Encoding the NP Consensus Protein Fused to 3 Copies of M2e (NPflu-3xM2e)

A full-length nucleoprotein (NP) consensus sequence, reflecting circulating human influenza lineages (seasonal A/H3N2 and A/H1N1 strains, as well as the 2009 pandemic A/H1N1 variants), was generated from complete NP protein sequences available at the NCBI Influenza Virus Sequence Database, accessed in May 2015. Briefly, a total of 1494 complete NP protein sequences, representing the spectrum of H3N2 (746 sequences from the period of 1968-2015), H1N1 (249 sequences from the period of 1977-2015) and H1N1v (499 sequences) influenza A diversity in humans from 1968 to 2015, were selected (after collapsing identical sequences) and downloaded. From these data, sequence alignments and consensus protein sequences were computed for each of the three subtypes on the CLC Main Workbench platform (version 6.8.4) using the default settings. Next, a global consensus was generated by giving the same weight to each of H3N2, H1N1 and H1N1v NP consensus and following the majority rule whenever applicable. When the three protein consensus sequence differed on a given position, the H3N2 value was chosen to reflect the overall predominance of this subtype during the 2011-2012, 2012-2013, and 2014-2015 flu seasons in the northern hemisphere preceding the time of design. The amino acid sequence of the NP global consensus was then processed to generate a codon-optimized nucleotide sequence for high expression in mammalian cells. Regions of very high (>80%) or low (<30%) GC content were avoided whenever possible, and cis-acting sequence motifs like internal TATA-boxes, chi-sites, ribosomal entry sites, ARE, INS, and CRS sequence elements, as well as repetitive sequences, RNA secondary structures and splice donor and acceptor sites, were avoided. The sequence was further edited to remove MV editing ($A_5G_3$)- and core gene end ($A_4CKT$)-like sequences on both strands. BsiWI and BssHII restriction sites were then added at the 5' and 3' ends, respectively, of the nucleotide sequence (NPflu) of the NP global consensus. The sequence respects the "rule of six", which stipulates that the number of nucleotides of the MV genome must be a multiple of 6 and has the sequence of SEQ ID No. 30.

A further construct encoding the NP consensus protein fused to three copies of M2e (NPflu-3xM2e) was generated by PCR amplification using the NPflu consensus gene as a template and the forward primer 5'-AGT<u>CGTACGG</u> CCACCATGGC CTCTC-3' 5seq id No; 36) containing BsiWI restriction site (underlined) and the reverse primer 5'—TCGGCGCGCG ATC<u>CTCCGGA</u> GTTGTCGTAC TCTTCGGCGT TG-3' (SEQ ID No.37) containing BspE1 and BssHII restriction enzyme sites (underlined). The resulting cDNA was cloned into the PCR4Blunt-TOPO plasmid. It contained unique BspE1 and BssHII restriction enzyme sites at the 3' extremity of the NPflu coding sequence which permitted subsequent insertion of the synthetic and codon-optimized 3xM2e sequence described above.

Supplementary Materials and Methods for the Construction and Characterization of Recombinant MV-NPflu&M2 and MV-NPflu-3xM2e Viruses Both NPflu and NPflu-3xM2e cDNAs were inserted into BsiWI/BssHII-digested pTM-MVSchw-ATU2(eGFP) vector, resulting in pTM-MV-ATU2-NPflu (SEQ ID No.11) and pTM-MV-ATU2-NPflu-3xM2e plasmids. (SEQ ID No.13) The plasmids pTM-MV-ATU2-NPflu and pTM-MV-ATU3-M2 were then digested with SalI restriction enzyme and ligated to produce the double recombinant pTM-MV-NPflu&M2 (SEQ ID No.10) plasmid.

Rescue of MV-ATU2-NPflu, MV-NPflu&M2 and MV-ATU2-NPflu-3xM2e recombinant viruses was performed in 293T-T7-MV helper cells as described above. The viruses were characterized by sequencing of their genome and by western blot assay of influenza NP and M2 (or M2e) expression (FIG. 9).

Supplementary Materials and Methods for the Construction and Characterization of Recombinant MV-ATU2-N-3xM2e Virus The N-3xM2e coding sequence was obtained by digestion with BsiWI and BssHII restriction enzymes of the pTM-MV-ATU3-N-3xM2e plasmid. The resulting DNA fragment was then inserted into the corresponding sites of pTM-MVSchw-ATU2(eGFP) vector and the resulting pTM-MV-ATU2-N-3xM2e construct (SEQ ID No.12) was checked by sequencing of the insert.

Rescue of MV-ATU2-N-3xM2e recombinant virus was performed in 293T-T7-MV helper cells as described above. The virus was characterized by sequencing of its genome and by western blot analysis of infected cell lysates. High level of expression of the N-3xM2e fusion protein was evidenced with anti-MV N antibodies and with the 14C2 anti-M2e monoclonal antibody, demonstrating that such fusion protein can be expressed either from ATU2 (FIG. 11) or from ATU3 (FIG. 2).

Supplementary Materials and Methods for the Characterization of Cellular Immune Responses Spleen cells were collected 7 to 10 days after a single administration of recombinant or parental measles virus and the frequency of influenza virus-specific IFN-γ-producing T cells was quantified in a standard ELISPOT assay. Briefly, 96-wells Multi-screen PVDF plates (Millipore) were coated with 10 µg/ml rat anti-mouse IFN-γ antibodies (R4-6A2, Becton-Dickinson) in PBS. Plates were washed and blocked with complete RPMI medium (RPMI 1640 supplemented with 10% FCS, 10 mM Hepes, $5 \times 10^{-5}$ M R-mercaptoethanol, non-essential amino acids, Sodium Pyruvate, 100 U/ml penicillin and 100 µg/ml styreptomycin) for 2 h. Various numbers of splenocytes (typically $4 \times 10^5$, $2 \times 10^5$ and $1 \times 10^5$) from immunized and control mice were then plated in triplicate in the presence or absence of the appropriate peptide (10 µM) and IL2 (10 U/ml). The cells were incubated for 20 h at 37° C., and after extensive washes, the spots were revealed by successive incubations with biotinylated rat anti-mouse IFNγ antibodies (XMG1.2, Becton-Dickinson), alkaline phosphatase-conjugated streptavidin (Becton-Dickinson) and 5-bromo-4-chloro-3-indolylphosphate/nitroblue tetrazolium (BCIP/NBT, Sigma) as the substrate. The spots were counted using the automated S6 Ultimate-V analyzer and associated Immunosoft software (CTL Analyzer). For each mouse, the number of peptide-specific IFNγ-producing cells was determined by calculating the difference between the number of spots generated in the absence and in the presence of the peptide. Results were expressed as the number of spot-forming cells (SFCs) per $10^6$ splenocytes.

The NP366 (H3N2) consensus peptide (AS-NENMDNM—SEQ ID No.41), the NP366 (Scotland) peptide (ASNENMDTM—SEQ ID No.42) and the NP263-276 conserved peptide (ALILRGSVAHKSCL—SEQ ID No.43) were synthesized by Eurogentec and used to measure the frequency of influenza-specific T cells. The measles H22-30 (RIVINREHL—SEQ ID No.44) and H446-454 (SNHNN-VYWL—SEQ ID No.45) peptides and the LCMV NP396-404 (FQPQNGQFI—SEQ ID No.46) peptide were used as positive and negative control peptides, respectively.

Results

Recombinant MVSchw Express the Full-Length M2 Consensus Protein and Replicate Efficiently A full-length M2 consensus sequence was designed by the inventors, reflecting circulating human influenza lineages, seasonal A/H3N2 and A/H1N1 strains, as well as the 2009 pandemic A/H1N1 variant strain, from complete coding sequences available at the NCBI in November 2011. This global consensus (M2raw) was generated from separate H3N2, H1N1 and H1N1v consensus, as described in materials and methods and was edited to remove potential MV editing- and polyadenylation sites. The global consensus amino acid sequence is identical to the H3N2 consensus with the exception of a single conservative substitution (Val51Ile) in the cytoplasmic domain, but different from the H1N1 (7 substitutions) and the H1N1v consensus (15 substitutions). When the M2 ectodomain (M2e) region only is considered, the global M2e consensus is identical to both H1N1 and H3N2 consensus, and differs at 4 positions from the H1N1v consensus (Table 1).

Both M2raw and a human codon-optimized version (M2opt) of the consensus gene were inserted as an additional transcription unit (ATU) into MV vector, either in position 3 (ATU2, FIG. 1A) or in position 1 (ATU1, not shown) of the genome. All four corresponding recombinant viruses were successfully rescued in helper 293-T7-MV, as indicated by the formation of syncytia in MV-infected Vero-NK cells (FIG. 10 for ATU2 viruses, not shown for ATU1 viruses) and by the sequencing of the ATU on the rescued virus genomes.

The growth of recombinant MV-ATU2 viruses was next analyzed in Vero-NK cells. Growth kinetics of both recombinant MV-ATU2-M2raw and MV-ATU2-M2opt were slightly delayed compared to that of parental MVSchw (FIG. 1B). Furthermore, the yields of recombinant viruses were 10 times lower than for the parental virus, with a maximum titer of $10^{6.4}$ TCID$_{50}$/ml. This may be due to the toxicity of the M2 ion channel for mammalian cells (Ilyinskii et al., 2007) and the high levels of M2 expression at the surface of MV-M2 infected cells.

Figure 10:
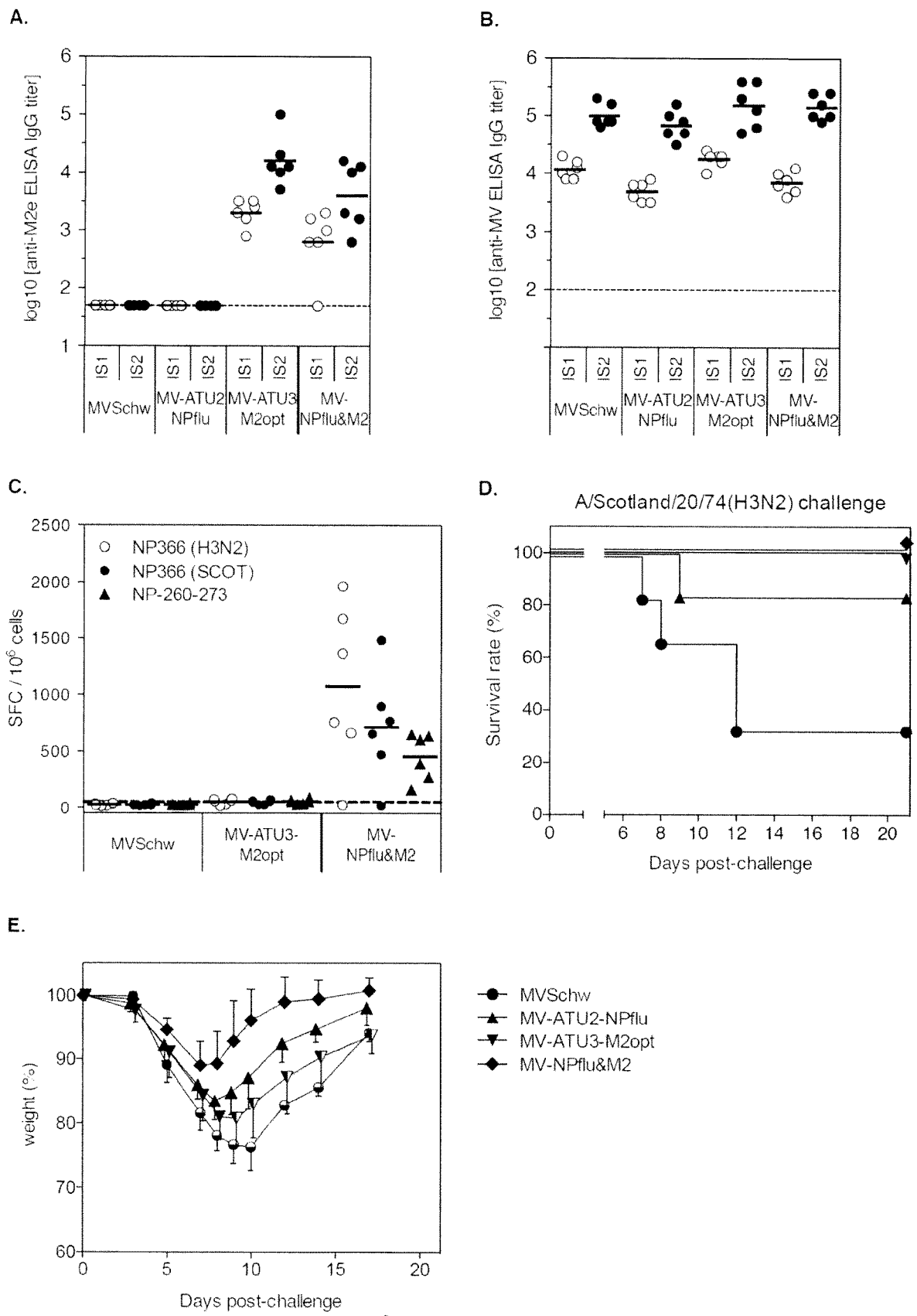

Indeed, expression of M2 consensus protein at the surface of infected cells was evidenced by immunofluorescence analysis of non-permeabilized cells with the 1402 mouse monoclonal antibody directed against the extracellular M2 ectodomain (FIG. 10). Furthermore, expression levels of M2 in Vero-NK cells infected by the recombinant MV-M2 viruses were analyzed by fluorescent western blotting of cell lysates and were shown to be much higher than expression levels in MDCK cells infected with A/PR/8/34 (PR8) or A/Scotland/20/74 (SCOT) influenza viruses (FIG. 1D-E). More precisely, lysates from MV-M2-infected Vero NK cells had to be diluted more than 1 in 4 (FIG. 1D) or up to 1 in 10 (FIG. 1E) to match band intensity of lysates from influenza-infected MDCK cells.

Recombinant MVSchw Express an Additional N Protein Fused to M2e Ectodomain and Replicate Efficiently To enhance M2e immunogenicity, we sought to express M2e as a fusion protein with measles nucleoprotein (N), thereby achieving multimerization and display of M2e on the viral nucleoprotein. To that end, one or three tandem copies of the 23 aa-consensus M2e sequence was genetically linked to the measles N C-terminus through a flexible SGGSGG linker (SEQ ID No.38), and the resulting protein was expressed from the ATU located in position 6 of the pTM-MVSchw-ATU3 vector (FIG. 2). In this approach, the measles N protein serves as a carrier to incorporate M2e into measles ribonucleoprotein (RNP) complexes.

Both recombinant MV-N-1xM2e and MV-N-3xM2e viruses were successfully rescued in helper 293-T7-MV, as indicated by the formation of syncytia in MV-infected Vero-NK cells (FIG. 2B) and by the sequencing of the ATU on the rescued virus genomes. Both recombinant viruses grew to titers in the $10^7$-$10^8$ TCID$_{50}$/ml range, which are similar to those achieved by parental MVSchwarz. This indicates that the expression of the hybrid N proteins from an additional gene in position 6 of the genome does not affect viral propagation in vitro. Expression of the N-M2e fusion proteins was analyzed by immunofluorescence of infected cells and western blotting of infected cell lysates. In addition to the authentic N band, an additional band was observed by western blotting with anti-MV N antibodies for each fusion protein at the expected size (FIG. 2D). These bands also reacted with the 14C2 anti-M2e monoclonal antibody (FIG. 2C), validating the correct expression of the M2e epitopes on its N carrier. It is noteworthy that several minor additional bands are visible on the blots, indicating degradation of authentic and fusion N proteins and susceptibility of measles N to proteolysis, as already evidenced by others (Rima, 1983). Intensity of the N-M2e bands was lower than that of the authentic N, indicating reduced expression levels of the N-M2e genes from the ATU located in the distal position 6 when compared to those of the authentic N gene located in the proximal position 1 of the antigenome. This was expected, since viral mRNAs are produced in decreasing amounts from the 3' to the 5' end of MV genomic RNA (Plumet et al., 2005). As illustrated in FIG. 2B, immunostaining with anti-MV N antibodies showed that N is mainly contained in large cytoplasmic inclusion bodies, as already described by others (Griffin, 2013). The role of these inclusion bodies in MV life cycle has not been extensively studied, but are likely the sites of viral genome transcription and replication as evidenced recently for other paramyxoviruses and rhabdoviruses (reviewed in Zhang et al., 2013). Interestingly, immunostaining with the 14C2 anti-M2e monoclonal antibody showed a similar localization of both N-M2e fusion proteins, indicating that their measles N region directed the fusion proteins to the sites of viral replication and likewise promoted their incorporation and multimerization into the active RNP complexes.

MV-M2 and MV-N-M2e Induce Th1-Type Immune Response

Figure 3:
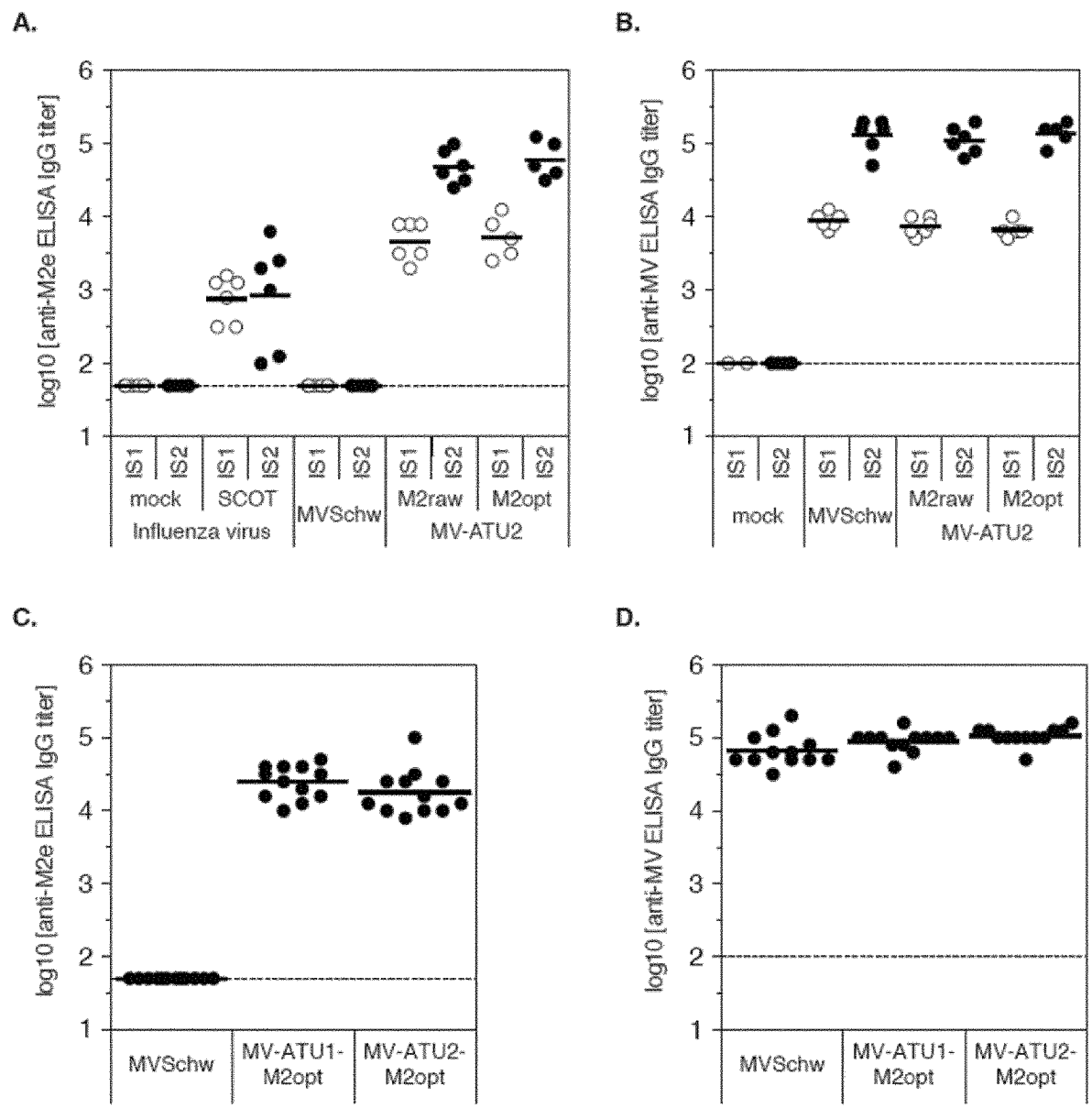
Figure 3:
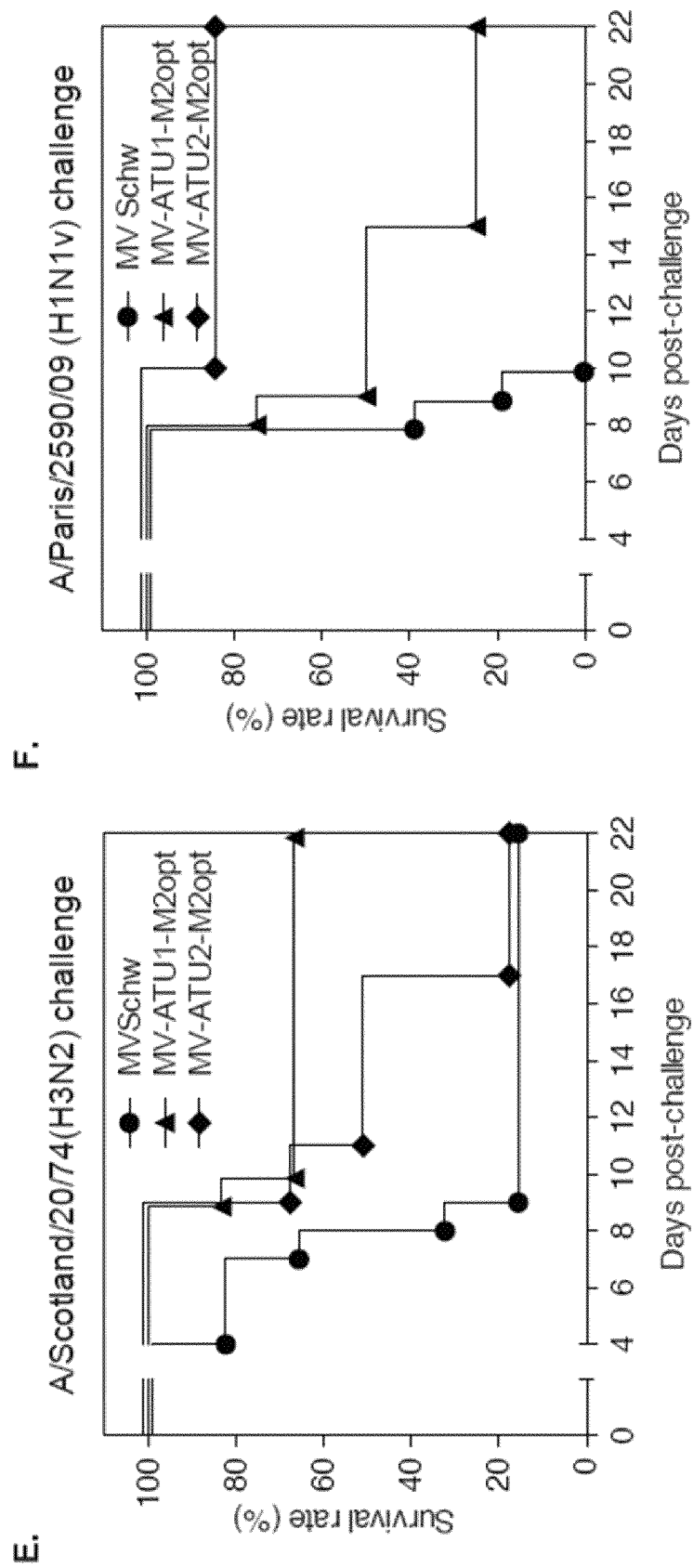

The immunogenicity of the recombinant MV-M2 viruses was investigated in genetically modified CD46-IFNAR mice susceptible to MV infection (Mrkic et al., 1998) and compared to the immunogenicity of M2 expressed during experimental influenza infection with the mouse-adapted A/Scotland/20/74 strain (FIG. 3).

M2e- and measles-specific antibody responses were evaluated for each individual mouse by indirect ELISA against M2e peptide and MV antigens, respectively. M2e peptide was biotinylated at its C-terminus and immobilized on streptavidine-coupled microtiter plates in order to ensure that the peptide was displayed onto the polystyrene wells in a conformation as close as possible to its natural conformation, where it is C-terminally linked to M2 transmembrane region and displayed on the cell surface. Indeed, preliminary experiments showed that recognition of the M2e peptide by the 14C2 monoclonal antibody as well as by polyclonal antibodies induced in mice by experimental influenza infection was much more efficient when the M2e peptide was biotinylated and immobilized, rather than adsorbed on the plastic surface of ELISA plates (not shown).

High titers of anti-M2e IgG were raised in all mice to similar levels after the first injection of recombinant MV-ATU2-M2 viruses (FIG. 3A) and MV-ATU1-M2 viruses (not shown), whereas preimmune sera (not shown) and sera from control animals that received empty MVSchw remained negative. These titers were higher for both MV-ATU2-M2raw and MV-ATU2-M2opt injected animals (average titer of 3.7±0.3 and 3.7±0.2 log 10, respectively) than for animals infected with the A/Scotland/20/74 virus (2.9±0.3 log 10 titer, $p<10^{-3}$). After the second injection, titers were boosted 10 to 20 times for animals immunized with MV vectors. Tallying with the results observed after the first injection, the four MV-M2 recombinant viruses induced similar high IgG titers, which felt in the $10^4$-$10^5$ range (FIGS. 3A and 3C). Noticeably, the second inoculation of A/Scotland/20/74 virus did not amplify the anti-M2 IgG response (2.9±0.8 log 10).

Figure 4:
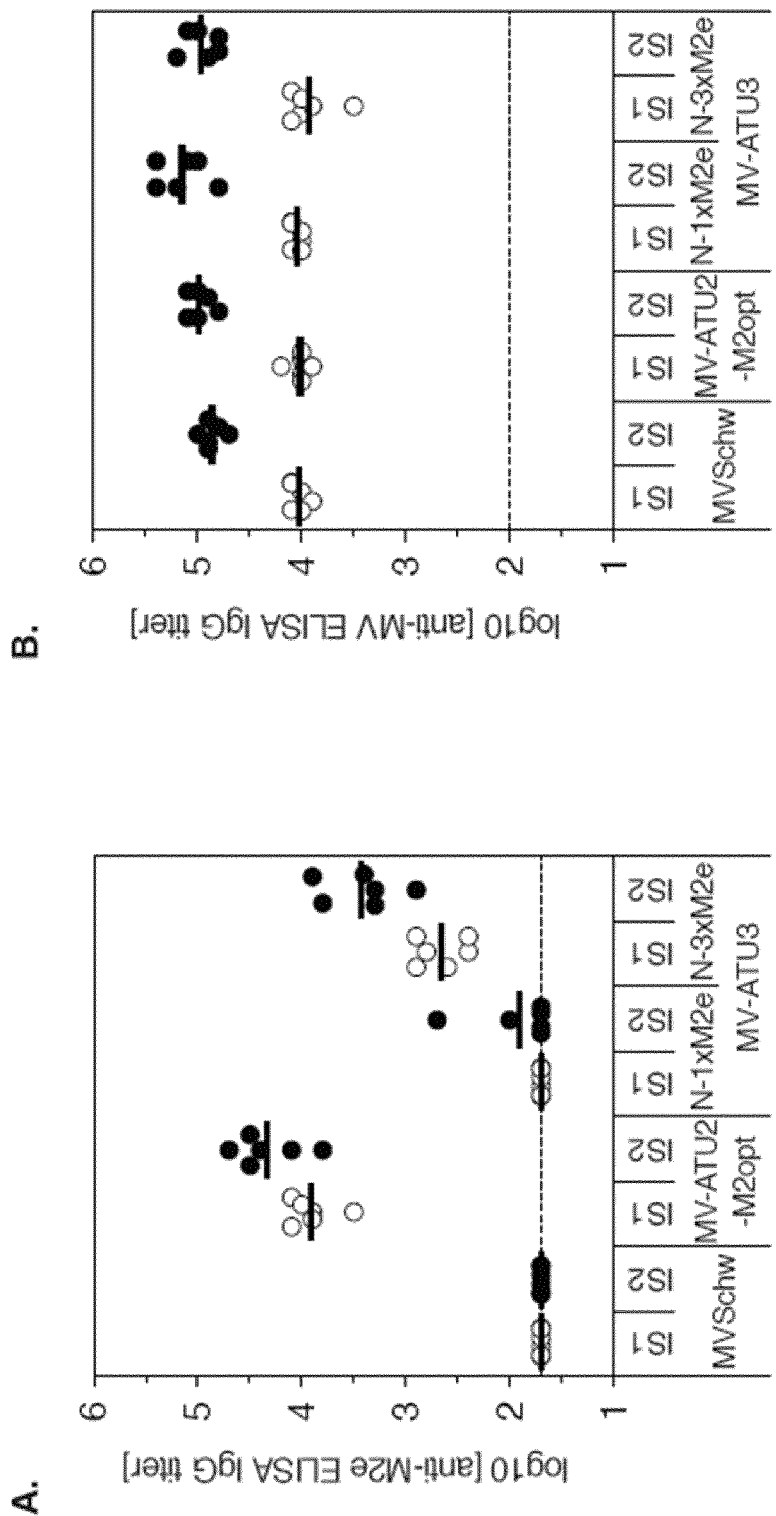
Figure 4:
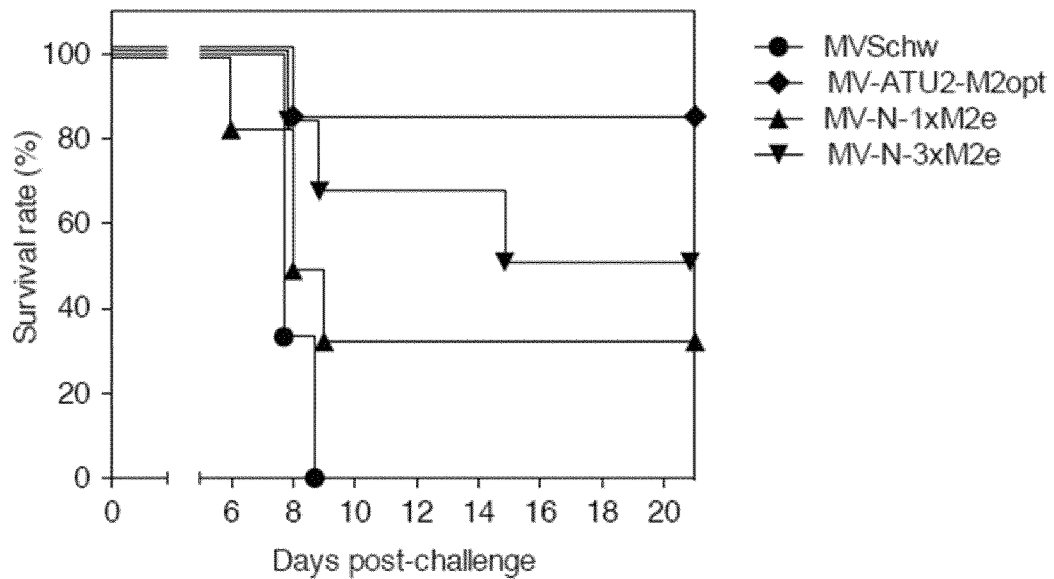

Next, the immunogenicity of the recombinant MV-N-M2e viruses was compared to that of the MV-ATU2-M2opt virus. Significant titers of anti-M2e IgG were raised in all mice after the first injection of recombinant MV-N-3xM2e virus (2.7±0.2 log 10 titer), whereas sera from control animals and sera from animals that received the MV-N-1xM2e remained negative (log 10 titers <1.7, FIG. 4A). After the second injection, titers were boosted up to 3.5±0.4 log 10 for animals immunized with the MV-3xM2e virus and an anti-M2 response was detected at low titers in 2 out of 6 mice immunized with the MV-N-1xM2e virus (2.0 and 2.7 log 10 titers). In contrast, a single injection of MV-ATU2-M2opt induced a high IgG titer (3.9±0.2 log 10 titer) that further increased after a second injection (4.3±0.3 log 10 titer).

To analyze the polarization of the immune response induced by the recombinant MV vaccines, we next measured the level of IgG1 and IgG2a isotypes three weeks after the second injection (FIG. 4C). Immunization with two doses of MV-ATU2-M2 or MV-N-3xM2e induced higher titers of IgG2a than IgG1 antibodies (average ratio IgG2a over IgG1 of 60 and 79 respectively), suggesting that the immune response was skewed towards a Th1-type response.

Interestingly, antibodies to MV were raised at similar levels in all mice that received either MVSchw, MV-M2 viruses (FIGS. 3B and 3D) or MV-N-M2e viruses (FIG. 4B). This indicates that expression of the full-length M2 protein by the recombinant viruses did not alter their replication in vivo nor modify their measles-specific immunogenicity, despite their delayed growth curve and reduced titers in in vitro experiments. This also indicates that the expression of the hybrid N-M2e proteins from an additional nucleoprotein gene did not affect replication and immunogenicity of measles virus in mice.

Altogether, these results demonstrated that the measles vector is capable of inducing very high levels of anti-M2e antibodies in CD46-IFNAR mice (H-2b 129/Sv background) whether the full-length M2 gene is expressed from an ATU or 3 tandem copies of the short 23-aa M2e sequence are fused to an extra copy of the N gene. Most interestingly, both vectorization strategy allowed to bypass the H-2 restriction of anti-M2e responses, which was described recently for DNA immunization, adenovirus vectorization and M2e-multiple antigenic peptides (MAP) immunization, and which evidenced very poor responsiveness in mice of the $H2^b$ haplotype (Misplon et al., 2010; Wolf et al., 2011). In addition, anti-M2e responses are likely Th1-skewed, a hallmark of live attenuated viruses and a highly desirable feature for an antiviral vaccine.

Protection of Mice after Homologous and Heterologous Challenge

To determine the protective efficacy of MV-ATU1-M2opt and MV-ATU2-M2opt, we examined the survival of CD46-IFNAR mice after intranasal lethal challenge with 10 LD50 of the homologous A/Scotland/20/74 (H3N2) strain or the heterologous A/Paris/2590/09 (H1N1v) strain. Mice were also monitored for weight change as a measure of illness. All mice immunized as a control with the parental MVSchw died within 10 days after challenge with A/Paris/2590/09 (H1N1v) (FIG. 3F). All but one control mice immunized with the parental MVSchw died within 10 days after challenge with the A/Scotland/20/74 (H3N2) (FIG. 3E). In contrast, mice immunized with MV-ATU1-M2 or MV-ATU2-M2 were partially protected against challenge, with a reduction in global mortality and delayed death time. Survival rates ranged from 17 to 83% and mice that survived the challenge, presented weight loss up to 25% of their initial body weight and began to recover on day 8-10 post challenge (not shown).

Figure 5:
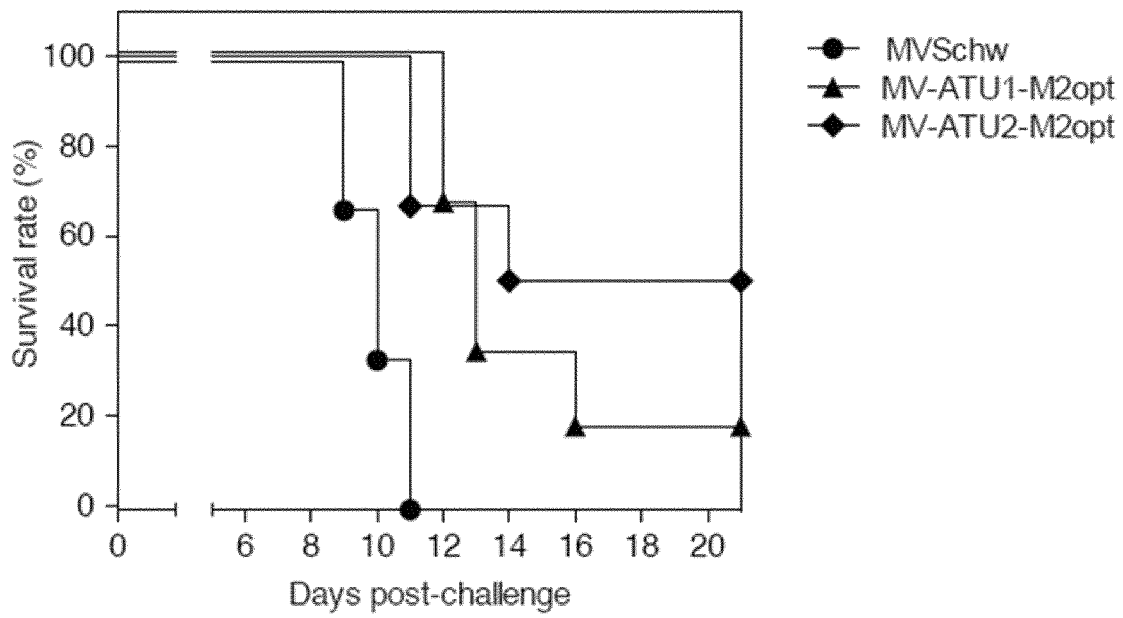

To confirm that the antibodies induced by vaccination with MV-M2 recombinant viruses were responsible for the observed protection, serum was prepared from CD46-IFNAR mice immunized with MV-ATU1-M2 or MV-ATU2-M2 and transferred to naïve C57BL/6 recipient mice. Each mouse received 400 µl of pooled immune serum by intraperitoneal injection, a dose sufficient to obtain anti-M2e circulating antibody titers in the recipient mice at approximately $1/10^{th}$ the levels present in the donor mice (preliminary experiments, not shown). The day after transfer, mice were challenged with homologous A/Scotland/20/74 (H3N2) and survival curves were recorded (FIG. 5). As was observed for donor immunized mice (FIG. 3E), mice transferred with either immune sera were partially protected against challenge, with a reduction in global mortality and delayed death time, whereas all mice transferred with control serum died within 11 days.

Together, these results indicate that recombinant MV-M2 viruses induced protective immunity against homologous H3N2 and heterologous H1N1v influenza in CD46-IFNAR mice, and that circulating antibodies against M2 present in the immunized animals contribute to the observed protection.

Antibodies Induced by N-M2e Fusion Proteins Recognize Native Tetrameric M2 and Protect Mice Against Homologous Challenge Although the mechanism of protection by anti-M2e antibodies remains poorly understood, it relies largely on Fc receptor-dependent elimination of influenza virus-infected cells, ADCC and Ab-dependant cell-mediated phagocytosis (El Bakkouri et al., 2011; Jegerlehner et al., 2004). Therefore, it is critical that anti-M2e antibodies raised by immunization are capable of recognizing native M2e, which is presented as a tetrameric complex at the surface of influenza-infected cells as on influenza virions. To investigate this point, we produced MDCK cells constitutively expressing the full-length consensus M2 protein at the cell surface, as described in materials and methods. We used these MDCK-M2 cells in a cell-based indirect ELISA to analyze binding of sera from MV-N-1xMe- and MV-N-3xM2e-immunized mice (FIG. 4D).

MV-N-3xM2e recombinant virus induced high levels of antibodies able to bind to MDCK-M2 cells (2.8±0.4 log 10 titer). The titers of anti-MDCK-M2 antibodies induced by N-displayed M2e in these MV-N-3xM2e-immunized mice were 20 times lower than those of antibodies induced by the native M2 consensus protein in MV-ATU2-M2-immunized mice (4.2±0.2 log 10 titer, $p<10^{-3}$). Sera from mice immunized with MV-N-1xM2e remained negative (log 10 titer <1.7). The hierarchy of binding titers was indeed comparable to that observed with the peptide ELISA (FIG. 4A) and confirmed that the N-1xM2e construct with a single copy of M2e is less immunogenic than the N-3xM2e construct expressing 3 tandem copies of the M2.

Altogether, these results demonstrated that the M2e peptide, displayed and multimerized on measles RNP complexes is able to induce antibodies recognizing the native tetrameric M2 protein expressed at the cell surface of MDCK-M2 cells.

To investigate the protective efficacy of MV-N-1xM2e and MV-N-3xM2e, we examined the survival of CD46-IFNAR mice after intranasal lethal challenge with the homologous A/Scotland/20/74 (H3N2) virus. All mice immunized with the parental MVSchw died within 9 days (FIG. 4E). In contrast, 2 and 3 out of 6 mice immunized with MV-N-1xM2e and MV-N-3xM2e respectively, survived up to 21 days after challenge. Noticeably, immunization with MV-N-3xM2e resulted in a delayed death time for mice that eventually succumbed to infection, and immunization with MV-ATU2-M2opt induced better protection, in agreement with the induction of higher anti-M2e and anti-native M2 antibody titers. Together, these results suggested that recombinant MV-N-3xM2e and, to a lesser extent, MV-N-1xM2e induces significant protective immunity against influenza in CD46-IFNAR mice.

Supplementary Results for the Construction and Characterization of Recombinant MV-M1 and MV-M1&M2 Viruses
Recombinant MVSchw can be Engineered to Express Full-Length M1 and M2 Consensus Proteins from Two ATUs We designed a full-length M1 consensus sequence, reflecting circulating human influenza lineages, seasonal A/H3N2 and A/H1N1 strains, as well as the 2009 pandemic A/H1N1v strain, from complete protein sequences available at the NCBI in January 2013. This global consensus was generated from separate H3N2, H1N1 and H1N1v consensus, as described in materials and methods. The corresponding nucleotide coding sequence was then generated, codon-optimized for high expression in mammalian cells, and further edited to remove influenza splice sites and prevent synthesis of truncated M2-like polypeptides. It was also edited to remove potential MV editing- and polyadenylation sites. Taking advantage of the gradient of gene expression generated by MV replication (Plumet et al., 2005), the resulting M1opt consensus gene was inserted as an ATU in position 3 (ATU2, FIG. 6A) of the MV vector and the M2opt consensus gene was inserted in position 6 (ATU3). This choice was made in an attempt to reduce M2 expression and negative impact on measles vector replication, which we observed previously when M2 was inserted in the more proximal ATU2 (FIG. 1).

Then, a measles vector with M1opt and M2opt consensus genes inserted in two distinct ATUs was produced by SalI restriction and ligation. The single and double recombinant viruses were successfully rescued in helper 293-T7-MV, as indicated by the formation of syncytia in MV-infected Vero-NK cells and by the sequencing of the ATUs on the rescued virus genomes. All recombinant viruses grew to titers in the $10^7$-$10^8$ TCID$_{50}$/ml range, which are similar to those achieved by parental MVSchwarz. Interestingly, M2 toxicity for mammalian cells did not impair growth of MV-ATU3-M2opt and MV-M1&M2 viruses, as it did for MV-ATU2-M2opt, suggesting that M2 expression levels from the distal ATU3 were reduced below toxicity levels, as expected.

Figure 6:
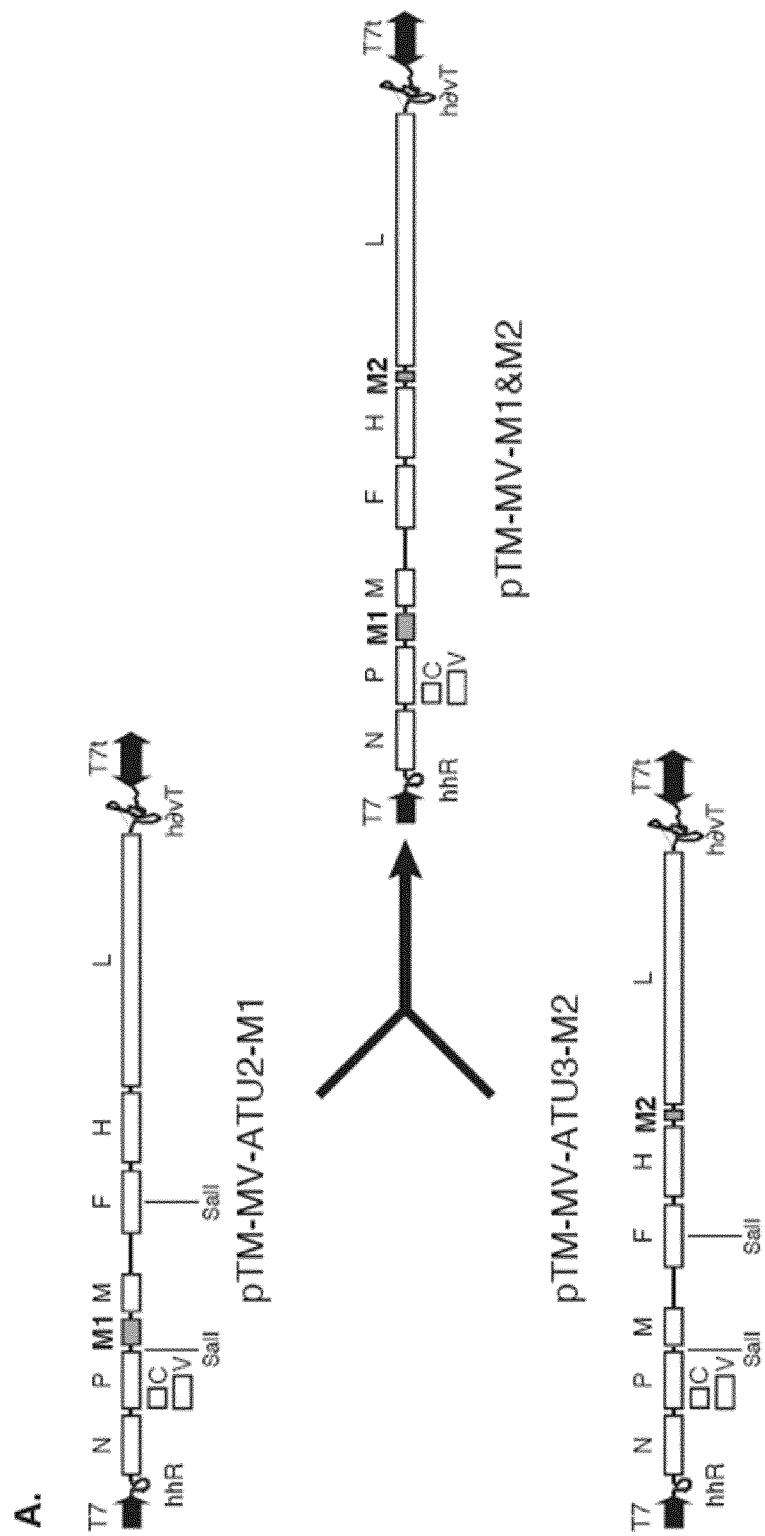
Figure 6:
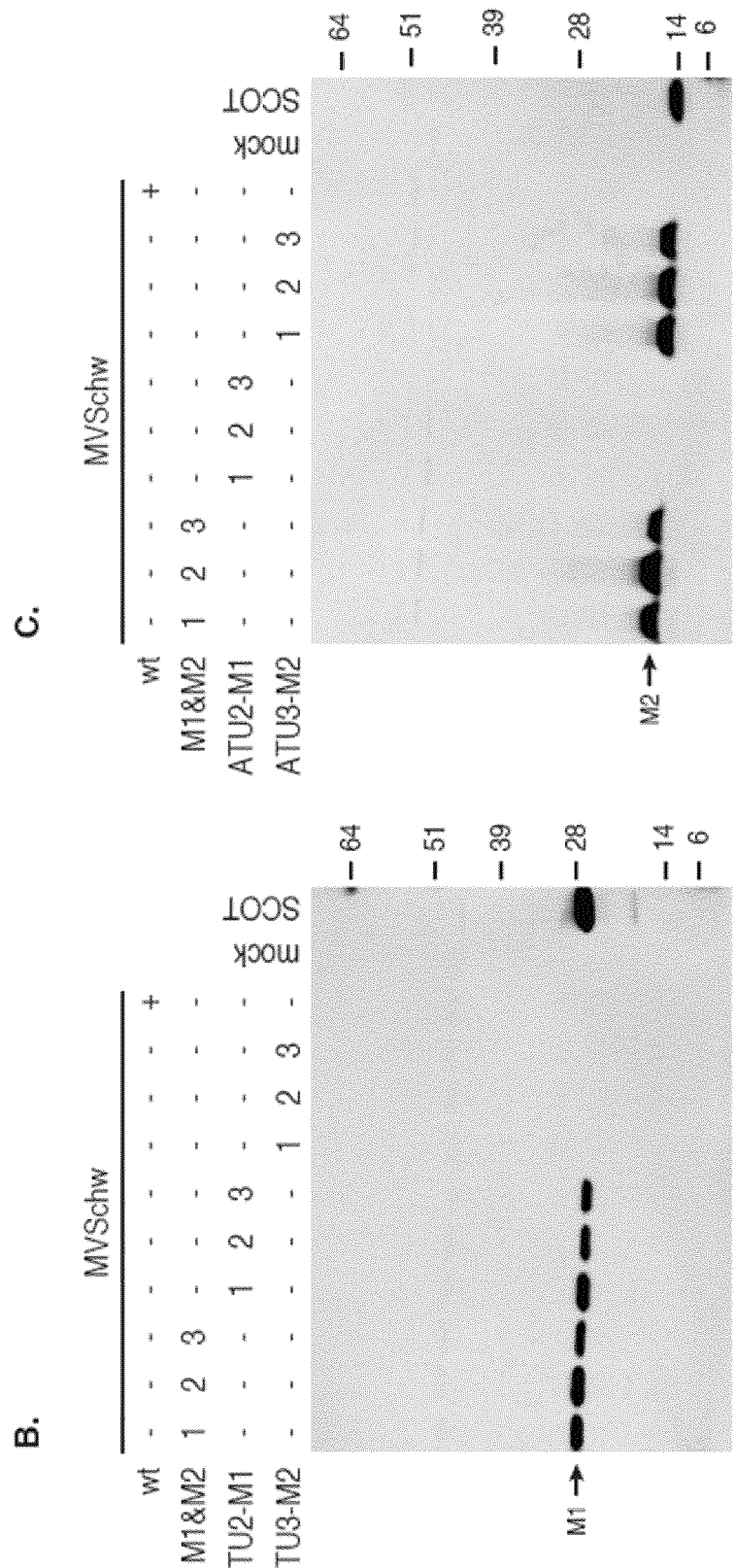

Expression of M1 and M2 in Vero-NK cells infected by either the single and double recombinant virus was analyzed by fluorescent western blotting of cell lysates. M2 expression levels were shown to be higher than expression levels in MDCK cells infected with A.Scotland/20/74 influenza virus (FIG. 6C), whereas M1 expression levels were shown to be somewhat lower (FIG. 6B). M1 and M2 expression levels of the double MV-M1&M2 recombinant virus were similar to those of the single recombinant viruses, MV-ATU2-M1opt and MV-ATU3-M2opt respectively.

Altogether, these data indicate that measles virus vector may be engineered in order to simultaneously express consensus genes coding for both M1 matrix and M2 ion channel from circulating influenza lineages. This double recombinant virus should drive the production of influenza virus-like particles (VLPs) covered with the M2 protein from infected cells and induce enhanced immune responses in immunized animals against both M1 and M2 influenza antigens.

Dual Recombinant Measles Virus Expressing Both M1 and M2 Consensus Proteins Exhibit Higher Protection Efficiency in Mice than Single Recombinant Viruses.

Figure 8:
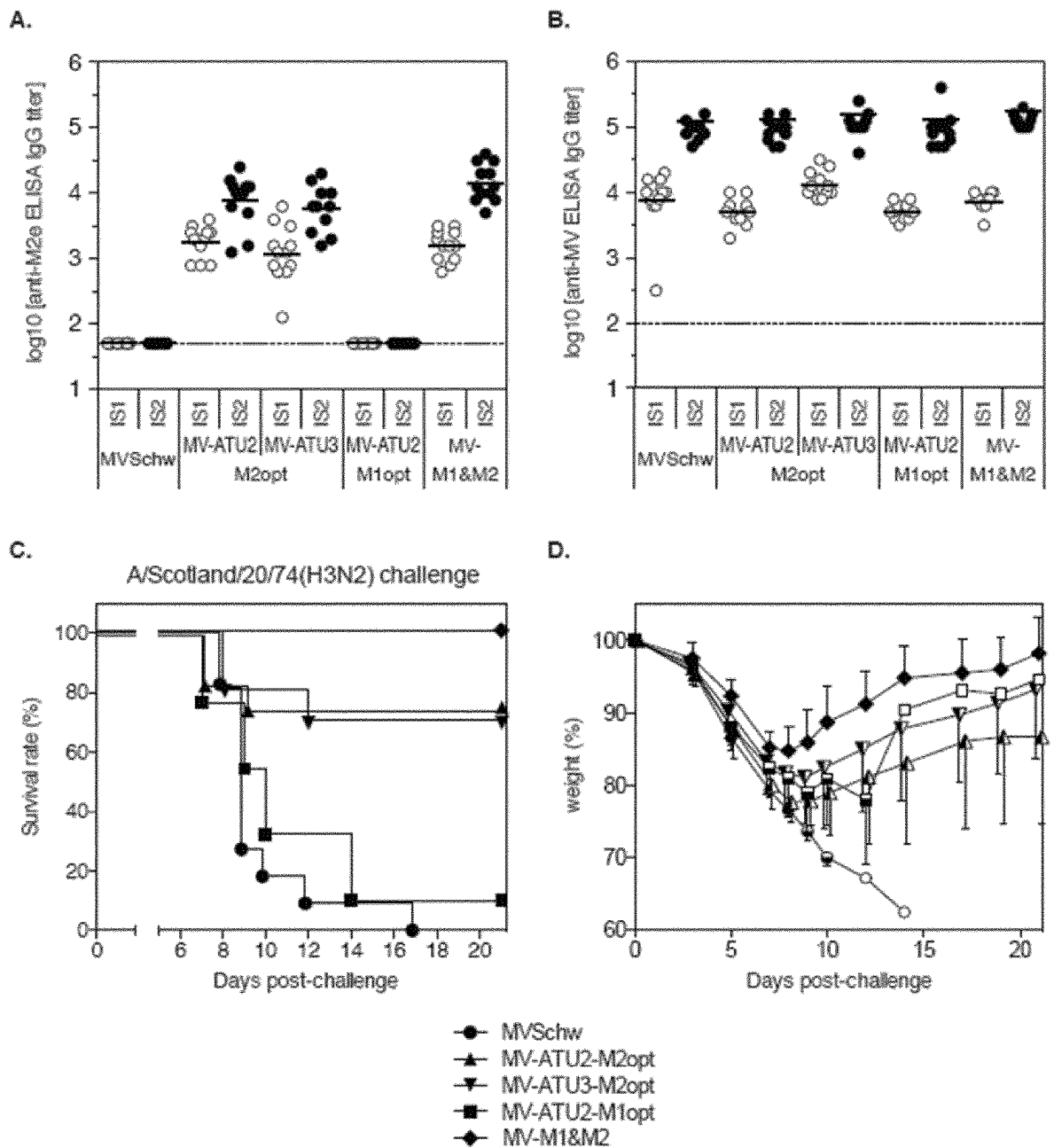

Immunogenicity of the dual recombinant MV-M1&M2 virus was investigated in CD46-IFNAR mice and compared to the immunogenicity of the single recombinant MV-ATU2-M2opt and MV-ATU3-M2opt viruses. High titers of anti-M2e IgG were raised in all mice after the first injection of either of the 3 recombinant viruses, whereas sera from control animals that received empty MVSchw or MV-ATU2-M1opt remained negative (FIG. 8A). After the second injection, titers were boosted up to similar levels for animals immunized with either MV-ATU2-M2opt or MV-ATU3-M2opt viruses (3.9±0.4 and 3.8±0.3 log 10 titers, respectively). Remarkably, significantly higher anti-M2e responses were detected in mice immunized with the dual recombinant MV-M1&M2 virus (4.1±0.3 log 10 titers) than in mice immunized with parental MV-ATU3-M2opt ($p<0.01$) or former MV-ATU2-M2opt ($p<0.1$) viruses.

Interestingly, antibodies to MV were raised at similar levels in all mice that received either MVSchw or MV-M1&M2 virus (FIG. 8B), indicating that the simultaneous expression of two foreign proteins by the dual recombinant virus did not alter its replication in vivo nor modify its measles-specific immunogenicity, as already observed for single recombinant viruses.

To investigate the protective efficacy of the dual recombinant MV-M1&M2 virus, we examined the survival of CD46-IFNAR mice after intranasal lethal challenge with the homologous A/Scotland/20/74 (H3N2) virus. Mice immunized with MV-ATU2-M1opt or the parental MVSchw presented a massive and rapid weight loss from day 3 post-challenge and most died within 12 days (FIG. 8C). Mice immunized with either MV-ATU2-M2opt or MV-ATU3-M2opt single recombinant viruses were partially protected against challenge, with a good reduction in global mortality. Survival rates were 75% and 70% respectively, and mice that survived the challenge, presented weight loss up to 25% of their initial body weight (FIG. 8D). In sharp contrast, all mice immunized with the dual recombinant MV-M1&M2 virus survived after challenge with reduced clinical symptoms and limited weight loss. Together, these results indicated that the dual recombinant MV-M1&M2 virus induces significantly better protective immunity against influenza in CD46-IFNAR mice than either of its parental MV-ATU2-M1opt or MV-ATU3-M2opt.

Recombinant MVSchw can be Engineered to Simultaneously Express Full-Length NP Consensus and M2 or M2e Consensus We designed a full-length NP consensus sequence, reflecting circulating human influenza lineages, seasonal A/H3N2 and A/H1N1 strains, as well as the 2009 pandemic A/H1N1v strain, from complete protein sequences available at the NCBI in May 2015. This global consensus was generated from separate H3N2, H1N1 and H1N1v consensus, as described in materials and methods. The corresponding nucleotide coding sequence was then generated, codon-optimized for high expression in mammalian cells, and further edited to remove potential MV editing- and poly-adenylation sites.

Two alternative strategies were then explored for simultaneous expression of NP and M2 consensus sequences.

First, similarly to the strategy used to express M1 and M2 sequences (see above), the resulting NPflu consensus gene was inserted as an ATU in position 3 (ATU2, FIG. 9A) of the MV vector and the M2opt consensus gene was inserted in position 6 (ATU3). Then, a measles vector with NPflu and M2opt consensus genes inserted in two distinct ATUs was produced by SalI restriction and ligation. The single MV-NPflu and double MV-NPflu&M2 recombinant viruses were successfully rescued in helper 293-T7-MV, as indicated by the formation of syncytia in MV-infected Vero-NK cells and by the sequencing of the ATUs on the rescued virus genomes. Both recombinant viruses grew with a delayed kinetic up to titers in the $10^7$ $TCID_{50}$/ml range, which are slightly lower to those achieved by parental MVSchwarz, indicating that expression of NPflu interferes to some extent with replication of the Measles virus genome and/or dissemination of the virus.

Second, NP and M2e were expressed as a chimeric NPflu-3xM2e antigen from the ATU located in position 3 of the pTM-MVSchw-ATU2 vector (FIG. 9B). In this approach, the NPflu consensus protein acted as a carrier and displayed 3 copies of the 23 aa-consensus M2e polypeptide at its C-terminus. It its most likely that the chimeric antigen will multimerize as authentic influenza NP does, thus enhancing immunogenicity of the M2e polypeptide. The recombinant MV-NPflu-3xM2e virus was successfully rescued in helper 293-T7-MV and was propagated in Vero-NK cells up to titers in the $10^7$ $TCID_{50}$/ml range which are similar to those achieved by parental MV-ATU2-NPflu although lower than those achieved by empty MVSchwarz vector.

Expression of NPflu and M2/M2e in Vero-NK cells infected by either single or double recombinant virus was analyzed by fluorescent western blotting of cell lysates. NPflu expressions levels were shown to be similar than expression levels in MDCK cells infected with A/Scotland/20/74 influenza virus (FIG. 9C), whereas M2 expression levels had already been shown to be higher (FIG. 6C). M2 expression levels of the double MV-NPflu&M2 recombinant virus were somewhat lower than those of the single MV-ATU3-M2opt recombinant virus (FIG. 9D), in accordance with the observed delayed growth of the former. NP expression levels of the double MV-NPflu&M2 recombinant virus were similar to those of the single MV-ATU2-NPflu recombinant virus.

Expression of the NPflu-M2e fusion protein was demonstrated by the presence of a band of higher molecular weight and expected size (64.6 kDa) than that of authentic NP (56 kDa). This band reacted with both anti-influenza virion antibodies and 14C2 anti-M2e monoclonal antibody (FIGS. 9C and 9D), validating the correct expression of the M2e epitopes on the NP carrier.

Altogether, these data indicate that measles virus vector may also be engineered in order to simultaneously express consensus genes coding for both NP nucleoprotein and M2 ion channel from circulating influenza lineages. M2 can be expressed either as a full length integral protein from a dedicated ATU, such as in the dual MV-NPflu&M2 recombinant virus, or as a fusion protein between its 23 aa-core M2e ectodomain and NPflu, such as in the single MV-NPflu-3xM2e recombinant virus.

Dual Recombinant Measles Virus Expressing Both NPflu and M2 Consensus Proteins Exhibit Higher Protection Efficiency in Mice than Single Recombinant Viruses Immunogenicity of the dual recombinant MV-NPflu&M2 virus was investigated in CD46-IFNAR mice and compared to the immunogenicity of the single recombinant MV-ATU3-M2opt viruses.

High titers of anti-M2e IgG were raised in all mice after the first injection of either of the recombinant viruses, whereas sera from control animals that received empty MVSchw or MV-ATU2-NPflu remained negative (FIG. 10A). After the second injection, titers were boosted up to lower levels for animals immunized with MV-NPflu&M2 (3.6±0.5 log 10 titers) than for animal immunized with MV-ATU3-M2opt viruses (4.2±0.4 log 10 titers, p<0.1), in accordance with the delayed growth curve and reduced yields in vitro of the former. Induction of an heterospecific cellular response was examined in mice that had been immunized with the dual MV-NPflu&M2 virus. Frequencies of influenza virus-specific IFN-γ-producing T cells in the spleens of immunized mice were quantified by ELISPOT, using the influenza virus NP366 immunodominant class I peptide and the NP260-273 class II peptide. IFNγ-producing CD8+ T cells were detected in response to the NP366 (H3N2) consensus class I peptide (SEQ ID No.41) when splenocytes were isolated from 5 out of 6 MV-NPflu&M2 immunized mice but not from control MVSchw and MV-ATU3-M2opt immunized mice (FIG. 10C). Influenza-specific T cell precursor frequencies ranging between 670 and 2000 per $10^6$ splenocytes (average 1300±510) were observed, demonstrating that a very strong heterospecific CD8+ T cell response was induced upon immunization with the dual MV-NPflu&M2 recombinant virus. These NP366 specific T cells were cross-reactive and able to recognize the NP366 (Scotland)—SEQ ID No.42) peptide corresponding to the A/Scotland/20/74 virus with similar efficiencies (860±340 SFC/$10^6$ splenocytes). IFNγ-producing CD4+ T cells were detected in response to the NP260-273 conserved class II peptide (SEQ ID No.43), albeit at slightly lower frequencies (520±150 SFC/$10^6$ splenocytes). To investigate the protective efficacy of the dual recombinant MV-NPflu&M2 virus, we examined the survival of CD46-IFNAR mice after intranasal lethal challenge with the homologous A/Scotland/20/74 (H3N2) virus. Mice immunized with the control parental MVSchw presented a massive and rapid weight loss from day 3 post-challenge (FIG.

10D) and 4 out of 6 mice died within 12 days (FIG. 10E). Mice immunized with either MV-ATU2-NPflu or MV-ATU3-M2opt single recombinant viruses were partially protected against challenge, with a reduction in global mortality and weight loss. Most mice survived the challenge and presented maximal weight loss of 16.5±2.9% (day 8) and 19.2±4.4% (day 9) of their initial body weight, respectively (FIG. 10E). In contrast, all mice immunized with the dual recombinant MV-NPflu&M2 virus survived after challenge with a net reduction of clinical symptoms (not shown) and a more transient weight loss: they presented a maximal weight loss of 11.0±3.7% at day 7 and quickly recovered thereafter.

Together, these results indicated that the dual recombinant MV-NPflu&M2 virus induces significantly better protective immunity against influenza in CD46-IFNAR mice than either of its parental MV-ATU2-NPflu or MV-ATU3-M2opt. Higher protective efficiency was correlated to the induction of both anti-M2e antibodies and anti-NP cellular responses. Tables

TABLE 1

Alignment of the M2e consensus amino acid sequences

| | |
|---|---|
| global consensus† | SLLTEVETPI RNEWGCRCND SSD (SEQ ID No. 21) |
| H1N1 consensus | ---------- ---------- --- |
| H1N1v consensus | ---------T -S--E---S- --- (SEQ ID No. 32) |
| H3N2 consensus | ---------- ---------- --- |

†used as immunogen in the reported experiments.
-indicates matching residues.

CONCLUSION

The objective of this preclinical study was to evaluate the proof-of-concept of a new universal influenza vaccine strategy based on a standard measles vaccine engineered to express a M2 consensus protein. The inventors found that the vaccines induced high titers of anti-M2e antibodies and protected mice from an intranasal lethal challenge with homologous or heterologous influenza viruses.

After two successive immunizations with recombinant MV-M2 or MV-NM2e viruses, mice were partially protected from intranasal infectious challenge with mouse-adapted A/Scotland/20/74 (H3N2) and A/Paris/2590/09 (H1N1v) viruses and passive transfer experiments demonstrated that anti-M2 antibodies contributed to the protection. The anti-M2e responses are likely Th1-skewed, a hallmark of live attenuated viruses and a highly desirable feature for an antiviral vaccine.

Interestingly, as already mentioned above, both vectorization strategy allowed to bypass the H-2 restriction of anti-M2e responses, which was evidenced recently and predicted very poor responsiveness of all mice of the H-$2^b$ MHC haplotype such as the CD46-IFNAR mice used in the study. This indicates that T cell responses induced against the measles vector likely supplied the T helper cellular response, which is needed to trigger B cells to produce anti-M2e antibodies. Remarkably, help was supplied whether M2 epitopes were linked to measles N within the N-M2e hybrid protein (like in a hapten-carrier conjugate) or co-expressed with MV proteins in the case of the MV-ATU1-M2 or MV-ATU2-M2 viruses.

Most interestingly, protection was conferred against challenge with the A/Scotland/20/74 virus but also with the pandemic A/Paris/2590/09 H1N1v strain, whose M2e sequence has an avian origin and differs at 4 positions from the global consensus sequence used for immunization. This result may be predictive of broad protection against a variety of subtypes, since, as an example, avian H5N1 viruses differs only at 3 of the 4 above mentioned positions.

Partial protection suggests that the recombinant vaccine might be improved. In that respect, expression of the hybrid N-M2e proteins as an additional nucleoprotein gene placed in position 6 of the genome (ATU3) did not affect replication in vitro and immunogenicity in mice. This gave the inventors the opportunity for further refinement of this strategy by placing the additional hybrid N-M2e genes upstream in the genome, such as in position 3 (ATU2) between the P and the M genes, thus increasing N-M2e expression and possibly immunogenicity and levels of protection. Levels of protection may also be improved by the co-expression of a second influenza consensus protein, such as an M1 or NP consensus, in a double recombinant measles vaccine. This approach would advantageously complete the induction of broad anti-M2 antibody responses by cellular responses targeting conserved influenza structural proteins. Indeed, the inventors showed that the measles vaccine can be further engineered to express either M1 and M2 consensus proteins, or NP and M2/M2e consensus proteins and that such double recombinant viruses provide enhanced protection against influenza in the IFNAR-CD46 mouse model than any single recombinant virus. Higher protection efficiency of the double MV-NP&M2 recombinant virus correlated to the induction of cross-reactive cellular responses against the NP protein. Interestingly, better protection efficiency of the double MV-M1&M2 recombinant virus correlated to the induction of higher anti-M2e antibody levels, strongly advocating in favor of the production of influenza VLP in cells infected by the double MV-M1&M2 recombinant virus.

Alternatively, partial protection might be indicative of the stringency of the mouse model. The inventors used mouse-adapted viruses for challenge, and relied on stocks prepared after a limited number of passages (less than 2) in cell culture. At the challenge doses used (10 LD50 and less than $10^3$ PFU), most control mice died quickly, CD46-IFNAR mice within 8 days (FIGS. 3 and 4) and immunocompetent C57BL/6 mice (FIG. 5) within 10 days. This match previous observation of the inventors in other mouse strains and is strongly indicative of the high virulence of the adapted viruses in laboratory strains of mice. In addition, CD46-IFNAR mice were established by backcrossing CD46-transgenic mice against IFNAR mice lacking the type 1 IFN receptor (IFNα/βR$^{-/-}$) and are expected to exhibit increased mortality and morbidity after influenza challenge as their IFNAR parents (Arimori et al., 2013).

Because recombinant MV-influenza vaccine can be easily and rapidly produced in large quantities and at low cost in most countries, recombinant MV-influenza vaccines might be used instead of the standard MV vaccine routinely used for infants worldwide, notably through the Expanded Program of Immunization of WHO. Interestingly, the induction of measles-specific immunity was not altered in the mouse preclinical model by the expression of any of the M1, M2 and NP transgenes, suggesting that MV-influenza vaccine might even replace the MV Schwarz strain in the combined measles, mumps, rubella vaccine or the measles, mumps, rubella, varicella vaccines.

In conclusion, the inventors have produced new recombinant MV-influenza viruses able to induce high levels of anti-M2 antibodies and cellular responses to influenza and broad protection from intranasal challenge, thus making the proof-of-concept of this strategy for universal influenza vaccine development. It could also help achieve wide vaccine coverage in both children and adults against zoonotic influenza viruses, such as avian H5N1, H9N2 and H7N9 viruses, in the regions that are affected by cases of animal to human transmission. These characterized universal influenza vaccine candidates deserve to be evaluated in a more adapted, non-immuno-compromised and genetically diverse, non-human-primate model, in which the protective potential of the induced immune responses against field isolates of seasonal and zoonotic influenza strains could be addressed.

REFERENCES

Arimori, Y., Nakamura, R., Yamada, H., Shibata, K., Maeda, N., Kase, T., Yoshikai, Y., 2013. Type I interferon limits influenza virus-induced acute lung injury by regulation of excessive inflammation in mice. Antiviral Res 99, 230-237

Bankamp B et al *Genetic characterization of Measles Vaccine Strains —The Journal of Infectious Diseases* 2011; 204:S533-S548

Deng L. et al *Vaccines* 2015, 3, 105-136

Bao, Y., Bolotov, P., Dernovoy, D., Kiryutin, B., Zaslaysky, L., Tatusova, T., Ostell, J., Lipman, D., 2008. The influenza virus resource at the National Center for Biotechnology Information. J Virol 82, 596-601.

Calain, P., Roux, L., 1993. The rule of six, a basic feature for efficient replication of Sendai virus defective interfering RNA. J Virol 67, 4822-4830.

Combredet, C., Labrousse, V., Mollet, L., Lorin, C., Delebecque, F., Hurtrel, B., McClure, H., Feinberg, M. B., Brahic, M., Tangy, F., 2003. A molecularly cloned Schwarz strain of measles virus vaccine induces strong immune responses in macaques and transgenic mice. J Virol 77, 11546-11554.

El Bakkouri, K., Descamps, F., De Filette, M., Smet, A., Festjens, E., Birkett, A., Van Rooijen, N., Verbeek, S., Fiers, W., Saelens, X., 2011. Universal vaccine based on ectodomain of matrix protein 2 of influenza A: Fc receptors and alveolar macrophages mediate protection. J Immunol 186, 1022-1031.

Griffin, D. E., 2013. Measles virus, in: Knipe, D. M., Howley, P. M. (Eds.), Fields Virology, 6th ed. Lippincott Williams & Wilkins, Philadelphia, Pa.

Hoffmann, E., Krauss, S., Perez, D., Webby, R., Webster, R. G., 2002. Eight-plasmid system for rapid generation of influenza virus vaccines. Vaccine 20, 3165-3170.

Ilyinskii, P. O., Gabai, V. L., Sunyaev, S. R., Thoidis, G., Shneider, A. M., 2007. Toxicity of influenza A virus matrix protein 2 for mammalian cells is associated with its intrinsic proton-channeling activity. Cell cycle 6, 2043-2047.

Jegerlehner, A., Schmitz, N., Storni, T., Bachmann, M. F., 2004. Influenza A vaccine based on the extracellular domain of M2: weak protection mediated via antibody-dependent NK cell activity. J Immunol 172, 5598-5605.

Marcel Jonges et al. *J. Clin. Microbiol*. March 2010 vol. 48 no. 3 928-940

Misplon, J. A., Lo, C. Y., Gabbard, J. D., Tompkins, S. M., Epstein, S. L., 2010. Genetic control of immune responses to influenza A matrix 2 protein (M2). Vaccine 28, 5817-5827.

Mrkic, B., Pavlovic, J., Rulicke, T., Volpe, P., Buchholz, C. J., Hourcade, D., Atkinson, J. P., Aguzzi, A., Cattaneo, R., 1998. Measles virus spread and pathogenesis in genetically modified mice. J Virol 72, 7420-7427.

Plumet, S., Duprex, W. P., Gerlier, D., 2005. Dynamics of viral RNA synthesis during measles virus infection. J Virol 79, 6900-6908.

Ramisse, F., Deramoudt, F. X., Szatanik, M., Bianchi, A., Binder, P., Hannoun, C., Alonso, J. M., 1998. Effective prophylaxis of influenza A virus pneumonia in mice by topical passive immunotherapy with polyvalent human immunoglobulins or F(ab')2 fragments. Clinical and experimental immunology 111, 583-587.

Reed, L. J., Muench, H., 1938. A simple method of estimating fifty percent endpoints. Am. J. Hyg. 27, 493-497.

Rima, B. K., 1983. The proteins of morbilliviruses. J Gen Virol 64 (Pt 6), 1205-1219.

Schneider, H., Kaelin, K., Billeter, M. A., 1997. Recombinant measles viruses defective for RNA editing and V protein synthesis are viable in cultured cells. Virology 227, 314-322.

Wolf, A. I., Mozdzanowska, K., Williams, K. L., Singer, D., Richter, M., Hoffmann, R., Caton, A. J., Otvos, L., Erikson, J., 2011. Vaccination with M2e-based multiple antigenic peptides: characterization of the B cell response and protection efficacy in inbred and outbred mice. PloS one 6, e28445.

Zhang, S., Chen, L., Zhang, G., Yan, Q., Yang, X., Ding, B., Tang, Q., Sun, S., Hu, Z., Chen, M., 2013. An amino acid of human parainfluenza virus type 3 nucleoprotein is critical for template function and cytoplasmic inclusion body formation. J Virol 87, 12457-12470.

The invention claimed is:

1. A recombinant measles virus (MV) comprising a recombinant genome comprising a cDNA comprising (i) a nucleotide sequence that encodes the sequence of a full-length antigenomic RNA of MV, and wherein one additional transcription unit (ATU) has been inserted upstream of the N gene (ATU1) or in the intergenic region(s) between the P and M genes (ATU2) or between the H and L genes (ATU3) of MV and, (ii) operably linked in frame into said ATU or ATUs, a heterologous polynucleotide that encodes at least a M2 or M2e antigen wherein the heterologous polynucleotide is provided as the insert cloned into the cDNA encoding the full-length antigenomic RNA of MV in a transfer vector
wherein the transfer vector is selected from the group consisting of:
pTM-MV-ATU1-M2raw having the sequence of SEQ ID No.1, pTM-MV-ATU2-M2raw having the sequence of SEQ ID No.3, pTM-MV-ATU1-M2opt having the sequence of SEQ ID No.2, pTM-MV-ATU2-M2opt having the sequence of SEQ ID No.4, pTM-MV-ATU3-M2opt having the sequence of SEQ ID No.8;
pTM-MV-ATU3-N-1xM2e having the sequence of SEQ ID No.5, pTM-MV-ATU3-N-3xM2e having the sequence of SEQ ID No.6 (N is the measles virus N protein);
pTM-MV-M1&M2 having the sequence of SEQ ID No.9;
pTM-MV-NPflu&M2 having the sequence of SEQ ID No.10 and pTM-MV-ATU2-NPflu having the sequence of SEQ ID No.11 which is the parental construct for pTM-MV-NPflu&M2;
pTM-MV-ATU2-NPflu-3xM2e having the sequence of SEQ ID No.13;
pTM-MV-ATU2-M1opt having the sequence of SEQ ID No.7; and
pTM-MV-ATU2-N-3xM2e having the sequence of SEQ ID No.12, where N is the measles virus Nucleoprotein.

2. The recombinant measles virus according to claim 1, wherein the measles virus is a live attenuated strain selected in the group of the Schwarz strain, the Moraten strain, the Zagreb and the AIK-C strain.

3. An immunogenic composition comprising a recombinant measles virus according claim 1, optionally comprising influenza VLPs and further comprising a pharmaceutical vehicle suitable for administration to a host and optionally an adjuvant of the immune response wherein said composition is optionally formulated for the administration in children.

4. An immunogenic composition according to claim 3, which further comprises Influenza Virus-Like Particles and is obtained from a supernatant or a lysate of cells producing the recombinant measles virus.

5. A method of inducing an immune response for prophylactic protection against flu in a subject, comprising administering the recombinant measles virus according to claim 3 to a subject.

6. A method of inducing formation of antibodies against influenza A virus in a subject and/or inducing a cellular immune response against influenza A virus in a subject, comprising administering the recombinant measles virus according to claim 3 to a subject.

7. A method of protecting a subject against a condition or a disease resulting from the infection by an influenza virus A in a human host, comprising administering the recombinant measles virus according to claim 3 to the subject.

8. The method of claim 7, further comprising protecting the subject from a measles virus infection.

9. A method of protecting a subject against a condition or a disease resulting from the infection by an influenza virus A in a subject, comprising administering a multivalent vaccine comprising the recombinant measles virus according to claim 3 to the subject, such as a combined measles, mumps, rubella and influenza multivalent vaccine or a measles, mumps, rubella, varicella and influenza multivalent vaccine.

10. A transfer vector selected from the group consisting of:
   pTM-MV-ATU1-M2raw having the sequence of SEQ ID No.1, pTM-MV-ATU2-M2raw having the sequence of SEQ ID No.3, pTM-MV-ATU1-M2opt having the sequence of SEQ ID No.2, pTM-MV-ATU2-M2opt having the sequence of SEQ ID No.4, pTM-MV-ATU3-M2opt having the sequence of SEQ ID No.8;
   pTM-MV-ATU3-N-1xM2e having the sequence of SEQ ID No.5, pTM-MV-ATU3-N-3xM2e having the sequence of SEQ ID No.6 (N is the measles virus N protein);
   pTM-MV-M1&M2 having the sequence of SEQ ID No.9;
   pTM-MV-NPflu&M2 having the sequence of SEQ ID No.10 and pTM-MV-ATU2-NPflu having the sequence of SEQ ID No.11 which is the parental construct for pTM-MV-NPflu&M2;
   pTM-MV-ATU2-NPflu-3xM2e having the sequence of SEQ ID No.13;
   pTM-MV-ATU2-M1opt having the sequence of SEQ ID No.7; and
   pTM-MV-ATU2-N-3xM2e having the sequence of SEQ ID No.12, where N is the measles virus Nucleoprotein.

11. A rescue system for the assembly of infectious recombinant measles virus particles and optionally influenza A VLP, comprising a mammalian cell or cell line, transformed with plasmid vectors suitable for the expression of a polymerase, and for the expression of the N, P and L proteins of a measles virus, wherein said cell is further transfected with a vector according to claim 10.

12. A rescue system according to claim 11, wherein the cell is the 293-T7-NP cell line deposited on Jun. 14, 2006 with the CNCM (Paris, France) under number I-3618 or the 293-Tnls7-NP cell line deposited on Aug. 4, 2006 with the CNCM (Paris, France) under number I-3662.

13. A cell transformed with nucleotide sequences expressing a polymerase, and nucleotide sequences expressing the N, P and L proteins of a measles virus, wherein said cell is further transfected with a vector according to claim 10 in conditions enabling production of recombinant measles virus.

14. A cell culture supernatant or lysate recovered from cells according to claim 13.

15. An immunogenic composition prepared from the cell culture supernatant or lysate according to claim 14.

16. A polynucleotide which is selected from the group consisting of:
   pTM-MV-ATU1-M2raw having the sequence of SEQ ID No.1, pTM-MV-ATU2-M2raw having the sequence of SEQ ID No.3, pTM-MV-ATU1-M2opt having the sequence of SEQ ID No.2, pTM-MV-ATU2-M2opt having the sequence of SEQ ID No.4, pTM-MV-ATU3-M2opt having the sequence of SEQ ID No.8,
   pTM-MV-ATU3-N-1xM2e having the sequence of SEQ ID No.5, pTM-MV-ATU3-N-3xM2e having the sequence of SEQ ID No.6,
   pTM-MV-M1&M2 having the sequence of SEQ ID No.9,
   pTM-MV-NPflu&M2 having the sequence of SEQ ID No.10 and pTM-MV-ATU2-NPflu having the sequence of SEQ ID No.11,
   pTM-MV-ATU2-NPflu-3xM2e having the sequence of SEQ ID No.13,
   pTM-MV-ATU2-M1opt having the sequence of SEQ ID No.7,
   pTM-MV-ATU2-N-3xM2e having the sequence of SEQ ID No.12,
   a polynucleotide having the sequence of SEQ ID No.17or a polynucleotide having the sequence of SEQ ID No.18,
   a polynucleotide having the sequence of SEQ ID No.20,
   a polynucleotide having the sequence of SEQ ID No.22,
   a polynucleotide having the sequence of SEQ ID No.24,
   a polynucleotide having the sequence of SEQ ID No.26,
   a polynucleotide having the sequence of SEQ ID No.27,
   a polynucleotide having the sequence of SEQ ID No. 30, and
   a polynucleotide encoding any of the polypeptide the sequence of which consists of a sequence selected the group consisting of: SEQ ID No.19, SEQ ID No.23, SEQ ID No.25, SEQ ID No.28, SEQ ID No.29, SEQ ID No.31, and SEQ ID No.32.

* * * * *

SEQUENCE LISTING

```
<160> NUMBER OF SEQ ID NOS: 46

<210> SEQ ID NO 1
<211> LENGTH: 19423
<212> TYPE: DNA
<213> ORGANISM: Artificial Sequence
<220> FEATURE:
<223> OTHER INFORMATION: pTM-MV-ATU1-M2raw
```

<220> FEATURE:
<221> NAME/KEY: misc_RNA
<222> LOCATION: (1)..(16350)
<223> OTHER INFORMATION: MV-ATU1-M2raw_antigenome
<220> FEATURE:
<221> NAME/KEY: misc_feature
<222> LOCATION: (53)..(508)
<223> OTHER INFORMATION: ATU1
<220> FEATURE:
<221> NAME/KEY: misc_feature
<222> LOCATION: (111)..(116)
<223> OTHER INFORMATION: BsiWI restriction site
<220> FEATURE:
<221> NAME/KEY: misc_feature
<222> LOCATION: (120)..(416)
<223> OTHER INFORMATION: ORF for M2 consensus protein : M2 raw
<220> FEATURE:
<221> NAME/KEY: misc_feature
<222> LOCATION: (417)..(422)
<223> OTHER INFORMATION: BssHII restriction site
<220> FEATURE:
<221> NAME/KEY: misc_feature
<222> LOCATION: (16351)..(19423)
<223> OTHER INFORMATION: plasmid_backbone

<400> SEQUENCE: 1
accaaacaaa gttgggtaag gatagttcaa tcaatgatca tcttctagtg cacttaggat 60
tcaagatcct attatcaggg acaagagcag gattagggat atccgagacg cgtacgacca 120
tgagccttct aaccgaggtc gaaacgccta tcagaaacga atgggggtgc agatgcaacg 180
attcaagtga ccctcttgtt gttgccgcga gtatcattgg gatcttgcac ttgatattgt 240
ggattcttga tcgtcttttc ttcaaatgca tctatcgact cttcaaacac ggtctgaaaa 300
gaggaccttc tacggaagga gtacctgagt ctatgaggga agaatatcga aaggaacagc 360
agaatgctgt ggatgctgac gacagtcatt ttgtcagcat agagctggag tgataagcgc 420
gcagcgctta gacgtctcgc gatcgattag tgcgagaggc cgagggccag aacaacatcc 480
gcctaccatc catcattgtt ataaaaaact taggattcaa gatcctatta tcagggacaa 540
gagcaggatt agggatatcc gagatggcca cacttttaag gagcttagca ttgttcaaaa 600
gaaacaagga caaaccaccc attacatcag gatccggtgg agccatcaga ggaatcaaac 660
acattattat agtaccaatc cctggagatt cctcaattac cactcgatcc agacttctgg 720
accggttggt gaggttaatt ggaaacccgg atgtgagcgg gcccaaacta acaggggcac 780
taataggtat attatcctta tttgtggagt ctccaggtca attgattcag aggatcaccg 840
atgaccctga cgttagcata aggctgttag aggttgtcca gagtgaccag tcacaatctg 900
gccttacctt cgcatcaaga ggtaccaaca tggaggatga ggcggaccaa tacttttcac 960
atgatgatcc aattagtagt gatcaatcca ggttcggatg gttcgggaac aaggaaatct 1020
cagatattga agtgcaagac cctgagggat tcaacatgat tctgggtacc atcctagccc 1080
aaatttgggt cttgctcgca aaggcggtta cggccccaga cacggcagct gattcggagc 1140
taagaaggtg gataaagtac acccaacaaa gaagggtagt tggtgaattt agattggaga 1200
gaaaatggtt ggatgtggtg aggaacagga ttgccgagga cctctcctta cgccgattca 1260
tggtcgctct aatcctggat atcaagagaa cacccggaaa caaacccagg attgctgaaa 1320
tgatatgtga cattgataca tatatcgtag aggcaggatt agccagtttt atcctgacta 1380
ttaagtttgg gatagaaact atgtatcctg ctcttggact gcatgaattt gctggtgagt 1440
tatccacact tgagtccttg atgaaccttt accagcaaat gggggaaact gcaccctaca 1500
tggtaatcct ggagaactca attcagaaca agttcagtgc aggatcatac cctctgctct 1560

-continued

```
ggagctatgc catgggagta ggagtggaac ttgaaaactc catgggaggt ttgaactttg    1620
gccgatctta ctttgatcca gcatatttta gattagggca agagatggta aggaggtcag    1680
ctggaaaggt cagttccaca ttggcatctg aactcggtat cactgccgag gatgcaaggc    1740
ttgtttcaga gattgcaatg catactactg aggacaagat cagtagagcg gttggaccca    1800
gacaagccca agtatcattt ctacacggtg atcaaagtga gaatgagcta ccgagattgg    1860
ggggcaagga agataggagg gtcaaacaga gtcgaggaga agccagggag agctacagag    1920
aaaccgggcc cagcagagca agtgatgcga gagctgccca tcttccaacc ggcacacccc    1980
tagacattga cactgcaacg gagtccagcc aagatccgca ggacagtcga aggtcagctg    2040
acgccctgct taggctgcaa gccatggcag gaatctcgga agaacaaggc tcagacacgg    2100
acacccctat agtgtacaat gacagaaatc ttctagacta ggtgcgagag gccgagggcc    2160
agaacaacat ccgcctacca tccatcattg ttataaaaaa cttaggaacc aggtccacac    2220
agccgccagc ccatcaacca tccactccca cgattggagc caatggcaga gagcaggca    2280
cgccatgtca aaaacggact ggaatgcatc cgggctctca aggccgagcc catcggctca    2340
ctggccatcg aggaagctat ggcagcatgg tcagaaatat cagacaaccc aggacaggag    2400
cgagccacct gcagggaaga gaaggcaggc agttcgggtc tcagcaaacc atgcctctca    2460
gcaattggat caactgaagg cggtgcacct cggcatccgcg gtcagggacc tggagagagc    2520
gatgacgacg ctgaaacttt gggaatcccc ccaagaaatc tccaggcatc aagcactggg    2580
ttacagtgtt attacgttta tgatcacagc ggtgaagcgg ttaagggaat ccaagatgct    2640
gactctatca tggttcaatc aggccttgat ggtgatagca ccctctcagg aggagacaat    2700
gaatctgaaa acagcgatgt ggatattggc gaacctgata ccgagggata tgctatcact    2760
gaccggggat ctgctcccat ctctatgggg ttcaggggctt ctgatgttga aactgcagaa    2820
ggaggggaga tccacgagct cctgagactc caatccagag gcaacaactt ccgaagctt    2880
gggaaaactc tcaatgttcc tccgcccccg gaccccggta gggccagcac ttccgggaca    2940
cccattaaaa agggcacaga cgcgagatta gcctcatttg gaacggagat cgcgtctta    3000
ttgacaggtg gtgcaaccca atgtgctcga aagtcacccct cggaaccatc agggccaggt    3060
gcacctgcgg ggaatgtccc cgagtgtgtg agcaatgccg cactgataca ggagtggaca    3120
cccgaatctg gtaccacaat ctccccgaga tcccagaata tgaagaagg gggagactat    3180
tatgatgatg agctgttctc tgatgtccaa gatattaaaa cagccttggc caaaatacac    3240
gaggataatc agaagataat ctccaagcta gaatcactgc tgttattgaa gggagaagtt    3300
gagtcaatta agaagcagat caacaggcaa aatatcagca tatccaccct ggaaggacac    3360
ctctcaagca tcatgatcgc cattcctgga cttgggaagg atcccaacga ccccactgca    3420
gatgtcgaaa tcaatcccga cttgaaaccc atcataggca gagattcagg ccgagcactg    3480
gccgaagttc tcaagaaacc cgttgccagc cgacaactcc aaggaatgac aaatggacgg    3540
accagttcca gaggacagct gctgaaggaa tttcagctaa agccgatcgg gaaaaagatg    3600
agctcagccg tcgggtttgt tcctgacacc ggccctgcat cacgcagtgt aatccgctcc    3660
attataaaat ccagccggct agaggaggat cggaagcgtt acctgatgac tctccttgat    3720
gatatcaaag gagccaatga tcttgccaag ttccaccaga tgctgatgaa gataataatg    3780
aagtagctac agctcaactt acctgccaac cccatgccag tcgacccaac tagtacaacc    3840
taaatccatt ataaaaaact taggagcaaa gtgattgcct cccaaggtcc acaatgacag    3900
agacctacga cttcgacaag tcggcatggg acatcaaagg gtcgatcgct ccgatacaac    3960
```

```
ccaccaccta cagtgatggc aggctggtgc cccaggtcag agtcatagat cctggtctag    4020
gcgacaggaa ggatgaatgc tttatgtaca tgtttctgct gggggttgtt gaggacagcg    4080
attccctagg gcctccaatc gggcgagcat ttgggttcct gcccttaggt gttggcagat    4140
ccacagcaaa gcccgaaaaa ctcctcaaag aggccactga gcttgacata gttgttagac    4200
gtacagcagg gctcaatgaa aaactggtgt tctacaacaa caccccacta actctcctca    4260
caccttggag aaaggtccta acaacaggga gtgtcttcaa cgcaaaccaa gtgtgcaatg    4320
cggttaatct gataccgctc gataccccgc agaggttccg tgttgtttat atgagcatca    4380
cccgtctttc ggataacggg tattacaccg ttcctagaag aatgctggaa ttcagatcgg    4440
tcaatgcagt ggccttcaac ctgctggtga cccttaggat tgacaaggcg ataggccctg    4500
ggaagatcat cgacaataca gagcaacttc ctgaggcaac atttatggtc cacatcggga    4560
acttcaggag aaagaagagt gaagtctact ctgccgatta ttgcaaaatg aaaatcgaaa    4620
agatgggcct ggttttttgca cttggtggga tagggggcac cagtcttcac attagaagca    4680
caggcaaaat gagcaagact ctccatgcac aactcgggtt caagaagacc ttatgttacc    4740
cgctgatgga tatcaatgaa gaccttaatc gattactctg gaggagcaga tgcaagatag    4800
taagaatcca ggcagttttg cagccatcag ttcctcaaga attccgcatt tacgacgacg    4860
tgatcataaa tgatgaccaa ggactattca aagttctgta gaccgtagtg cccagcaatg    4920
cccgaaaacg acccccctca caatgacagc cagaaggccc ggacaaaaaa gcccctccg    4980 aaagactcca cggaccaagc gagaggccag ccagcagccg acggcaagcg cgaacaccag    5040
gcggccccag cacagaacag ccctgacaca aggccaccac cagccacccc aatctgcatc    5100
ctcctcgtgg gaccccgag gaccaacccc caaggctgcc cccgatccaa accaccaacc    5160
gcatccccac cacccccggg aaagaaaccc ccagcaattg gaaggcccct ccccctcttc    5220
ctcaacacaa gaactccaca accgaaccgc acaagcgacc gaggtgaccc aaccgcaggc    5280
atccgactcc ctagacagat cctctctccc cggcaaacta aacaaaactt agggccaagg    5340
aacatacaca cccaacagaa cccagacccc ggcccacggc gccgcgcccc caaccccga    5400 caaccagagg gagcccccaa ccaatcccgc cggctccccc ggtgcccaca ggcagggaca    5460
ccaacccccg aacagaccca gcacccaacc atcgacaatc caagacgggg gggcccccc    5520 aaaaaaggc cccagggggc cgacagccag caccgcgagg aagcccaccc accccacaca    5580
cgaccacggc aaccaaacca gaacccagac cacccctggg caccagctcc cagactcggc    5640
catcaccccg cagaaaggaa aggccacaac ccgcgcaccc cagccccgat ccggcgggga    5700
gccacccaac ccgaaccagc acccaagagc gatccccgaa ggaccccga accgcaaagg    5760 acatcagtat cccacagcct ctccaagtcc cccggtctcc tcctcttctc gaagggacca    5820
aaagatcaat ccaccacacc cgacgacact caactcccca cccctaaagg agacaccggg    5880
aatcccagaa tcaagactca tccaatgtcc atcatgggtc tcaaggtgaa cgtctctgcc    5940
atattcatgg cagtactgtt aactctccaa acacccaccg gtcaaatcca ttggggcaat    6000
ctctctaaga taggggtggt aggaatagga agtgcaagct acaaagttat gactcgttcc    6060
agccatcaat cattagtcat aaaattaatg cccaatataa ctctcctcaa taactgcacg    6120
agggtagaga ttgcagaata caggagacta ctgagaacag ttttggaacc aattagagat    6180
gcacttaatg caatgaccca gaatataaga ccggttcaga gtgtagcttc aagtaggaga    6240
cacaagagat ttgcgggagt agtcctggca ggtgcggccc taggcgttgc cacagctgct    6300
```

```
cagataacag ccggcattgc acttcaccag tccatgctga actctcaagc catcgacaat    6360
ctgagagcga gcctggaaac tactaatcag gcaattgaga caatcagaca agcagggcag    6420
gagatgatat tggctgttca gggtgtccaa gactacatca ataatgagct gataccgtct    6480
atgaaccaac tatcttgtga tttaatcggc cagaagctcg ggctcaaatt gctcagatac    6540
tatacagaaa tcctgtcatt atttggcccc agtttacggg accccatatc tgcggagata    6600
tctatccagg cttttgagcta tgcgcttgga ggagacatca ataaggtgtt agaaaagctc    6660
ggatacagtg gaggtgattt actgggcatc ttagagagcg gaggaataaa ggcccggata    6720
actcacgtcg acacagagtc ctacttcatt gtcctcagta tagcctatcc gacgctgtcc    6780
gagattaagg gggtgattgt ccaccggcta gaggggtct cgtacaacat aggctctcaa     6840
gagtggtata ccactgtgcc caagtatgtt gcaacccaag ggtaccttat ctcgaatttt    6900
gatgagtcat cgtgtacttt catgccagag gggactgtgt gcagccaaaa tgccttgtac    6960
ccgatgagtc ctctgctcca agaatgcctc cggggtaca ccaagtcctg tgctcgtaca     7020
ctcgtatccg ggtcttttgg gaaccggttc attttatcac aagggaacct aatagccaat    7080
tgtgcatcaa tcctttgcaa gtgttacaca acaggaacga tcattaatca agaccctgac    7140
aagatcctaa catacattgc tgccgatcac tgcccggtag tcgaggtgaa cggcgtgacc    7200
atccaagtcg ggagcaggag gtatccagac gctgtgtact tgcacagaat tgacctcggt    7260
cctcccatat cattggagag gttggacgta gggacaaatc tggggaatgc aattgctaag    7320
ttggaggatg ccaaggaatt gttggagtca tcggaccaga tattgaggag tatgaaaggt    7380
ttatcgagca ctagcatagt ctacatcctg attgcagtgt gtcttggagg gttgataggg    7440
atccccgctt taatatgttg ctgcaggggg cgttgtaaca aaaagggaga acaagttggt    7500
atgtcaagac caggcctaaa gcctgatctt acgggaacat caaaatccta tgtaaggtcg    7560
ctctgatcct ctacaactct tgaaacacaa atgtcccaca agtctcctct tcgtcatcaa    7620
gcaaccaccg cacccagcat caagcccacc tgaaattatc tccggcttcc ctctggccga    7680
acaatatcgg tagttaatca aaacttaggg tgcaagatca tccacaatgt caccacaacg    7740
agaccggata aatgccttct acaaagataa cccccatccc aagggaagta ggatagtcat    7800
taacagagaa catcttatga ttgatagacc ttatgttttg ctggctgttc tgtttgtcat    7860
gtttctgagc ttgatcgggt tgctagccat tgcaggcatt agacttcatc gggcagccat    7920
ctacaccgca gagatccata aaagcctcag caccaatcta gatgtaacta actcaatcga    7980
gcatcaggtc aaggacgtgc tgacaccact cttcaaaatc atcggtgatg aagtgggcct    8040
gaggacacct cagagattca ctgacctagt gaaattaatc tctgacaaga ttaaattcct    8100
taatccggat agggagtacg acttcagaga tctcacttgg tgtatcaacc cgccagagag    8160
aatcaaattg gattatgatc aatactgtgc agatgtggct gctgaagagc tcatgaatgc    8220
attggtgaac tcaactctac tggagaccag aacaaccaat cagttcctag ctgtctcaaa    8280
gggaaactgc tcagggccca ctacaatcag aggtcaattc tcaaacatgt cgctgtccct    8340
gttagacttg tatttaggtc gaggttacaa tgtgtcatct atagtcacta tgacatccca    8400
gggaatgtat gggggaactt acctagtgga aaagcctaat ctgagcagca aaagtcaga     8460 gttgtcacaa ctgagcatgt accgagtgtt tgaagtaggt gttatcagaa atccgggttt    8520
gggggctccg gtgttccata tgacaaacta tcttgagcaa ccagtcagta atgatctcag    8580
caactgtatg gtggctttgg gggagctcaa actcgcagcc ctttgtcacg ggaagattc     8640 tatcacaatt ccctatcagg gatcagggaa aggtgtcagc ttccagctcg tcaagctagg    8700
```

```
tgtctggaaa tccccaaccg acatgcaatc ctgggtcccc ttatcaacgg atgatccagt    8760
gatagacagg ctttacctct catctcacag aggtgttatc gctgacaatc aagcaaaatg    8820
ggctgtcccg acaacacgaa cagatgacaa gttgcgaatg gagacatgct tccaacaggc    8880
gtgtaagggt aaaatccaag cactctgcga gaatcccgag tgggcaccat tgaaggataa    8940
caggattcct tcatacgggg tcttgtctgt tgatctgagt ctgacagttg agcttaaaat    9000
caaaattgct tcgggattcg ggccattgat cacacacggt tcaggatgg acctatacaa     9060
atccaaccac aacaatgtgt attggctgac tatcccgcca atgaagaacc tagccttagg    9120
tgtaatcaac acattggagt ggataccgag attcaaggtt agtccctacc tcttcactgt    9180
cccaattaag gaagcaggcg aagactgcca tgccccaaca tacctacctg cggaggtgga    9240
tggtgatgtc aaactcagtt ccaatctggt gattctacct ggtcaagatc tccaatatgt    9300
tttggcaacc tacgatactt ccagggttga acatgctgtg gtttattacg tttacagccc    9360
aagccgctca ttttcttact tttatccttt taggttgcct ataaaggggg tccccatcga    9420
attacaagtg gaatgcttca catgggacca aaaactctgg tgccgtcact tctgtgtgct    9480
tgcggactca gaatctggtg gacatatcac tcactctggg atggtgggca tgggagtcag    9540
ctgcacagtc acccgggaag atggaaccaa tcgcagatag ggctgctagt gaaccaatca    9600
catgatgtca cccagacatc aggcataccc actagtgtga aatagacatc agaattaaga    9660
aaaacgtagg gtccaagtgg ttccccgtta tggactcgct atctgtcaac cagatcttat    9720
accctgaagt tcacctagat agcccgatag ttaccaataa gatagtagcc atcctggagt    9780
atgctcgagt ccctcacgct tacagcctgg aggacccta actgtgtcag aacatcaagc     9840
accgcctaaa aaacggattt tccaaccaaa tgattataaa caatgtggaa gttgggaatg    9900
tcatcaagtc caagcttagg agttatccgg cccactctca tattccatat ccaaattgta    9960
atcaggattt atttaacata gaagacaaag agtcaacgag gaagatccgt gaactcctca   10020
aaaagggggaa ttcgctgtac tccaaagtca gtgataaggt tttccaatgc ttaagggaca   10080
ctaactcacg gcttggccta ggctccgaat tgagggagga catcaaggag aaagttatta   10140
acttgggagt ttacatgcac agctcccagt ggtttgagcc ctttctgttt tggtttacag   10200
tcaagactga gatgaggtca gtgattaaat cacaaaccca tacttgccat aggaggagac   10260
acacacctgt attcttcact ggtagttcag ttgagttgct aatctctcgt gaccttgttg   10320
ctataatcag taaagagtct caacatgtat attacctgac atttgaactg gttttgatgt   10380
attgtgatgt catagagggg aggttaatga cagagaccgc tatgactatt gatgctaggt   10440
atacagagct tctaggaaga gtcagataca tgtggaaact gatagatggt ttcttccctg   10500
cactcgggaa tccaacttat caaattgtag ccatgctgga gcctctttca cttgcttacc   10560
tgcagctgag ggatataaca gtagaactca gaggtgcttt ccttaaccac tgctttactg   10620
aaatacatga tgttcttgac caaaacgggt ttctgatga aggtacttat catgagttaa    10680
ctgaagctct agattacatt ttcataactg atgacataca tctgacaggg gagattttct   10740
cattttttcag aagtttcggc cacccccagac ttgaagcagt aacggctgct gaaaatgtta  10800
ggaaatacat gaatcagcct aaagtcattg tgtatgagac tctgatgaaa ggtcatgcca   10860
tattttgtgg aatcataatc aacggctatc gtgacaggca cggaggcagt tggccaccgc   10920
tgaccctccc cctgcatgct gcagacacaa tccggaatgc tcaagcttca ggtgaagggt   10980
taacacatga gcagtgcgtt gataactgga aatcttttgc tggagtgaaa tttggctgct   11040
```

-continued

```
ttatgcctct tagcctggat agtgatctga caatgtacct aaaggacaag gcacttgctg   11100
ctctccaaag ggaatgggat tcagtttacc cgaaagagtt cctgcgttac gaccctccca   11160
agggaaccgg gtcacggagg cttgtagatg ttttccttaa tgattcgagc tttgacccat   11220
atgatgtgat aatgtatgtt gtaagtggag cttacctcca tgaccctgag ttcaacctgt   11280
cttacagcct gaaagaaaag gagatcaagg aaacaggtag acttttttgct aaaatgactt   11340
acaaaatgag ggcatgccaa gtgattgctg aaaatctaat ctcaaacggg attggcaaat   11400
attttaagga caatgggatg gccaaggatg agcacgattt gactaaggca ctccacactc   11460
tagctgtctc aggagtcccc aaagatctca agaaagtca caggggggggg ccagtcttaa   11520
aaacctactc ccgaagccca gtccacacaa gtaccaggaa cgtgagagca gcaaaagggt   11580
ttatagggtt ccctcaagta attcggcagg accaagacac tgatcatccg gagaatatgg   11640
aagcttacga gacagtcagt gcatttatca cgactgatct caagaagtac tgccttaatt   11700
ggagatatga gaccatcagc ttgtttgcac agaggctaaa tgagatttac ggattgccct   11760
catttttcca gtggctgcat aagaggcttg agacctctgt cctgtatgta agtgaccctc   11820
attgcccccc cgaccttgac gcccatatcc cgttatataa agtccccaat gatcaaatct   11880
tcattaagta ccctatggga ggtatagaag ggtattgtca gaagctgtgg accatcagca   11940
ccattcccta tctataccctg gctgcttatg agagcggagt aaggattgct tcgttagtgc   12000
aaggggacaa tcagaccata gccgtaacaa aaagggtacc cagcacatgg ccctacaacc   12060
ttaagaaacg ggaagctgct agagtaacta gagattactt tgtaattctt aggcaaaggc   12120
tacatgatat tggccatcac ctcaaggcaa atgagacaat tgtttcatca cattttttg    12180
tctattcaaa aggaatatat tatgatgggc tacttgtgtc ccaatcactc aagagcatcg   12240
caagatgtgt attctggtca gagactatag ttgatgaaac aagggcagca tgcagtaata   12300
ttgctacaac aatggctaaa agcatcgaga gaggttatga ccgttacctt gcatattccc   12360
tgaacgtcct aaaagtgata cagcaaattc tgatctctct tggcttcaca atcaattcaa   12420
ccatgacccg ggatgtagtc ataccctcc tcacaaacaa cgacctctta ataaggatgg    12480
cactgttgcc cgctcctatt gggggatgat tatctgaa tatgagcagg ctgtttgtca     12540
gaaacatcgg tgatccagta acatcatcaa ttgctgatct caagagaatg attctcgcct   12600
cactaatgcc tgaagagacc ctccatcaag taatgacaca acaaccgggg gactcttcat    12660
tcctagactg ggctagcgac ccttactcag caaatcttgt atgtgtccag agcatcacta    12720
gactcctcaa gaacataact gcaaggtttg tcctgatcca tagtccaaac ccaatgttaa    12780
aaggattatt ccatgatgac agtaaagaag aggacgaggg actggcggca ttcctcatgg   12840
acaggcatat tatagtacct agggcagctc atgaaatcct ggatcatagt gtcacagggg   12900
caagagagtc tattgcaggc atgctggata ccacaaaagg cttgattcga gccagcatga    12960
ggaaggggggg gttaacctct cgagtgataa ccagattgtc caattatgac tatgaacaat   13020
tcagagcagg gatggtgcta ttgacaggaa gaaagagaaa tgtcctcatt gacaaagagt    13080
catgttcagt gcagctggcg agagctctaa gaagccatat gtgggcgagg ctagctcgag    13140
gacggcctat ttacgccctt gaggtccctg atgtactaga atctatgcga ggccaccttα    13200
ttcggcgtca tgagacatgt gtcatctgcg agtgtggatc agtcaactac ggatggtttt   13260
ttgtcccctc gggttgccaa ctggatgata ttgacaagga acatcatcc ttgagagtcc    13320
catatattgg ttctaccact gatgagagaa cagacatgaa gcttgccttc gtaagagccc   13380
caagtcgatc cttgcgatct gctgttagaa tagcaacagt gtactcatgg gcttacggtg   13440
```

```
atgatgatag ctcttggaac gaagcctggt tgttggctag gcaaagggcc aatgtgagcc    13500
tggaggagct aagggtgatc actcccatct caacttcgac taatttagcg cataggttga    13560
gggatcgtag cactcaagtg aaatactcag gtacatccct tgtccgagtg gcgaggtata    13620
ccacaatctc caacgacaat ctctcatttg tcatatcaga taagaaggtt gatactaact    13680
ttatatacca acaaggaatg cttctagggt tgggtgtttt agaaacattg tttcgactcg    13740
agaaagatac cggatcatct aacacggtat tacatcttca cgtcgaaaca gattgttgcg    13800
tgatcccgat gatagatcat cccaggatac ccagctcccg caagctagag ctgagggcag    13860
agctatgtac caacccattg atatatgata atgcacctttaattgacaga gatgcaacaa    13920 ggctatacac ccagagccat aggaggcacc ttgtggaatt tgttacatgg tccacacccc    13980
aactatatca cattttagct aagtccacag cactatctat gattgacctg gtaacaaaat    14040
ttgagaagga ccatatgaat gaaatttcag ctctcatagg ggatgacgat atcaatagtt    14100
tcataactga gtttctgctc atagagccaa gattattcac tatctacttg ggccagtgtg    14160
cggccatcaa ttgggcattt gatgtacatt atcatagacc atcagggaaa tatcagatgg    14220
gtgagctgtt gtcatcgttc ctttctagaa tgagcaaagg agtgtttaag gtgcttgtca    14280
atgctctaag ccacccaaag atctacaaga aattctggca ttgtggtatt atagagccta    14340
tccatggtcc ttcacttgat gctcaaaact tgcacacaac tgtgtgcaac atggtttaca    14400
catgctatat gacctacctc gacctgttgt tgaatgaaga gttagaagag ttcacatttc    14460
tcttgtgtga aagcgacgag gatgtagtac cggacagatt cgacaacatc caggcaaaac    14520
acttatgtgt tctggcagat ttgtactgtc aaccagggac ctgcccacca attcgaggtc    14580
taagaccggt agagaaatgt gcagttctaa ccgaccatat caaggcagag gctatgttat    14640
ctccagcagg atcttcgtgg aacataaatc caattattgt agaccattac tcatgctctc    14700
tgacttatct ccggcgagga tcgatcaaac agataagatt gagagttgat ccaggattca    14760
ttttcgacgc cctcgctgag gtaaatgtca gtcagccaaa gatcggcagc aacaacatct    14820
caaatatgag catcaaggct ttcagacccc cacacgatga tgttgcaaaa ttgctcaaag    14880
atatcaacac aagcaagcac aatcttccca tttcaggggg caatctcgcc aattatgaaa    14940
tccatgcttt ccgcagaatc gggttgaact catctgcttg ctacaaagct gttgagatat    15000
caacattaat taggagatgc cttgagccag gggaggacgg cttgttcttg ggtgagggat    15060
cgggttctat gttgatcact tataaagaga tacttaaaact aaacaagtgc ttctataata    15120
gtggggtttc cgccaattct agatctggtc aaagggaatt agcaccctat ccctccgaag    15180
ttggccttgt cgaacacaga atgggagtag gtaatattgt caaagtgctc tttaacggga    15240
ggcccgaagt cacgtgggta ggcagtgtag attgcttcaa tttcatagtt agtaatatcc    15300
ctacctctag tgtggggttt atccattcag atatagagac cttgcctgac aaagatacta    15360
tagagaagct agaggaattg gcagccatct tatcgatggc tctgctcctg ggcaaaatag    15420
gatcaatact ggtgattaag cttatgcctt tcagcgggga ttttgttcag ggatttataa    15480
gttatgtagg gtctcattat agagaagtga accttgtata ccctagatac agcaacttca    15540
tctctactga atcttatttg gttatgacag atctcaaggc taaccggcta atgaatcctg    15600
aaaagattaa gcagcagata attgaatcat ctgtgaggac ttcacctgga cttataggtc    15660
acatcctatc cattaagcaa ctaagctgca tacaagcaat tgtgggagac gcagttagta    15720
gaggtgatat caatcctact ctgaaaaaac ttacacctat agagcaggtg ctgatcaatt    15780
```

```
gcgggttggc aattaacgga cctaagctgt gcaaagaatt gatccaccat gatgttgcct   15840
cagggcaaga tggattgctt aattctatac tcatcctcta cagggagttg caagattca    15900 aagacaacca aagaagtcaa caagggatgt ccacgctta ccccgtattg gtaagtagca    15960
ggcaacgaga acttatatct aggatcaccc gcaaattctg ggggcacatt cttctttact   16020
ccgggaacaa aaagttgata aataagttta tccagaatct caagtccggc tatctgatac   16080
tagacttaca ccagaatatc ttcgttaaga atctatccaa gtcagagaaa cagattatta   16140
tgacgggggg tttgaaacgt gagtgggttt ttaaggtaac agtcaaggag accaaagaat   16200
ggtataagtt agtcggatac agtgccctga ttaaggacta attggttgaa ctccggaacc   16260
ctaatcctgc cctaggtggt taggcattat ttgcaatata ttaaagaaaa ctttgaaaat   16320
acgaagtttc tattcccagc tttgtctggt ggccggcatg gtcccagcct cctcgctggc   16380
gccggctggg caacattccg aggggaccgt cccctcggta atggcgaatg ggacgcggcc   16440
gatccggctg ctaacaaagc ccgaaaggaa gctgagttgg ctgctgccac cgctgagcaa   16500
taactagcat aaccccttgg ggcctctaaa cgggtcttga ggggttttt gctgaaagga    16560 ggaactatat ccggatgcgg ccgcgggccc tatggtaccc agcttttgtt ccctttagtg   16620
agggttaatt ccgagcttgg cgtaatcatg gtcatagctg tttcctgtgt gaaattgtta   16680
tccgctcaca attccacaca acataggagc cggaagcata agtgtaaag cctggggtgc     16740 ctaatgagtg aggtaactca cattaattgc gttgcgctca ctgcccgctt ccagtcggg    16800 aaacctgtcg tgccagctgc attaatgaat cggccaacgc gcggggagag gcggtttgcg   16860
tattgggcgc tcttccgctt cctcgctcac tgactcgctg cgctcggtcg ttcggctgcg   16920
gcgagcggta tcagctcact caaaggcggt aatacggtta ccacagaat caggggataa    16980 cgcaggaaag aacatgtgag caaaaggcca gcaaaaggcc aggaaccgta aaaaggccgc   17040
gttgctggcg ttttttccata ggctcggccc cctgacgag catcacaaaa atcgacgctc   17100
aagtcagagg tggcgaaacc cgacaggact ataaagatac caggcgttcc ccctggaag    17160 ctcctcgtg cgctctcctg ttccgaccct gccgcttacc ggatacctgt ccgcctttct   17220
cccttcggga agcgtggcgc tttctcaatg ctcacgctgt aggtatctca gttcggtgta   17280
ggtcgttcgc tccaagctgg gctgtgtgca cgaaccccc gttcagcccg accgctgcgc    17340
cttatccggt aactatcgtc ttgagtccaa cccggtaaga cacgacttat cgccactggc   17400
agcagccact ggtaacagga ttagcagagc gaggtatgta ggcggtgcta cagagttctt   17460
gaagtggtgg cctaactacg gctacactag aaggacagta tttggtatct gcgctctgct   17520
gaagccagtt accttcggaa aaagagttgg tagctcttga tccggcaaac aaaccaccgc   17580
tggtagcggt ggtttttttg tttgcaagca gcagattacg cgcagaaaaa aaggatctca   17640
agaagatcct ttgatctttt ctacggggtc tgacgctcag tggaacgaaa actcacgtta   17700
agggattttg gtcatgagat tatcaaaaag gatcttcacc tagatccttt taaattaaaa   17760
atgaagtttt aaatcaatct aaagtatata tgagtaaact tggtctgaca gttaccaatg   17820
cttaatcagt gaggcaccta tctcagcgat ctgtctattt cgttcatcca tagttgcctg   17880
actgcccgtc gtgtagataa ctacgatacg ggagggctta ccatctggcc ccagtgctgc   17940
aatgataccg cgagacccac gctcaccggc tccagattta tcagcaataa accagccagc   18000
cggaagggcc gagcgcagaa gtggtcctgc aactttatcc gcctccatcc agtctattaa   18060
ttgttgccgg gaagctagag taagtagttc gccagttaat agtttgcgca acgttgttgc   18120
cattgctaca ggcatcgtgg tgtcacgctc gtcgtttggt atggcttcat tcagctccgg   18180
```

```
ttcccaacga tcaaggcgag ttacatgatc ccccatgttg tgaaaaaaag cggttagctc  18240
cttcggtcct ccgatcgttg tcagaagtaa gttggccgca gtgttatcac tcatgcttat  18300
ggcagcactg cataattctc ttactgtcat gccatccgta agatgctttt ctgtgactgg  18360
tgagtactca accaagtcat tctgagaata gtgtatgcgg cgaccgagtt gctcttgccc  18420
ggcgtcaata cgggataata ccgcgccaca tagcagaact ttaaaagtgc tcatcattgg  18480
aaaacgttct tcggggcgaa aactctcaag gatcttaccg ctgttgagat ccagttcgat  18540
gtaacccact cgtgcaccca actgatcttc agcatctttt actttcacca gcgtttctgg  18600
gtgagcaaaa acaggaaggc aaaatgccgc aaaaaaggga ataagggcga cacggaaatg  18660
ttgaatactc atactcttcc tttttcaata ttattgaagc atttatcagg gttattgtct  18720
catgagcgga tacatatttg aatgtattta gaaaaataaa caaatagggg ttccgcgcac  18780
atttccccga aaagtgccac ctgaaattgt aaacgttaat attttgttaa aattcgcgtt  18840
aaatttttgt taaatcagct cattttttaa ccaataggcc gaaatcggca aaatccctta  18900
taaatcaaaa gaatagaccg agatagggtt gagtgttgtt ccagtttgga acaagagtcc  18960
actattaaag aacgtggact ccaacgtcaa agggcgaaaa accgtctatc agggcgatgg  19020
cccactacgt gaaccatcac cctaatcaag ttttttgggg tcgaggtgcc gtaaagcact  19080
aaatcggaac cctaaaggga gcccccgatt tagagcttga cggggaaagc cggcgaacgt  19140
ggcgagaaag gaagggaaga aagcgaaagg agcgggcgct agggcgctgg caagtgtagc  19200
ggtcacgctg cgcgtaacca ccacacccgc cgcgcttaat gcgccgctac agggcgcgtc  19260
ccattcgcca ttcaggctgc gcaactgttg ggaagggcga tcggtgcggg cctcttcgct  19320
attacgccag ccaccgcggt ggcggccgct aatacgactc actatagggc caactttgtt  19380
tggtctgatg agtccgtgag gacgaaaccc ggagtcccgg gtc                   19423
```

```
<210> SEQ ID NO 2
<211> LENGTH: 19423
<212> TYPE: DNA
<213> ORGANISM: Artificial Sequence
<220> FEATURE:
<223> OTHER INFORMATION: pTM-MV-ATU1-M2opt
<220> FEATURE:
<221> NAME/KEY: misc_RNA
<222> LOCATION: (1)..(16350)
<223> OTHER INFORMATION: MV-ATU1-M2opt_antigenome
<220> FEATURE:
<221> NAME/KEY: misc_feature
<222> LOCATION: (53)..(508)
<223> OTHER INFORMATION: ATU1
<220> FEATURE:
<221> NAME/KEY: misc_feature
<222> LOCATION: (111)..(116)
<223> OTHER INFORMATION: BsiWI restriction site
<220> FEATURE:
<221> NAME/KEY: misc_feature
<222> LOCATION: (120)..(416)
<223> OTHER INFORMATION: ORF for M2 consensus protein : M2opt
<220> FEATURE:
<221> NAME/KEY: misc_feature
<222> LOCATION: (417)..(422)
<223> OTHER INFORMATION: BssHII restriction site
<220> FEATURE:
<221> NAME/KEY: misc_feature
<222> LOCATION: (16351)..(19423)
<223> OTHER INFORMATION: plasmid_backbone

<400> SEQUENCE: 2
accaaacaaa gttgggtaag gatagttcaa tcaatgatca tcttctagtg cacttaggat     60
```

-continued

```
tcaagatcct attatcaggg acaagagcag gattagggat atccgagacg cgtacgacca      120
tgagcctgct gaccgaggtg gaaaccccca tcagaaacga gtggggctgc cggtgcaacg      180
acagcagcga tcctctggtg gtggccgcca gcatcatcgg catcctgcac ctgatcctgt      240
ggattctgga ccggctgttc ttcaagtgca tctacagact gttcaagcac ggcctgaaga      300
gaggccccag cacagaaggc gtgcccgaga gcatgcggga agagtaccgg aaagaacagc      360
agaacgccgt ggacgccgac gacagccact tcgtgtccat cgagctggaa tgataagcgc      420
gcagcgctta gacgtctcgc gatcgattag tgcgagaggc cgagggccag aacaacatcc      480
gcctaccatc catcattgtt ataaaaaact taggattcaa gatcctatta tcagggacaa      540
gagcaggatt agggatatcc gagatggcca cacttttaag gagcttagca ttgttcaaaa      600
gaaacaagga caaccaccc attacatcag gatccgtgg agccatcaga ggaatcaaac      660
acattattat agtaccaatc cctggagatt cctcaattac cactcgatcc agacttctgg      720
accggttggt gaggttaatt ggaaacccgg atgtgagcgg gcccaaacta acaggggcac      780
taataggtat attatcctta tttgtggagt ctccaggtca attgattcag aggatcaccg      840
atgaccctga cgttagcata aggctgttag aggttgtcca gagtgaccag tcacaatctg      900
gccttacctt cgcatcaaga ggtaccaaca tggaggatga ggcggaccaa tactttcac      960 atgatgatcc aattagtagt gatcaatcca ggttcggatg gttcgggaac aaggaaatct     1020
cagatattga agtgcaagac cctgagggat tcaacatgat tctgggtacc atcctagccc     1080
aaatttgggt cttgctcgca aaggcggtta cggccccaga cacggcagct gattcggagc     1140
taagaaggtg gataaagtac acccaacaaa gaagggtagt tggtgaattt agattggaga     1200
gaaaatggtt ggatgtggtg aggaacagga ttgccgagga cctctcctta cgccgattca     1260
tggtcgctct aatcctggat atcaagagaa cacccgaaa caaacccagg attgctgaaa     1320
tgatatgtga cattgataca tatatcgtag aggcaggatt agccagtttt atcctgacta     1380
ttaagtttgg gatagaaact atgtatcctg ctcttggact gcatgaattt gctggtgagt     1440
tatccacact tgagtccttg atgaaccttt accagcaaat gggggaaact gcaccctaca     1500
tggtaatcct ggagaactca attcagaaca agttcagtgc aggatcatac cctctgctct     1560
ggagctatgc catgggagta ggagtggaac ttgaaaactc catgggaggt ttgaactttg     1620
gccgatctta ctttgatcca gcatatttta gattagggca agagatggta aggaggtcag     1680
ctggaaaggt cagttccaca ttggcatctg aactcggtat cactgccgag gatgcaaggc     1740
ttgtttcaga gattgcaatg catactactg aggacaagat cagtagagcg gttggacccca     1800 gacaagccca agtatcattt ctacacggtg atcaaagtga gaatgagcta ccgagattgg     1860
ggggcaagga agataggagg gtcaaacaga gtcgaggaga agccagggag agctacagag     1920
aaaccgggcc cagcagagca agtgatgcga gagctgccca tcttccaacc ggcacacccc     1980
tagacattga cactgcaacg gagtccagcc aagatccgca ggacagtcga aggtcagctg     2040
acgccctgct taggctgcaa gccatggcag gaatctcgga agaacaaggc tcagacacgg     2100 acaccctat agtgtacaat gacagaaatc ttctagacta ggtgcgagag gccgagggcc     2160
agaacaacat ccgcctacca tccatcattg ttataaaaaa cttaggaacc aggtccacac     2220
agccgccagc ccatcaacca tccactccca cgattggagc caatggcaga agagcaggca     2280
cgccatgtca aaaacggact ggaatgcatc cgggctctca aggccgagcc catcggctca     2340
ctggccatcg aggaagctat ggcagcatgg tcagaaatat cagacaaccc aggacaggag     2400
cgagccacct gcagggaaga gaaggcaggc agttcgggtc tcagcaaacc atgcctctca     2460
```

```
gcaattggat caactgaagg cggtgcacct cgcatccgcg gtcagggacc tggagagagc    2520
gatgacgacg ctgaaacttt gggaatcccc ccaagaaatc tccaggcatc aagcactggg    2580
ttacagtgtt attacgttta tgatcacagc ggtgaagcgg ttaagggaat ccaagatgct    2640
gactctatca tggttcaatc aggccttgat ggtgatagca ccctctcagg aggagacaat    2700
gaatctgaaa acagcgatgt ggatattggc gaacctgata ccgagggata tgctatcact    2760
gaccggggat ctgctcccat ctctatgggg ttcaggcctt ctgatgttga aactgcagaa    2820 ggagggggaga tccacgagct cctgagactc aatccagag gcaacaactt ccgaagctt    2880 gggaaaactc tcaatgttcc tccgcccccg gaccccggta gggccagcac ttccgggaca    2940
cccattaaaa agggcacaga cgcgagatta gcctcatttg aacggagat cgcgtcttta    3000 ttgacaggtg gtgcaaccca atgtgctcga aagtcaccct cggaaccatc agggccaggt    3060
gcacctgcgg ggaatgtccc cgagtgtgtg agcaatgccg cactgataca ggagtggaca    3120
cccgaatctg gtaccacaat ctccccgaga tcccagaata tgaagaagg gggagactat    3180 tatgatgatg agctgttctc tgatgtccaa gatattaaaa cagccttggc caaaatacac    3240
gaggataatc agaagataat ctccaagcta gaatcactgc tgttattgaa gggagaagtt    3300
gagtcaatta agaagcagat caacaggcaa aatatcagca tatccaccct ggaaggacac    3360
ctctcaagca tcatgatcgc cattcctgga cttgggaagg atcccaacga ccccactgca    3420
gatgtcgaaa tcaatcccga cttgaaaccc atcataggca gagattcagg ccgagcactg    3480
gccgaagttc tcaagaaacc cgttgccagc cgacaactcc aaggaatgac aaatggacgg    3540
accagttcca gaggacagct gctgaaggaa tttcagctaa agccgatcgg gaaaaagatg    3600
agctcagccg tcgggtttgt tcctgacacc ggccctgcat cacgcagtgt aatccgctcc    3660
attataaaat ccagccggct agaggaggat cggaagcgtt acctgatgac tctccttgat    3720
gatatcaaag gagccaatga tcttgccaag ttccaccaga tgctgatgaa gataataatg    3780
aagtagctac agctcaactt acctgccaac cccatgccag tcgacccaac tagtacaacc    3840
taaatccatt ataaaaaact taggagcaaa gtgattgcct cccaaggtcc acaatgacag    3900
agacctacga cttcgacaag tcggcatggg acatcaaagg gtcgatcgct ccgatacaac    3960
ccaccaccta cagtgatggc aggctggtgc cccaggtcag agtcatagat cctggtctag    4020
gcgacaggaa ggatgaatgc tttatgtaca tgtttctgct gggggttgtt gaggacagcg    4080
attccctagg gcctccaatc gggcgagcat ttgggttcct gcccttaggt gttggcagat    4140
ccacagcaaa gcccgaaaaa ctcctcaaag aggccactga gcttgacata gttgttagac    4200
gtacagcagg gctcaatgaa aaactggtgt tctacaacaa caccccacta actctcctca    4260
caccttggag aaaggtccta acaacaggga gtgtcttcaa cgcaaaccaa gtgtgcaatg    4320
cggttaatct gataccgctc gataccccgc agaggttccg tgttgtttat atgagcatca    4380
cccgtctttc ggataacggg tattacaccg ttcctagaag aatgctggaa ttcagatcgg    4440
tcaatgcagt ggccttcaac ctgctggtga cccttaggat tgacaaggcg ataggccctg    4500
ggaagatcat cgacaataca gagcaacttc ctgaggcaac atttatggtc cacatcggga    4560
acttcaggag aaagaagagt gaagtctact ctgccgatta ttgcaaaatg aaaatcgaaa    4620
agatgggcct ggttttttgca cttggtggga taggggcac cagtcttcac attagaagca    4680
caggcaaaat gagcaagact ctccatgcac aactcgggtt caagaagacc ttatgttacc    4740
cgctgatgga tatcaatgaa gaccttaatc gattactctg gaggagcaga tgcaagatag    4800
```

```
taagaatcca ggcagttttg cagccatcag ttcctcaaga attccgcatt tacgacgacg    4860
tgatcataaa tgatgaccaa ggactattca aagttctgta gaccgtagtg cccagcaatg    4920
cccgaaaacg accccccctca caatgacagc cagaaggccc ggacaaaaaa gcccctccg    4980 aaagactcca cggaccaagc gagaggccag ccagcagccg acggcaagcg cgaacaccag    5040
gcggccccag cacagaacag ccctgacaca aggccaccac cagccacccc aatctgcatc    5100
ctcctcgtgg accccgag accaacccc caaggctgcc cccgatccaa accaccaacc    5160 gcatcccac cacccccggg aaagaaaccc ccagcaattg aaggcccct cccctcttc    5220 ctcaacacaa gaactccaca accgaaccgc acaagcgacc gaggtgaccc aaccgcaggc    5280
atccgactcc ctagacagat cctctctccc cggcaaacta aacaaaactt agggccaagg    5340
aacatacaca cccaacagaa cccagacccc ggcccacggc gccgcgcccc aaccccga    5400 caaccagagg gagcccccaa ccaatcccgc cggctccccc ggtgcccaca ggcagggaca    5460 ccaaccccg aacagaccca gcacccaacc atcgacaatc caagacgggg gggccccccc    5520 aaaaaaggc cccagggggc cgacagccag caccgcgagg aagcccaccc accccacaca    5580
cgaccacggc aaccaaacca gaacccagac caccctgggc caccagctcc cagactcggc    5640
catcaccccg cagaaaggaa aggccacaac ccgcgcaccc cagccccgat ccggcgggga    5700
gccacccaac ccgaaccagc acccaagagc gatccccgaa ggaccccga accgcaaagg    5760 acatcagtat cccacagcct ctccaagtcc cccggtctcc tcctcttctc gaagggacca    5820
aaagatcaat ccaccacacc cgacgacact caactcccca ccctaaagg agacaccggg    5880 aatcccagaa tcaagactca tccaatgtcc atcatgggtc tcaaggtgaa cgtctctgcc    5940
atattcatgg cagtactgtt aactctccaa acacccaccg gtcaaatcca ttggggcaat    6000
ctctctaaga taggggtggt aggaatagga agtgcaagct acaaagttat gactcgttcc    6060
agccatcaat cattagtcat aaaattaatg cccaatataa ctctcctcaa taactgcacg    6120
agggtagaga ttgcagaata caggagacta ctgagaacga ttttggaacc aattagagat    6180
gcacttaatg caatgaccca gaatataaga ccggttcaga gtgtagcttc aagtaggaga    6240
cacaagagat ttgcgggagt agtcctggca ggtgcggccc taggcgttgc cacagctgct    6300
cagataacag ccggcattgc acttcaccag tccatgctga actctcaagc catcgacaat    6360
ctgagagcga gcctggaaac tactaatcag gcaattgaga caatcagaca agcagggcag    6420
gagatgatat tggctgttca gggtgtccaa gactacatca ataatgagct gataccgtct    6480
atgaaccaac tatcttgtga tttaatcggc cagaagctcg ggctcaaatt gctcagatac    6540
tatacagaaa tcctgtcatt atttggcccc agtttacggg accccatatc tgcggagata    6600
tctatccagg cttttgagcta tgcgcttgga ggagacatca ataaggtgtt agaaaagctc    6660
ggatacagtg gaggtgattt actgggcatc ttagagagcg gaggaataaa ggcccggata    6720
actcacgtcg acacagagtc ctacttcatt gtcctcagta tagcctatcc gacgctgtcc    6780
gagattaagg gggtgattgt ccaccggcta gaggggtct cgtacaacat aggctctcaa    6840
gagtggtata ccactgtgcc caagtatgtt gcaacccaag ggtaccttat ctcgaatttt    6900
gatgagtcat cgtgtactt catgccgag gggactgtgt gcagccaaaa tgccttgtac    6960
ccgatgagtc ctctgctcca agaatgcctc cggggggtaca ccaagtcctg tgctcgtaca    7020
ctcgtatccg ggtcttttgg gaaccggttc atttttatcac aagggaacct aatagccaat    7080
tgtgcatcaa tcctttgcaa gtgttacaca acaggaacga tcattaatca agaccctgac    7140
aagatcctaa catacattgc tgccgatcac tgcccggtag tcgaggtgaa cggcgtgacc    7200
```

```
atccaagtcg ggagcaggag gtatccagac gctgtgtact tgcacagaat tgacctcggt    7260
cctcccatat cattggagag gttggacgta gggacaaatc tggggaatgc aattgctaag    7320
ttggaggatg ccaaggaatt gttggagtca tcggaccaga tattgaggag tatgaaaggt    7380
ttatcgagca ctagcatagt ctacatcctg attgcagtgt gtcttggagg gttgataggg    7440
atccccgctt taatatgttg ctgcaggggg cgttgtaaca aaagggaga acaagttggt    7500 atgtcaagac caggcctaaa gcctgatctt acgggaacat caaaatccta tgtaaggtcg    7560
ctctgatcct ctacaactct tgaaacacaa atgtcccaca agtctcctct tcgtcatcaa    7620
gcaaccaccg cacccagcat caagcccacc tgaaattatc tccggcttcc ctctggccga    7680
acaatatcgg tagttaatca aaacttaggg tgcaagatca tccacaatgt caccacaacg    7740
agaccggata aatgccttct acaaagataa ccccatccc aagggaagta ggatagtcat    7800
taacagagaa catcttatga ttgatagacc ttatgttttg ctggctgttc tgtttgtcat    7860
gtttctgagc ttgatcgggt tgctagccat tgcaggcatt agacttcatc gggcagccat    7920
ctacaccgca gagatccata aaagcctcag caccaatcta gatgtaacta actcaatcga    7980
gcatcaggtc aaggacgtgc tgacaccact cttcaaaatc atcggtgatg aagtgggcct    8040
gaggacacct cagagattca ctgacctagt gaaattaatc tctgacaaga ttaaattcct    8100
taatccggat agggagtacg acttcagaga tctcacttgg tgtatcaacc cgccagagag    8160
aatcaaattg gattatgatc aatactgtgc agatgtggct gctgaagagc tcatgaatgc    8220
attggtgaac tcaactctac tggagaccag aacaaccaat cagttcctag ctgtctcaaa    8280
gggaaactgc tcagggccca ctacaatcag aggtcaattc tcaaacatgt cgctgtccct    8340
gttagacttg tatttaggtc gaggttacaa tgtgtcatct atagtcacta tgacatccca    8400
gggaatgtat gggggaactt acctagtgga aaagcctaat ctgagcagca aaggtcaga    8460 gttgtcacaa ctgagcatgt accgagtgtt tgaagtaggt gttatcagaa atccgggttt    8520
gggggctccg gtgttccata tgacaaacta tcttgagcaa ccagtcagta atgatctcag    8580
caactgtatg gtggctttgg gggagctcaa actcgcagcc ctttgtcacg ggaagattc    8640 tatcacaatt ccctatcagg gatcagggaa aggtgtcagc ttccagctcg tcaagctagg    8700
tgtctggaaa tccccaaccg acatgcaatc ctgggtcccc ttatcaacgg atgatccagt    8760
gatagacagg ctttacctct catctcacag aggtgttatc gctgacaatc aagcaaaatg    8820
ggctgtcccg acaacacgaa cagatgacaa gttgcgaatg gagacatgct ccaacaggc    8880 gtgtaagggt aaaatccaag cactctgcga gaatcccgag tgggcaccat tgaaggataa    8940
caggattcct tcatacgggg tcttgtctgt tgatctgagt ctgacagttg agcttaaaat    9000
caaaattgct tcgggattcg ggccattgat cacacacggt tcaggatgg acctatacaa    9060 atccaaccac aacaatgtgt attggctgac tatcccgcca atgaagaacc tagccttagg    9120
tgtaatcaac acattggagt ggataccgag attcaaggtt agtccctacc tcttcactgt    9180
cccaattaag gaagcaggcg aagactgcca tgccccaaca tacctacctg cggaggtgga    9240
tggtgatgtc aaactcagtt ccaatctggt gattctacct ggtcaagatc tccaatatgt    9300
tttggcaacc tacgatactt ccaggggttga acatgctgtg gttttattcg tttacagccc    9360
aagccgctca ttttcttact tttatcctt taggttgcct ataaaggggg tccccatcga    9420 attcaagtg gaatgcttca catgggacca aaaactctgg tgccgtcact tctgtgtgct    9480
tgcggactca gaatctggtg gacatatcac tcactctggg atggtgggca tgggagtcag    9540
```

```
ctgcacagtc acccgggaag atggaaccaa tcgcagatag ggctgctagt gaaccaatca    9600
catgatgtca cccagacatc aggcataccc actagtgtga aatagacatc agaattaaga    9660
aaaacgtagg gtccaagtgg ttccccgtta tggactcgct atctgtcaac cagatcttat    9720
accctgaagt tcacctagat agcccgatag ttaccaataa gatagtagcc atcctggagt    9780
atgctcgagt ccctcacgct tacagcctgg aggaccctac actgtgtcag aacatcaagc    9840
accgcctaaa aaacggattt tccaaccaaa tgattataaa caatgtggaa gttgggaatg    9900
tcatcaagtc caagcttagg agttatccgg cccactctca tattccatat ccaaattgta    9960
atcaggattt atttaacata gaagacaaag agtcaacgag gaagatccgt gaactcctca   10020
aaaggggaa ttcgctgtac tccaaagtca gtgataaggt tttccaatgc ttaagggaca   10080
ctaactcacg gcttggccta ggctccgaat tgagggagga catcaaggag aaagttatta   10140
acttgggagt ttacatgcac agctcccagt ggtttgagcc ctttctgttt tggtttacag   10200
tcaagactga gatgaggtca gtgattaaat cacaaaccca tacttgccat aggaggagac   10260
acacacctgt attcttcact ggtagttcag ttgagttgct aatctctcgt gaccttgttg   10320
ctataatcag taaagagtct caacatgtat attacctgac atttgaactg gttttgatgt   10380
attgtgatgt catagagggg aggttaatga cagagaccgc tatgactatt gatgctaggt   10440
atacagagct tctaggaaga gtcagataca tgtggaaact gatagatggt ttcttccctg   10500
cactcgggaa tccaacttat caaattgtag ccatgctgga gcctctttca cttgcttacc   10560
tgcagctgag ggatataaca gtagaactca gaggtgcttt ccttaaccac tgctttactg   10620
aaatacatga tgttcttgac caaaacgggt tttctgatga aggtacttat catgagttaa   10680
ctgaagctct agattacatt ttcataactg atgacataca tctgacaggg gagattttct   10740
catttttcag aagtttcggc cacccccgac ttgaagcagt aacggctgct gaaaatgtta   10800
ggaaatacat gaatcagcct aaagtcattg tgtatgagac tctgatgaaa ggtcatgcca   10860
tattttgtgg aatcataatc aacggctatc gtgacaggca cggaggcagt tggccaccgc   10920
tgacctctcc cctgcatgct gcagacacaa tccggaatgc tcaagcttca ggtgaagggt   10980
taacacatga gcagtgcgtt gataactgga aatcttttgc tggagtgaaa tttggctgct   11040
ttatgcctct tagcctggat agtgatctga caatgtacct aaaggacaag gcacttgctg   11100
ctctccaaag ggaatgggat tcagtttacc cgaaagagtt cctgcgttac gaccctccca   11160
agggaaccgg gtcacggagg cttgtagatg ttttccttaa tgattcgagc tttgacccat   11220
atgatgtgat aatgtatgtt gtaagtggag cttacctcca tgaccctgag ttcaacctgt   11280
cttacagcct gaaagaaaag gagatcaagg aaacaggtag acttttttgct aaaatgactt   11340
acaaaatgag ggcatgccaa gtgattgctg aaaatctaat ctcaaacggg attggcaaat   11400
attttaagga caatgggatg gccaaggatg agcacgattt gactaaggca ctccacactc   11460
tagctgtctc aggagtcccc aaagatctca agaaagtca cagggggggg ccagtcttaa   11520
aaacctactc ccgaagccca gtccacacaa gtaccaggaa cgtgagagca gcaaaagggt   11580
ttataggggtt ccctcaagta attcggcagg accaagacac tgatcatccg gagaatatgg   11640
aagcttacga gacagtcagt gcatttatca cgactgatct caagaagtac tgccttaatt   11700
ggagatatga gaccatcagc ttgtttgcac agaggctaaa tgagatttac ggattgccct   11760
catttttcca gtggctgcat aagaggcttg agacctctgt cctgtatgta agtgaccctc   11820
attgccccc cgaccttgac gcccatatcc cgttatataa agtccccaat gatcaaatct   11880
tcattaagta ccctatggga ggtatagaag ggtattgtca gaagctgtgg accatcagca   11940
```

```
ccattccctc tctatacctg gctgcttatg agagcggagt aaggattgct tcgttagtgc   12000
aaggggacaa tcagaccata gccgtaacaa aaagggtacc cagcacatgg ccctacaacc   12060
ttaagaaacg ggaagctgct agagtaacta gagattactt tgtaattctt aggcaaaggc   12120
tacatgatat tggccatcac ctcaaggcaa atgagacaat tgtttcatca cattttttg    12180 tctattcaaa aggaatatat tatgatgggc tacttgtgtc ccaatcactc aagagcatcg   12240
caagatgtgt attctggtca gagactatag ttgatgaaac aagggcagca tgcagtaata   12300
ttgctacaac aatggctaaa agcatcgaga gaggttatga ccgttacctt gcatattccc   12360
tgaacgtcct aaaagtgata cagcaaattc tgatctctct tggcttcaca atcaattcaa   12420
ccatgacccg ggatgtagtc ataccctcc tcacaaacaa cgacctctta ataaggatgg    12480
cactgttgcc cgctcctatt gggggatga attatctgaa tatgagcagg ctgtttgtca    12540
gaaacatcgg tgatccagta acatcatcaa ttgctgatct caagagaatg attctcgcct   12600
cactaatgcc tgaagagacc ctccatcaag taatgacaca acaaccgggg gactcttcat   12660
tcctagactg ggctagcgac ccttactcag caaatcttgt atgtgtccag agcatcacta   12720
gactcctcaa gaacataact gcaaggtttg tcctgatcca tagtccaaac ccaatgttaa   12780
aaggattatt ccatgatgac agtaaagaag aggacgaggg actggcggca ttcctcatgg   12840
acaggcatat tatagtacct agggcagctc atgaaatcct ggatcatagt gtcacagggg   12900
caagagagtc tattgcaggc atgctggata ccacaaaagg cttgattcga ccagcatga    12960 ggaaggggg gttaacctct cgagtgataa ccagattgtc caattatgac tatgaacaat    13020
tcagagcagg gatggtgcta ttgacaggaa gaaagagaaa tgtcctcatt gacaaagagt   13080
catgttcagt gcagctggcg agagctcaa gaagccatat gtgggcgagg ctagctcgag    13140
gacggcctat ttacggcctt gaggtccctg atgtactaga atctatgcga ggccacctta   13200
ttcggcgtca tgagacatgt gtcatctgcg agtgtggatc agtcaactac ggatggtttt   13260
ttgtcccctc gggttgccaa ctggatgata ttgacaagga acatcatcc ttgagagtcc    13320 catatattgg ttctaccact gatgagagaa cagacatgaa gcttgccttc gtaagagccc   13380
caagtcgatc cttgcgatct gctgttagaa tagcaacagt gtactcatgg gcttacggtg   13440
atgatgatag ctcttggaac gaagcctggt tgttggctag gcaaagggcc aatgtgagcc   13500
tggaggagct aagggtgatc actcccatct caacttcgac taatttagcg cataggttga   13560
gggatcgtag cactcaagtg aaatactcag gtacatccct tgtccgagtg gcgaggtata   13620
ccacaatctc caacgacaat ctctcatttg tcatatcaga taagaaggtt gatactaact   13680
ttatatacca acaaggaatg cttctagggt tgggtgtttt agaaacattg tttcgactcg   13740
agaaagatac cggatcatct aacacggtat tacatcttca cgtcgaaaca gattgttgcg   13800
tgatcccgat gatagatcat cccaggatac ccagctcccg caagctagag ctgagggcag   13860
agctatgtac caacccattg atatatgata atgcaccttt aattgacaga gatgcaacaa   13920
ggctatacac ccagagccat aggaggcacc ttgtggaatt tgttacatgg tccacacccc   13980
aactatatca cattttagct aagtccacag cactatctat gattgacctg gtaacaaaat   14040
ttgagaagga ccatatgaat gaaatttcag ctctcatagg ggatgacgat atcaatagtt   14100
tcataactga gtttctgctc atagagccaa gattattcac tatctacttg ggccagtgtg   14160
cggccatcaa ttgggcattt gatgtacatt atcatagacc atcagggaaa tatcagatgg   14220
gtgagctgtt gtcatcgttc ctttctagaa tgagcaaagg agtgtttaag gtgcttgtca   14280
```

```
atgctctaag ccacccaaag atctacaaga aattctggca ttgtggtatt atagagccta    14340
tccatggtcc ttcacttgat gctcaaaact tgcacacaac tgtgtgcaac atggtttaca    14400
catgctatat gacctacctc gacctgttgt tgaatgaaga gttagaagag ttcacatttc    14460
tcttgtgtga aagcgacgag gatgtagtac cggacagatt cgacaacatc caggcaaaac    14520
acttatgtgt tctggcagat tgtactgtc aaccagggac ctgcccacca attcgaggtc     14580
taagaccggt agagaaatgt gcagttctaa ccgaccatat caaggcagag gctatgttat    14640
ctccagcagg atcttcgtgg aacataaatc caattattgt agaccattac tcatgctctc    14700
tgacttatct ccggcgagga tcgatcaaac agataagatt gagagttgat ccaggattca    14760
ttttcgacgc cctcgctgag gtaaatgtca gtcagccaaa gatcggcagc aacaacatct    14820
caaatatgag catcaaggct ttcagacccc cacacgatga tgttgcaaaa ttgctcaaag    14880
atatcaacac aagcaagcac aatcttccca tttcagggg caatctcgcc aattatgaaa     14940
tccatgcttt ccgcagaatc gggttgaact catctgcttg ctacaaagct gttgagatat    15000
caacattaat taggagatgc cttgagccag gggaggacgg cttgttcttg ggtgagggat    15060
cgggttctat gttgatcact tataaagaga tacttaaact aaacaagtgc ttctataata    15120 gtgggtttc cgccaattct agatctggtc aaagggaatt agcaccctat ccctccgaag     15180
ttggccttgt cgaacacaga atgggagtag gtaatattgt caaagtgctc tttaacggga    15240
ggcccgaagt cacgtgggta ggcagtgtag attgcttcaa tttcatagtt agtaatatcc    15300
ctacctctag tgtggggttt atccattcag atatagagac cttgcctgac aaagatacta    15360
tagagaagct agaggaattg gcagccatct tatcgatggc tctgctcctg ggcaaaatag    15420
gatcaatact ggtgattaag cttatgcctt tcagcgggga ttttgttcag ggatttataa    15480
gttatgtagg gtctcattat agagaagtga accttgtata ccctagatac agcaacttca    15540
tctctactga atcttatttg gttatgacag atctcaaggc taaccggcta atgaatcctg    15600
aaaagattaa gcagcagata attgaatcat ctgtgaggac ttcacctgga cttataggtc    15660
acatcctatc cattaagcaa ctaagctgca tacaagcaat tgtgggagac gcagttagta    15720
gaggtgatat caatcctact ctgaaaaaac ttacacctat agagcaggtg ctgatcaatt    15780
gcgggttggc aattaacgga cctaagctgt gcaaagaatt gatccaccat gatgttgcct    15840
cagggcaaga tggattgctt aattctatac tcatcctcta cagggagttg caagattca     15900 aagacaacca aagaagtcaa caagggatgt tccacgctta ccccgtattg gtaagtagca    15960
ggcaacgaga acttatatct aggatcaccc gcaaattctg ggggcacatt cttctttact    16020
ccgggaacaa aaagttgata aataagttta tccagaatct caagtccggc tatctgatac    16080
tagacttaca ccagaatatc ttcgttaaga atctatccaa gtcagagaaa cagattatta    16140
tgacgggggg tttgaaacgt gagtgggttt ttaaggtaac agtcaaggag accaaagaat    16200
ggtataagtt agtcggatac agtgccctga ttaaggacta attggttgaa ctccggaacc    16260
ctaatcctgc cctaggtggt taggcattat ttgcaatata ttaaagaaaa cttgaaaat    16320 acgaagtttc tattcccagc tttgtctggt ggccggcatg gtcccagcct cctcgctggc    16380
gccggctggg caacattccg aggggaccgt ccctcggta atggcgaatg ggacgcggcc    16440
gatccggctg ctaacaaagc ccgaaaggaa gctgagttgg ctgctgccac cgctgagcaa    16500
taactagcat aaccccttgg ggcctctaaa cgggtcttga ggggtttttt gctgaaagga    16560
ggaactatat ccggatgcgg ccgcgggccc tatggtaccc agcttttgtt ccctttagtg    16620
agggttaatt ccgagcttgg cgtaatcatg gtcatagctg tttcctgtgt gaaattgtta    16680
```

```
tccgctcaca attccacaca acataggagc cggaagcata aagtgtaaag cctggggtgc    16740
ctaatgagtg aggtaactca cattaattgc gttgcgctca ctgcccgctt tccagtcggg    16800
aaacctgtcg tgccagctgc attaatgaat cggccaacgc gcggggagag gcggtttgcg    16860
tattgggcgc tcttccgctt cctcgctcac tgactcgctg cgctcggtcg ttcggctgcg    16920
gcgagcggta tcagctcact caaaggcggt aatacggtta ccacagaat cagggataa     16980 cgcaggaaag aacatgtgag caaaaggcca gcaaaaggcc aggaaccgta aaaaggccgc    17040
gttgctggcg tttttccata ggctccgccc ccctgacgag catcacaaaa atcgacgctc    17100
aagtcagagg tggcgaaacc cgacaggact ataaagatac caggcgttcc ccctggaag    17160 ctccctcgtg cgctctcctg ttccgaccct gccgcttacc ggatacctgt ccgcctttct    17220
cccttcggga agcgtggcgc tttctcaatg ctcacgctgt aggtatctca gttcggtgta    17280
ggtcgttcgc tccaagctgg gctgtgtgca cgaaccccc gttcagcccg accgctgcgc     17340
cttatccggt aactatcgtc ttgagtccaa cccggtaaga cacgacttat cgccactggc    17400
agcagccact ggtaacagga ttagcagagc gaggtatgta ggcggtgcta cagagttctt    17460
gaagtggtgg cctaactacg gctacactag aaggacagta tttggtatct gcgctctgct    17520
gaagccagtt accttcggaa aaagagttgg tagctcttga tccggcaaac aaaccaccgc    17580
tggtagcggt ggtttttttg tttgcaagca gcagattacg cgcagaaaaa aaggatctca    17640
agaagatcct ttgatctttt ctacggggtc tgacgctcag tggaacgaaa actcacgtta    17700
agggattttg gtcatgagat tatcaaaaag gatcttcacc tagatccttt taaattaaaa    17760
atgaagtttt aaatcaatct aaagtatata tgagtaaact tggtctgaca gttaccaatg    17820
cttaatcagt gaggcaccta tctcagcgat ctgtctattt cgttcatcca tagttgcctg    17880
actgcccgtc gtgtagataa ctacgatacg ggagggctta ccatctggcc ccagtgctgc    17940
aatgataccg cgagacccac gctcaccggc tccagattta tcagcaataa accagccagc    18000
cggaagggcc gagcgcagaa gtggtcctgc aactttatcc gcctccatcc agtctattaa    18060
ttgttgccgg gaagctagag taagtagttc gccagttaat agtttgcgca acgttgttgc    18120
cattgctaca ggcatcgtgg tgtcacgctc gtcgtttggt atggcttcat tcagctccgg    18180
ttcccaacga tcaaggcgag ttacatgatc ccccatgttg tgaaaaaaag cggttagctc    18240
cttcggtcct ccgatcgttg tcagaagtaa gttggccgca gtgttatcac tcatgcttat    18300
ggcagcactg cataattctc ttactgtcat gccatccgta agatgctttt ctgtgactgg    18360
tgagtactca accaagtcat tctgagaata gtgtatgcgg cgaccgagtt gctcttgccc    18420
ggcgtcaata cgggataata ccgcgccaca tagcagaact ttaaaagtgc tcatcattgg    18480
aaaacgttct cggggcgaa aactctcaag gatcttaccg ctgttgagat ccagttcgat    18540
gtaacccact cgtgcaccca actgatcttc agcatctttt actttcacca gcgtttctgg    18600
gtgagcaaaa acaggaaggc aaaatgccgc aaaaaaggga ataagggcga cacggaaatg    18660
ttgaatactc atactcttcc tttttcaata ttattgaagc atttatcagg gttattgtct    18720
catgagcgga tacatatttg aatgtattta gaaaaataaa caaatagggg ttccgcgcac    18780
atttccccga aaagtgccac ctgaaattgt aaacgttaat attttgttaa aattcgcgtt    18840
aaatttttgt taaatcagct catttttaa ccaataggcc gaaatcggca aaatccctta    18900
taaatcaaaa gaatagaccg agatagggt gagtgttgtt ccagtttgga acaagagtcc    18960
actattaaag aacgtggact ccaacgtcaa agggcgaaaa accgtctatc agggcgatgg    19020
```

-continued

```
cccactacgt gaaccatcac cctaatcaag ttttttgggg tcgaggtgcc gtaaagcact  19080
aaatcggaac cctaaaggga gcccccgatt tagagcttga cggggaaagc cggcgaacgt  19140
ggcgagaaag gaagggaaga aagcgaaagg agcgggcgct agggcgctgg caagtgtagc  19200
ggtcacgctg cgcgtaacca ccacacccgc cgcgcttaat gcgccgctac agggcgcgtc  19260
ccattcgcca ttcaggctgc gcaactgttg ggaagggcga tcggtgcggg cctcttcgct  19320
attacgccag ccaccgcggt ggcggccgct aatacgactc actatagggc caactttgtt  19380
tggtctgatg agtccgtgag gacgaaaccc ggagtcccgg gtc                   19423
```

<210> SEQ ID NO 3
<211> LENGTH: 19375
<212> TYPE: DNA
<213> ORGANISM: Artificial Sequence
<220> FEATURE:
<223> OTHER INFORMATION: pTM-MV-ATU2-M2raw
<220> FEATURE:
<221> NAME/KEY: misc_RNA
<222> LOCATION: (1)..(16302)
<223> OTHER INFORMATION: MV-ATU2-M2raw_antigenome
<220> FEATURE:
<221> NAME/KEY: misc_feature
<222> LOCATION: (3378)..(3785)
<223> OTHER INFORMATION: ATU2
<220> FEATURE:
<221> NAME/KEY: misc_feature
<222> LOCATION: (3444)..(3449)
<223> OTHER INFORMATION: BsiWI restriction site
<220> FEATURE:
<221> NAME/KEY: misc_feature
<222> LOCATION: (3453)..(3749)
<223> OTHER INFORMATION: ORF for M2 consensus protein : M2raw
<220> FEATURE:
<221> NAME/KEY: misc_feature
<222> LOCATION: (3750)..(3755)
<223> OTHER INFORMATION: BssHII restriction site
<220> FEATURE:
<221> NAME/KEY: misc_feature
<222> LOCATION: (16303)..(19375)
<223> OTHER INFORMATION: plasmid_backone

<400> SEQUENCE: 3

```
accaaacaaa gttgggtaag gatagttcaa tcaatgatca tcttctagtg cacttaggat     60
tcaagatcct attatcaggg acaagagcag gattagggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtgaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
```

```
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg aacttgaaa    1140 actccatggg aggtttgaac tttgccgat cttactttga tccagcatat tttagattag    1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc aacggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag ggccagaaca acatccgcct accatccatc attgttataa   1740
aaaacttagg aaccaggtcc acacagccgc cagcccatca accatccact cccacgattg   1800
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat cccccaaga    2100 aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aaggggagaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctgaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga acccgttgc cagccgacaa    3060 ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
```

```
cagatgctga tgaagataat aatgaagtag ctacagctca acttacctgc caaccccatg    3360
ccagtcgacc caactagcct accctccatc attgttataa aaaacttagg aaccaggtcc    3420
acacagccgc cagcccatca acgcgtacga ccatgagcct tctaaccgag gtcgaaacgc    3480
ctatcagaaa cgaatggggg tgcagatgca acgattcaag tgaccctctt gttgttgccg    3540
cgagtatcat tgggatcttg cacttgatat tgtggattct tgatcgtctt ttcttcaaat    3600
gcatctatcg actcttcaaa cacggtctga aagaggacc ttctacggaa ggagtacctg     3660
agtctatgag ggaagaatat cgaaaggaac agcagaatgc tgtggatgct gacgacagtc    3720
attttgtcag catagagctg gagtgataag cgcgcagcgc ttagacgtct cgcgatcgat    3780
actagtacaa cctaaatcca ttataaaaaa cttaggagca aagtgattgc ctcccaaggt    3840
ccacaatgac agagacctac gacttcgaca agtcggcatg ggacatcaaa gggtcgatcg    3900
ctccgataca acccaccacc tacagtgatg gcaggctggt gccccaggtc agagtcatag    3960
atcctggtct aggcgacagg aaggatgaat gctttatgta catgtttctg ctggggttg     4020 ttgaggacag cgattcccta gggcctccaa tcgggcgagc atttgggttc ctgcccttag    4080
gtgttggcag atccacagca aagcccgaaa aactcctcaa agaggccact gagcttgaca    4140
tagttgttag acgtacagca gggctcaatg aaaaactggt gttctacaac aacaccccac    4200
taactctcct cacaccttgg agaaaggtcc taacaacagg gagtgtcttc aacgcaaacc    4260
aagtgtgcaa tgcggttaat ctgataccgc tcgataccc gcagaggttc cgtgttgttt      4320
atatgagcat cacccgtctt tcggataacg ggtattacac cgttcctaga agaatgctgg    4380
aattcagatc ggtcaatgca gtggccttca acctgctggt gacccttagg attgacaagg    4440
cgataggccc tgggaagatc atcgacaata cagagcaact tcctgaggca acatttatgg    4500
tccacatcgg gaacttcagg agaaagaaga gtgaagtcta ctctgccgat tattgcaaaa    4560
tgaaaatcga aagatgggc ctggtttttg cacttggtgg gataggggc accagtcttc      4620 acattagaag cacaggcaaa atgagcaaga ctctccatgc acaactcggg ttcaagaaga    4680
ccttatgtta cccgctgatg gatatcaatg aagaccttaa tcgattactc tggaggagca    4740
gatgcaagat agtaagaatc caggcagttt tgcagccatc agttcctcaa gaattccgca    4800
tttacgacga cgtgatcata aatgatgacc aaggactatt caaagttctg tagaccgtag    4860
tgcccagcaa tgcccgaaaa cgaccccct cacaatgaca gccagaaggc ccggacaaaa     4920
aagccccctc cgaaagactc cacggaccaa gcgagaggcc agccagcagc cgacggcaag    4980
cgcgaacacc aggcggcccc agcacagaac agccctgaca caaggccacc accagccacc    5040
ccaatctgca tcctcctcgt gggaccccg aggaccaacc cccaaggctg ccccgatcc       5100 aaaccaccaa ccgcatcccc accacccccg ggaaagaaac cccagcaat tggaaggccc     5160 ctccccctct tcctcaacac aagaactcca caaccgaacc gcacaagcga ccgaggtgac    5220
ccaaccgcag gcatccgact ccctagacag atcctctctc cccggcaaac taaacaaaac    5280
ttagggccaa ggaacataca cacccaacag aaccagacc ccggcccacg cgccgcgcc      5340 cccaaccccc gacaaccaga gggagccccc aaccaatccc gccggctccc ccggtgccca    5400
caggcaggga caccaacccc cgaacagacc cagcacccaa ccatcgacaa tccaagacgg    5460 gggggcccc ccaaaaaaag gccccagggg ccgacagcc agcaccgcga ggaagcccac       5520
ccaccccaca cacgaccacg gcaaccaaac cagaacccag accaccctgg gccaccagct    5580
cccagactcg gccatcaccc cgcagaaagg aaaggccaca acccgcgcac cccagccccg    5640
atccggcggg gagccaccca acccgaacca gcacccaaga gcgatccccg aaggaccccc    5700
```

```
gaaccgcaaa ggacatcagt atcccacagc ctctccaagt cccccggtct cctcctcttc    5760
tcgaagggac caaaagatca atccaccaca cccgacgaca ctcaactccc cacccctaaa    5820
ggagacaccg ggaatcccag aatcaagact catccaatgt ccatcatggg tctcaaggtg    5880
aacgtctctg ccatattcat ggcagtactg ttaactctcc aaacacccac cggtcaaatc    5940
cattggggca atctctctaa gatagggtg gtaggaatag gaagtgcaag ctacaaagtt    6000
atgactcgtt ccagccatca atcattagtc ataaaattaa tgcccaatat aactctcctc    6060
aataactgca cgagggtaga gattgcagaa tacaggagac tactgagaac agttttggaa    6120
ccaattagag atgcacttaa tgcaatgacc cagaatataa daccggttca gagtgtagct    6180
tcaagtagga gacacaagag atttgcggga gtagtcctgg caggtgcggc cctaggcgtt    6240
gccacagctg ctcagataac agccggcatt gcacttcacc agtccatgct gaactctcaa    6300
gccatcgaca atctgagagc gagcctggaa actactaatc aggcaattga gacaatcaga    6360
caagcagggc aggagatgat attggctgtt cagggtgtcc aagactacat caataatgag    6420
ctgataccgt ctatgaacca actatcttgt gatttaatcg gccagaagct cgggctcaaa    6480
ttgctcagat actatacaga aatcctgtca ttatttggcc ccagtttacg ggaccccata    6540
tctgcggaga tatctatcca ggctttgagc tatgcgcttg gaggagacat caataaggtg    6600
ttagaaaagc tcggatacag tggaggtgat ttactgggca tcttagagag cggaggaata    6660
aaggcccgga taactcacgt cgacacagag tcctacttca ttgtcctcag tatagcctat    6720
ccgacgctgt ccgagattaa gggggtgatt gtccaccggc tagaggggt ctcgtacaac    6780 ataggctctc aagagtggta taccactgtg cccaagtatg ttgcaaccca agggtacctt    6840
atctcgaatt ttgatgagtc atcgtgtact ttcatgccag agggactgt gtgcagccaa    6900 aatgccttgt acccgatgag tcctctgctc caagaatgcc tccgggggta caccaagtcc    6960
tgtgctcgta cactcgtatc cgggtctttt gggaaccggt tcatttatc acaagggaac    7020 ctaatagcca attgtgcatc aatcctttgc aagtgttaca caacaggaac gatcattaat    7080
caagaccctg acaagatcct aacatacatt gctgccgatc actgcccggt agtcgaggtg    7140
aacggcgtga ccatccaagt cgggagcagg aggtatccag acgctgtgta cttgcacaga    7200
attgacctcg gtcctcccat atcattggag aggttggacg tagggacaaa tctggggaat    7260
gcaattgcta agttggagga tgccaaggaa ttgttggagt catcggacca gatattgagg    7320
agtatgaaag gtttatcgag cactagcata gtctacatcc tgattgcagt gtgtcttgga    7380
gggttgatag ggatccccgc tttaatatgt tgctgcaggg ggcgttgtaa caaaaaggga    7440
gaacaagttg gtatgtcaag accaggccta aagcctgatc ttacgggaac atcaaaatcc    7500
tatgtaaggt cgctctgatc ctctacaact cttgaaacac aaatgtccca caagtctcct    7560
cttcgtcatc aagcaaccac cgcacccagc atcaagccca cctgaaatta ctccggctt    7620 ccctctggcc gaacaatatc ggtagttaat caaaacttag ggtgcaagat catccacaat    7680
gtcaccacaa cgagaccgga taaatgcctt ctacaaagat aaccccatc ccaagggaag    7740 taggatagtc attaacagag aacatcttat gattgataga ccttatgttt tgctggctgt    7800
tctgtttgtc atgtttctga gcttgatcgg gttgctagcc attgcaggca ttagacttca    7860
tcgggcagcc atctacaccg cagagatcca taaaagcctc agcaccaatc tagatgtaac    7920
taactcaatc gagcatcagg tcaaggacgt gctgacacca ctcttcaaaa tcatcggtga    7980
tgaagtgggc ctgaggacac ctcagagatt cactgaccta gtgaaattaa tctctgacaa    8040
```

```
gattaaattc cttaatccgg atagggagta cgacttcaga gatctcactt ggtgtatcaa    8100
cccgccagag agaatcaaat tggattatga tcaatactgt gcagatgtgg ctgctgaaga    8160
gctcatgaat gcattggtga actcaactct actggagacc agaacaacca atcagttcct    8220
agctgtctca aagggaaact gctcagggcc cactacaatc agaggtcaat tctcaaacat    8280
gtcgctgtcc ctgttagact tgtatttagg tcgaggttac aatgtgtcat ctatagtcac    8340
tatgacatcc cagggaatgt atgggggaac ttacctagtg aaaagccta atctgagcag    8400 caaaaggtca gagttgtcac aactgagcat gtaccgagtg tttgaagtag gtgttatcag    8460
aaatccgggt ttgggggctc cggtgttcca tatgacaaac tatcttgagc aaccagtcag    8520
taatgatctc agcaactgta tggtggcttt ggggggagctc aaactcgcag ccctttgtca    8580
cggggaagat tctatcacaa ttccctatca gggatcaggg aaaggtgtca gcttccagct    8640
cgtcaagcta ggtgtctgga aatccccaac cgacatgcaa tcctgggtcc ccttatcaac    8700
ggatgatcca gtgatagaca ggcttttacct ctcatctcac agaggtgtta tcgctgacaa    8760
tcaagcaaaa tgggctgtcc cgacaacacg aacagatgac aagttgcgaa tggagacatg    8820
cttccaacag gcgtgtaagg gtaaaatcca agcactctgc gagaatcccg agtgggcacc    8880
attgaaggat aacaggattc cttcatacgg ggtcttgtct gttgatctga gtctgacagt    8940
tgagcttaaa atcaaaattg cttcgggatt cgggccattg atcacacacg gttcagggat    9000
ggacctatac aaatccaacc acaacaatgt gtattggctg actatcccgc caatgaagaa    9060
cctagcctta ggtgtaatca acacattgga gtggataccg agattcaagg ttagtcccta    9120
cctcttcact gtcccaatta aggaagcagg cgaagactgc catgccccaa catacctacc    9180 tgccggaggtg gatggtgatg tcaaactcag ttccaatctg gtgattctac ctggtcaaga    9240
tctccaatat gttttggcaa cctacgatac ttccaggggtt gaacatgctg tggttattaa    9300
cgtttacagc ccaagccgct cattttctta cttttatcct tttaggtttgc ctataaaggg    9360 ggtccccatc gaattacaag tggaatgctt cacatgggac caaaaactct ggtgccgtca    9420
cttctgtgtg cttgcggact cagaatctgg tggacatatc actcactctg ggatggtggg    9480
catgggagtc agctgcacag tcacccggga agatggaacc aatcgcagat agggctgcta    9540
gtgaaccaat cacatgatgt cacccagaca tcaggcatac ccactagtgt gaaatagaca    9600
tcagaattaa gaaaaacgta gggtccaagt ggttccccgt tatggactcg ctatctgtca    9660
accagatctt ataccctgaa gttcacctag atagcccgat agttaccaat aagatagtag    9720
ccatcctgga gtatgctcga gtccctcacg cttacagcct ggaggaccct acactgtgtc    9780
agaacatcaa gcaccgccta aaaaacggat tttccaacca aatgattata acaatgtgg    9840 aagttgggaa tgtcatcaag tccaagctta ggagttatcc ggcccactct catattccat    9900
atccaaattg taatcaggat ttatttaaca tagaagacaa agagtcaacg aggaagatcc    9960
gtgaactcct caaaaggggg aattcgctgt actccaaagt cagtgataag gttttccaat   10020
gcttaaggga cactaactca cggcttggcc taggctccga attgagggag acatcaaggg   10080
agaaagttat taacttggga gtttacatgc acagctccca gtggtttgag ccctttctgt   10140
tttggtttac agtcaagact gagatgaggt cagtgattaa atcacaaacc catacttgcc   10200
ataggaggag acacacacct gtattcttca ctggtagttc agttgagttg ctaatctctc   10260
gtgaccttgt tgctataatc agtaaagagt ctcaacatgt atattacctg acatttgaac   10320
tggttttgat gtattgtgat gtcatagagg ggaggttaat gacagagacc gctatgacta   10380
ttgatgctag gtatacagag cttctaggaa gagtcagata catgtggaaa ctgatagatg   10440
```

```
gtttcttccc tgcactcggg aatccaactt atcaaattgt agccatgctg gagcctcttt    10500
cacttgctta cctgcagctg agggatataa cagtagaact cagaggtgct ttccttaacc    10560
actgctttac tgaaatacat gatgttcttg accaaaacgg ttttctgat gaaggtactt     10620 atcatgagtt aactgaagct ctagattaca ttttcataac tgatgacata catctgacag    10680
gggagatttt ctcattttc agaagtttcg gccaccccag acttgaagca gtaacggctg     10740
ctgaaaatgt taggaaatac atgaatcagc ctaaagtcat tgtgtatgag actctgatga    10800
aaggtcatgc catattttgt ggaatcataa tcaacggcta tcgtgacagg cacggaggca    10860
gttggccacc gctgaccctc ccctgcatg ctgcagacac aatccggaat gctcaagctt     10920
caggtgaagg gttaacacat gagcagtgcg ttgataactg gaaatctttt gctggagtga    10980
aatttggctg ctttatgcct cttagcctgg atagtgatct gacaatgtac ctaaaggaca    11040
aggcacttgc tgctctccaa agggaatggg attcagttta cccgaaagag ttcctgcgtt    11100
acgaccctcc caagggaacc gggtcacgga ggcttgtaga tgttttcctt aatgattcga    11160
gctttgaccc atatgatgtg ataatgtatg ttgtaagtgg agcttacctc catgaccctg    11220
agttcaacct gtcttacagc ctgaaagaaa aggagatcaa ggaaacaggt agactttttg    11280
ctaaaatgac ttacaaaatg agggcatgcc aagtgattgc tgaaaatcta atctcaaacg    11340
ggattggcaa atatttaag gacaatggga tggccaagga tgagcacgat ttgactaagg     11400
cactccacac tctagctgtc tcaggagtcc ccaaagatct caaagaaagt cacagggggg    11460
ggccagtctt aaaaacctac tcccgaagcc cagtccacac aagtaccagg aacgtgagag    11520
cagcaaaagg gtttataggg ttccctcaag taattcggca ggaccaagac actgatcatc    11580
cggagaatat ggaagcttac gagacagtca gtgcatttat cacgactgat ctcaagaagt    11640
actgccttaa ttggagatat gagaccatca gcttgtttgc acagaggcta aatgagattt    11700
acggattgcc ctcattttc cagtggctgc ataagaggct tgagacctct gtcctgtatg    11760
taagtgaccc tcattgcccc cccgaccttg acgcccatat cccgttatat aaagtcccca    11820
atgatcaaat cttcattaag taccctatgg gaggtataga agggtattgt cagaagctgt    11880
ggaccatcag caccattccc tatctatacc tggctgctta tgagagcgga gtaaggattg    11940
cttcgttagt gcaaggggac aatcagacca tagccgtaac aaaaagggta cccagcacat    12000 ggcccctacaa ccttaagaaa cgggaagctg ctagagtaac tagagattac tttgtaattc    12060
ttaggcaaag gctacatgat attggccatc acctcaaggc aaatgagaca attgtttcat    12120
cacatttttt tgtctattca aaaggaatat attatgatgg gctacttgtg tcccaatcac    12180
tcaagagcat cgcaagatgt gtattctggt cagagactat agttgatgaa caagggcag     12240 catgcagtaa tattgctaca acaatggcta aaagcatcga gagaggttat gaccgttacc    12300
ttgcatattc cctgaacgtc ctaaaagtga tacagcaaat tctgatctct cttggcttca    12360
caatcaattc aaccatgacc cgggatgtag tcataccct cctcacaaac aacgacctct     12420
taataaggat ggcactgttg cccgctccta ttgggggat gaattatctg aatatgagca     12480
ggctgtttgt cagaaacatc ggtgatccag taacatcatc aattgctgat ctcaagagaa    12540
tgattctcgc ctcactaatg cctgaagaga ccctccatca agtaatgaca caacaaccgg    12600
gggactcttc attcctagac tgggctagcg acccttactc agcaaatctt gtatgtgtcc    12660
agagcatcac tagactcctc aagaacataa ctgcaaggtt tgtcctgatc catagtccaa    12720
acccaatgtt aaaaggatta ttccatgatg acagtaaaga gaggacgag ggactggcgg     12780
```

-continued

```
cattcctcat ggacaggcat attatagtac ctagggcagc tcatgaaatc ctggatcata    12840
gtgtcacagg ggcaagagag tctattgcag gcatgctgga taccacaaaa ggcttgattc    12900
gagccagcat gaggaagggg gggttaacct ctcgagtgat aaccagattg tccaattatg    12960
actatgaaca attcagagca gggatggtgc tattgacagg aagaaagaga aatgtcctca    13020
ttgacaaaga gtcatgttca gtgcagctgg cgagagctct aagaagccat atgtgggcga    13080
ggctagctcg aggacggcct atttacggcc ttgaggtccc tgatgtacta aatctatgc     13140 gaggccacct tattcggcgt catgagacat gtgtcatctg cgagtgtgga tcagtcaact    13200
acggatggtt ttttgtcccc tcgggttgcc aactggatga tattgacaag gaaacatcat    13260
ccttgagagt cccatatatt ggttctacca ctgatgagag aacagacatg aagcttgcct    13320
tcgtaagagc cccaagtcga tccttgcgat ctgctgttag aatagcaaca gtgtactcat    13380
gggcttacgg tgatgatgat agctcttgga acgaagcctg gttgttggct aggcaaaggg    13440
ccaatgtgag cctggaggag ctaagggtga tcactcccat ctcaacttcg actaatttag    13500
cgcataggtt gagggatcgt agcactcaag tgaaatactc aggtacatcc cttgtccgag    13560
tggcgaggta taccacaatc tccaacgaca atctctcatt tgtcatatca gataagaagg    13620
ttgatactaa ctttatatac caacaaggaa tgcttctagg gttgggtgtt ttagaaacat    13680
tgtttcgact cgagaaagat accggatcat ctaacacggt attacatctt cacgtcgaaa    13740
cagattgttg cgtgatcccg atgatagatc atcccaggat acccagctcc cgcaagctag    13800
agctgagggc agagctatgt accaacccat tgatatatga taatgcaccc ttaattgaca    13860
gagatgcaac aaggctatac acccagagcc ataggaggca ccttgtggaa tttgttacat    13920
ggtccacacc ccaactatat cacattttag ctaagtccac agcactatct atgattgacc    13980
tggtaacaaa atttgagaag gaccatatga atgaaatttc agctctcata ggggatgacg    14040
atatcaatag tttcataact gagtttctgc tcatagagcc aagattattc actatctact    14100
tgggccagtg tgcggccatc aattgggcat ttgatgtaca ttatcataga ccatcaggga    14160
aatatcagat gggtgagctg ttgtcatcgt tcctttctag aatgagcaaa ggagtgttta    14220
aggtgcttgt caatgctcta agccacccaa agatctacaa gaaattctgg cattgtggta    14280
ttatagagcc tatccatggt ccttcacttg atgctcaaaa cttgcacaca actgtgtgca    14340
acatggttta cacatgctat atgacctacc tcgacctgtt gttgaatgaa gagttagaag    14400
agttcacatt tctcttgtgt gaaagcgacg aggatgtagt accggacaga ttcgacaaca    14460
tccaggcaaa acacttatgt gttctggcag atttgtactg tcaaccaggg acctgcccac    14520
caattcgagg tctaagaccg gtagagaaat gtgcagttct aaccgaccat atcaaggcag    14580
aggctatgtt atctccagca ggatcttcgt ggaacataaa tccaattatt gtagaccatt    14640
actcatgctc tctgacttat ctccggcgag gatcgatcaa acagataaga ttgagagttg    14700
atccaggatt cattttcgac gccctcgctg aggtaaatgt cagtcagcca aagatcggca    14760
gcaacaacat ctcaaatatg agcatcaagg ctttcagacc cccacacgat gatgttgcaa    14820
aattgctcaa agatatcaac acaagcaagc acaatcttcc catttcaggg ggcaatctcg    14880
ccaattatga aatccatgct ttccgcagaa tcgggttgaa ctcatctgct tgctacaaag    14940
ctgttgagat atcaacatta attaggagat gccttgagcc aggggaggac ggcttgttct    15000
tgggtgaggg atcgggttct atgttgatca cttataaaga gatacttaaa ctaaacaagt    15060
gcttctataa tagtgggggtt tccgccaatt ctagatctgg tcaaagggaa ttagcaccct    15120
atccctccga agttggcctt gtcgaacaca gaatgggagt aggtaatatt gtcaaagtgc    15180
```

```
tctttaacgg gaggcccgaa gtcacgtggg taggcagtgt agattgcttc aatttcatag   15240
ttagtaatat ccctacctct agtgtggggt ttatccattc agatatagag accttgcctg   15300
acaaagatac tatagagaag ctagaggaat tggcagccat cttatcgatg gctctgctcc   15360
tgggcaaaat aggatcaata ctggtgatta agcttatgcc tttcagcggg gattttgttc   15420
agggatttat aagttatgta gggtctcatt atagagaagt gaaccttgta taccctagat   15480
acagcaactt catctctact gaatcttatt tggttatgac agatctcaag gctaaccggc   15540
taatgaatcc tgaaaagatt aagcagcaga taattgaatc atctgtgagg acttcacctg   15600
gacttatagg tcacatccta tccattaagc aactaagctg catacaagca attgtgggag   15660
acgcagttag tagaggtgat atcaatccta ctctgaaaaa acttacacct atagagcagg   15720
tgctgatcaa ttgcgggttg gcaattaacg gacctaagct gtgcaaagaa ttgatccacc   15780
atgatgttgc ctcagggcaa gatggattgc ttaattctat actcatcctc tacagggagt   15840
tggcaagatt caaagacaac caaagaagtc aacaagggag gttccacgct taccccgtat   15900
tggtaagtag caggcaacga gaacttatat ctaggatcac ccgcaaattc tggggggcaca  15960 ttcttcttta ctccgggaac aaaaagttga taaataagtt tatccagaat ctcaagtccg   16020
gctatctgat actagactta caccagaata tcttcgttaa gaatctatcc aagtcagaga   16080
aacagattat tatgacgggg ggtttgaaac gtgagtgggg ttttaaggta acagtcaagg   16140
agaccaaaga atggtataag ttagtcggat acagtgccct gattaaggac taattggttg   16200
aactccggaa ccctaatcct gccctaggtg gttaggcatt atttgcaata tattaaagaa   16260
aactttgaaa atacgaagtt tctattccca gctttgtctg gtggccggca tggtcccagc   16320
ctcctcgctg gcgccggctg ggcaacattc cgagggacc gtcccctcgg taatggcgaa    16380
tgggacgcgg ccgatccggc tgctaacaaa gcccgaaagg aagctgagtt ggctgctgcc   16440
accgctgagc aataactagc ataaccccctt ggggcctcta acgggtctt gagggggtttt  16500 ttgctgaaag gaggaactat atccggatgc ggccgcgggc cctatggtac ccagcttttg   16560 tccccttag tgagggttaa ttccgagctt ggcgtaatca tggtcatagc tgtttcctgt    16620
gtgaaattgt tatccgctca caattccaca caacatagga gccggaagca taagtgtaa   16680 agcctgggt gcctaatgag tgaggtaact cacattaatt gcgttgcgct cactgcccgc    16740
tttccagtcg ggaaacctgt cgtgccagct gcattaatga atcggccaac gcgcgggag    16800 aggcggtttg cgtattgggc gctcttccgc ttcctcgctc actgactcgc tgcgctcggt   16860
cgttcggctg cggcgagcgg tatcagctca ctcaaaggcg gtaatacggt tatccacaga   16920
atcaggggat aacgcaggaa agaacatgtg agcaaaaggc cagcaaaagg ccaggaaccg   16980
taaaaaggcc gcgttgctgg cgttttccca taggctcggc ccccctgacg agcatcacaa   17040
aaatcgacgc tcaagtcaga ggtggcgaaa cccgacagga ctataaagat accaggcgtt   17100 ccccctgga agctccctcg tgcgctctcc tgttccgacc ctgccgctta ccggatacct    17160
gtccgccttt ctcccttcgg gaagcgtggc gctttctcaa tgctcacgct gtaggtatct   17220
cagttcggtg taggtcgttc gctccaagct gggctgtgtg cacgaacccc ccgttcagcc   17280
cgaccgctgc gccttatccg gtaactatcg tcttgagtcc aacccggtaa gacacgactt   17340
atcgccactg gcagcagcca ctggtaacag gattagcaga gcgaggtatg taggcggtgc   17400
tacagagttc ttgaagtggt ggcctaacta cggctacact agaaggacag tatttggtat   17460
ctgcgctctg ctgaagccag ttaccttcgg aaaaagagtt ggtagctctt gatccggcaa   17520
```

```
acaaaccacc gctggtagcg gtggtttttt tgtttgcaag cagcagatta cgcgcagaaa    17580
aaaaggatct caagaagatc ctttgatctt ttctacgggg tctgacgctc agtggaacga    17640
aaactcacgt taagggattt tggtcatgag attatcaaaa aggatcttca cctagatcct    17700
tttaaattaa aaatgaagtt ttaaatcaat ctaaagtata tatgagtaaa cttggtctga    17760
cagttaccaa tgcttaatca gtgaggcacc tatctcagcg atctgtctat ttcgttcatc    17820
catagttgcc tgactgcccg tcgtgtagat aactacgata cgggagggct taccatctgg    17880
ccccagtgct gcaatgatac cgcgagaccc acgctcaccg gctccagatt tatcagcaat    17940
aaaccagcca gccggaaggg ccgagcgcag aagtggtcct gcaactttat ccgcctccat    18000
ccagtctatt aattgttgcc gggaagctag agtaagtagt tcgccagtta atagtttgcg    18060
caacgttgtt gccattgcta caggcatcgt ggtgtcacgc tcgtcgtttg gtatggcttc    18120
attcagctcc ggttcccaac gatcaaggcg agttacatga tcccccatgt tgtgaaaaaa    18180
agcggttagc tccttcggtc ctccgatcgt tgtcagaagt aagttggccg cagtgttatc    18240
actcatgctt atggcagcac tgcataattc tcttactgtc atgccatccg taagatgctt    18300
ttctgtgact ggtgagtact caaccaagtc attctgagaa tagtgtatgc ggcgaccgag    18360
ttgctcttgc ccggcgtcaa tacgggataa taccgcgcca catagcagaa ctttaaaagt    18420
gctcatcatt ggaaaacgtt cttcggggcg aaaactctca aggatcttac cgctgttgag    18480
atccagttcg atgtaaccca ctcgtgcacc caactgatct tcagcatctt ttactttcac    18540
cagcgtttct gggtgagcaa aacaggaag gcaaaatgcc gcaaaaaagg gaataagggc    18600
gacacggaaa tgttgaatac tcatactctt cctttttcaa tattattgaa gcatttatca    18660
gggttattgt ctcatgagcg gatacatatt tgaatgtatt tagaaaaata aacaaatagg    18720
ggttccgcgc acatttcccc gaaaagtgcc acctgaaatt gtaaacgtta atattttgtt    18780
aaaattcgcg ttaaattttt gttaaatcag ctcattttt aaccaatagg ccgaaatcgg    18840
caaaatccct tataaatcaa agaatagac cgagataggg ttgagtgttg ttccagtttg    18900
gaacaagagt ccactattaa agaacgtgga ctccaacgtc aaagggcgaa aaaccgtcta    18960
tcagggcgat ggcccactac gtgaaccatc accctaatca agttttttgg ggtcgaggtg    19020
ccgtaaagca ctaaatcgga accctaaagg agcccccga tttagagctt gacggggaaa    19080
gccggcgaac gtggcgagaa aggaagggaa gaaagcgaaa ggagcgggcg ctagggcgct    19140
ggcaagtgta gcggtcacgc tgcgcgtaac caccacaccc gccgcgctta atgcgccgct    19200
acagggcgcg tcccattcgc cattcaggct gcgcaactgt tgggaagggc gatcggtgcg    19260
ggcctcttcg ctattacgcc agccaccgcg gtggcggccg ctaatacgac tcactatagg    19320
gccaactttg tttggtctga tgagtccgtg aggacgaaac ccggagtccc gggtc         19375
```

<210> SEQ ID NO 4
<211> LENGTH: 19375
<212> TYPE: DNA
<213> ORGANISM: Artificial Sequence
<220> FEATURE:
<223> OTHER INFORMATION: pTM-MV-ATU2-M2opt
<220> FEATURE:
<221> NAME/KEY: misc_RNA
<222> LOCATION: (1)..(16302)
<223> OTHER INFORMATION: MV-ATU2-M2opt_antigenome
<220> FEATURE:
<221> NAME/KEY: misc_feature
<222> LOCATION: (3378)..(3785)
<223> OTHER INFORMATION: ATU2
<220> FEATURE:
<221> NAME/KEY: misc_feature

```
<222> LOCATION: (3453)..(3749)
<223> OTHER INFORMATION: ORF for M2 consensus protein : M2opt
<220> FEATURE:
<221> NAME/KEY: misc_feature
<222> LOCATION: (16303)..(19375)
<223> OTHER INFORMATION: plasmid_backone

<400> SEQUENCE: 4
```

| | | | | | |
|---|---|---|---|---|---|
| accaaacaaa | gttgggtaag | gatagttcaa | tcaatgatca | tcttctagtg | cacttaggat | 60 |
| tcaagatcct | attatcaggg | acaagagcag | gattagggat | atccgagatg | gccacacttt | 120 |
| taaggagctt | agcattgttc | aaaagaaaca | aggacaaacc | acccattaca | tcaggatccg | 180 |
| gtggagccat | cagaggaatc | aaacacatta | ttatagtacc | aatccctgga | gattcctcaa | 240 |
| ttaccactcg | atccagactt | ctggaccggt | tggtgaggtt | aattggaaac | ccggatgtga | 300 |
| gcgggcccaa | actaacaggg | gcactaatag | gtatattatc | cttatttgtg | gagtctccag | 360 |
| gtcaattgat | tcagaggatc | accgatgacc | ctgacgttag | cataaggctg | ttagaggttg | 420 |
| tccagagtga | ccagtcacaa | tctggcctta | ccttcgcatc | aagaggtacc | aacatggagg | 480 |
| atgaggcgga | ccaatacttt | tcacatgatg | atccaattag | tagtgatcaa | tccaggttcg | 540 |
| gatggttcgg | gaacaaggaa | atctcagata | ttgaagtgca | agaccctgag | ggattcaaca | 600 |
| tgattctggg | taccatccta | gcccaaattt | gggtcttgct | cgcaaaggcg | gttacggccc | 660 |
| cagacacggc | agctgattcg | gagctaagaa | ggtggataaa | gtacacccaa | caagaagggg | 720 |
| tagttggtga | atttagattg | gagagaaaat | ggttggatgt | ggtgaggaac | aggattgccg | 780 |
| aggacctctc | cttacgccga | ttcatggtcg | ctctaatcct | ggatatcaag | agaacacccg | 840 |
| gaaacaaacc | caggattgct | gaaatgatat | gtgacattga | tacatatatc | gtagaggcag | 900 |
| gattagccag | ttttatcctg | actattaagt | tgggataga | aactatgtat | cctgctcttg | 960 |
| gactgcatga | atttgctggt | gagttatcca | cacttgagtc | cttgatgaac | ctttaccagc | 1020 |
| aaatggggga | aactgcaccc | tacatggtaa | tcctggagaa | ctcaattcag | aacaagttca | 1080 |
| gtgcaggatc | ataccctctg | ctctggagct | atgccatggg | agtaggagtg | aacttgaaa | 1140 |
| actccatggg | aggtttgaac | tttgccgat | cttactttga | tccagcatat | tttagattag | 1200 |
| ggcaagagat | ggtaaggagg | tcagctggaa | aggtcagttc | cacattggca | tctgaactcg | 1260 |
| gtatcactgc | cgaggatgca | aggcttgttt | cagagattgc | aatgcatact | actgaggaca | 1320 |
| agatcagtag | agcggttgga | cccagacaag | cccaagtatc | atttctacac | ggtgatcaaa | 1380 |
| gtgagaatga | gctaccgaga | ttgggggca | aggaagatag | gagggtcaaa | cagagtcgag | 1440 |
| gagaagccag | ggagagctac | agagaaaccg | ggcccagcag | agcaagtgat | gcgagagctg | 1500 |
| cccatcttcc | aaccggcaca | cccctagaca | ttgacactgc | aacggagtcc | agccaagatc | 1560 |
| cgcaggacag | tcgaaggtca | gctgacgccc | tgcttaggct | gcaagccatg | caggaatct | 1620 |
| cggaagaaca | aggctcagac | acggacaccc | ctatagtgta | caatgacaga | aatcttctag | 1680 |
| actaggtgcg | agaggccgag | ggccagaaca | acatccgcct | accatccatc | attgttataa | 1740 |
| aaaacttagg | aaccaggtcc | acacagccgc | cagcccatca | accatccact | cccacgattg | 1800 |
| gagccaatgg | cagaagagca | ggcacgccat | gtcaaaaacg | gactggaatg | catccgggct | 1860 |
| ctcaaggccg | agcccatcgg | ctcactggcc | atcgaggaag | ctatgcagc | atggtcagaa | 1920 |
| atatcagaca | acccaggaca | ggagcgagcc | acctgcaggg | aagagaaggc | aggcagttcg | 1980 |
| ggtctcagca | aaccatgcct | ctcagcaatt | ggatcaactg | aaggcggtgc | acctcgcatc | 2040 |
| cgcggtcagg | gacctggaga | gagcgatgac | gacgctgaaa | ctttgggaat | ccccccaaga | 2100 |

```
aatctccagg catcaagcac tgggttacag tgttattacg tttatgatca cagcggtgaa    2160
gcggttaagg gaatccaaga tgctgactct atcatggttc aatcaggcct tgatggtgat    2220
agcaccctct caggaggaga caatgaatct gaaaacagcg atgtggatat tggcgaacct    2280
gataccgagg gatatgctat cactgaccgg ggatctgctc ccatctctat ggggttcagg    2340
gcttctgatg ttgaaactgc agaaggaggg gagatccacg agctcctgag actccaatcc    2400
agaggcaaca actttccgaa gcttgggaaa actctcaatg ttcctccgcc cccgaccccc    2460
ggtagggcca gcacttccgg acacccatt aaaaagggca cagacgcgag attagcctca     2520
tttggaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aaggggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg acacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga acccgttgc cagccgacaa     3060 ctccaaggaa tgacaaatgg acggaccagt tccagaggac agctgctgaa ggaatttcag    3120
ctaaagccga tcgggaaaaa gatgagctca gccgtcgggt tgttcctga caccggccct     3180 gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagcct accctccatc attgttataa aaaacttagg aaccaggtcc    3420
acacagccgc cagcccatca acgcgtacga ccatgagcct gctgaccgag gtggaaaccc    3480
ccatcagaaa cgagtggggc tgccggtgca acgacagcag cgatcctctg gtggtggccg    3540
ccagcatcat cggcatcctg cacctgatcc tgtggattct ggaccggctg ttcttcaagt    3600
gcatctacag actgttcaag cacggcctga agagaggccc cagcacagaa ggcgtgcccg    3660
agagcatgcg ggaagagtac cggaaagaac agcagaacgc cgtggacgcc gacgacagcc    3720
acttcgtgtc catcgagctg gaatgataag cgcgcagcgc ttagacgtct cgcgatcgat    3780
actagtacaa cctaaatcca ttataaaaaa cttaggagca aagtgattgc ctcccaaggt    3840
ccacaatgac agagacctac gacttcgaca gtcggcatg ggacatcaaa gggtcgatcg     3900
ctccgataca accccaccac tacagtgatg gcaggctggt gccccaggtc agagtcatag    3960
atcctggtct aggcgacagg aaggatgaat gctttatgta catgtttctg ctgggggttg    4020
ttgaggacag cgattcccta gggcctccaa tcgggcgagc atttgggttc ctgcccttag    4080
gtgttggcag atccacagca aagcccgaaa aactcctcaa agaggccact gagcttgaca    4140
tagttgttag acgtacagca gggctcaatg aaaaactggt gttctacaac aacaccccac    4200
taactctcct cacaccttgg agaaaggtcc taacaacagg gagtgtcttc aacgcaaacc    4260
aagtgtgcaa tgcggttaat ctgatacccgc tcgataccc gcagaggttc cgtgttgttt     4320
atatgagcat caccccgtctt tcggataacg ggtattacac cgttcctaga agaatgctgg    4380
aattcagatc ggtcaatgca gtggccttca acctgctggt gacccttagg attgacaagg    4440
cgataggccc tggaagatc atcgacaata cagagcaact tcctgaggca acatttatgg      4500
```

```
tccacatcgg gaacttcagg agaaagaaga gtgaagtcta ctctgccgat tattgcaaaa   4560
tgaaaatcga aaagatgggc ctggttttg  cacttggtgg gatagggggc accagtcttc   4620
acattagaag cacaggcaaa atgagcaaga ctctccatgc acaactcggg ttcaagaaga   4680
ccttatgtta cccgctgatg gatatcaatg aagaccttaa tcgattactc tggaggagca   4740
gatgcaagat agtaagaatc caggcagttt tgcagccatc agttcctcaa gaattccgca   4800
tttacgacga cgtgatcata aatgatgacc aaggactatt caaagttctg tagaccgtag   4860
tgcccagcaa tgcccgaaaa cgaccccct  cacaatgaca gccagaaggc ccggacaaaa   4920
aagccccctc cgaaagactc cacggaccaa gcgagaggcc agccagcagc cgacggcaag   4980
cgcgaacacc aggcggcccc agcacagaac agccctgaca caaggccacc accagccacc   5040
ccaatctgca tcctcctcgt gggacccccg aggaccaacc cccaaggctg ccccgatcc    5100 aaaccaccaa ccgcatcccc accacccccg ggaaagaaac cccagcaat  tggaaggccc    5160 ctcccctct  tcctcaacac aagaactcca caaccgaacc gcacaagcga ccgaggtgac    5220
ccaaccgcag gcatccgact ccctagacag atcctctctc cccggcaaac taaacaaaac   5280
ttagggccaa ggaacataca cacccaacag aacccagacc ccggcccacg gcgccgcgcc   5340
cccaaccccc gacaaccaga gggagccccc aaccaatccc gccggctccc ccggtgccca   5400
caggcaggga caccaacccc cgaacagacc cagcacccaa ccatcgacaa tccaagacgg   5460
gggggccccc ccaaaaaaag gccccaggg  gccgacagcc agcaccgcga ggaagcccac   5520
ccaccccaca cacgaccacg gcaaccaaac cagaacccag accaccctgg gccaccagct   5580
cccagactcg gccatcaccc cgcagaaagg aaaggccaca accgcgcac  cccagccccg    5640 atccggcggg gagccaccca acccgaacca gcacccaaga gcgatccccg aaggacccc    5700 gaaccgcaaa ggacatcagt atcccacagc ctctccaagt ccccggtct  cctcctcttc    5760 tcgaagggac caaagatca  atccaccaca cccgacgaca ctcaactccc cacccctaaa   5820
ggagacaccg ggaatcccag aatcaagact catccaatgt ccatcatggg tctcaaggtg   5880
aacgtctctg ccatattcat ggcagtactg ttaactctcc aaacacccac cggtcaaatc   5940 cattgggca  atctctctaa gataggggtg gtaggaatag gaagtgcaag ctacaaagtt   6000
atgactcgtt ccagccatca atcattagtc ataaaattaa tgcccaatat aactctcctc   6060
aataactgca cgagggtaga gattgcagaa tacaggagac tactgagaac agttttggaa   6120
ccaattagag atgcacttaa tgcaatgacc cagaatataa gaccggttca gagtgtagct   6180
tcaagtagga gacacaagag atttgcggga gtagtcctgg caggtgcggc cctaggcgtt   6240
gccacagctg ctcagataac agccggcatt gcacttcacc agtccatgct gaactctcaa   6300
gccatcgaca atctgagagc gagcctggaa actactaatc aggcaattga gacaatcaga   6360
caagcagggc aggagatgat attggctgtt caggggtgtcc aagactacat caataatgag   6420
ctgataccgt ctatgaacca actatcttgt gatttaatcg gccagaagct cgggctcaaa   6480
ttgctcagat actatacaga aatcctgtca ttatttggcc ccagtttacg ggaccccata   6540
tctgcggaga tatctatcca ggctttgagc tatgcgcttg gaggagacat caataaggtg   6600
ttagaaaagc tcgatacag  tggaggtgat ttactgggca tcttagagag cggaggaata   6660
aaggcccgga taactcacgt cgacacagag tcctacttca ttgtcctcag tatagcctat   6720
ccgacgctgt ccgagattaa gggggtgatt gtccaccggc tagaggggt  ctcgtacaac   6780 ataggctctc aagagtggta taccactgtg cccaagtatg ttgcaaccca agggtacctt   6840
```

```
atctcgaatt ttgatgagtc atcgtgtact ttcatgccag aggggactgt gtgcagccaa     6900
aatgccttgt acccgatgag tcctctgctc caagaatgcc tccggggta caccaagtcc      6960
tgtgctcgta cactcgtatc cgggtctttt gggaaccggt tcattttatc acaagggaac    7020
ctaatagcca attgtgcatc aatcctttgc aagtgttaca caacaggaac gatcattaat    7080
caagaccctg acaagatcct aacatacatt gctgccgatc actgcccggt agtcgaggtg    7140
aacggcgtga ccatccaagt cgggagcagg aggtatccag acgctgtgta cttgcacaga    7200
attgacctcg gtcctcccat atcattggag aggttggacg tagggacaaa tctggggaat    7260
gcaattgcta agttggagga tgccaaggaa ttgttggagt catcggacca gatattgagg    7320
agtatgaaag gtttatcgag cactagcata gtctacatcc tgattgcagt gtgtcttgga    7380
gggttgatag ggatccccgc tttaatatgt tgctgcaggg ggcgttgtaa caaaaaggga    7440
gaacaagttg gtatgtcaag accaggccta agcctgatc ttacgggaac atcaaaatcc      7500
tatgtaaggt cgctctgatc ctctacaact cttgaaacac aaatgtccca caagtctcct    7560
cttcgtcatc aagcaaccac cgcacccagc atcaagccca cctgaaatta tctccggctt    7620
ccctctggcc gaacaatatc ggtagttaat caaaacttag ggtgcaagat catccacaat    7680
gtcaccacaa cgagaccgga taaatgcctt ctacaaagat aaccccatc ccaagggaag      7740
taggatagtc attaacagag aacatcttat gattgataga ccttatgttt tgctggctgt    7800
tctgtttgtc atgtttctga gcttgatcgg gttgctagcc attgcaggca ttagacttca    7860
tcgggcagcc atctacaccg cagagatcca taaaagcctc agcaccaatc tagatgtaac    7920
taactcaatc gagcatcagg tcaaggacgt gctgacacca ctcttcaaaa tcatcggtga    7980
tgaagtgggc ctgaggacac ctcagagatt cactgaccta gtgaaattaa tctctgacaa    8040
gattaaattc cttaatccgg ataggagta cgacttcaga gatctcactt ggtgtatcaa      8100
cccgccagag agaatcaaat tggattatga tcaatactgt gcagatgtgg ctgctgaaga    8160
gctcatgaat gcattggtga actcaactct actggagacc agaacaacca atcagttcct    8220
agctgtctca aagggaaact gctcagggcc cactacaatc agaggtcaat tctcaaacat    8280
gtcgctgtcc ctgttagact tgtatttagg tcgaggttac aatgtgtcat ctatagtcac    8340
tatgacatcc cagggaatgt atgggggaac ttacctagtg gaaaagccta atctgagcag    8400
caaaaggtca gagttgtcac aactgagcat gtaccgagtg tttgaagtag gtgttatcag    8460
aaatccgggt ttgggggctc cggtgttcca tatgacaaac tatcttgagc aaccagtcag    8520
taatgatctc agcaactgta tggtggcttt ggggagctc aaactcgcag cccttttgtca     8580
cggggaagat tctatcacaa ttccctatca gggatcaggg aaaggtgtca gcttccagct    8640
cgtcaagcta ggtgtctgga atcccccaac cgacatgcaa tcctgggtcc ccttatcaac    8700
ggatgatcca gtgatagaca ggctttacct ctcatctcac agaggtgtta tcgctgacaa    8760
tcaagcaaaa tgggctgtcc cgacaacacg aacagatgac aagttgcgaa tggagacatg    8820
cttccaacag gcgtgtaagg gtaaaatcca agcactctgc gagaatcccg agtgggcacc    8880
attgaaggat aacaggattc cttcatacgg ggtcttgtct gttgatctga gtctgacagt    8940
tgagcttaaa atcaaaattg cttcgggatt cgggccattg atcacacacg gttcagggat    9000
ggacctatac aaatccaacc acaacaatgt gtattggctg actatcccgc caatgaagaa    9060
cctagcctta ggtgtaatca acacattgga gtggataccg agattcaagg ttagtcccta    9120
cctcttcact gtcccaatta aggaagcagg cgaagactgc catgccccaa catacctacc    9180
tgcggaggtg gatggtgatg tcaaactcag ttccaatctg gtgattctac ctggtcaaga    9240
```

```
tctccaatat gttttggcaa cctacgatac ttccagggtt gaacatgctg tggtttatta    9300
cgtttacagc ccaagccgct cattttctta cttttatcct tttaggttgc ctataaaggg    9360
ggtccccatc gaattacaag tggaatgctt cacatgggac caaaaactct ggtgccgtca    9420
cttctgtgtg cttgcggact cagaatctgg tggacatatc actcactctg ggatggtggg    9480
catgggagtc agctgcacag tcacccggga agatggaacc aatcgcagat agggctgcta    9540
gtgaaccaat cacatgatgt cacccagaca tcaggcatac ccactagtgt gaaatagaca    9600
tcagaattaa gaaaaacgta gggtccaagt ggttccccgt tatggactcg ctatctgtca    9660
accagatctt atacccctgaa gttcacctag atagcccgat agttaccaat aagatagtag    9720
ccatcctgga gtatgctcga gtccctcacg cttacagcct ggaggaccct acactgtgtc    9780
agaacatcaa gcaccgccta aaaacggat tttccaacca aatgattata aacaatgtgg    9840
aagttgggaa tgtcatcaag tccaagctta ggagttatcc ggcccactct catattccat    9900
atccaaattg taatcaggat ttatttaaca tagaagacaa agagtcaacg aggaagatcc    9960
gtgaactcct caaaaagggg aattcgctgt actccaaagt cagtgataag gttttccaat   10020
gcttaaggga cactaactca cggcttggcc taggctccga attgagggag gacatcaagg   10080
agaaagttat taacttggga gtttacatgc acagctccca gtggtttgag ccctttctgt   10140
tttggtttac agtcaagact gagatgaggt cagtgattaa atcacaaacc catacttgcc   10200
ataggaggag acacacacct gtattcttca ctggtagttc agttgagttg ctaatctctc   10260
gtgaccttgt tgctataatc agtaaagagt ctcaacatgt atattacctg acatttgaac   10320
tggttttgat gtattgtgat gtcatagagg ggaggttaat gacagagacc gctatgacta   10380
ttgatgctag gtacagagag cttctaggaa gagtcagata catgtggaaa ctgatagatg   10440
gtttcttccc tgcactcggg aatccaactt atcaaattgt agccatgctg gagcctcttt   10500
cacttgctta cctgcagctg agggatataa cagtagaact cagaggtgct ttccttaacc   10560
actgctttac tgaaatacat gatgttcttg accaaaacgg gttttctgat gaaggtactt   10620
atcatgagtt aactgaagct ctagattaca ttttcataac tgatgacata catctgacag   10680
gggagatttt ctcatttttc agaagtttcg gccaccccag acttgaagca gtaacggctg   10740
ctgaaaatgt taggaaatac atgaatcagc ctaaagtcat tgtgtatgag actctgatga   10800
aaggtcatgc catattttgt ggaatcataa tcaacggcta tcgtgacagg cacggaggca   10860
gttggccacc gctgaccctc cccctgcatg ctgcagacac aatccggaat gctcaagctt   10920
caggtgaagg gttaacacat gagcagtgcg ttgataactg gaaatctttt gctggagtga   10980
aatttggctg ctttatgcct cttagcctgg atagtgatct gacaatgtac ctaaaggaca   11040
aggcacttgc tgctctccaa agggaatggg attcagttta cccgaaagag ttcctgcgtt   11100
acgaccctcc caagggaacc gggtcacgga ggcttgtaga tgttttcctt aatgattcga   11160
gctttgaccc atatgatgtg ataatgtatg ttgtaagtgg agcttacctc catgaccctg   11220
agttcaacct gtcttacagc ctgaaagaaa aggagatcaa ggaaacaggt agacttttg    11280
ctaaaatgac ttacaaaatg agggcatgcc aagtgattgc tgaaaatcta atctcaaacg   11340
ggattggcaa atattttaag gacaatggga tggccaagga tgagcacgat ttgactaagg   11400
cactccacac tctagctgtc tcaggagtcc ccaaagatct caaagaaagt cacaggggg    11460
ggccagtctt aaaaacctac tcccgaagcc cagtccacac aagtaccagg aacgtgagag   11520
cagcaaaagg gtttataggg ttccctcaag taattcggca ggaccaagac actgatcatc   11580
```

```
cggagaatat ggaagcttac gagacagtca gtgcatttat cacgactgat ctcaagaagt    11640
actgccttaa ttggagatat gagaccatca gcttgtttgc acagaggcta aatgagattt    11700
acggattgcc ctcatttttc cagtggctgc ataagaggct tgagacctct gtcctgtatg    11760
taagtgaccc tcattgcccc cccgaccttg acgcccatat cccgttatat aaagtcccca    11820
atgatcaaat cttcattaag taccctatgg gaggtataga agggtattgt cagaagctgt    11880
ggaccatcag caccattccc tatctatacc tggctgctta tgagagcgga gtaaggattg    11940
cttcgttagt gcaaggggac aatcagacca tagccgtaac aaaaagggta cccagcacat    12000
ggccctacaa ccttaagaaa cgggaagctg ctagagtaac tagagattac tttgtaattc    12060
ttaggcaaag gctacatgat attggccatc acctcaaggc aaatgagaca attgtttcat    12120
cacatttttt tgtctattca aaaggaatat attatgatgg gctacttgtg tcccaatcac    12180
tcaagagcat cgcaagatgt gtattctggt cagagactat agttgatgaa acaagggcag    12240
catgcagtaa tattgctaca acaatggcta aaagcatcga gagaggttat gaccgttacc    12300
ttgcatattc cctgaacgtc ctaaaagtga tacagcaaat tctgatctct cttggcttca    12360
caatcaattc aaccatgacc cgggatgtag tcataccect cctcacaaac aacgacctct    12420
taataaggat ggcactgttg cccgctccta ttgggggat gaattatctg aatatgagca    12480
ggctgtttgt cagaaacatc ggtgatccag taacatcatc aattgctgat ctcaagagaa    12540
tgattctcgc ctcactaatg cctgaagaga ccctccatca gtaatgacaa caacaaccgg    12600
gggactcttc attcctagac tgggctagcg acccttactc agcaaatctt gtatgtgtcc    12660
agagcatcac tagactcctc aagaacataa ctgcaaggtt tgtcctgatc catagtccaa    12720
acccaatgtt aaaaggatta ttccatgatg acagtaaaga agaggacgag gactggcgg    12780 cattcctcat ggacaggcat attatagtac ctagggcagc tcatgaaatc ctggatcata    12840
gtgtcacagg ggcaagagag tctattgcag gcatgctgga taccacaaaa ggcttgattc    12900
gagccagcat gaggaagggg gggttaacct ctcgagtgat aaccagattg tccaattatg    12960
actatgaaca attcagagca gggatggtgc tattgacagg aagaaagaga aatgtcctca    13020
ttgacaaaga gtcatgttca gtgcagctgg cgagagctct aagaagccat atgtgggcga    13080
ggctagctcg aggacggcct atttacggcc ttgaggtccc tgatgtacta gaatctatgc    13140
gaggccacct tattcggcgt catgagacat gtgtcatctg cgagtgtgga tcagtcaact    13200
acggatggtt ttttgtcccc tcgggttgcc aactggatga tattgacaag gaaacatcat    13260
ccttgagagt cccatatatt ggttctacca ctgatgagag aacagacatg aagcttgcct    13320
tcgtaagagc cccaagtcga tccttgcgat ctgctgttag aatagcaaca gtgtactcat    13380
gggcttacgg tgatgatgat agctcttgga acgaagcctg gttgttggct aggcaaaggg    13440
ccaatgtgag cctggaggag ctaagggtga tcactcccat ctcaacttcg actaatttag    13500
cgcataggtt gagggatcgt agcactcaag tgaaatactc aggtacatcc cttgtccgag    13560
tggcgaggta taccacaatc tccaacgaca atctctcatt tgtcatatca gataagaagg    13620
ttgatactaa cttttatatac caacaaggaa tgcttctagg gttgggtgtt ttagaaacat    13680
tgtttcgact cgagaaagat accggatcat ctaaacggt attacatctt cacgtcgaaa    13740
cagattgttg cgtgatcccg atgatagatc atcccaggat acccagctcc cgcaagctag    13800
agctgagggc agagctatgt accaacccat tgatatatga taatgcacct ttaattgaca    13860
gagatgcaac aaggctatac acccagagcc ataggaggca ccttgtggaa tttgttacat    13920
ggtccacacc ccaactatat cacatttttag ctaagtccac agcactatct atgattgacc    13980
```

```
tggtaacaaa atttgagaag gaccatatga atgaaatttc agctctcata ggggatgacg   14040
atatcaatag tttcataact gagtttctgc tcatagagcc aagattattc actatctact   14100
tgggccagtg tgcggccatc aattgggcat ttgatgtaca ttatcataga ccatcaggga   14160
aatatcagat gggtgagctg ttgtcatcgt tcctttctag aatgagcaaa ggagtgttta   14220
aggtgcttgt caatgctcta agccacccaa agatctacaa gaaattctgg cattgtggta   14280
ttatagagcc tatccatggt ccttcacttg atgctcaaaa cttgcacaca actgtgtgca   14340
acatggttta cacatgctat atgacctacc tcgacctgtt gttgaatgaa gagttagaag   14400
agttcacatt tctcttgtgt gaaagcgacg aggatgtagt accggacaga ttcgacaaca   14460
tccaggcaaa acacttatgt gttctggcag atttgtactg tcaaccaggg acctgcccac   14520
caattcgagg tctaagaccg gtagagaaat gtgcagttct aaccgaccat atcaaggcag   14580
aggctatgtt atctccagca ggatcttcgt ggaacataaa tccaattatt gtagaccatt   14640
actcatgctc tctgacttat ctccggcgag gatcgatcaa acagataaga ttgagagttg   14700
atccaggatt cattttcgac gccctcgctg aggtaaatgt cagtcagcca agatcggca   14760 gcaacaacat ctcaaatatg agcatcaagg ctttcagacc cccacacgat gatgttgcaa   14820
aattgctcaa agatatcaac acaagcaagc acaatcttcc catttcaggg ggcaatctcg   14880
ccaattatga aatccatgct ttccgcagaa tcggggttgaa ctcatctgct tgctacaaag   14940
ctgttgagat atcaacatta attaggagat gccttgagcc aggggaggac ggcttgttct   15000
tgggtgaggg atcgggttct atgttgatca cttataaaga gatacttaaa ctaaacaagt   15060
gcttctataa tagtggggtt tccgccaatt ctagatctgg tcaaagggaa ttagcaccct   15120
atccctccga agttggcctt gtcgaacaca gaatgggagt aggtaatatt gtcaaagtgc   15180
tctttaacgg gaggcccgaa gtcacgtggg taggcagtgt agattgcttc aatttcatag   15240
ttagtaatat ccctacctct agtgtggggt ttatccattc agatatagag accttgcctg   15300
acaaagatac tatagagaag ctagaggaat tggcagccat cttatcgatg gctctgctcc   15360
tgggcaaaat aggatcaata ctggtgatta agcttatgcc tttcagcggg gattttgttc   15420
agggatttat aagttatgta gggtctcatt atagagaagt gaaccttgta taccctagat   15480
acagcaactt catctctact gaatcttatt tggttatgac agatctcaag gctaaccggc   15540
taatgaatcc tgaaaagatt aagcagcaga taattgaatc atctgtgagg acttcacctg   15600
gacttatagg tcacatccta tccattaagc aactaagctg catacaagca attgtgggag   15660
acgcagttag tagaggtgat atcaatccta ctctgaaaaa acttacacct atagagcagg   15720
tgctgatcaa ttgcgggttg gcaattaacg gacctaagct gtgcaaagaa ttgatccacc   15780
atgatgttgc ctcagggcaa gatggattgc ttaattctat actcatcctc tacagggagt   15840
tggcaagatt caaagacaac caaagaagtc aacaaggat gttccacgct taccccgtat   15900
tggtaagtag caggcaacga gaacttatat ctaggatcac ccgcaaattc tgggggcaca   15960
ttcttcttta ctccgggaac aaaaagttga taaataagtt tatccagaat ctcaagtccg   16020
gctatctgat actagactta caccagaata tcttcgttaa gaatctatcc aagtcagaga   16080
aacagattat tatgacgggg ggtttgaaac gtgagtgggt ttttaaggta acagtcaagg   16140
agaccaaaga atggtataag ttagtcggat acagtgccct gattaaggac taattggttg   16200
aactccggaa ccctaatcct gccctaggtg gttaggcatt atttgcaata tattaaagaa   16260
aactttgaaa atacgaagtt tctattccca gctttgtctg gtggccggca tggtcccagc   16320
```

```
ctcctcgctg gcgccggctg ggcaacattc cgaggggacc gtcccctcgg taatggcgaa    16380
tgggacgcgg ccgatccggc tgctaacaaa gcccgaaagg aagctgagtt ggctgctgcc    16440
accgctgagc aataactagc ataacccctt ggggcctcta aacgggtctt gagggg tttt   16500 ttgctgaaag gaggaactat atccggatgc ggccgcgggc cctatggtac ccagcttttg    16560 ttcccttag tgagggttaa ttccgagctt ggcgtaatca tggtcatagc tgtttcctgt     16620
gtgaaattgt tatccgctca caattccaca acataggag gccggaagca taaagtgtaa     16680 agcctgggt gcctaatgag tgaggtaact cacattaatt gcgttgcgct cactgcccgc     16740
tttccagtcg ggaaacctgt cgtgccagct gcattaatga atcggccaac gcgcggggag    16800
aggcggtttg cgtattgggc gctcttccgc ttcctcgctc actgactcgc tgcgctcggt    16860
cgttcggctg cggcgagcgg tatcagctca ctcaaaggcg gtaatacggt tatccacaga    16920
atcaggggat aacgcaggaa agaacatgtg agcaaaaggc cagcaaaagg ccaggaaccg    16980
taaaaaggcc gcgttgctgg cgttttttcca taggctcggc cccctgacg agcatcacaa    17040 aaatcgacgc tcaagtcaga ggtggcgaaa cccgacagga ctataaagat accaggcgtt    17100
cccccctgga agctccctcg tgcgctctcc tgttccgacc ctgccgctta ccggatacct    17160
gtccgccttt ctcccttcgg gaagcgtggc gctttctcaa tgctcacgct gtaggtatct    17220
cagttcggtg taggtcgttc gctccaagct gggctgtgtg cacgaacccc cgttcagcc     17280 cgaccgctgc gccttatccg gtaactatcg tcttgagtcc aacccggtaa gacacgactt    17340
atcgccactg gcagcagcca ctggtaacag gattagcaga gcgaggtatg taggcggtgc    17400
tacagagttc ttgaagtggt ggcctaacta cggctacact agaaggacag tatttggtat    17460
ctgcgctctg ctgaagccag ttaccttcgg aaaaagagtt ggtagctctt gatccggcaa    17520
acaaaccacc gctggtagcg gtggtttttt tgtttgcaag cagcagatta cgcgcagaaa    17580
aaaaggatct caagaagatc ctttgatctt ttctacgggg tctgacgctc agtggaacga    17640
aaactcacgt taagggattt tggtcatgag attatcaaaa aggatcttca cctagatcct    17700
tttaaattaa aaatgaagtt ttaaatcaat ctaaagtata tatgagtaaa cttggtctga    17760
cagttaccaa tgcttaatca gtgaggcacc tatctcagcg atctgtctat ttcgttcatc    17820
catagttgcc tgactgcccg tcgtgtagat aactacgata cgggagggct taccatctgg    17880
ccccagtgct gcaatgatac cgcgagaccc acgctcaccg gctccagatt tatcagcaat    17940
aaaccagcca gccggaaggg ccgagcgcag aagtggtcct gcaactttat ccgcctccat    18000
ccagtctatt aattgttgcc gggaagctag agtaagtagt tcgccagtta atagtttgcg    18060
caacgttgtt gccattgcta caggcatcgt ggtgtcacgc tcgtcgtttg gtatggcttc    18120
attcagctcc ggttcccaac gatcaaggcg agttacatga tcccccatgt tgtgaaaaaa    18180
agcggttagc tccttcggtc ctccgatcgt tgtcagaagt aagttggccg cagtgttatc    18240
actcatgctt atggcagcac tgcataattc tcttactgtc atgccatccg taagatgctt    18300
ttctgtgact ggtgagtact caaccaagtc attctgagaa tagtgtatgc ggcgaccgag    18360
ttgctcttgc ccggcgtcaa tacgggataa taccgcgcca catagcagaa ctttaaaagt    18420
gctcatcatt ggaaaacgtt cttcgggggcg aaaactctca aggatcttac cgctgttgag    18480
atccagttcg atgtaaccca ctcgtgcacc caactgatct tcagcatctt ttactttcac    18540
cagcgtttct gggtgagcaa aaacaggaag gcaaaatgcc gcaaaaaagg gaataagggc    18600
gacacggaaa tgttgaatac tcatactctt cctttttcaa tattattgaa gcattttatca   18660 gggttattgt ctcatgagcg gatacatatt tgaatgtatt tagaaaaata acaaataggg    18720
```

```
ggttccgcgc acatttcccc gaaaagtgcc acctgaaatt gtaaacgtta atattttgtt    18780
aaaattcgcg ttaaattttt gttaaatcag ctcattttt  aaccaatagg ccgaaatcgg    18840
caaaatccct tataaatcaa agaatagac  cgagataggg ttgagtgttg ttccagtttg    18900
gaacaagagt ccactattaa agaacgtgga ctccaacgtc aaagggcgaa aaaccgtcta    18960
tcagggcgat ggcccactac gtgaaccatc accctaatca agttttttgg ggtcgaggtg    19020
ccgtaaagca ctaaatcgga accctaaagg gagcccccga tttagagctt gacggggaaa    19080
gccggcgaac gtggcgagaa aggaagggaa gaaagcgaaa ggagcgggcg ctagggcgct    19140
ggcaagtgta gcggtcacgc tgcgcgtaac caccacaccc gccgcgctta atgcgccgct    19200
acagggcgcg tcccattcgc cattcaggct gcgcaactgt tgggaagggc gatcggtgcg    19260
ggcctcttcg ctattacgcc agccaccgcg gtggcggccg ctaatacgac tcactatagg    19320
gccaactttg tttggtctga tgagtccgtg aggacgaaac ccggagtccc gggtc         19375
```

<210> SEQ ID NO 5
<211> LENGTH: 20749
<212> TYPE: DNA
<213> ORGANISM: Artificial Sequence
<220> FEATURE:
<223> OTHER INFORMATION: pTM-MV-ATU3-N-1xM2e
<220> FEATURE:
<221> NAME/KEY: misc_RNA
<222> LOCATION: (1)..(17676)
<223> OTHER INFORMATION: MV-ATU3-N-1xM2e_antigenome
<220> FEATURE:
<221> NAME/KEY: misc_feature
<222> LOCATION: (9176)..(10957)
<223> OTHER INFORMATION: ATU3
<220> FEATURE:
<221> NAME/KEY: misc_feature
<222> LOCATION: (9246)..(9251)
<223> OTHER INFORMATION: BsiWI restriction site
<220> FEATURE:
<221> NAME/KEY: misc_feature
<222> LOCATION: (9255)..(10922)
<223> OTHER INFORMATION: ORF for N-1xM2e fusion protein : N-1xM2e_ORF
<220> FEATURE:
<221> NAME/KEY: misc_feature
<222> LOCATION: (10926)..(10931)
<223> OTHER INFORMATION: BssHII restriction site
<220> FEATURE:
<221> NAME/KEY: misc_feature
<222> LOCATION: (17677)..(20749)
<223> OTHER INFORMATION: plasmid_backbone

<400> SEQUENCE: 5
accaaacaaa gttgggtaag gatagttcaa tcaatgatca tcttctagtg cacttaggat 60
tcaagatcct attatcaggg acaagagcag gattagggat atccgagatg gccacacttt 120
taaggagctt agcattgttc aaaagaaaca aggacaaacc acccattaca tcaggatccg 180
gtggagccat cagaggaatc aaacacatta ttatagtacc aatccctgga gattcctcaa 240
ttaccactcg atccagactt ctggaccggt tggtgaggtt aattggaaac ccggatgtga 300
gcgggcccaa actaacaggg gcactaatag gtatattatc cttatttgtg gagtctccag 360
gtcaattgat tcagaggatc accgatgacc ctgacgttag cataaggctg ttagaggttg 420
tccagagtga ccagtcacaa tctggcctta ccttcgcatc aagaggtacc aacatggagg 480
atgaggcgga ccaatacttt tcacatgatg atccaattag tagtgatcaa tccaggttcg 540
gatggttcgg gaacaaggaa atctcagata ttgaagtgca agaccctgag ggattcaaca 600
tgattctggg taccatccta gcccaaattt gggtcttgct cgcaaaggcg gttacggccc 660

-continued

```
cagacacggc agctgattcg gagctaagaa ggtggataaa gtacacccaa caagaaggg      720 tagttggtga atttagattg gagagaaaat ggttggatgt ggtgaggaac aggattgccg      780
aggacctctc cttacgccga ttcatggtcg ctctaatcct ggatatcaag agaacacccg      840
gaaacaaacc caggattgct gaaatgatat gtgacattga tacatatatc gtagaggcag      900
gattagccag ttttatcctg actattaagt ttgggataga aactatgtat cctgctcttg      960
gactgcatga atttgctggt gagttatcca cacttgagtc cttgatgaac ctttaccagc     1020
aaatggggga aactgcaccc tacatggtaa tcctggagaa ctcaattcag aacaagttca     1080
gtgcaggatc ataccctctg ctctggagct atgccatggg agtaggagtg aacttgaaa      1140 actccatggg aggtttgaac tttggccgat cttactttga tccagcatat tttagattag     1200
ggcaagagat ggtaaggagg tcagctggaa aggtcagttc cacattggca tctgaactcg     1260
gtatcactgc cgaggatgca aggcttgttt cagagattgc aatgcatact actgaggaca     1320
agatcagtag agcggttgga cccagacaag cccaagtatc atttctacac ggtgatcaaa     1380
gtgagaatga gctaccgaga ttgggggca aggaagatag gagggtcaaa cagagtcgag      1440
gagaagccag ggagagctac agagaaaccg ggcccagcag agcaagtgat gcgagagctg     1500
cccatcttcc aaccggcaca cccctagaca ttgacactgc aacggagtcc agccaagatc     1560
cgcaggacag tcgaaggtca gctgacgccc tgcttaggct gcaagccatg gcaggaatct     1620
cggaagaaca aggctcagac acggacaccc ctatagtgta caatgacaga atcttctag     1680 actaggtgcg agaggccgag ggccagaaca acatccgcct accatccatc attgttataa     1740
aaaacttagg aaccaggtcc acacagccgc cagcccatca accatccact cccacgattg     1800
gagccaatgg cagaagagca ggcacgccat gtcaaaaacg gactggaatg catccgggct     1860
ctcaaggccg agcccatcgg ctcactggcc atcgaggaag ctatggcagc atggtcagaa     1920
atatcagaca acccaggaca ggagcgagcc acctgcaggg aagagaaggc aggcagttcg     1980
ggtctcagca aaccatgcct ctcagcaatt ggatcaactg aaggcggtgc acctcgcatc     2040
cgcggtcagg gacctggaga gagcgatgac gacgctgaaa ctttgggaat cccccaaga     2100 aatctccagg catcaagcac tgggttacag tgttattacg tttatgatca cagcggtgaa     2160
gcggttaagg gaatccaaga tgctgactct atcatggttc aatcaggcct tgatggtgat     2220
agcaccctct caggaggaga caatgaatct gaaaacagcg atgtggatat ggcgaacct     2280 gataccgagg gatatgctat cactgaccgg ggatctgctc ccatctctat ggggttcagg     2340
gcttctgatg ttgaaactgc agaaggaggg gagatccacg agctcctgag actccaatcc     2400
agaggcaaca actttccgaa gcttgggaaa actctcaatg ttcctccgcc cccggacccc     2460
ggtagggcca gcacttccgg gacacccatt aaaaagggca cagacgcgag attagcctca     2520
tttggaacgg agatcgcgtc tttattgaca ggtggtgcaa cccaatgtgc tcgaaagtca     2580
ccctcggaac catcagggcc aggtgcacct gcggggaatg tccccgagtg tgtgagcaat     2640
gccgcactga tacaggagtg gacacccgaa tctggtacca caatctcccc gagatcccag     2700
aataatgaag aaggggagac tattatgat gatgagctgt tctctgatgt ccaagatatt     2760
aaaacagcct tggccaaaat acacgaggat aatcagaaga taatctccaa gctagaatca     2820
ctgctgttat tgaagggaga agttgagtca attaagaagc agatcaacag gcaaaatatc     2880
agcatatcca ccctggaagg acacctctca agcatcatga tcgccattcc tggacttggg     2940
aaggatccca acgaccccac tgcagatgtc gaaatcaatc ccgacttgaa acccatcata     3000
ggcagagatt caggccgagc actggccgaa gttctcaaga aacccgttgc cagccgacaa     3060
```

```
ctccaaggaa tgacaaatgg acggaccagt tccagaggac agctgctgaa ggaatttcag      3120
ctaaagccga tcgggaaaaa gatgagctca gccgtcgggt ttgttcctga caccggccct      3180
gcatcacgca gtgtaatccg ctccattata aaatccagcc ggctagagga ggatcggaag      3240
cgttacctga tgactctcct tgatgatatc aaaggagcca atgatcttgc caagttccac      3300
cagatgctga tgaagataat aatgaagtag ctacagctca acttacctgc caaccccatg      3360
ccagtcgacc caactagtac aacctaaatc cattataaaa aacttaggag caaagtgatt      3420
gcctcccaag gtccacaatg acagagacct acgacttcga caagtcggca tgggacatca      3480
aagggtcgat cgctccgata caacccacca cctacagtga tggcaggctg gtgccccagg      3540
tcagagtcat agatcctggt ctaggcgaca ggaaggatga atgctttatg tacatgtttc      3600
tgctgggggt tgttgaggac agcgattccc tagggcctcc aatcgggcga gcatttgggt      3660
tcctgccctt aggtgttggc agatccacag caaagcccga aaaactcctc aaagaggcca      3720
ctgagcttga catagttgtt agacgtacag cagggctcaa tgaaaaactg gtgttctaca      3780
acaacacccc actaactctc ctcacacctt ggagaaaggt cctaacaaca gggagtgtct      3840
tcaacgcaaa ccaagtgtgc aatgcggtta atctgatacc gctcgatacc ccgcagaggt      3900
tccgtgttgt ttatatgagc atcacccgtc tttcggataa cgggtattac accgttccta      3960
gaagaatgct ggaattcaga tcggtcaatg cagtggcctt caacctgctg gtgacccta      4020 ggattgacaa ggcgataggc cctgggaaga tcatcgacaa tacagagcaa cttcctgagg      4080
caacatttat ggtccacatc gggaacttca ggagaaagaa gagtgaagtc tactctgccg      4140
attattgcaa aatgaaaatc gaaaagatgg gcctggtttt tgcacttggt gggatagggg      4200
gcaccagtct tcacattaga agcacaggca aaatgagcaa gactctccat gcacaactcg      4260
ggttcaagaa gaccttatgt tacccgctga tggatatcaa tgaagacctt aatcgattac      4320
tctggaggag cagatgcaag atagtaagaa tccaggcagt tttgcagcca tcagttcctc      4380
aagaattccg catttacgac gacgtgatca taaatgatga ccaaggacta ttcaaagttc      4440
tgtagaccgt agtgcccagc aatgcccgaa acgaccccc ctcacaatga cagccagaag      4500 gccccggacaa aaaagccccc tccgaaagac tccacgacc aagcgagagg ccagccagca      4560
gccgacggca agcgcgaaca ccaggcggcc ccagcacaga acagccctga cacaaggcca      4620
ccaccagcca ccccaatctg catcctcctc gtgggacccc cgaggaccaa ccccaaggc      4680 tgcccccgat ccaaaccacc aaccgcatcc ccaccacccc cgggaaagaa accccccagca      4740 attggaaggc ccctccccct cttcctcaac acaagaactc cacaaccgaa ccgcacaagc      4800
gaccgaggtg acccaaccgc aggcatccga ctccctagac agatcctctc tccccggcaa      4860
actaaacaaa acttagggcc aaggaacata cacacccaac agaacccaga ccccggccca      4920
cggcgccgcg ccccaacccc ccgacaacca gagggagccc ccaaccaatc ccgccggctc      4980
ccccggtgcc cacaggcagg acaccaaccc cccgaacaga cccagcaccc aaccatcgac      5040
aatccaagac gggggggccc ccccaaaaaa aggccccag gggccgacag ccagcaccgc      5100
gaggaagccc accccacccca cacacgacca cggcaaccaa accagaaccc agaccaccct      5160
gggccaccag ctcccagact cggccatcac ccccagaaa ggaaaggcca caacccgcgc      5220
accccagccc cgatccggcg gggagccacc caacccgaac cagcacccaa gagcgatccc      5280
cgaaggaccc ccgaaccgca aaggacatca gtatcccaca gcctctccaa gtccccggt      5340 ctcctcctct tctcgaaggg accaaaagat caatccacca cacccgacga cactcaactc      5400
```

```
cccaccccta aaggagacac cgggaatccc agaatcaaga ctcatccaat gtccatcatg   5460
ggtctcaagg tgaacgtctc tgccatattc atggcagtac tgttaactct ccaaacaccc   5520
accggtcaaa tccattgggg caatctctct aagatagggg tggtaggaat aggaagtgca   5580
agctacaaag ttatgactcg ttccagccat caatcattag tcataaaatt aatgcccaat   5640
ataactctcc tcaataactg cacgagggta gagattgcag aatacaggag actactgaga   5700
acagttttgg aaccaattag agatgcactt aatgcaatga cccagaatat aagaccggtt   5760
cagagtgtag cttcaagtag gagacacaag agatttgcgg gagtagtcct ggcaggtgcg   5820
gccctaggcg ttgccacagc tgctcagata acagccggca ttgcacttca ccagtccatg   5880
ctgaactctc aagccatcga caatctgaga gcgagcctgg aaactactaa tcaggcaatt   5940
gagacaatca gacaagcagg gcaggagatg atattggctg ttcagggtgt ccaagactac   6000
atcaataatg agctgatacc gtctatgaac caactatctt gtgatttaat cggccagaag   6060
ctcgggctca aattgctcag atactataca gaaatcctgt cattatttgg ccccagttta   6120 cgggaccccca tatctgcgga gatatctatc caggctttga gctatgcgct tggaggagac   6180
atcaataagg tgttagaaaa gctcggatac agtggaggtg atttactggg catcttagag   6240
agcggaggaa taaaggcccg ataactcac gtcgacacag agtcctactt cattgtcctc   6300
agtatagcct atccgacgct gtccgagatt aagggggtga ttgtccaccg gctagagggg   6360
gtctcgtaca acataggctc tcaagagtgg tataccactg tgcccaagta tgttgcaacc   6420
caagggtacc ttatctcgaa ttttgatgag tcatcgtgta ctttcatgcc agaggggact   6480
gtgtgcagcc aaaatgcctt gtacccgatg agtcctctgc tccaagaatg cctccggggg   6540
tacaccaagt cctgtgctcg tacactcgta tccgggtctt ttgggaaccg gttcattta   6600 tcacaaggga acctaatagc caattgtgca tcaatccttt gcaagtgtta cacaacagga   6660
acgatcatta atcaagaccc tgacaagatc ctaacataca ttgctgccga tcactgcccg   6720
gtagtcgagg tgaacggcgt gaccatccaa gtcgggagca ggaggtatcc agacgctgtg   6780
tacttgcaca gaattgacct cggtcctccc atatcattgg agaggttgga cgtagggaca   6840
aatctgggga atgcaattgc taagttggag gatgccaagg aattgttgga gtcatcggac   6900
cagatattga ggagtatgaa aggtttatcg agcactagca tagtctacat cctgattgca   6960
gtgtgtcttg gagggttgat agggatcccc gctttaatat gttgctgcag ggggcgttgt   7020
aacaaaaagg gagaacaagt tggtatgtca agaccaggcc taaagcctga tcttacggga   7080
acatcaaaat cctatgtaag gtcgctctga tcctctacaa ctcttgaaac acaaatgtcc   7140
cacaagtctc ctcttcgtca tcaagcaacc accgcaccca gcatcaagcc cacctgaaat   7200
tatctccggc ttccctctgg ccgaacaata tcggtagtta atcaaaactt agggtgcaag   7260
atcatccaca atgtcaccac aacgagaccg gataaatgcc ttctacaaag ataacccca   7320 tcccaaggga agtaggatag tcattaacag agaacatctt atgattgata gaccttatgt   7380
tttgctggct gttctgtttg tcatgtttct gagcttgatc gggttgctag ccattgcagg   7440
cattagactt catcgggcag ccatctacac cgcagagatc cataaaagcc tcagcaccaa   7500
tctagatgta actaactcaa tcgagcatca ggtcaaggac gtgctgacac cactcttcaa   7560
aatcatcggt gatgaagtgg gcctgaggac acctcagaga ttcactgacc tagtgaaatt   7620
aatctctgac aagattaaat tccttaatcc ggatagggag tacgacttca gagatctcac   7680
ttggtgtatc aacccgccag agagaatcaa attggattat gatcaatact gtgcagatgt   7740
ggctgctgaa gagctcatga atgcattggt gaactcaact ctactggaga ccagaacaac   7800
```

```
caatcagttc ctagctgtct caaagggaaa ctgctcaggg cccactacaa tcagaggtca    7860
attctcaaac atgtcgctgt ccctgttaga cttgtattta ggtcgaggtt acaatgtgtc    7920
atctatagtc actatgacat cccagggaat gtatggggga acttacctag tggaaaagcc    7980
taatctgagc agcaaaaggt cagagttgtc acaactgagc atgtaccgag tgtttgaagt    8040
aggtgttatc agaaatccgg gtttgggggc tccggtgttc catatgacaa actatcttga    8100
gcaaccagtc agtaatgatc tcagcaactg tatggtggct ttgggggagc tcaaactcgc    8160 agcccttttgt cacggggaag attctatcac aattccctat cagggatcag ggaaaggtgt    8220
cagcttccag ctcgtcaagc taggtgtctg gaaatcccca accgacatgc aatcctgggt    8280
ccccttatca acggatgatc cagtgataga caggctttac ctctcatctc acagaggtgt    8340
tatcgctgac aatcaagcaa aatgggctgt cccgacaaca cgaacagatg acaagttgcg    8400
aatggagaca tgcttccaac aggcgtgtaa gggtaaaatc caagcactct gcgagaatcc    8460
cgagtgggca ccattgaagg ataacaggat tccttcatac gggtcttgt ctgttgatct     8520 gagtctgaca gttgagctta aaatcaaaat tgcttcggga ttcgggccat tgatcacaca    8580
cggttcaggg atggacctat acaaatccaa ccacaacaat gtgtattggc tgactatccc    8640
gccaatgaag aacctagcct taggtgtaat caacacattg gagtggatac cgagattcaa    8700
ggttagtccc tacctcttca ctgtcccaat taaggaagca ggcgaagact gccatgcccc    8760
aacataccta cctgcggagg tggatggtga tgtcaaactc agttccaatc tggtgattct    8820
acctggtcaa gatctccaat atgttttggc aacctacgat acttccaggg ttgaacatgc    8880
tgtggtttat tacgtttaca gcccaagccg ctcattttct tactttttatc cttttaggtt    8940 gcctataaag ggggtcccca tcgaattaca agtggaatgc ttcacatggg accaaaaact    9000
ctggtgccgt cacttctgtg tgcttgcgga ctcagaatct ggtggacata tcactcactc    9060
tgggatggtg ggcatgggag tcagctgcac agtcacccgg gaagatggaa ccaatcgcag    9120 ataggggctgc tagtgaacca atcacatgat gtcacccaga catcaggcat acccactagt    9180
ctaccctcca tcattgttat aaaaaactta ggaaccaggt ccacacagcc gccagcccat    9240
caacgcgtac ggagatggcc acactttaa ggagcttagc attgttcaaa agaaacaagg     9300
acaaaccacc cattacatca ggatccggtg gagccatcag aggaatcaaa cacattatta    9360
tagtaccaat ccctggagat tcctcaatta ccactcgatc cagacttctg gaccggttgg    9420
tgaggttaat tggaaacccg gatgtgagcg ggcccaaact aacagggggca ctaataggta   9480 tattatcctt atttgtggag tctccaggtc aattgattca gaggatcacc gatgaccctg    9540
acgttagcat aaggctgtta gaggttgtcc agagtgacca gtcacaatct ggccttacct    9600
tcgcatcaag aggtaccaac atggaggatg aggcggacca atactttttca catgatgatc    9660 caattagtag tgatcaatcc aggttcggat ggttcgggaa caaggaaatc tcagatattg    9720
aagtgcaaga ccctgaggga ttcaacatga ttctgggtac catcctagcc caaatttggg    9780
tcttgctcgc aaaggcggtt acggccccag acacggcagc tgattcggag ctaagaaggt    9840
ggataaagta cacccaacaa agaagggtag ttggtgaatt tagattggag agaaaatggt    9900
tggatgtggt gaggaacagg attgccgagg acctctcctt acgccgattc atggtcgctc    9960
taatcctgga tatcaagaga acacccggaa acaaacccag gattgctgaa atgatatgtg   10020
acattgatac atatatcgta gaggcaggat tagccagttt tatcctgact attaagtttg   10080
ggatagaaac tatgtatcct gctcttggac tgcatgaatt tgctggtgag ttatccacac   10140
```

```
ttgagtcctt gatgaacctt taccagcaaa tgggggaaac tgcaccctac atggtaatcc    10200
tggagaactc aattcagaac aagttcagtg caggatcata ccctctgctc tggagctatg    10260
ccatgggagt aggagtggaa cttgaaaact ccatgggagg tttgaacttt ggccgatctt    10320
actttgatcc agcatatttt agattagggc aagagatggt aaggaggtca gctggaaagg    10380
tcagttccac attggcatct gaactcggta tcactgccga ggatgcaagg cttgtttcag    10440
agattgcaat gcatactact gaggacaaga tcagtagagc ggttggaccc agacaagccc    10500
aagtatcatt tctacacggt gatcaaagtg agaatgagct accgagattg ggggcaagg     10560
aagataggag ggtcaaacag agtcgaggag aagccaggga gagctacaga gaaaccgggc    10620
ccagcagagc aagtgatgcg agagctgccc atcttccaac cggcacaccc ctagacattg    10680
acactgcaac ggagtccagc caagatccgc aggacagtcg aaggtcagct gacgccctgc    10740
ttaggctgca agccatggca ggaatctcgg aagaacaagg ctcagacacg dacacccta     10800
tagtgtacaa tgacagaaat cttctagact ccggaggatc tggcggctct ctgctgaccg    10860
aggtggaaac ccccatcaga aacgagtggg gctgccggtg caacgacagc tctgattgat    10920
aacgagcgcg cagcgcttag acgtctcgcg atcgatgcta gtgtgaaata gacatcagaa    10980
ttaagaaaaa cgtagggtcc aagtggttcc ccgttatgga ctcgctatct gtcaaccaga    11040
tcttataccc tgaagttcac ctagatagcc cgatagttac caataagata gtagccatcc    11100
tggagtatgc tcgagtccct cacgcttaca gcctggagga ccctacactg tgtcagaaca    11160
tcaagcaccg cctaaaaaac ggattttcca accaaatgat tataaacaat gtggaagttg    11220
ggaatgtcat caagtccaag cttaggagtt atccggccca ctctcatatt ccatatccaa    11280
attgtaatca ggatttattt aacatagaag acaaagagtc aacgaggaag atccgtgaac    11340
tcctcaaaaa ggggaattcg ctgtactcca aagtcagtga taaggttttc caatgcttaa    11400
gggacactaa ctcacggctt ggcctaggct ccgaattgag ggaggacatc aaggagaaag    11460
ttattaactt gggagtttac atgcacagct cccagtggtt tgagcccttt ctgttttggt    11520
ttacagtcaa gactgagatg aggtcagtga ttaaatcaca aacccatact tgccataggb    11580
ggagacacac acctgtattc ttcactggta gttcagttga gttgctaatc tctcgtgacc    11640
ttgttgctat aatcagtaaa gagtctcaac atgtatatta cctgacattt gaactggttt    11700
tgatgtattg tgatgtcata gaggggaggt taatgacaga daccgctatg actattgatg    11760
ctaggtatac agagcttcta ggaagagtca gatacatgtg gaaactgata gatggtttct    11820
tccctgcact cggaatcca acttatcaaa ttgtagccat gctggagcct cttcacttg      11880
cttacctgca gctgagggat ataacagtag aactcagagg tgctttcctt aaccactgct    11940
ttactgaaat acatgatgtt cttgaccaaa acgggttttc tgatgaaggt acttatcatg    12000
agttaactga agctctagat tacatttca taactgatga catacatctg acaggggaga    12060
ttttctcatt tttcagaagt ttcggccacc ccagacttga agcagtaacg gctgctgaaa    12120
atgttaggaa atacatgaat cagcctaaag tcattgtgta tgagactctg atgaaaggtc    12180
atgccatatt ttgtggaatc ataatcaacg gctatcgtga caggcacgga ggcagttggc    12240
caccgctgac cctcccctg catgctgcag acacaatccg gaatgctcaa gcttcaggtc     12300
aagggttaac acatgagcag tgcgttgata actggaaatc ttttgctgga gtgaaattttg   12360
gctgctttat gcctcttagc ctggatagtg atctgacaat gtacctaaag gacaaggcac    12420
ttgctgctct ccaaagggaa tgggattcag tttacccgaa agagttcctg cgttacgacc    12480
ctcccaaggg aaccgggtca cggaggcttg tagatgtttt ccttaatgat tcgagctttg    12540
```

```
acccatatga tgtgataatg tatgttgtaa gtggagctta cctccatgac cctgagttca   12600
acctgtctta cagcctgaaa gaaaaggaga tcaaggaaac aggtagactt tttgctaaaa   12660
tgacttacaa aatgagggca tgccaagtga ttgctgaaaa tctaatctca aacgggattg   12720
gcaaatattt taaggacaat gggatggcca aggatgagca cgatttgact aaggcactcc   12780
acactctagc tgtctcagga gtccccaaag atctcaaaga aagtcacagg gggggccag    12840 tcttaaaaac ctactcccga agcccagtcc acacaagtac caggaacgtg agagcagcaa   12900
aagggtttat agggttccct caagtaattc ggcaggacca agacactgat catccggaga   12960
atatggaagc ttacgagaca gtcagtgcat ttatcacgac tgatctcaag aagtactgcc   13020
ttaattggag atatgagacc atcagcttgt ttgcacagag gctaaatgag atttacggat   13080
tgccctcatt tttccagtgg ctgcataaga ggcttgagac ctctgtcctg tatgtaagtg   13140
accctcattg ccccccgac  cttgacgccc atatcccgtt atataaagtc cccaatgatc   13200
aaatcttcat taagtaccct atgggaggta tagaagggta ttgtcagaag ctgtggacca   13260
tcagcaccat tccctatcta tacctggctg cttatgagag cggagtaagg attgcttcgt   13320
tagtgcaagg ggacaatcag accatagccg taacaaaaag ggtacccagc acatggccct   13380
acaaccttaa gaaacgggaa gctgctagag taactagaga ttactttgta attcttaggc   13440
aaaggctaca tgatattggc catcacctca aggcaaatga gacaattgtt tcatcacatt   13500
tttttgtcta ttcaaaagga atatattatg atgggctact tgtgtcccaa tcactcaaga   13560
gcatcgcaag atgtgtattc tggtcagaga ctatagttga tgaaacaagg gcagcatgca   13620
gtaatattgc tacaacaatg gctaaaagca tcgagagagg ttatgaccgt taccttgcat   13680
attccctgaa cgtcctaaaa gtgatacagc aaattctgat ctctcttggc ttcacaatca   13740
attcaaccat gacccgggat gtagtcatac ccctcctcac aaacaacgac ctcttaataa   13800
ggatggcact gttgcccgct cctattgggg ggatgaatta tctgaatatg agcaggctgt   13860
ttgtcagaaa catcggtgat ccagtaacat catcaattgc tgatctcaag agaatgattc   13920
tcgcctcact aatgcctgaa gagaccctcc atcaagtaat gacacaacaa ccggggact   13980 cttcattcct agactgggct agcgacccct actcagcaaa tcttgtatgt gtccagagca   14040
tcactagact cctcaagaac ataactgcaa ggtttgtcct gatccatagt ccaaacccaa   14100
tgttaaaagg attattccat gatgacagta agaagagga  cgagggactg gcggcattcc   14160
tcatggacag gcatattata gtacctaggg cagctcatga aatcctggat catagtgtca   14220
caggggcaag agagtctatt gcaggcatgc tggataccac aaaaggcttg attcgagcca   14280
gcatgaggaa gggggggtta acctctcgag tgataaccag attgtccaat tatgactatg   14340
aacaattcag agcagggatg gtgctattga caggaagaaa gagaaatgtc ctcattgaca   14400
aagagtcatg ttcagtgcag ctggcgagag ctctaagaag ccatatgtgg gcgaggctag   14460
ctcgaggacg gccatatttac ggccttgagg tccctgatgt actagaatct atgcgaggcc   14520
accttattcg gcgtcatgag acatgtgtca tctgcgagtg tggatcagtc aactacggat   14580
ggttttttgt cccctcgggt tgccaactgg atgatattga caaggaaaca tcatccttga   14640
gagtcccata tattggttct accactgatg agagaacaga catgaagctt gccttcgtaa   14700
gagccccaag tcgatccttg cgatctgctg ttagaatagc aacagtgtac tcatgggctt   14760
acggtgatga tgatagctct tggaacgaag cctggttgtt ggctaggcaa agggccaatg   14820
tgagcctgga ggagctaagg gtgatcactc ccatctcaac ttcgactaat ttagcgcata   14880
```

```
ggttgaggga tcgtagcact caagtgaaat actcaggtac atcccttgtc cgagtggcga   14940
ggtataccac aatctccaac gacaatctct catttgtcat atcagataag aaggttgata   15000
ctaactttat ataccaacaa ggaatgcttc tagggttggg tgttttagaa acattgtttc   15060
gactcgagaa agataccgga tcatctaaca cggtattaca tcttcacgtc gaaacagatt   15120
gttgcgtgat cccgatgata gatcatccca ggatacccag ctcccgcaag ctagagctga   15180
gggcagagct atgtaccaac ccattgatat atgataatgc acctttaatt gacagagatg   15240
caacaaggct atacacccag agccatagga ggcaccttgt ggaatttgtt acatggtcca   15300
caccccaact atatcacatt ttagctaagt ccacagcact atctatgatt gacctggtaa   15360
caaaatttga aaggaccat atgaatgaaa tttcagctct catagggat gacgatatca    15420
atagtttcat aactgagttt ctgctcatag agccaagatt attcactatc tacttgggcc   15480
agtgtgcggc catcaattgg gcatttgatg tacattatca tagaccatca gggaaatatc   15540
agatgggtga gctgttgtca tcgttccttt ctagaatgag caaggagtg tttaaggtgc    15600
ttgtcaatgc tctaagccac ccaaagatct acaagaaatt ctggcattgt ggtattatag   15660
agcctatcca tggtccttca cttgatgctc aaaacttgca cacaactgtg tgcaacatgg   15720
tttacacatg ctatatgacc tacctcgacc tgttgttgaa tgaagagtta aaagagttca   15780
catttctctt gtgtgaaagc gacgaggatg tagtaccgga cagattcgac aacatccagg   15840
caaaacactt atgtgttctg gcagatttgt actgtcaacc agggacctgc ccaccaattc   15900
gaggtctaag accggtagag aaatgtgcag ttctaaccga ccatatcaag gcagaggcta   15960
tgttatctcc agcaggatct tcgtggaaca taaatccaat tattgtagac cattactcat   16020
gctctctgac ttatctccgg cgaggatcga tcaaacagat aagattgaga gttgatccag   16080
gattcatttt cgacgccctc gctgaggtaa atgtcagtca gccaaagatc ggcagcaaca   16140
acatctcaaa tatgagcatc aaggctttca gaccccaca cgatgatgtt gcaaaattgc    16200
tcaaagatat caacacaagc aagcacaatc ttcccatttc aggggggcaat ctcgccaatt   16260
atgaaatcca tgctttccgc agaatcgggt tgaactcatc tgcttgctac aaagctgttg   16320
agatatcaac attaattagg agatgccttg agccagggga ggacggcttg ttcttgggtg   16380
agggatcggg ttctatgttg atcacttata aagagatact taaactaaac aagtgcttct   16440
ataatagtgg ggtttccgcc aattctagat ctggtcaaag gaattagca ccctatccct    16500
ccgaagttgg ccttgtcgaa cacagaatgg gagtaggtaa tattgtcaaa gtgctcttta   16560
acgggaggcc cgaagtcacg tgggtaggca gtgtagattg cttcaatttc atagttagta   16620
atatccctac ctctagtgtg gggtttatcc attcagatat agagaccttg cctgacaaag   16680
atactataga gaagctagag gaattggcag ccatcttatc gatggctctg ctcctgggca   16740
aaataggatc aatactggtg attaagctta tgcctttcag cggggatttt gttcagggat   16800
ttataagtta tgtagggtct cattatagag aagtgaacct tgtataccct agatacagca   16860
acttcatctc tactgaatct tatttggtta tgacagatct caaggctaac cggctaatga   16920
atcctgaaaa gattaagcag cagataattg aatcatctgt gaggacttca cctggactta   16980
taggtcacat cctatccatt aagcaactaa gctgcataca agcaattgtg ggagacgcag   17040
ttagtagagg tgatatcaat cctactctga aaaaacttac acctatagag caggtgctga   17100
tcaattgcgg gttggcaatt aacggaccta agctgtgcaa agaattgatc caccatgatg   17160
ttgcctcagg gcaagatgga ttgcttaatt ctatactcat cctctacagg gagttggcaa   17220
gattcaaaga caaccaaaga agtcaacaag ggatgttcca cgcttacccc gtattggtaa   17280
```

```
gtagcaggca acgagaactt atatctagga tcacccgcaa attctggggg cacattcttc   17340
tttactccgg gaacaaaaag ttgataaata agtttatcca gaatctcaag tccggctatc   17400
tgatactaga cttacaccag aatatcttcg ttaagaatct atccaagtca gagaaacaga   17460
ttattatgac gggggtttg aaacgtgagt gggtttttaa ggtaacagtc aaggagacca   17520
aagaatggta taagttagtc ggatacagtg ccctgattaa ggactaattg gttgaactcc   17580
ggaaccctaa tcctgccta ggtggttagg cattatttgc aatatattaa agaaaacttt   17640
gaaaatacga agtttctatt cccagctttg tctggtggcc ggcatggtcc cagcctcctc   17700
gctggcgccg gctgggcaac attccgaggg gaccgtcccc tcggtaatgg cgaatgggac   17760
gcggccgatc cggctgctaa caaagcccga aaggaagctg agttggctgc tgccaccgct   17820
gagcaataac tagcataacc ccttggggcc tctaaacggg tcttgagggg ttttttgctg   17880
aaaggaggaa ctatatccgg atgcggccgc gggccctatg gtacccagct tttgttccct   17940
ttagtgaggg ttaattccga gcttggcgta atcatggtca tagctgtttc ctgtgtgaaa   18000
ttgttatccg ctcacaattc cacacaacat aggagccgga agcataaagt gtaaagcctg   18060
gggtgcctaa tgagtgaggt aactcacatt aattgcgttg cgctcactgc ccgctttcca   18120
gtcgggaaac ctgtcgtgcc agctgcatta atgaatcggc caacgcgcgg ggagaggcgg   18180
tttgcgtatt gggcgctctt ccgcttcctc gctcactgac tcgctgcgct cggtcgttcg   18240
gctgcggcga gcggtatcag ctcactcaaa ggcggtaata cggttatcca cagaatcagg   18300
ggataacgca ggaaagaaca tgtgagcaaa aggccagcaa aaggccagga accgtaaaaa   18360
ggccgcgttg ctggcgtttt tccataggct cggccccct gacgagcatc acaaaaatcg   18420
acgctcaagt cagaggtggc gaaacccgac aggactataa agataccagg cgttccccc   18480 tggaagctcc ctcgtgcgct ctcctgttcc gaccctgccg cttaccggat acctgtccgc   18540
ctttctccct tcgggaagcg tggcgctttc tcaatgctca cgctgtaggt atctcagttc   18600
ggtgtaggtc gttcgctcca agctgggctg tgtgcacgaa ccccccgttc agcccgaccg   18660
ctgcgcctta tccggtaact atcgtcttga gtccaacccg gtaagacacg acttatcgcc   18720
actggcagca gccactggta acaggattag cagagcgagg tatgtaggcg gtgctacaga   18780
gttcttgaag tggtggccta actacggcta cactagaagg acagtatttg gtatctgcgc   18840
tctgctgaag ccagttacct tcggaaaaag agttggtagc tcttgatccg gcaaacaaac   18900
caccgctggt agcggtggtt tttttgtttg caagcagcag attacgcgca gaaaaaagg   18960 atctcaagaa gatcctttga tcttttctac ggggtctgac gctcagtgga acgaaaactc   19020
acgttaaggg attttggtca tgagattatc aaaaaggatc ttcacctaga tccttttaaa   19080
ttaaaaatga agttttaaat caatctaaag tatatatgag taaacttggt ctgacagtta   19140
ccaatgctta atcagtgagg cacctatctc agcgatctgt ctatttcgtt catccatagt   19200
tgcctgactg cccgtcgtgt agataactac gatacgggag gcttaccat ctggccccag   19260 tgctgcaatg ataccgcgag acccacgctc accggctcca gatttatcag caataaacca   19320
gccagccgga agggccgagc gcagaagtgg tcctgcaact ttatccgcct ccatccagtc   19380
tattaattgt tgccgggaag ctagagtaag tagttcgcca gttaatagtt tgcgcaacgt   19440
tgttgccatt gctacaggca tcgtggtgtc acgctcgtcg tttggtatgg cttcattcag   19500
ctccggttcc caacgatcaa ggcgagttac atgatccccc atgttgtgaa aaaaagcggt   19560
tagctccttc ggtcctccga tcgttgtcag aagtaagttg gccgcagtgt tatcactcat   19620
```

-continued

```
gcttatggca gcactgcata attctcttac tgtcatgcca tccgtaagat gcttttctgt  19680
gactggtgag tactcaacca agtcattctg agaatagtgt atgcggcgac cgagttgctc  19740
ttgcccggcg tcaatacggg ataataccgc gccacatagc agaactttaa aagtgctcat  19800
cattggaaaa cgttcttcgg ggcgaaaact ctcaaggatc ttaccgctgt tgagatccag  19860
ttcgatgtaa cccactcgtg cacccaactg atcttcagca tcttttactt tcaccagcgt  19920
ttctgggtga gcaaaaacag gaaggcaaaa tgccgcaaaa aagggaataa gggcgacacg  19980
gaaatgttga atactcatac tcttcctttt tcaatattat tgaagcattt atcagggtta  20040
ttgtctcatg agcggataca tatttgaatg tatttagaaa aataaacaaa taggggttcc  20100
gcgcacattt ccccgaaaag tgccacctga aattgtaaac gttaatattt tgttaaaatt  20160
cgcgttaaat ttttgttaaa tcagctcatt ttttaaccaa taggccgaaa tcggcaaaat  20220
cccttataaa tcaaaagaat agaccgagat agggttgagt gttgttccag tttggaacaa  20280
gagtccacta ttaaagaacg tggactccaa cgtcaaaggg cgaaaaaccg tctatcaggg  20340
cgatggccca ctacgtgaac catcacccta atcaagtttt ttggggtcga ggtgccgtaa  20400
agcactaaat cggaacccta aagggagccc ccgatttaga gcttgacggg gaaagccggc  20460
gaacgtggcg agaaaggaag ggaagaaagc gaaaggagcg ggcgctaggg cgctggcaag  20520
tgtagcggtc acgctgcgcg taaccaccac acccgccgcg cttaatgcgc cgctacaggg  20580
cgcgtcccat tcgccattca ggctgcgcaa ctgttgggaa gggcgatcgg tgcgggcctc  20640
ttcgctatta cgccagccac cgcggtggcg gccgctaata cgactcacta tagggccaac  20700
tttgtttggt ctgatgagtc cgtgaggacg aaacccggag tcccgggtc             20749
```

<210> SEQ ID NO 6
<211> LENGTH: 20905
<212> TYPE: DNA
<213> ORGANISM: Artificial Sequence
<220> FEATURE:
<223> OTHER INFORMATION: pTM-MV-ATU3-N-3xM2e
<220> FEATURE:
<221> NAME/KEY: misc_RNA
<222> LOCATION: (1)..(17832)
<223> OTHER INFORMATION: MV-ATU3-N-3xM2e_antigenome
<220> FEATURE:
<221> NAME/KEY: misc_feature
<222> LOCATION: (9176)..(11113)
<223> OTHER INFORMATION: ATU3
<220> FEATURE:
<221> NAME/KEY: misc_feature
<222> LOCATION: (9246)..(9251)
<223> OTHER INFORMATION: BsiWI restriction site
<220> FEATURE:
<221> NAME/KEY: misc_feature
<222> LOCATION: (9255)..(11078)
<223> OTHER INFORMATION: ORF for N-3xM2e fusion protein : N-3xM2e_ORF
<220> FEATURE:
<221> NAME/KEY: misc_feature
<222> LOCATION: (11082)..(11087)
<223> OTHER INFORMATION: BssHII restriction site
<220> FEATURE:
<221> NAME/KEY: misc_feature
<222> LOCATION: (17833)..(20905)
<223> OTHER INFORMATION: plasmid_backbone

<400> SEQUENCE: 6

```
accaaacaaa gttgggtaag gatagttcaa tcaatgatca tcttctagtg cacttaggat     60
tcaagatcct attatcaggg acaagagcag gattagggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
```

```
ttaccactcg atccagactt ctggaccggt tggtgaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caagaaggg    720 tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggca aggaagatag gagggtcaaa cagagtcgag   1440
gagaagccag ggagagctac agagaaaccg ggcccagcag agcaagtgat gcgagagctg   1500
cccatcttcc aaccggcaca ccctagaca ttgacactgc aacggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga atcttctag   1680 actaggtgcg agaggccgag ggccagaaca acatccgcct accatccatc attgttataa   1740
aaaacttagg aaccaggtcc acacagccgc cagcccatca accatccact cccacgattg   1800
gagccaatgg cagaagagca ggcacgccat gtcaaaaacg gactgaaatg catccgggct   1860
ctcaaggccg agcccatcgg ctcactggcc atcgaggaag ctatggcagc atggtcagaa   1920
atatcagaca cccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa cttgggaat ccccccaaga   2100 aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
```

```
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aaggggGAGA ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg cacctctca agcatcatga tcgccattcc tggacttggg    2940
aaggatccca acgacccca c tgcagatgtc gaaatcaatc ccgacttgaa acccatcata    3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt tgttcctga cccggccct     3180 gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagtac aacctaaatc cattataaaa aacttaggag caaagtgatt    3420
gcctcccaag gtccacaatg acagagacct acgacttcga caagtcggca tgggacatca    3480
aagggtcgat cgctccgata caacccacca cctacagtga tggcaggctg gtgccccagg    3540
tcagagtcat agatcctggt ctaggcgaca ggaaggatga atgctttatg tacatgtttc    3600 tgctggggt tgttgaggac agcgattccc tagggcctcc aatcgggcga gcatttgggt    3660
tcctgccctt aggtgttggc agatccacag caaagcccga aaaactcctc aaagaggcca    3720
ctgagcttga catagttgtt agacgtacag cagggctcaa tgaaaaactg gtgttctaca    3780
acaacacccc actaactctc ctcacaccct ggagaaaggt cctaacaaca gggagtgtct    3840
tcaacgcaaa ccaagtgtgc aatgcggtta atctgatacc gctcgatacc ccgcagaggt    3900
tccgtgttgt ttatatgagc atcacccgtc tttcggataa cgggtattac accgttccta    3960
gaagaatgct ggaattcaga tcggtcaatg cagtggcctt caacctgctg gtgaccctta    4020
ggattgacaa ggcgataggc cctgggaaga tcatcgacaa tacagagcaa cttcctgagg    4080
caacatttat ggtccacatc gggaacttca ggagaaagaa gagtgaagtc tactctgccg    4140
attattgcaa aatgaaaatc gaaaagatgg gcctggtttt tgcacttggt gggatagggg    4200
gcaccagtct tcacattaga agcacaggca aaatgagcaa gactctccat gcacaactcg    4260
ggttcaagaa gaccttatgt tacccgctga tggatatcaa tgaagacctt aatcgattac    4320
tctggaggag cagatgcaag atagtaagaa tccaggcagt tttgcagcca tcagttcctc    4380
aagaattccg catttacgac gacgtgatca taaatgatga ccaaggacta ttcaaagttc    4440
tgtagaccgt agtgcccagc aatgcccgaa aacgaccccc ctcacaatga cagccagaag    4500
gcccggacaa aaaagccccc tccgaaagac tccacggacc aagcgagagg ccagccagca    4560
gccgacggca agcgcgaaca ccaggcggcc ccagcacaga acagccctga cacaaggcca    4620
ccaccagcca ccccaatctg catcctcctc gtgggacccc cgaggaccaa cccccaaggc    4680 tgccccgat ccaaaccacc aaccgcatcc ccaccaccc cggaaagaa acccccagca     4740 attggaaggc ccctcccct cttcctcaac acaagaactc cacaaccgaa ccgcacaagc     4800
gaccgaggtg acccaaccgc aggcatccga ctccctagac agatcctctc tccccggcaa    4860
actaaacaaa acttagggcc aaggaacata cacacccaac agaacccaga ccccggccca    4920
cggcgccgcg ccccaacccc ccgacaacca gagggagccc ccaaccaatc ccgccggctc    4980
```

```
ccccggtgcc cacaggcagg gacaccaacc cccgaacaga cccagcaccc aaccatcgac      5040
aatccaagac ggggggggccc ccccaaaaaa aggcccccag gggccgacag ccagcaccgc      5100
gaggaagccc acccacccca cacacgacca cggcaaccaa accagaaccc agaccaccct      5160
gggccaccag ctcccagact cggccatcac cccgcagaaa ggaaaggcca aacccgcgc       5220 accccagccc cgatccggcg gggagccacc caacccgaac cagcacccaa gagcgatccc      5280
cgaaggaccc ccgaaccgca aaggacatca gtatcccaca gcctctccaa gtccccggt      5340 ctcctcctct tctcgaaggg accaaaagat caatccacca caccccgacga cactcaactc      5400 cccacccta aaggagacac cgggaatccc agaatcaaga ctcatccaat gtccatcatg      5460
ggtctcaagg tgaacgtctc tgccatattc atggcagtac tgttaactct ccaaacaccc      5520
accggtcaaa tccattgggg caatctctct aagataggggg tggtaggaat aggaagtgca      5580
agctacaaag ttatgactcg ttccagccat caatcattag tcataaaatt aatgcccaat      5640
ataactctcc tcaataactg cacgagggta gagattgcag aatacaggag actactgaga      5700
acagttttgg aaccaattag agatgcactt aatgcaatga cccagaatat aagaccggtt      5760
cagagtgtag cttcaagtag gagacacaag agatttgcgg gagtagtcct ggcaggtgcg      5820
gccctaggcg ttgccacagc tgctcagata acagccggca ttgcacttca ccagtccatg      5880
ctgaactctc aagccatcga caatctgaga gcgagcctgg aaaactactaa tcaggcaatt      5940 gagacaatca gacaagcagg gcaggagatg atattggctg ttcagggtgt ccaagactac      6000
atcaataatg agctgatacc gtctatgaac caactatctt gtgatttaat cggccagaag      6060
ctcgggctca aattgctcag atactataca gaaatcctgt cattatttgg ccccagttta      6120
cgggacccca tatctgcgga gatatctatc caggctttga gctatgcgct tggaggagac      6180
atcaataagg tgttagaaaa gctcggatac agtggaggtg atttactggg catcttagag      6240
agcggaggaa taaaggcccg gataactcac gtcgacacag agtccctactt cattgtcctc      6300 agtatagcct atccgacgct gtccgagatt aaggggtga ttgtccaccg gctagagggg      6360
gtctcgtaca acataggctc tcaagagtgg tataccactg tgcccaagta tgttgcaacc      6420
caagggtacc ttatctcgaa ttttgatgag tcatcgtgta ctttcatgcc agaggggact      6480
gtgtgcagcc aaaatgcctt gtacccgatg agtcctctgc tccaagaatg cctccgggg       6540 tacaccaagt cctgtgctcg tacactcgta tccgggtctt ttgggaaccg gttcatttta      6600
tcacaaggga acctaatagc caattgtgca tcaatccttt gcaagtgtta cacaacagga      6660
acgatcatta tcaagaccc tgacaagatc ctaacataca ttgctgccga tcactgcccg      6720
gtagtcgagg tgaacggcgt gaccatccaa gtcgggagca ggaggtatcc agacgctgtg      6780
tacttgcaca gaattgacct cggtcctccc atatcattgg agaggttgga cgtagggaca      6840
aatctgggga atgcaattgc taagttggag gatgccaagg aattgttgga gtcatcggac      6900
cagatattga ggagtatgaa aggttttatcg agcactagca tagtctacat cctgattgca      6960
gtgtgtcttg gagggttgat agggatcccc gctttaatat gttgctgcag ggggcgttgt      7020
aacaaaaagg gagaacaagt tggtatgtca agaccaggcc taaagcctga tcttacggga      7080
acatcaaaat cctatgtaag gtcgctctga tcctctacaa ctcttgaaac acaaatgtcc      7140
cacaagtctc ctcttcgtca tcaagcaacc accgcaccca gcatcaagcc cacctgaaat      7200
tatctccggc ttccctctgg ccgaacaata tcggtagtta atcaaaactt agggtgcaag      7260
atcatccaca atgtcaccac aacgagaccg gataaatgcc ttctacaaag ataaccccca      7320
```

```
tcccaaggga agtaggatag tcattaacag agaacatctt atgattgata gaccttatgt   7380
tttgctggct gttctgtttg tcatgtttct gagcttgatc gggttgctag ccattgcagg   7440
cattagactt catcgggcag ccatctacac cgcagagatc cataaaagcc tcagcaccaa   7500
tctagatgta actaactcaa tcgagcatca ggtcaaggac gtgctgacac cactcttcaa   7560
aatcatcggt gatgaagtgg gcctgaggac acctcagaga ttcactgacc tagtgaaatt   7620
aatctctgac aagattaaat tccttaatcc ggatagggag tacgacttca gagatctcac   7680
ttggtgtatc aacccgccag agagaatcaa attggattat gatcaatact gtgcagatgt   7740
ggctgctgaa gagctcatga atgcattggt gaactcaact ctactggaga ccagaacaac   7800
caatcagttc ctagctgtct caaagggaaa ctgctcaggg cccactacaa tcagaggtca   7860
attctcaaac atgtcgctgt ccctgttaga cttgtattta ggtcgaggtt acaatgtgtc   7920
atctatagtc actatgacat cccagggaat gtatggggga acttacctag tggaaaagcc   7980
taatctgagc agcaaaaggt cagagttgtc acaactgagc atgtaccgag tgtttgaagt   8040
aggtgttatc agaaatccgg gtttgggggc tccggtgttc catatgacaa actatctcga   8100
gcaaccagtc agtaatgatc tcagcaactg tatggtggct ttgggggagc tcaaactcgc   8160 agcccttgt cacggggaag attctatcac aattccctat cagggatcag ggaaaggtgt   8220
cagcttccag ctcgtcaagc taggtgtctg gaaatcccca accgacatgc aatcctgggt   8280
ccccttatca acggatgatc cagtgataga caggctttac ctctcatctc acagaggtgt   8340
tatcgctgac aatcaagcaa aatgggctgt cccgacaaca cgaacagatg acaagttgcg   8400
aatggagaca tgcttccaac aggcgtgtaa gggtaaaatc caagcactct gcgagaatcc   8460
cgagtgggca ccattgaagg ataacaggat tccttcatac ggggtcttgt ctgttgatct   8520
gagtctgaca gttgagctta aaatcaaaat tgcttcggga ttcgggccat tgatcacaca   8580
cggttcaggg atggacctat acaaatccaa ccacaacaat gtgtattggc tgactatccc   8640
gccaatgaag aacctagcct taggtgtaat caacacattg gagtggatac cgagattcaa   8700
ggttagtccc tacctcttca ctgtcccaat taaggaagca ggcgaagact gccatgcccc   8760
aacataccta cctgcggagg tggatggtga tgtcaaactc agttccaatc tggtgattct   8820
acctggtcaa gatctccaat atgtttttgg caacctacgat acttccaggg ttgaacatgc   8880
tgtggtttat tacgtttaca gcccaagccg ctcattttct tactttttatc cttttaggtt   8940 gcctataaag ggggtcccca tcgaattaca agtggaatgc ttcacatggg accaaaaact   9000
ctggtgccgt cacttctgtg tgcttgcgga ctcagaatct ggtggacata tcactcactc   9060
tgggatggtg ggcatgggag tcagctgcac agtcacccgg gaagatggaa ccaatcgcag   9120
atagggctgc tagtgaacca atcacatgat gtcacccaga catcaggcat acccactagt   9180
ctaccctcca tcattgttat aaaaaactta ggaaccaggt ccacacagcc gccagcccat   9240
caacgcgtac ggagatggcc acacttttaa ggagcttagc attgttcaaa agaaacaagg   9300
acaaaccacc cattacatca ggatccggtg gagccatcag aggaatcaaa acattatta   9360 tagtaccaat ccctggagat tcctcaatta ccactcgatc cagacttctg gaccggttgg   9420
tgaggttaat tggaaacccg gatgtgagcg ggcccaaact aacagggca ctaataggta   9480 tattatcctt atttgtggag tctccaggtc aattgattca gaggatcacc gatgaccctg   9540
acgttagcat aaggctgtta gaggttgtcc agagtgacca gtcacaatct ggccttacct   9600
tcgcatcaag aggtaccaac atggaggatg aggcggacca atacttttca catgatgatc   9660
caattagtag tgatcaatcc aggttcggat ggttcgggaa caaggaaatc tcagatattg   9720
```

```
aagtgcaaga ccctgaggga ttcaacatga ttctgggtac catcctagcc caaatttggg   9780
tcttgctcgc aaaggcggtt acggcccag acacggcagc tgattcggag ctaagaaggt    9840
ggataaagta cacccaacaa agaagggtag ttggtgaatt tagattggag agaaaatggt   9900
tggatgtggt gaggaacagg attgccgagg acctctcctt acgccgattc atggtcgctc   9960
taatcctgga tatcaagaga acacccggaa acaaacccag gattgctgaa atgatatgtg  10020
acattgatac atatatcgta gaggcaggat tagccagttt tatcctgact attaagtttg  10080
ggatagaaac tatgtatcct gctcttggac tgcatgaatt tgctggtgag ttatccacac  10140
ttgagtcctt gatgaacctt taccagcaaa tgggggaaac tgcaccctac atggtaatcc  10200
tggagaactc aattcagaac aagttcagtg caggatcata ccctctgctc tggagctatg  10260
ccatgggagt aggagtggaa cttgaaaact ccatgggagg tttgaacttt ggccgatctt  10320
actttgatcc agcatatttt agattagggc aagagatggt aaggaggtca gctggaaagg  10380
tcagttccac attggcatct gaactcgta tcactgccga ggatgcaagg cttgtttcag    10440
agattgcaat gcatactact gaggacaaga tcagtagagc ggttggaccc agacaagccc  10500
aagtatcatt tctacacggt gatcaaagtg agaatgagct accgagattg ggggcaagg    10560
aagataggag ggtcaaacag agtcgaggag aagccaggga gagctacaga gaaaccgggc  10620
ccagcagagc aagtgatgcg agagctgccc atcttccaac cggcacaccc ctagacattg  10680
acactgcaac ggagtccagc caagatccgc aggacagtcg aaggtcagct gacgccctgc  10740
ttaggctgca agccatggca ggaatctcgg aagaacaagg ctcagacacg gacacccta    10800
tagtgtacaa tgacagaaat cttctagact ccggaggatc tggcggctct ctgctgaccg  10860
aggtggaaac ccccatcaga aacgagtggg gctgccggtg caacgacagc tctgatggcg  10920
gcggaagcct gctgacagaa gtggaaacac ctattcggaa tgagtgggga tgcagatgca  10980
atgactccag cgacggcgga ggcagtctgc tgactgaagt ggaaacccca attcgcaacg  11040
aatggggatg tcgctgtaac gatagcagcg actgataacg agcgcgcagc gcttagacgt  11100
ctcgcgatcg atgctagtgt gaaatagaca tcagaattaa gaaaaacgta gggtccaagt  11160
ggttccccgt tatggactcg ctatctgtca accagatctt ataccctgaa gttcacctag  11220
atagcccgat agttaccaat aagatagtag ccatcctgga gtatgctcga gtccctcacg  11280
cttacagcct ggaggaccct acactgtgtc agaacatcaa gcaccgccta aaaaacggat  11340
tttccaacca aatgattata aacaatgtgg aagttgggaa tgtcatcaag tccaagctta  11400
ggagttatcc ggcccactct catattccat atccaaattg taatcaggat ttatttaaca  11460
tagaagacaa agagtcaacg aggaagatcc gtgaactcct caaaaagggg aattcgctgt  11520
actccaaagt cagtgataag gttttccaat gcttaaggga cactaactca cggcttggcc  11580
taggctccga attgagggag gacatcaagg agaaagttat taacttggga gtttacatgc  11640
acagctccca gtggtttgag cccttttctgt tttggtttac agtcaagact gagatgaggt  11700
cagtgattaa atcacaaacc catacttgcc ataggaggag acacacacct gtattcttca  11760
ctggtagttc agttgagttg ctaatctctc gtgaccttgt tgctataatc agtaaagagt  11820
ctcaacatgt atattacctg acatttgaac tggttttgat gtattgtgat gtcatagagg  11880
ggaggttaat gacagagacc gctatgacta ttgatgctag gtatacagag cttctaggaa  11940
gagtcagata catgtggaaa ctgatagatg gtttcttccc tgcactcggg aatccaactt  12000
atcaaattgt agccatgctg gagcctcttt cacttgctta cctgcagctg agggatataa  12060
```

```
cagtagaact cagaggtgct ttccttaacc actgctttac tgaaatacat gatgttcttg   12120
accaaaacgg gttttctgat gaaggtactt atcatgagtt aactgaagct ctagattaca   12180
ttttcataac tgatgacata catctgacag gggagatttt ctcatttttc agaagtttcg   12240
gccaccccag acttgaagca gtaacggctg ctgaaaatgt taggaaatac atgaatcagc   12300
ctaaagtcat tgtgtatgag actctgatga aaggtcatgc catattttgt ggaatcataa   12360
tcaacggcta tcgtgacagg cacggaggca gttggccacc gctgaccctc cccctgcatg   12420
ctgcagacac aatccggaat gctcaagctt caggtgaagg gttaacacat gagcagtgcg   12480
ttgataactg gaaatctttt gctggagtga aatttggctg cttatgcct cttagcctgg    12540 atagtgatct gacaatgtac ctaaaggaca aggcacttgc tgctctccaa agggaatggg   12600
attcagttta cccgaaagag ttcctgcgtt acgaccctcc caagggaacc gggtcacgga   12660
ggcttgtaga tgttttcctt aatgattcga gctttgaccc atatgatgtg ataatgtatg   12720
ttgtaagtgg agcttacctc catgaccctg agttcaacct gtcttacagc ctgaaagaaa   12780
aggagatcaa ggaaacaggt agacttttg ctaaaatgac ttacaaaatg agggcatgcc    12840
aagtgattgc tgaaaatcta atctcaaacg ggattggcaa atattttaag gacaatggga   12900
tggccaagga tgagcacgat ttgactaagg cactccacac tctagctgtc tcaggagtcc   12960
ccaaagatct caaagaaagt cacagggggg ggccagtctt aaaaacctac tcccgaagcc   13020
cagtccacac aagtaccagg aacgtgagag cagcaaaagg gttatagggg ttccctcaag   13080
taattcggca ggaccaagac actgatcatc cggagaatat ggaagcttac gagacagtca   13140
gtgcatttat cacgactgat ctcaagaagt actgccttaa ttggagatat gagaccatca   13200
gcttgtttgc acagaggcta aatgagattt acggattgcc ctcatttttc cagtggctgc   13260
ataagaggct tgagacctct gtcctgtatg taagtgaccc tcattgcccc cccgaccttg   13320
acgcccatat cccgttatat aaagtcccca atgatcaaat cttcattaag taccctatgg   13380
gaggtataga agggtattgt cagaagctgt ggaccatcag caccattccc tatctatacc   13440
tggctgctta tgagagcgga gtaaggattg cttcgttagt gcaaggggac aatcagacca   13500
tagccgtaac aaaaagggta cccagcacat ggccctacaa ccttaagaaa cgggaagctg   13560
ctagagtaac tagagattac tttgtaattc ttaggcaaag gctacatgat attggccatc   13620
acctcaaggc aaatgagaca attgtttcat cacatttttt tgtctattca aaaggaatat   13680
attatgatgg gctacttgtg tcccaatcac tcaagagcat cgcaagatgt gtattctggt   13740
cagagactat agttgatgaa acaagggcag catgcagtaa tattgctaca acaatggcta   13800
aaagcatcga gagaggttat gaccgttacc ttgcatattc cctgaacgtc ctaaaagtga   13860
tacagcaaat tctgatctct cttggcttca caatcaattc aaccatgacc cgggatgtag   13920
tcatacccct cctcacaaac aacgacctct taataaggat ggcactgttg cccgctccta   13980 ttgggggat gaattatctg aatatgagca ggctgtttgt cagaaacatc ggtgatccag   14040
taacatcatc aattgctgat ctcaagagaa tgattctcgc ctcactaatg cctgaagaga   14100
ccctccatca gtaatgacaa caacaaccgg gggactcttc attcctagac tgggctagcg   14160 accctactc agcaaatctt gtatgtgtcc agagcatcac tagactcctc aagaacataa   14220
ctgcaaggtt tgtcctgatc catagtccaa acccaatgtt aaaaggatta ttccatgatg   14280
acagtaaaga agaggacgag ggactggcgg cattcctcat ggacaggcat attatagtac   14340
ctagggcagc tcatgaaatc ctggatcata gtgtcacagg ggcaagagag tctattgcag   14400
gcatgctgga taccacaaaa ggcttgattc gagccagcat gaggaagggg gggttaacct   14460
```

```
ctcgagtgat aaccagattg tccaattatg actatgaaca attcagagca gggatggtgc   14520
tattgacagg aagaaagaga aatgtcctca ttgacaaaga gtcatgttca gtgcagctgg   14580
cgagagctct aagaagccat atgtgggcga ggctagctcg aggacggcct atttacggcc   14640
ttgaggtccc tgatgtacta gaatctatgc gaggccacct tattcggcgt catgagacat   14700
gtgtcatctg cgagtgtgga tcagtcaact acggatggtt ttttgtcccc tcgggttgcc   14760
aactggatga tattgacaag gaaacatcat ccttgagagt cccatatatt ggttctacca   14820
ctgatgagag aacagacatg aagcttgcct tcgtaagagc cccaagtcga tccttgcgat   14880
ctgctgttag aatagcaaca gtgtactcat gggcttacgg tgatgatgat agctcttgga   14940
acgaagcctg gttgttggct aggcaaaggg ccaatgtgag cctggaggag ctaagggtga   15000
tcactcccat ctcaacttcg actaatttag cgcataggtt gagggatcgt agcactcaag   15060
tgaaatactc aggtacatcc cttgtccgag tggcgaggta taccacaatc tccaacgaca   15120
atctctcatt tgtcatatca gataagaagg ttgatactaa cttatatac caacaaggaa   15180
tgcttctagg gttgggtgtt ttagaaacat tgtttcgact cgagaaagat accggatcat   15240
ctaacacggt attacatctt cacgtcgaaa cagattgttg cgtgatcccg atgatagatc   15300
atcccaggat acccagctcc cgcaagctag agctgagggc agagctatgt accaacccat   15360
tgatatatga taatgcacct ttaattgaca gagatgcaac aaggctatac cccagagcc   15420
ataggaggca ccttgtggaa tttgttacat ggtccacacc ccaactatat cacattttag   15480
ctaagtccac agcactatct atgattgacc tggtaacaaa atttgagaag gaccatatga   15540
atgaaatttc agctctcata ggggatgacg atatcaatag tttcataact gagtttctgc   15600
tcatagagcc aagattattc actatctact tgggccagtg tgcggccatc aattgggcat   15660
ttgatgtaca ttatcataga ccatcaggga aatatcagat gggtgagctg ttgtcatcgt   15720
tcctttctag aatgagcaaa ggagtgttta aggtgcttgt caatgctcta agccaccccaa   15780
agatctacaa gaaattctgg cattgtggta ttatagagcc tatccatggt ccttcacttg   15840
atgctcaaaa cttgcacaca actgtgtgca acatggttta cacatgctat atgacctacc   15900
tcgacctgtt gttgaatgaa gagttagaag agttcacatt tctcttgtgt gaaagcgacg   15960
aggatgtagt accggacaga ttcgacaaca tccaggcaaa acacttatgt gttctggcag   16020
atttgtactg tcaaccaggg acctgcccac caattcgagg tctaagaccg gtagagaaat   16080
gtgcagttct aaccgaccat atcaaggcag aggctatgtt atctccagca ggatcttcgt   16140
ggaacataaa tccaattatt gtagaccatt actcatgctc tctgacttat ctccggcgag   16200
gatcgatcaa acagataaga ttgagagttg atccaggatt cattttcgac gccctcgctg   16260
aggtaaatgt cagtcagcca aagatcggca gcaacaacat ctcaaatatg agcatcaagg   16320
cttcagacc cccacacgat gatgttgcaa aattgctcaa agatatcaac acaagcaagc   16380
acaatcttcc catttcaggg ggcaatctcg ccaattatga aatccatgct ttccgcagaa   16440
tcgggttgaa ctcatctgct tgctacaaag ctgttgagat atcaacatta attaggagat   16500
gccttgagcc agggggaggac ggcttgttct tgggtgaggg atcgggttct atgttgatca   16560
cttataaaga gatacttaaa ctaaacaagt gcttctataa tagtgggggtt tccgccaatt   16620
ctagatctgg tcaaagggaa ttagcaccct atccctccga agttggcctt gtcgaacaca   16680
gaatgggagt aggtaatatt gtcaaagtgc tctttaacgg gaggcccgaa gtcacgtggg   16740
taggcagtgt agattgcttc aatttcatag ttagtaatat ccctacctct agtgtggggt   16800
```

```
ttatccattc agatatagag accttgcctg acaaagatac tatagagaag ctagaggaat    16860
tggcagccat cttatcgatg gctctgctcc tgggcaaaat aggatcaata ctggtgatta    16920
agcttatgcc tttcagcggg gattttgttc agggatttat aagttatgta gggtctcatt    16980
atagagaagt gaaccttgta taccctagat acagcaactt catctctact gaatcttatt    17040
tggttatgac agatctcaag gctaaccggc taatgaatcc tgaaaagatt aagcagcaga    17100
taattgaatc atctgtgagg acttcacctg gacttatagg tcacatccta tccattaagc    17160
aactaagctg catacaagca attgtgggag acgcagttag tagaggtgat atcaatccta    17220
ctctgaaaaa acttacacct atagagcagg tgctgatcaa ttgcgggttg gcaattaacg    17280
gacctaagct gtgcaaagaa ttgatccacc atgatgttgc ctcagggcaa gatggattgc    17340
ttaattctat actcatcctc tacagggagt tggcaagatt caaagacaac caaagaagtc    17400
aacagggat gttccacgct taccccgtat tggtaagtag caggcaacga gaacttatat    17460
ctaggatcac ccgcaaattc tgggggcaca ttcttctta ctccgggaac aaaaagttga    17520
taaataagtt tatccagaat ctcaagtccg gctatctgat actagactta caccagaata    17580
tcttcgttaa gaatctatcc aagtcagaga acagattat tatgacgggg ggtttgaaac    17640
gtgagtgggt ttttaaggta acagtcaagg agaccaaaga atggtataag ttagtcggat    17700
acagtgccct gattaaggac taattggttg aactccggaa ccctaatcct gccctaggtg    17760
gttaggcatt atttgcaata tattaaagaa actttgaaa atacgaagtt tctattccca    17820
gctttgtctg gtggccggca tggtcccagc ctcctcgctg gcgccggctg ggcaacattc    17880
cgaggggacc gtcccctcgg taatggcgaa tgggacgcgg ccgatccggc tgctaacaaa    17940
gcccgaaagg aagctgagtt ggctgctgcc accgctgagc aataactagc ataacccctt    18000
ggggcctcta acgggtctt gagggggtttt ttgctgaaag gaggaactat atccggatgc    18060
ggccgcgggc cctatggtac ccagcttttg ttcccttag tgagggttaa ttccgagctt    18120
ggcgtaatca tggtcatagc tgtttcctgt gtgaaattgt tatccgctca caattccaca    18180
caacatagga gccggaagca taaagtgtaa agcctggggt gcctaatgag tgaggtaact    18240
cacattaatt gcgttgcgct cactgcccgc tttccagtcg ggaaacctgt cgtgccagct    18300
gcattaatga atcggccaac gcgcggggag aggcggtttg cgtattgggc gctcttccgc    18360
ttcctcgctc actgactcgc tgcgctcggt cgttcggctg cggcgagcgg tatcagctca    18420
ctcaaaggcg gtaatacggt tatccacaga atcagggat aacgcaggaa agaacatgtg    18480
agcaaaaggc cagcaaaagg ccaggaaccg taaaaaggcc gcgttgctgg cgttttccca    18540
taggctcggc cccctgacg agcatcacaa aaatcgacgc tcaagtcaga ggtggcgaaa    18600
cccgacagga ctataaagat accaggcgtt cccccctgga agctccctcg tgcgctctcc    18660
tgttccgacc ctgccgctta ccggatacct gtccgccttt ctcccttcgg gaagcgtggc    18720
gctttctcaa tgctcacgct gtaggtatct cagttcggtg taggtcgttc gctccaagct    18780
gggctgtgtg cacgaacccc ccgttcagcc cgaccgctgc gccttatccg gtaactatcg    18840
tcttgagtcc aacccggtaa gacacgactt atcgccactg gcagcagcca ctggtaacag    18900
gattagcaga gcgaggtatg taggcggtgc tacagagttc ttgaagtggt ggcctaacta    18960
cggctacact agaaggacag tatttggtat ctgcgctctg ctgaagccag ttaccttcgg    19020
aaaaagagtt ggtagctctt gatccggcaa acaaaccacc gctggtagcg gtggtttttt    19080
tgtttgcaag cagcagatta cgcgcagaaa aaaaggatct caagaagatc ctttgatctt    19140
ttctacgggg tctgacgctc agtggaacga aaactcacgt taagggattt tggtcatgag    19200
```

```
attatcaaaa aggatcttca cctagatcct tttaaattaa aaatgaagtt ttaaatcaat  19260
ctaaagtata tatgagtaaa cttggtctga cagttaccaa tgcttaatca gtgaggcacc  19320
tatctcagcg atctgtctat ttcgttcatc catagttgcc tgactgcccg tcgtgtagat  19380
aactacgata cgggagggct taccatctgg ccccagtgct gcaatgatac cgcgagaccc  19440
acgctcaccg gctccagatt tatcagcaat aaaccagcca gccggaaggg ccgagcgcag  19500
aagtggtcct gcaactttat ccgcctccat ccagtctatt aattgttgcc gggaagctag  19560
agtaagtagt tcgccagtta atagtttgcg caacgttgtt gccattgcta caggcatcgt  19620
ggtgtcacgc tcgtcgtttg gtatggcttc attcagctcc ggttcccaac gatcaaggcg  19680
agttacatga tcccccatgt tgtgaaaaaa agcggttagc tccttcggtc ctccgatcgt  19740
tgtcagaagt aagttggccg cagtgttatc actcatgctt atggcagcac tgcataattc  19800
tcttactgtc atgccatccg taagatgctt ttctgtgact ggtgagtact caaccaagtc  19860
attctgagaa tagtgtatgc ggcgaccgag ttgctcttgc ccggcgtcaa tacgggataa  19920
taccgcgcca catagcagaa ctttaaaagt gctcatcatt ggaaaacgtt cttcggggcg  19980
aaaactctca aggatcttac cgctgttgag atccagttcg atgtaaccca ctcgtgcacc  20040
caactgatct tcagcatctt ttactttcac cagcgtttct gggtgagcaa aaacaggaag  20100
gcaaaatgcc gcaaaaaagg gaataagggc gacacggaaa tgttgaatac tcatactctt  20160
cctttttcaa tattattgaa gcatttatca gggttattgt ctcatgagcg gatacatatt  20220
tgaatgtatt tagaaaaata aacaaatagg ggttccgcgc acatttcccc gaaaagtgcc  20280
acctgaaatt gtaaacgtta atattttgtt aaaattcgcg ttaaattttt gttaaatcag  20340
ctcatttttt aaccaatagg ccgaaatcgg caaaatccct tataaatcaa aagaatagac  20400
cgagataggg ttgagtgttg ttccagtttg gaacaagagt ccactattaa agaacgtgga  20460
ctccaacgtc aaagggcgaa aaaccgtcta tcagggcgat ggcccactac gtgaaccatc  20520
accctaatca agttttttgg ggtcgaggtg ccgtaaagca ctaaatcgga accctaaagg  20580
gagcccccga tttagagctt gacggggaaa gccggcgaac gtggcgagaa aggaagggaa  20640
gaaagcgaaa ggagcgggcg ctagggcgct ggcaagtgta gcggtcacgc tgcgcgtaac  20700
caccacaccc gccgcgctta atgcgccgct acagggcgcg tcccattcgc cattcaggct  20760
gcgcaactgt tgggaagggc gatcggtgcg ggcctcttcg ctattacgcc agccaccgcg  20820
gtggcggccg ctaatacgac tcactatagg gccaactttg tttggtctga tgagtccgtg  20880
aggacgaaac ccggagtccc gggtc                                        20905
```

```

<210> SEQ ID NO 7
<211> LENGTH: 19843
<212> TYPE: DNA
<213> ORGANISM: Artificial Sequence
<220> FEATURE:
<223> OTHER INFORMATION: pTM-MV-ATU2-M1opt
<220> FEATURE:
<221> NAME/KEY: misc_RNA
<222> LOCATION: (1)..(16770)
<223> OTHER INFORMATION: MV-ATU2-M1opt_antigenome
<220> FEATURE:
<221> NAME/KEY: misc_feature
<222> LOCATION: (3378)..(4253)
<223> OTHER INFORMATION: ATU2
<220> FEATURE:
<221> NAME/KEY: misc_feature
<222> LOCATION: (3444)..(3449)
<223> OTHER INFORMATION: BsiWI restriction site
<220> FEATURE:
```

```
<221> NAME/KEY: misc_feature
<222> LOCATION: (3453)..(4214)
<223> OTHER INFORMATION: ORF for M1 consensus protein : M1opt
<220> FEATURE:
<221> NAME/KEY: misc_feature
<222> LOCATION: (4218)..(4223)
<223> OTHER INFORMATION: BssHII restriction site
<220> FEATURE:
<221> NAME/KEY: misc_feature
<222> LOCATION: (16771)..(19843)
<223> OTHER INFORMATION: plasmid_backbone

<400> SEQUENCE: 7
```

| | | | | | |
|---|---|---|---|---|---|
| accaaacaaa | gttgggtaag | gatagttcaa | tcaatgatca | tcttctagtg | cacttaggat | 60 |
| tcaagatcct | attatcaggg | acaagagcag | gattagggat | atccgagatg | ccacacttt | 120 |
| taaggagctt | agcattgttc | aaaagaaaca | aggacaaacc | acccattaca | tcaggatccg | 180 |
| gtggagccat | cagaggaatc | aaacacatta | ttatagtacc | aatccctgga | gattcctcaa | 240 |
| ttaccactcg | atccagactt | ctggaccggt | tggtgaggtt | aattggaaac | ccggatgtga | 300 |
| gcgggcccaa | actaacaggg | gcactaatag | gtatattatc | cttatttgtg | gagtctccag | 360 |
| gtcaattgat | tcagaggatc | accgatgacc | ctgacgttag | cataaggctg | ttagaggttg | 420 |
| tccagagtga | ccagtcacaa | tctggcctta | ccttcgcatc | aagaggtacc | aacatggagg | 480 |
| atgaggcgga | ccaatacttt | tcacatgatg | atccaattag | tagtgatcaa | tccaggttcg | 540 |
| gatggttcgg | gaacaaggaa | atctcagata | ttgaagtgca | agaccctgag | ggattcaaca | 600 |
| tgattctggg | taccatccta | gcccaaattt | gggtcttgct | cgcaaaggcg | gttacggccc | 660 |
| cagacacggc | agctgattcg | gagctaagaa | ggtggataaa | gtacacccaa | caagaaggg | 720 |
| tagttggtga | atttagattg | gagagaaaat | ggttggatgt | ggtgaggaac | aggattgccg | 780 |
| aggacctctc | cttacgccga | ttcatggtcg | ctctaatcct | ggatatcaag | agaacacccg | 840 |
| gaaacaaacc | caggattgct | gaaatgatat | gtgacattga | tacatatatc | gtagaggcag | 900 |
| gattagccag | ttttatcctg | actattaagt | ttgggataga | aactatgtat | cctgctcttg | 960 |
| gactgcatga | atttgctggt | gagttatcca | cacttgagtc | cttgatgaac | ctttaccagc | 1020 |
| aaatggggga | aactgcaccc | tacatggtaa | tcctggagaa | ctcaattcag | aacaagttca | 1080 |
| gtgcaggatc | atacctctg | ctctggagct | atgccatggg | agtaggagtg | aacttgaaa | 1140 |
| actccatggg | aggtttgaac | tttgccgat | cttactttga | tccagcatat | tttagattag | 1200 |
| ggcaagagat | ggtaaggagg | tcagctggaa | aggtcagttc | cacattggca | tctgaactcg | 1260 |
| gtatcactgc | cgaggatgca | aggcttgttt | cagagattgc | aatgcatact | actgaggaca | 1320 |
| agatcagtag | agcggttgga | cccagacaag | cccaagtatc | atttctacac | ggtgatcaaa | 1380 |
| gtgagaatga | gctaccgaga | ttgggggca | aggaagatag | gagggtcaaa | cagagtcgag | 1440 |
| gagaagccag | ggagagctac | agagaaaccg | ggcccagcag | agcaagtgat | gcgagagctg | 1500 |
| cccatcttcc | aaccggcaca | cccctagaca | ttgacactgc | aacggagtcc | agccaagatc | 1560 |
| cgcaggacag | tcgaaggtca | gctgacgccc | tgcttaggct | gcaagccatg | gcaggaatct | 1620 |
| cggaagaaca | aggctcagac | acggacaccc | ctatagtgta | caatgacaga | aatcttctag | 1680 |
| actaggtgcg | agaggccgag | ggccagaaca | acatccgcct | accatccatc | attgttataa | 1740 |
| aaaacttagg | aaccaggtcc | acacagccgc | cagcccatca | accatccact | cccacgattg | 1800 |
| gagccaatgg | cagaagagca | ggcacgccat | gtcaaaaacg | gactggaatg | catccgggct | 1860 |
| ctcaaggccg | agcccatcgg | ctcactggcc | atcgaggaag | ctatggcagc | atggtcagaa | 1920 |
| atatcagaca | acccaggaca | ggagcgagcc | acctgcaggg | aagagaaggc | aggcagttcg | 1980 |

```
ggtctcagca aaccatgcct ctcagcaatt ggatcaactg aaggcggtgc acctcgcatc    2040
cgcggtcagg gacctggaga gagcgatgac gacgctgaaa ctttgggaat cccccccaaga   2100
aatctccagg catcaagcac tgggttacag tgttattacg tttatgatca cagcggtgaa    2160
gcggttaagg gaatccaaga tgctgactct atcatggttc aatcaggcct tgatggtgat    2220
agcaccctct caggaggaga caatgaatct gaaacagcg atgtggatat tggcgaacct     2280
gataccgagg gatatgctat cactgaccgg ggatctgctc ccatctctat ggggttcagg    2340
gcttctgatg ttgaaactgc agaaggaggg gagatccacg agctcctgag actccaatcc    2400
agaggcaaca actttccgaa gcttgggaaa actctcaatg ttcctccgcc cccggacccc    2460
ggtagggcca gcacttccgg gacacccatt aaaaagggca cagacgcgag attagcctca    2520
tttggaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aaggggggaga ctattatgat gatgagctgt tctctgatgt ccaagatatt   2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctgaagg cacctctca agcatcatga tcgccattcc tggacttggg      2940
aaggatccca acgaccccac tgcagatgtc gaaatcaatc ccgacttgaa acccatcata    3000
ggcagagatt caggccgagc actggccgaa gttctcaaga accccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt ttgttcctga caccggccct    3180
gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagcct accctccatc attgttataa aaacttagg aaccaggtcc     3420
acacagccgc cagcccatca acgcgtacga ccatgagcct gctgaccgag gtggaaacct    3480
acgtgctgag catcatcccc agcgggccctc tgaaggccga gatcgctcag cggctggaag   3540
atgtgttcgc cggcaagaac accgacctgg aagccctgat ggaatggctg aaaaccggc     3600
ccatcctgag cccccctgacc aagggcatcc tgggcttcgt gttcaccctg accgtgccct   3660
ctgagagagg cctgcagcgg agaagattcg tgcagaacgc cctgaacggc aacggcgacc    3720
ccaacaacat ggaccgggcc gtgaagctgt accggaagct gaagagagag atcaccttcc    3780
acggcgccaa agagatcgcc ctgagctact ctgctggcgc cctggcctct tgcatgggcc    3840
tgatctacaa ccggatgggc gccgtgacaa cagaggtggc cttttggcctc gtgtgcgcca   3900
catgcgagca gatcgccgac agccagcacc ggtcccacag acagatggtc accaccacca    3960
accccctgat ccggcacgag aacagaatgg tgctggcctc caccaccgcc aaggccatgg    4020
aacagatggc cggcagctct gagcaggccg ccgaagctat ggaagtggcc tctcaggccc    4080
ggcagatggt gcaggccatg agagccatcg gcacccaccc tagcagcagc accggcctga    4140
aggacgacct gctggaaaat ctgcaagctt accagaaaag aatgggcgtg cagatgcagc    4200
ggtttaagta atgacgagcg cgcagcgctt agacgtctcg cgatcgatac tagtacaacc    4260
taaatccatt ataaaaaact taggagcaaa gtgattgcct cccaaggtcc acaatgacag    4320
```

```
agacctacga cttcgacaag tcggcatggg acatcaaagg gtcgatcgct ccgatacaac    4380
ccaccaccta cagtgatggc aggctggtgc cccaggtcag agtcatagat cctggtctag    4440
gcgacaggaa ggatgaatgc tttatgtaca tgtttctgct gggggttgtt gaggacagcg    4500
attccctagg gcctccaatc gggcgagcat ttgggttcct gcccttaggt gttggcagat    4560
ccacagcaaa gcccgaaaaa ctcctcaaag aggccactga gcttgacata gttgttagac    4620
gtacagcagg gctcaatgaa aaactggtgt tctacaacaa cacccactc actctcctca    4680 caccttggag aaaggtccta acaacaggga gtgtcttcaa cgcaaaccaa gtgtgcaatg    4740
cggttaatct gataccgctc gatccccgc agaggttccg tgttgtttat atgagcatca    4800
cccgtctttc ggataacggg tattacaccg ttcctagaag aatgctggaa ttcagatcgg    4860
tcaatgcagt ggccttcaac ctgctggtga cccttaggat tgacaaggcg ataggccctg    4920
ggaagatcat cgacaataca gagcaacttc ctgaggcaac atttatggtc cacatcggga    4980
acttcaggag aaagaagagt gaagtctact ctgccgatta ttgcaaaatg aaaatcgaaa    5040
agatgggcct ggttttgca cttggtggga taggggcac cagtcttcac attagaagca    5100
caggcaaaat gagcaagact ctccatgcac aactcgggtt caagaagacc ttatgttacc    5160
cgctgatgga tatcaatgaa gaccttaatc gattactctg gaggagcaga tgcaagatag    5220
taagaatcca ggcagttttg cagccatcag ttcctcaaga attccgcatt tacgacgacg    5280
tgatcataaa tgatgaccaa ggactattca agttctgta ccgtagtg cccagcaatg    5340 cccgaaaacg accccctca caatgacagc cagaaggccc ggacaaaaaa gcccctccg    5400 aaagactcca cggaccaagc gagaggccag ccagcagccg acggcaagcg cgaacaccag    5460
gcggccccag cacagaacag ccctgacaca aggccaccac cagccacccc aatctgcatc    5520
ctcctcgtgg gaccccgag gaccaacccc caaggctgcc cccgatccaa accaccaacc    5580
gcatccccac cacccccggg aaagaaaccc ccagcaattg aaggcccct ccccctcttc    5640 ctcaacacaa gaactccaca accgaaccgc acaagcgacc gaggtgaccc aaccgcaggc    5700
atccgactcc ctagacagat cctctctccc cggcaaacta aacaaaactt agggccaagg    5760
aacatacaca cccaacagaa cccagacccc ggcccacggc gccgcgcccc caaccccga    5820 caaccagagg gagcccccaa ccaatcccgc cggctccccc ggtgcccaca ggcagggaca    5880 ccaaccccg aacagaccca gcacccaacc atcgacaatc caagacgggg gggcccccc    5940 aaaaaaaggc cccaggggc cgacagccag caccgcgagg aagcccaccc accccacaca    6000
cgaccacggc aaccaaacca gaacccagac caccctgggc caccagctcc cagactcggc    6060
catcaccccg cagaaaggaa aggccacaac ccgcgcaccc cagccccgat ccggcgggga    6120
gccacccaac ccgaaccagc acccaagagc gatccccgaa ggaccccccga accgcaaagg    6180 acatcagtat cccacagcct ctccaagtcc cccggtctcc tcctcttctc gaagggacca    6240
aaagatcaat ccaccacacc cgacgacact caactcccca cccctaaagg agacaccggg    6300
aatcccagaa tcaagactca tccaatgtcc atcatgggtc tcaaggtgaa cgtctctgcc    6360
atattcatgg cagtactgtt aactctccaa acacccaccg gtcaaatcca ttggggcaat    6420
ctctctaaga taggggtggt aggaatagga agtgcaagct acaaagttat gactcgttcc    6480
agccatcaat cattagtcat aaaattaatg cccaatataa ctctcctcaa taactgcacg    6540
agggtagaga ttgcagaata caggagacta ctgagaacag ttttggaacc aattagagat    6600
gcacttaatg caatgaccca gaatataaga ccggttcaga gtgtagcttc aagtaggaga    6660
cacaagagat ttgcgggagt agtcctggca ggtgcggccc taggcgttgc cacagctgct    6720
```

```
cagataacag ccggcattgc acttcaccag tccatgctga actctcaagc catcgacaat    6780
ctgagagcga gcctggaaac tactaatcag gcaattgaga caatcagaca agcagggcag    6840
gagatgatat tggctgttca gggtgtccaa gactacatca ataatgagct gataccgtct    6900
atgaaccaac tatcttgtga tttaatcggc cagaagctcg ggctcaaatt gctcagatac    6960
tatacagaaa tcctgtcatt atttggcccc agtttacggg accccatatc tgcggagata    7020
tctatccagg ctttgagcta tgcgcttgga ggagacatca ataaggtgtt agaaaagctc    7080
ggatacagtg gaggtgattt actgggcatc ttagagagcg aggaataaaa ggcccggata    7140
actcacgtcg acacagagtc ctacttcatt gtcctcagta tagcctatcc gacgctgtcc    7200
gagattaagg gggtgattgt ccaccggcta gaggggggtct cgtacaacat aggctctcaa    7260
gagtggtata ccactgtgcc caagtatgtt gcaacccaag ggtaccttat ctcgaatttt    7320
gatgagtcat cgtgtacttt catgccagag gggactgtgt gcagccaaaa tgccttgtac    7380
ccgatgagtc ctctgctcca agaatgcctc cgggggtaca ccaagtcctg tgctcgtaca    7440
ctcgtatccg ggtcttttgg gaaccggttc attttatcac aagggaacct aatagccaat    7500
tgtgcatcaa tcctttgcaa gtgttacaca acaggaacga tcattaatca agaccctgac    7560
aagatcctaa catacattgc tgccgatcac tgcccggtag tcgaggtgaa cggcgtgacc    7620
atccaagtcg ggagcaggag gtatccgacg gctgtgtact gcacagaat tgacctcggt    7680 cctcccatat cattggagag gttggacgta gggacaaatc tggggaatgc aattgctaag    7740
ttggaggatg ccaaggaatt gttggagtca tcggaccaga tattgaggag tatgaaaggt    7800
ttatcgagca ctagcatagt ctacatcctg attgcagtgt gtcttggagg ttgatagggg    7860
atccccgctt taatatgttg ctgcaggggg cgttgtaaca aaaagggaga acaagttggt    7920
atgtcaagac caggcctaaa gcctgatctt acgggaacat caaaatccta tgtaaggtcg    7980
ctctgatcct ctacaactct tgaaacacaa atgtcccaca agtctcctct tcgtcatcaa    8040
gcaaccaccg cacccagcat caagcccacc tgaaattatc tccggcttcc ctctggccga    8100
acaatatcgg tagttaatca aaacttaggg tgcaagatca tccacaatgt caccacaacg    8160
agaccggata aatgccttct acaaagataa ccccatccc aagggaagta ggatagtcat    8220
taacagagaa catcttatga ttgatagacc ttatgttttg ctggctgttc tgtttgtcat    8280
gtttctgagc ttgatcgggt tgctagccat tgcaggcatt agacttcatc gggcagccat    8340
ctacaccgca gagatccata aaagcctcag caccaatcta gatgtaacta actcaatcga    8400
gcatcaggtc aaggacgtgc tgacaccact cttcaaaatc atcggtgatg aagtgggcct    8460
gaggacacct cagagattca ctgacctagt gaaattaatc tctgacaaga ttaaattcct    8520
taatccggat agggagtacg acttcagaga tctcacttgg tgtatcaacc cgccagagag    8580
aatcaaattg gattatgatc aatactgtgc agatgtggct gctgaagagc tcatgaatgc    8640
attggtgaac tcaactctac tggagaccag aacaaccaat cagttcctag ctgtctcaaa    8700
gggaaactgc tcagggccca ctacaatcag aggtcaattc tcaaacatgt cgctgtccct    8760
gttagacttg tatttaggtc gaggttacaa tgtgtcatct atagtcacta tgacatccca    8820
gggaatgtat gggggaactt acctagtgga aaagcctaat ctgagcagca aaaggtcaga    8880
gttgtcacaa ctgagcatgt accgagtgtt tgaagtaggt gttatcagaa atccgggttt    8940
gggggctccg tgttccata tgacaaaacta tcttgagcaa ccagtcagta atgatctcag    9000
caactgtatg gtggctttgg gggagctcaa actcgcagcc ctttgtcacg gggaagattc    9060
```

```
tatcacaatt ccctatcagg gatcagggaa aggtgtcagc ttccagctcg tcaagctagg    9120
tgtctggaaa tccccaaccg acatgcaatc ctgggtcccc ttatcaacgg atgatccagt    9180
gatagacagg ctttacctct catctcacag aggtgttatc gctgacaatc aagcaaaatg    9240
ggctgtcccg acaacacgaa cagatgacaa gttgcgaatg gagacatgct tccaacaggc    9300
gtgtaagggt aaaatccaag cactctgcga gaatcccgag tgggcaccat tgaaggataa    9360
caggattcct tcatacgggg tcttgtctgt tgatctgagt ctgacagttg agcttaaaat    9420
caaaattgct tcgggattcg ggccattgat cacacacggt tcagggatgg acctatacaa    9480
atccaaccac aacaatgtgt attggctgac tatcccgcca atgaagaacc tagccttagg    9540
tgtaatcaac acattggagt ggataccgag attcaaggtt agtccctacc tcttcactgt    9600
cccaattaag gaagcaggcg aagactgcca tgccccaaca tacctacctg cggaggtgga    9660
tggtgatgtc aaactcagtt ccaatctggt gattctacct ggtcaagatc tccaatatgt    9720
tttggcaacc tacgatactt ccaggggttga acatgctgtg gtttattacg tttacagccc    9780
aagccgctca ttttcttact tttatccttt taggttgcct ataaagggg tccccatcga    9840
attacaagtg gaatgcttca catgggacca aaaactctgg tgccgtcact tctgtgtgct    9900
tgcggactca gaatctggtg gacatatcac tcactctggg atggtgggca tgggagtcag    9960
ctgcacagtc acccgggaag atggaaccaa tcgcagatag ggctgctagt gaaccaatca   10020
catgatgtca cccagacatc aggcataccc actagtgtga aatagacatc agaattaaga   10080
aaaacgtagg gtccaagtgg ttccccgtta tggactcgct atctgtcaac cagatcttat   10140
accctgaagt tcacctagat agcccgatag ttaccaataa gatagtagcc atcctggagt   10200
atgctcgagt ccctcacgct tacagcctgg aggaccctac actgtgtcag aacatcaagc   10260
accgcctaaa aaacggattt tccaaccaaa tgattataaa caatgtggaa gttgggaatg   10320
tcatcaagtc caagcttagg agttatccgg cccactctca tattccatat ccaaattgta   10380
atcaggattt atttaacata gaagacaaag agtcaacgag gaagatccgt gaactcctca   10440
aaagggggaa ttcgctgtac tccaaagtca gtgataaggt tttccaatgc ttaagggaca   10500
ctaactcacg gcttggccta ggctccgaat tgagggagga catcaaggag aaagttatta   10560
acttgggagt ttacatgcac agctcccagt ggtttgagcc cttctgtttt tggtttacag   10620
tcaagactga gatgaggtca gtgattaaat cacaaaccca tacttgccat aggaggagac   10680
acacacctgt attcttcact ggtagttcag ttgagttgct aatctctcgt gaccttgttg   10740
ctataatcag taaagagtct caacatgtat attacctgac atttgaactg gttttgatgt   10800
attgtgatgt catagagggg aggttaatga cagagaccgc tatgactatt gatgctaggt   10860
atacagagct tctaggaaga gtcagataca tgtggaaact gatagatggt ttcttccctg   10920
cactcgggaa tccaacttat caaattgtag ccatgctgga gcctctttca cttgcttacc   10980
tgcagctgag ggatataaca gtagaactca gaggtgcttt ccttaaccac tgctttactg   11040
aaatacatga tgttcttgac caaaacgggt tttctgatga aggtacttat catgagttaa   11100
ctgaagctct agattacatt ttcataactg atgacataca tctgacaggg gagattttct   11160
cattttcag aagtttcggc cacccccgac ttgaagcagt aacggctgct gaaaatgtta   11220
ggaaatacat gaatcagcct aaagtcattg tgtatgagac tctgatgaaa ggtcatgcca   11280
tattttgtgg aatcataatc aacggctatc gtgacaggca cggaggcagt tggccaccgc   11340
tgaccctccc cctgcatgct gcagacacaa tccggaatgc tcaagcttca ggtgaagggt   11400
taacacatga gcagtgcgtt gataactgga aatctttgc tggagtgaaa tttggctgct   11460
```

```
ttatgcctct tagcctggat agtgatctga caatgtacct aaaggacaag gcacttgctg    11520
ctctccaaag ggaatgggat tcagtttacc cgaaagagtt cctgcgttac gaccctccca    11580
agggaaccgg gtcacggagg cttgtagatg ttttccttaa tgattcgagc tttgacccat    11640
atgatgtgat aatgtatgtt gtaagtggag cttacctcca tgaccctgag ttcaacctgt    11700
cttacagcct gaaagaaaag gagatcaagg aaacaggtag acttttttgct aaaatgactt    11760
acaaaatgag ggcatgccaa gtgattgctg aaaatctaat ctcaaacggg attggcaaat    11820
attttaagga caatgggatg gccaaggatg agcacgattt gactaaggca ctccacactc    11880
tagctgtctc aggagtcccc aaagatctca agaaagtca cagggggggg ccagtcttaa    11940
aaacctactc ccgaagccca gtccacacaa gtaccaggaa cgtgagagca gcaaaagggt    12000
ttatagggtt ccctcaagta attcggcagg accaagacac tgatcatccg gagaatatgg    12060
aagcttacga gacagtcagt gcatttatca cgactgatct caagaagtac tgccttaatt    12120
ggagatatga gaccatcagc ttgtttgcac agaggctaaa tgagatttac ggattgccct    12180
cattttttcca gtggctgcat aagaggcttg agacctctgt cctgtatgta agtgaccctc    12240
attgccccccc cgaccttgac gcccatatcc cgttatataa agtccccaat gatcaaatct    12300
tcattaagta ccctatggga ggtatagaag ggtattgtca gaagctgtgg accatcagca    12360
ccattcccta tctataccctg gctgcttatg agagcggagt aaggattgct tcgttagtgc    12420
aaggggacaa tcagaccata gccgtaacaa aaagggtacc cagcacatgg ccctacaacc    12480
ttaagaaacg ggaagctgct agagtaacta gagattactt tgtaattctt aggcaaaggc    12540
tacatgatat tggccatcac ctcaaggcaa atgagacaat tgtttcatca catttttttg    12600
tctattcaaa aggaatatat tatgatgggc tacttgtgtc ccaatcactc aagagcatcg    12660
caagatgtgt attctggtca gagactatag ttgatgaaac aagggcagca tgcagtaata    12720
ttgctacaac aatggctaaa agcatcgaga gaggttatga ccgttacctt gcatattccc    12780
tgaacgtcct aaaagtgata cagcaaattc tgatctctct tggcttcaca atcaattcaa    12840
ccatgacccg ggatgtagtc atacccctcc tcacaaacaa cgacctctta ataaggatgg    12900
cactgttgcc cgctcctatt gggggggatga attatctgaa tatgagcagg ctgtttgtca    12960
gaaacatcgg tgatccagta acatcatcaa ttgctgatct caagagaatg attctcgcct    13020
cactaatgcc tgaagagacc ctccatcaag taatgacaca acaaccgggg gactcttcat    13080
tcctagactg ggctagcgac ccttactcag caaatcttgt atgtgtccag agcatcacta    13140
gactcctcaa gaacataact gcaaggtttg tcctgatcca tagtccaaac ccaatgttaa    13200
aaggattatt ccatgatgac agtaaagaag aggacgaggg actggcggca ttcctcatgg    13260
acaggcatat tatagtacct agggcagctc atgaaatcct ggatcatagt gtcacagggg    13320
caagagagtc tattgcaggc atgctggata ccacaaaagg cttgattcga ccagcatga    13380
ggaaggggggg gttaacctct cgagtgataa ccagattgtc caattatgac tatgaacaat    13440
tcagagcagg gatggtgcta ttgacaggaa gaaagagaaa tgtcctcatt gacaaagagt    13500
catgttcagt gcagctggcg agagctctaa gaagccatat gtgggcgagg ctagctcgag    13560
gacggcctat ttacggcctt gaggtccctg atgtactaga atctatgcga ggccacctta    13620
ttcggcgtca tgagacatgt gtcatctgcg agtgtggatc agtcaactac ggatggtttt    13680
ttgtccccctc gggttgccaa ctggatgata ttgacaagga aacatcatcc ttgagagtcc    13740
catatattgg ttctaccact gatgagagaa cagacatgaa gcttgccttc gtaagagccc    13800
```

```
caagtcgatc cttgcgatct gctgttagaa tagcaacagt gtactcatgg gcttacggtg    13860
atgatgatag ctcttggaac gaagcctggt tgttggctag gcaaagggcc aatgtgagcc    13920
tggaggagct aagggtgatc actcccatct caacttcgac taatttagcg cataggttga    13980
gggatcgtag cactcaagtg aaatactcag gtacatccct tgtccgagtg gcgaggtata    14040
ccacaatctc caacgacaat ctctcatttg tcatatcaga taagaaggtt gatactaact    14100
ttatatacca acaaggaatg cttctagggt tgggtgtttt agaaacattg tttcgactcg    14160
agaaagatac cggatcatct aacacggtat tacatcttca cgtcgaaaca gattgttgcg    14220
tgatcccgat gatagatcat cccaggatac ccagctcccg caagctagag ctgagggcag    14280
agctatgtac caacccattg atatatgata atgcaccttt aattgacaga gatgcaacaa    14340
ggctatacac ccagagccat aggaggcacc ttgtggaatt tgttacatgg tccacacccc    14400
aactatatca cattttagct aagtccacag cactatctat gattgacctg gtaacaaaat    14460
ttgagaagga ccatatgaat gaaatttcag ctctcatagg ggatgacgat atcaatagtt    14520
tcataactga gtttctgctc atagagccaa gattattcac tatctacttg ggccagtgtg    14580
cggccatcaa ttgggcattt gatgtacatt atcatagacc atcagggaaa tatcagatgg    14640
gtgagctgtt gtcatcgttc ctttctagaa tgagcaaagg agtgtttaag gtgcttgtca    14700
atgctctaag ccacccaaag atctacaaga aattctggca ttgtggtatt atagagccta    14760
tccatggtcc ttcacttgat gctcaaaact tgcacacaac tgtgtgcaac atggtttaca    14820
catgctatat gacctacctc gacctgttgt tgaatgaaga gttagaagag ttcacatttc    14880
tcttgtgtga aagcgacgag gatgtagtac cggacagatt cgacaacatc caggcaaaac    14940
acttatgtgt tctggcagat ttgtactgtc aaccagggac ctgcccacca attcgaggtc    15000
taagaccggt agagaaatgt gcagttctaa ccgaccatat caaggcagag gctatgttat    15060
ctccagcagg atcttcgtgg aacataaatc caattattgt agaccattac tcatgctctc    15120
tgacttatct ccggcgagga tcgatcaaac agataagatt gagagttgat ccaggattca    15180
ttttcgacgc cctcgctgag gtaaatgtca gtcagccaaa gatcggcagc aacaacatct    15240
caaatatgag catcaaggct ttcagacccc cacacgatga tgttgcaaaa ttgctcaaag    15300
atatcaacac aagcaagcac aatcttccca tttcaggggg caatctcgcc aattatgaaa    15360
tccatgcttt ccgcagaatc gggttgaact catctgcttg ctacaaagct gttgagatat    15420
caacattaat taggagatgc cttgagccag gggaggacgg cttgttcttg ggtgagggat    15480
cgggttctat gttgatcact tataaagaga tacttaaact aaacaagtgc ttctataata    15540
gtgggggttttc cgccaattct agatctggtc aaagggaatt agcaccctat ccctccgaag    15600
ttggccttgt cgaacacaga atgggagtag gtaatattgt caaagtgctc tttaacggga    15660
ggcccgaagt cacgtgggta ggcagtgtag attgcttcaa tttcatagtt agtaatatcc    15720
ctacctctag tgtgggggttt atccattcag atatagagac cttgcctgac aaagatacta    15780
tagagaagct agaggaattg gcagccatct tatcgatggc tctgctcctg ggcaaaatag    15840
gatcaatact ggtgattaag cttatgcctt tcagcgggga ttttgttcag ggatttataa    15900
gttatgtagg gtctcattat agagaagtga accttgtata ccctagatac agcaacttca    15960
tctctactga atcttatttg gttatgacag atctcaaggc taaccggcta atgaatcctg    16020
aaaagattaa gcagcagata attgaatcat ctgtgaggac ttcacctgga cttataggtc    16080
acatcctatc cattaagcaa ctaagctgca tacaagcaat tgtgggagac gcagttagta    16140
gaggtgatat caatcctact ctgaaaaaac ttacacctat agagcaggtg ctgatcaatt    16200
```

```
gcgggttggc aattaacgga cctaagctgt gcaaagaatt gatccaccat gatgttgcct   16260
cagggcaaga tggattgctt aattctatac tcatcctcta cagggagttg gcaagattca   16320
aagacaacca aagaagtcaa caagggatgt tccacgctta ccccgtattg gtaagtagca   16380
ggcaacgaga acttatatct aggatcaccc gcaaattctg ggggcacatt cttctttact   16440
ccgggaacaa aaagttgata aataagttta tccagaatct caagtccggc tatctgatac   16500
tagacttaca ccagaatatc ttcgttaaga atctatccaa gtcagagaaa cagattatta   16560
tgacgggggg tttgaaacgt gagtgggttt taaggtaac agtcaaggag accaaagaat    16620
ggtataagtt agtcggatac agtgccctga ttaaggacta attggttgaa ctccggaacc   16680
ctaatcctgc cctaggtggt taggcattat ttgcaatata ttaaagaaaa ctttgaaaat   16740
acgaagtttc tattcccagc tttgtctggt ggccggcatg gtcccagcct cctcgctggc   16800
gccggctggg caacattccg aggggaccgt cccctcggta atggcgaatg ggacgcggcc   16860
gatccggctg ctaacaaagc ccgaaaggaa gctgagttgg ctgctgccac cgctgagcaa   16920
taactagcat aaccccttgg ggcctctaaa cgggtcttga ggggtttttt gctgaaagga   16980
ggaactatat ccggatgcgg ccgcgggccc tatggtaccc agcttttgtt ccctttagtg   17040
agggttaatt ccgagcttgg cgtaatcatg gtcatagctg tttcctgtgt gaaattgtta   17100
tccgctcaca attccacaca acataggagc cggaagcata aagtgtaaag cctggggtgc   17160
ctaatgagtg aggtaactca cattaattgc gttgcgctca ctgcccgctt tccagtcggg   17220
aaacctgtcg tgccagctgc attaatgaat cggccaacgc gcggggagag gcggtttgcg   17280
tattgggcgc tcttccgctt cctcgctcac tgactcgctg cgctcggtcg ttcggctgcg   17340
gcgagcggta tcagctcact caaaggcggt aatacggtta ccacagaat cagggqataa    17400
cgcaggaaag aacatgtgag caaaaggcca gcaaaggcc aggaaccgta aaaaggccgc     17460
gttgctggcg tttttccata ggctcggccc ccctgacgag catcacaaaa atcgacgctc   17520
aagtcagagg tggcgaaacc cgacaggact ataaagatac caggcgttcc ccctggaag    17580
ctccctcgtg cgctctcctg ttccgaccct gccgcttacc ggatacctgt ccgcctttct   17640
cccttcggga agcgtggcgc tttctcaatg ctcacgctgt aggtatctca gttcggtgta   17700
ggtcgttcgc tccaagctgg gctgtgtgca cgaaccccccg ttcagcccg accgctgcgc    17760
cttatccggt aactatcgtc ttgagtccaa cccggtaaga cacgacttat cgccactggc   17820
agcagccact ggtaacagga ttagcagagc gaggtatgta ggcggtgcta cagagttctt   17880
gaagtggtgg cctaactacg gctacactag aaggacagta tttggtatct gcgctctgct   17940
gaagccagtt accttcggaa aaagagttgg tagctcttga tccggcaaac aaaccaccgc   18000
tggtagcggt ggttttttg tttgcaagca gcagattacg cgcagaaaaa aaggatctca    18060
agaagatcct ttgatctttt ctacggggtc tgacgctcag tggaacgaaa actcacgtta   18120
agggattttg gtcatgagat tatcaaaaag gatcttcacc tagatccttt taaattaaaa   18180
atgaagtttt aaatcaatct aaagtatata tgagtaaact tggtctgaca gttaccaatg   18240
cttaatcagt gaggcaccta tctcagcgat ctgtctattt cgttcatcca tagttgcctg   18300
actgcccgtc gtgtagataa ctacgatacg ggagggctta ccatctggcc ccagtgctgc   18360
aatgataccg cgagacccac gctcaccggc tccagattta tcagcaataa accagccagc   18420
cggaagggcc gagcgcagaa gtggtcctgc aactttatcc gcctccatcc agtctattaa   18480
ttgttgccgg gaagctagag taagtagttc gccagttaat agtttgcgca acgttgttgc   18540
```

```
cattgctaca ggcatcgtgg tgtcacgctc gtcgtttggt atggcttcat tcagctccgg  18600
ttcccaacga tcaaggcgag ttacatgatc ccccatgttg tgaaaaaaag cggttagctc  18660
cttcggtcct ccgatcgttg tcagaagtaa gttggccgca gtgttatcac tcatgcttat  18720
ggcagcactg cataattctc ttactgtcat gccatccgta agatgctttt ctgtgactgg  18780
tgagtactca accaagtcat tctgagaata gtgtatgcgg cgaccgagtt gctcttgccc  18840
ggcgtcaata cgggataata ccgcgccaca tagcagaact ttaaaagtgc tcatcattgg  18900
aaaacgttct tcggggcgaa aactctcaag gatcttaccg ctgttgagat ccagttcgat  18960
gtaacccact cgtgcaccca actgatcttc agcatctttt actttcacca gcgtttctgg  19020
gtgagcaaaa acaggaaggc aaaatgccgc aaaaaaggga ataagggcga cacggaaatg  19080
ttgaatactc atactcttcc tttttcaata ttattgaagc atttatcagg gttattgtct  19140
catgagcgga tacatatttg aatgtattta gaaaaataaa caaatagggg ttccgcgcac  19200
atttccccga aaagtgccac ctgaaattgt aaacgttaat attttgttaa aattcgcgtt  19260
aaatttttgt taaatcagct cattttttaa ccaataggcc gaaatcggca aaatccctta  19320
taaatcaaaa gaatagaccg agatagggtt gagtgttgtt ccagtttgga acaagagtcc  19380
actattaaag aacgtggact ccaacgtcaa agggcgaaaa accgtctatc agggcgatgg  19440
cccactacgt gaaccatcac cctaatcaag ttttttgggg tcgaggtgcc gtaaagcact  19500
aaatcggaac cctaaaggga gcccccgatt tagagcttga cggggaaagc cggcgaacgt  19560
ggcgagaaag gaagggaaga aagcgaaagg agcgggcgct agggcgctgg caagtgtagc  19620
ggtcacgctg cgcgtaacca ccacacccgc cgcgcttaat gcgccgctac agggcgcgtc  19680
ccattcgcca ttcaggctgc gcaactgttg ggaagggcga tcggtgcggg cctcttcgct  19740
attacgccag ccaccgcggt ggcggccgct aatacgactc actatagggc caactttgtt  19800
tggtctgatg agtccgtgag gacgaaaccc ggagtcccgg gtc                   19843
```

<210> SEQ ID NO 8
<211> LENGTH: 19375
<212> TYPE: DNA
<213> ORGANISM: Artificial Sequence
<220> FEATURE:
<223> OTHER INFORMATION: pTM-MV-ATU3-M2opt
<220> FEATURE:
<221> NAME/KEY: misc_RNA
<222> LOCATION: (1)..(16302)
<223> OTHER INFORMATION: MV-ATU3-M2opt_antigenome
<220> FEATURE:
<221> NAME/KEY: misc_feature
<222> LOCATION: (9176)..(9583)
<223> OTHER INFORMATION: ATU3
<220> FEATURE:
<221> NAME/KEY: misc_feature
<222> LOCATION: (9246)..(9251)
<223> OTHER INFORMATION: BsiWI restriction site
<220> FEATURE:
<221> NAME/KEY: misc_feature
<222> LOCATION: (9255)..(9551)
<223> OTHER INFORMATION: ORF for M2 consensus protein : M2opt
<220> FEATURE:
<221> NAME/KEY: misc_feature
<222> LOCATION: (9552)..(9557)
<223> OTHER INFORMATION: BssHII restriction site
<220> FEATURE:
<221> NAME/KEY: misc_feature
<222> LOCATION: (16303)..(19375)
<223> OTHER INFORMATION: plasmid_backbone

<400> SEQUENCE: 8

```
accaaacaaa gttgggtaag gatagttcaa tcaatgatca tcttctagtg cacttaggat     60
```

-continued

```
tcaagatcct attatcaggg acaagagcag gattagggat atccgagatg ccacacttt     120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtgaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag tttatcctg actattaagt ttgggataga aactatgtat cctgctcttg     960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc atacctctg ctctggagct atgccatggg agtaggagtg aacttgaaa    1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggca aggaagatag gagggtcaaa cagagtcgag   1440
gagaagccag ggagagctac agagaaaccg ggcccagcag agcaagtgat gcgagagctg   1500
cccatcttcc aaccggcaca ccctagaca ttgacactgc aacggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga atcttctag   1680
actaggtgcg agaggccgag ggccagaaca acatccgcct accatccatc attgttataa   1740
aaaacttagg aaccaggtcc acacagccgc cagcccatca accatccact cccacgattg   1800
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat cccccaaga   2100
aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
```

```
agaggcaaca actttccgaa gcttgggaaa actctcaatg ttcctccgcc cccggacccc    2460
ggtagggcca gcacttccgg gacacccatt aaaaagggca cagacgcgag attagcctca    2520
tttggaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aagggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg cacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt tgttcctga caccggccct    3180 gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagtac aacctaaatc cattataaaa aacttaggag caaagtgatt    3420
gcctcccaag gtccacaatg acagagacct acgacttcga caagtcggca tgggacatca    3480
aagggtcgat cgctccgata caacccacca cctacagtga tggcaggctg gtgccccagg    3540
tcagagtcat agatcctggt ctaggcgaca ggaaggatga atgctttatg tacatgtttc    3600
tgctgggggt tgttgaggac agcgattccc tagggcctcc aatcgggcga gcatttgggt    3660
tcctgccctt aggtgttggc agatccacag caaagcccga aaaactcctc aaagaggcca    3720
ctgagcttga catagttgtt agacgtacag cagggctcaa tgaaaaactg gtgttctaca    3780
acaacacccc actaactctc ctcacacctt ggagaaaggt cctaacaaca gggagtgtct    3840
tcaacgcaaa ccaagtgtgc aatgcggtta atctgatacc gctcgatacc ccgcagaggt    3900
tccgtgttgt ttatatgagc atcacccgtc tttcggataa cgggtattac accgttccta    3960
gaagaatgct ggaattcaga tcggtcaatg cagtggcctt caacctgctg gtgacccta    4020 ggattgacaa ggcgataggc cctgggaaga tcatcgacaa tacagagcaa cttcctgagg    4080
caacatttat ggtccacatc gggaacttca ggagaaagaa gagtgaagtc tactctgccg    4140
attattgcaa aatgaaaatc gaaaagatgg gcctggtttt tgcacttggt gggataggg    4200 gcaccagtct tcacattaga agcacaggca aaatgagcaa gactctccat gcacaactcg    4260
ggttcaagaa gaccttatgt tacccgctga tggatatcaa tgaagacctt aatcgattac    4320
tctggaggag cagatgcaag atagtaagaa tccaggcagt tttgcagcca tcagttcctc    4380
aagaattccg catttacgac gacgtgatca taaatgatga ccaaggacta ttcaaagttc    4440
tgtagaccgt agtgcccagc aatgcccgaa acgaccccc ctcacaatga cagccagaag    4500
gcccggacaa aaaagccccc tccgaaagac tccacggacc aagcgagagg ccagccagca    4560
gccgacggca agcgcgaaca ccaggcggcc ccagcacaga acagccctga cacaaggcca    4620
ccaccagcca ccccaatctg catcctcctc gtgggacccc cgaggaccaa ccccaaggc    4680 tgcccccgat ccaaaccacc aaccgcatcc ccaccacccc cggaaagaa accccagca    4740 attggaaggc ccctccccct cttcctcaac acaagaactc cacaaccgaa ccgcacaagc    4800
```

```
gaccgaggtg acccaaccgc aggcatccga ctccctagac agatcctctc tccccggcaa    4860
actaaacaaa acttagggcc aaggaacata cacacccaac agaacccaga ccccggccca    4920
cggcgccgcg cccccaaccc ccgacaacca gagggagccc ccaaccaatc ccgccggctc    4980
ccccggtgcc cacaggcagg gacaccaacc cccgaacaga cccagcaccc aaccatcgac    5040
aatccaagac ggggggggccc ccccaaaaaa aggcccccag gggccgacag ccagcaccgc    5100
gaggaagccc acccacccca cacacgacca cggcaaccaa accagaaccc agaccaccct    5160
gggccaccag ctcccagact cggccatcac cccgcagaaa ggaaaggcca aacccgcgc     5220 accccagccc cgatccggcg gggagccacc caacccgaac cagcacccaa gagcgatccc    5280
cgaaggaccc ccgaaccgca aaggacatca gtatcccaca gcctctccaa gtccccggt    5340 ctcctcctct tctcgaaggg accaaaagat caatccacca cacccgacga cactcaactc    5400 cccacccta aaggagacac cgggaatccc agaatcaaga ctcatccaat gtccatcatg    5460
ggtctcaagg tgaacgtctc tgccatattc atggcagtac tgttaactct ccaaacaccc    5520
accggtcaaa tccattgggg caatctctct aagatagggg tggtaggaat aggaagtgca    5580
agctacaaag ttatgactcg ttccagccat caatcattag tcataaaatt aatgcccaat    5640
ataactctcc tcaataactg cacgagggta gagattgcag aatacaggag actactgaga    5700
acagttttgg aaccaattag agatgcactt aatgcaatga cccagaatat aagaccggtt    5760
cagagtgtag cttcaagtag gagacacaag agatttgcgg gagtagtcct ggcaggtgcg    5820
gccctaggcg ttgccacagc tgctcagata acagccggca ttgcacttca ccagtccatg    5880
ctgaactctc aagccatcga caatctgaga gcgagcctgg aaactactaa tcaggcaatt    5940
gagacaatca gacaagcagg gcaggagatg atattggctg ttcagggtgt ccaagactac    6000
atcaataatg agctgatacc gtctatgaac caactatctt gtgatttaat cggccagaag    6060
ctcgggctca aattgctcag atactataca gaaatcctgt cattatttgg ccccagttta    6120
cgggacccca tatctgcgga gatatctatc caggctttga gctatgcgct tggaggagac    6180
atcaataagg tgttagaaaa gctcggatac agtggaggtg atttactggg catcttagag    6240
agcggaggaa taaaggcccg gataactcac gtcgacacag agtcctactt cattgtcctc    6300
agtatagcct atccgacgct gtccgagatt aaggggtga ttgtccaccg gctagagggg    6360
gtctcgtaca acataggctc tcaagagtgg tataccactg tgcccaagta tgttgcaacc    6420
caagggtacc ttatctcgaa ttttgatgag tcatcgtgta ctttcatgcc agagggact     6480 gtgtgcagcc aaaaatgcct tgtacccgatg agtcctctgc tccaagaatg cctccggggg    6540
tacaccaagt cctgtgctcg tacactcgta tccgggtctt ttgggaaccg gttcatttta    6600
tcacaaggga acctaatagc caattgtgca tcaatccttt gcaagtgtta cacaacagga    6660
acgatcatta tcaagaccc tgacaagatc ctaacataca ttgctgccga tcactgcccg    6720
gtagtcgagg tgaacggcgt gaccatccaa gtcgggagca ggaggtatcc agacgctgtg    6780
tacttgcaca gaattgacct cggtcctccc atatcattgg agaggttgga cgtagggaca    6840
aatctgggga atgcaattgc taagttggag gatgccaagg aattgttgga gtcatcggac    6900
cagatattga ggagtatgaa aggtttatcg agcactagca tagtctacat cctgattgca    6960
gtgtgtcttg gagggttgat agggatcccc gctttaatat gttgctgcag ggggcgttgt    7020
aacaaaaagg gagaacaagt tggtatgtca agaccaggcc taaagcctga tcttacggga    7080
acatcaaaat cctatgtaag gtcgctctga tcctctacaa ctcttgaaac acaaatgtcc    7140
```

```
cacaagtctc ctcttcgtca tcaagcaacc accgcaccca gcatcaagcc cacctgaaat   7200
tatctccggc ttccctctgg ccgaacaata tcggtagtta atcaaaactt agggtgcaag   7260
atcatccaca atgtcaccac aacgagaccg gataaatgcc ttctacaaag ataacccca   7320 tcccaaggga agtaggatag tcattaacag agaacatctt atgattgata gaccttatgt   7380
tttgctggct gttctgtttg tcatgtttct gagcttgatc gggttgctag ccattgcagg   7440
cattagactt catcgggcag ccatctacac cgcagagatc cataaaagcc tcagcaccaa   7500
tctagatgta actaactcaa tcgagcatca ggtcaaggac gtgctgacac cactcttcaa   7560
aatcatcggt gatgaagtgg gcctgaggac acctcagaga ttcactgacc tagtgaaatt   7620
aatctctgac aagattaaat tccttaatcc ggatagggag tacgacttca gagatctcac   7680
ttggtgtatc aacccgccag agagaatcaa attggattat gatcaatact gtgcagatgt   7740
ggctgctgaa gagctcatga atgcattggt gaactcaact ctactggaga ccagaacaac   7800
caatcagttc ctagctgtct caaagggaaa ctgctcaggg cccactacaa tcagaggtca   7860
attctcaaac atgtcgctgt ccctgttaga cttgtattta ggtcgaggtt acaatgtgtc   7920
atctatagtc actatgacat cccagggaat gtatggggga acttacctag tggaaaagcc   7980
taatctgagc agcaaaaggt cagagttgtc acaactgagc atgtaccgag tgtttgaagt   8040
aggtgttatc agaaatccgg gtttgggggc tccggtgttc catatgacaa actatcttga   8100
gcaaccagtc agtaatgatc tcagcaactg tatggtggct ttgggggagc tcaaactcgc   8160 agcccttttgt cacggggaag attctatcac aattccctat cagggatcag ggaaaggtgt   8220
cagcttccag ctcgtcaagc taggtgtctg gaaatcccca accgacatgc aatcctgggt   8280
ccccttatca acggatgatc cagtgataga caggctttac ctctcatctc acagaggtgt   8340
tatcgctgac aatcaagcaa aatgggctgt cccgacaaca cgaacagatg acaagttgcg   8400
aatggagaca tgcttccaac aggcgtgtaa gggtaaaatc caagcactct gcgagaatcc   8460
cgagtgggca ccattgaagg ataacaggat tccttcatac ggggtcttgt ctgttgatct   8520
gagtctgaca gttgagctta aaatcaaaat tgcttcggga ttcgggccat tgatcacaca   8580
cggttcaggg atggacctat acaaatccaa ccacaacaat gtgtattggc tgactatccc   8640
gccaatgaag aacctagcct taggtgtaat caacacattg gagtggatac cgagattcaa   8700
ggttagtccc tacctcttca ctgtcccaat taaggaagca ggcgaagact gccatgcccc   8760 aacatacccta cctgcggagg tggatggtga tgtcaaactc agttccaatc tggtgattct   8820
acctggtcaa gatctccaat atgttttggc aacctacgat acttccaggg ttgaacatgc   8880
tgtggtttat tacgtttaca gcccaagccg ctcatttttct tacttttatc cttttaggtt   8940
gcctataaag ggggtccca tcgaattaca agtggaatgc ttcacatggg accaaaaact   9000
ctggtgccgt cacttctgtg tgcttgcgga ctcagaatct ggtggacata tcactcactc   9060
tgggatggtg ggcatgggag tcagctgcac agtcacccgg gaagatggaa ccaatcgcag   9120 ataggctgc tagtgaacca atcacatgat gtcacccaga catcaggcat acccactagt   9180
ctaccctcca tcattgttat aaaaaactta ggaaccaggt ccacacagcc gccagcccat   9240
caacgcgtac gaccatgagc ctgctgaccg aggtggaaac ccccatcaga acgagtgggg   9300
gctgccggtg caacgacagc agcgatcctc tggtggtggc cgccagcatc atcggcatcc   9360
tgcacctgat cctgtggatt ctggaccggc tgttcttcaa gtgcatctac agactgttca   9420
agcacggcct gaagagaggc cccagcacag aaggcgtgcc cgagagcatg cgggaagagt   9480
accggaaaga acagcagaac gccgtggacg ccgacgacag ccacttcgtg tccatcgagc   9540
```

```
tggaatgata agcgcgcagc gcttagacgt ctcgcgatcg atgctagtgt gaaatagaca    9600
tcagaattaa gaaaaacgta gggtccaagt ggttccccgt tatggactcg ctatctgtca    9660
accagatctt ataccctgaa gttcacctag atagcccgat agttaccaat aagatagtag    9720
ccatcctgga gtatgctcga gtccctcacg cttacagcct ggaggaccct acactgtgtc    9780
agaacatcaa gcaccgccta aaaaacggat tttccaacca aatgattata aacaatgtgg    9840
aagttgggaa tgtcatcaag tccaagctta ggagttatcc ggcccactct catattccat    9900
atccaaattg taatcaggat ttatttaaca tagaagacaa agagtcaacg aggaagatcc    9960
gtgaactcct caaaaggggg aattcgctgt actccaaagt cagtgataag gttttccaat   10020
gcttaaggga cactaactca cggcttggcc taggctccga attgagggag gacatcaagg   10080
agaaagttat taacttggga gtttacatgc acagctccca gtggtttgag ccctttctgt   10140
tttggtttac agtcaagact gagatgaggt cagtgattaa atcacaaacc catacttgcc   10200
ataggaggag acacacacct gtattcttca ctggtagttc agttgagttg ctaatctctc   10260
gtgaccttgt tgctataatc agtaaagagt ctcaacatgt atattacctg acatttgaac   10320
tggttttgat gtattgtgat gtcatagagg ggaggttaat gacagagacc gctatgacta   10380
ttgatgctag gtatacagag cttctaggaa gagtcagata catgtggaaa ctgatagatg   10440
gtttcttccc tgcactcggg aatccaactt atcaaattgt agccatgctg gagcctcttt   10500
cacttgctta cctgcagctg agggatataa cagtagaact cagaggtgct ttccttaacc   10560
actgctttac tgaaatacat gatgttcttg accaaaacgg gttttctgat gaaggtactt   10620
atcatgagtt aactgaagct ctagattaca ttttcataac tgatgacata catctgacag   10680
gggagatttt ctcattttc agaagtttcg gccaccccag acttgaagca gtaacggctg   10740
ctgaaaatgt taggaaatac atgaatcagc ctaaagtcat tgtgtatgag actctgatga   10800
aaggtcatgc catattttgt ggaatcataa tcaacggcta tcgtgacagg cacggaggca   10860
gttggccacc gctgaccctc cccctgcatg ctgcagacac aatccggaat gctcaagctt   10920
caggtgaagg gttaacacat gagcagtgcg ttgataactg gaaatctttt gctggagtga   10980
aatttggctg ctttatgcct cttagcctgg atagtgatct gacaatgtac ctaaaggaca   11040
aggcacttgc tgctctccaa agggaatggg attcagttta cccgaaagag ttcctgcgtt   11100
acgaccctcc caagggaacc gggtcacgga ggcttgtaga tgttttcctt aatgattcga   11160
gctttgaccc atatgatgtg ataatgtatg ttgtaagtgg agcttacctc catgaccctg   11220
agttcaacct gtcttacagc ctgaaagaaa aggagatcaa ggaaacaggt agactttttg   11280
ctaaaatgac ttacaaaatg agggcatgcc aagtgattgc tgaaaatcta atctcaaacg   11340
ggattggcaa atattttaag gacaatggga tggccaagga tgagcacgat ttgactaagg   11400
cactccacac tctagctgtc tcaggagtcc ccaaagatct caaagaaagt cacagggggg   11460
ggccagtctt aaaaacctac tcccgaagcc cagtccacac aagtaccagg aacgtgagag   11520
cagcaaaagg gtttataggg ttccctcaag taattcggca ggaccaagac actgatcatc   11580
cggagaatat ggaagcttac gagacagtca gtgcatttat cacgactgat ctcaagaagt   11640
actgccttaa ttggagatat gagaccatca gcttgttttgc acagaggcta aatgagtttt   11700
acggattgcc ctcattttc cagtggctgc ataagaggct tgagacctct gtcctgtatg   11760
taagtgaccc tcattgcccc cccgacctttg acgcccatat cccgttatat aaagtcccca   11820
atgatcaaat cttcattaag taccctatgg gaggtataga agggtattgt cagaagctgt   11880
```

```
ggaccatcag caccattccc tatctatacc tggctgctta tgagagcgga gtaaggattg    11940
cttcgttagt gcaagggggac aatcagacca tagccgtaac aaaaagggta cccagcacat    12000
ggccctacaa ccttaagaaa cgggaagctg ctagagtaac tagagattac tttgtaattc    12060
ttaggcaaag gctacatgat attggccatc acctcaaggc aaatgagaca attgtttcat    12120 cacattttt tgtctattca aaaggaatat attatgatgg gctacttgtg tcccaatcac    12180
tcaagagcat cgcaagatgt gtattctggt cagagactat agttgatgaa acaagggcag    12240
catgcagtaa tattgctaca acaatggcta aaagcatcga gagaggttat gaccgttacc    12300
ttgcatattc cctgaacgtc ctaaaagtga tacagcaaat tctgatctct cttggcttca    12360
caatcaattc aaccatgacc cgggatgtag tcataccct cctcacaaac aacgacctct    12420
taataaggat ggcactgttg cccgctccta ttgggggggat gaattatctg aatatgagca    12480
ggctgtttgt cagaaacatc ggtgatccag taacatcatc aattgctgat ctcaagagaa    12540
tgattctcgc ctcactaatg cctgaagaga ccctccatca agtaatgaca caacaaccgg    12600
gggactcttc attcctagac tgggctagcg acccttactc agcaaatctt gtatgtgtcc    12660
agagcatcac tagactcctc aagaacataa ctgcaaggtt tgtcctgatc catagtccaa    12720
acccaatgtt aaaaggatta ttccatgatg acagtaaaga agaggacgag ggactggcgg    12780
cattcctcat ggacaggcat attatagtac ctagggcagc tcatgaaatc ctggatcata    12840
gtgtcacagg ggcaagagag tctattgcag gcatgctgga taccacaaaa ggcttgattc    12900
gagccagcat gaggaagggg gggttaacct ctcgagtgat aaccagattg tccaattatg    12960
actatgaaca attcagagca gggatggtgc tattgacagg aagaaagaga atgtcctca    13020 ttgacaaaga gtcatgttca gtgcagctgg cgagagctct aagaagccat atgtgggcga    13080
ggctagctcg aggacggcct atttacggcc ttgaggtccc tgatgtacta aatctatgc    13140 gaggccacct tattcggcgt catgagacat gtgtcatctg cgagtgtgga tcagtcaact    13200
acggatggtt ttttgtcccc tcgggttgcc aactggatga tattgacaag gaaacatcat    13260
ccttgagagt cccatatatt ggttctacca ctgatgagag aacagacatg aagcttgcct    13320
tcgtaagagc cccaagtcga tccttgcgat ctgctgttag aatagcaaca gtgtactcat    13380
gggcttacgg tgatgatgat agctcttgga acgaagcctg gttgttggct aggcaaaggg    13440
ccaatgtgag cctggaggag ctaagggtga tcactcccat ctcaacttcg actaatttag    13500
cgcataggtt gagggatcgt agcactcaag tgaaatactc aggtacatcc cttgtccgag    13560
tggcgaggta taccacaatc tccaacgaca atctctcatt tgtcatatca gataagaagg    13620
ttgatactaa ctttatatac caacaaggaa tgcttctagg gttgggtgtt ttagaaacat    13680
tgtttcgact cgagaaagat accggatcat ctaacacggt attacatctt cacgtcgaaa    13740
cagattgttg cgtgatcccg atgatagatc atcccaggat acccagctcc cgcaagctag    13800
agctgagggc agagctatgt accaacccat tgatatatga taatgcacct ttaattgaca    13860
gagatgcaac aaggctatac acccagagcc ataggaggca ccttgtggaa tttgttacat    13920
ggtccacacc ccaactatat cacatttag ctaagtccac agcactatct atgattgacc    13980
tggtaacaaa atttgagaag gaccatatga atgaaatttc agctctcata ggggatgacg    14040
atatcaatag tttcataact gagtttctgc tcatagagcc aagattattc actatctact    14100
tgggccagtg tgcggccatc aattgggcat ttgatgtaca ttatcataga ccatcaggga    14160
aatatcagat gggtgagctg ttgtcatcgt tcctttctag aatgagcaaa ggagtgttta    14220
aggtgcttgt caatgctcta agccacccca agatctacaa gaaattctgg cattgtggta    14280
```

```
ttatagagcc tatccatggt ccttcacttg atgctcaaaa cttgcacaca actgtgtgca   14340
acatggttta cacatgctat atgacctacc tcgacctgtt gttgaatgaa gagttagaag   14400
agttcacatt tctcttgtgt gaaagcgacg aggatgtagt accggacaga ttcgacaaca   14460
tccaggcaaa acacttatgt gttctggcag atttgtactg tcaaccaggg acctgcccac   14520
caattcgagg tctaagaccg gtagagaaat gtgcagttct aaccgaccat atcaaggcag   14580
aggctatgtt atctccagca ggatcttcgt ggaacataaa tccaattatt gtagaccatt   14640
actcatgctc tctgacttat ctccggcgag gatcgatcaa acagataaga ttgagagttg   14700
atccaggatt cattttcgac gccctcgctg aggtaaatgt cagtcagcca agatcggca   14760
gcaacaacat ctcaaatatg agcatcaagg ctttcagacc cccacacgat gatgttgcaa   14820
aattgctcaa agatatcaac acaagcaagc acaatcttcc catttcaggg ggcaatctcg   14880
ccaattatga aatccatgct ttccgcagaa tcgggttgaa ctcatctgct tgctacaaag   14940
ctgttgagat atcaacatta attaggagat gccttgagcc aggggaggac ggcttgttct   15000
tgggtgaggg atcgggttct atgttgatca cttataaaga gatacttaaa ctaaacaagt   15060
gcttctataa tagtggggtt tccgccaatt ctagatctgg tcaaagggaa ttagcaccct   15120
atccctccga agttggcctt gtcgaacaca gaatgggagt aggtaatatt gtcaaagtgc   15180
tctttaacgg gaggcccgaa gtcacgtggg taggcagtgt agattgcttc aatttcatag   15240
ttagtaatat ccctacctct agtgtggggt ttatccattc agatatagag accttgcctg   15300
acaaagatac tatagagaag ctagaggaat tggcagccat cttatcgatg gctctgctcc   15360
tgggcaaaat aggatcaata ctggtgatta agcttatgcc tttcagcggg gattttgttc   15420
agggatttat aagttatgta gggtctcatt atagagaagt gaaccttgta taccctagat   15480
acagcaactt catctctact gaatcttatt tggttatgac agatctcaag gctaaccggc   15540
taatgaatcc tgaaaagatt aagcagcaga taattgaatc atctgtgagg acttcacctg   15600
gacttatagg tcacatccta tccattaagc aactaagctg catacaagca attgtgggag   15660
acgcagttag tagaggtgat atcaatccta ctctgaaaaa acttacacct atagagcagg   15720
tgctgatcaa ttgcgggttg gcaattaacg gacctaagct gtgcaaagaa ttgatccacc   15780
atgatgttgc ctcagggcaa gatggattgc ttaattctat actcatcctc tacagggagt   15840
tggcaagatt caaagacaac caaagaagtc aacaagggat gttccacgct taccccgtat   15900
tggtaagtag caggcaacga gaacttatat ctaggatcac ccgcaaattc tgggggcaca   15960
ttcttctttta ctccgggaac aaaaagttga taaataagtt tatccagaat ctcaagtccg   16020
gctatctgat actagactta caccagaata tcttcgttaa gaatctatcc aagtcagaga   16080
aacagattat tatgacgggg ggtttgaaac gtgagtgggg ttttaaggta acagtcaagg   16140
agaccaaaga atggtataag ttagtcggat acagtgccct gattaaggac taattggttg   16200
aactccggaa ccctaatcct gccctaggtg ttaggcatt atttgcaata tattaaagaa   16260
aactttgaaa atacgaagtt tctattccca gctttgtctg gtggccggca tggtcccagc   16320
ctcctcgctg gcgccggctg ggcaacattc cgagggacc gtccctcgg taatggcgaa   16380
tgggacgcgg ccgatccggc tgctaacaaa gcccgaaagg aagctgagtt ggctgctgcc   16440
accgctgagc aataactagc ataacccctt ggggcctcta aacgggtctt gaggggtttt   16500
ttgctgaaag gaggaactat atccggatgc ggccgcgggc cctatggtac ccagcttttg   16560
ttcccttttag tgagggttaa ttccgagctt ggcgtaatca tggtcatagc tgtttcctgt   16620
```

```
gtgaaattgt tatccgctca caattccaca caacatagga gccggaagca taaagtgtaa   16680
agcctggggt gcctaatgag tgaggtaact cacattaatt gcgttgcgct cactgcccgc   16740
tttccagtcg ggaaacctgt cgtgccagct gcattaatga atcggccaac gcgcggggag   16800
aggcggtttg cgtattgggc gctcttccgc ttcctcgctc actgactcgc tgcgctcggt   16860
cgttcggctg cggcgagcgg tatcagctca ctcaaaggcg gtaatacggt tatccacaga   16920
atcaggggat aacgcaggaa agaacatgtg agcaaaaggc cagcaaaagg ccaggaaccg   16980
taaaaaggcc gcgttgctgg cgttttccca taggctcggc cccctgacg agcatcacaa   17040 aaatcgacgc tcaagtcaga ggtggcgaaa cccgacagga ctataaagat accaggcgtt   17100 ccccctgga agctccctcg tgcgctctcc tgttccgacc ctgccgctta ccggatacct   17160
gtccgccttt ctcccttcgg gaagcgtggc gctttctcaa tgctcacgct gtaggtatct   17220
cagttcggtg taggtcgttc gctccaagct gggctgtgtg cacgaacccc ccgttcagcc   17280
cgaccgctgc gccttatccg gtaactatcg tcttgagtcc aacccggtaa gacacgactt   17340
atcgccactg gcagcagcca ctggtaacag gattagcaga gcgaggtatg taggcggtgc   17400
tacagagttc ttgaagtggt ggcctaacta cggctacact agaaggacag tatttggtat   17460
ctgcgctctg ctgaagccag ttaccttcgg aaaaagagtt ggtagctctt gatccggcaa   17520
acaaaccacc gctggtagcg gtggtttttt tgtttgcaag cagcagatta cgcgcagaaa   17580
aaaaggatct caagaagatc ctttgatctt ttctacgggg tctgacgctc agtggaacga   17640
aaactcacgt taagggattt tggtcatgag attatcaaaa aggatcttca cctagatcct   17700
tttaaattaa aaatgaagtt ttaaatcaat ctaaagtata tatgagtaaa cttggtctga   17760
cagttaccaa tgcttaatca gtgaggcacc tatctcagcg atctgtctat ttcgttcatc   17820
catagttgcc tgactgcccg tcgtgtagat aactacgata cgggagggct taccatctgg   17880
ccccagtgct gcaatgatac cgcgagaccc acgctcaccg gctccagatt tatcagcaat   17940
aaaccagcca gccggaaggg ccgagcgcag aagtggtcct gcaactttat ccgcctccat   18000
ccagtctatt aattgttgcc gggaagctag agtaagtagt tcgccagtta atagtttgcg   18060
caacgttgtt gccattgcta caggcatcgt ggtgtcacgc tcgtcgtttg gtatggcttc   18120
attcagctcc ggttcccaac gatcaaggcg agttacatga tcccccatgt tgtgaaaaaa   18180
agcggttagc tccttcggtc ctccgatcgt tgtcagaagt aagttggccg cagtgttatc   18240
actcatgctt atggcagcac tgcataattc tcttactgtc atgccatccg taagatgctt   18300
ttctgtgact ggtgagtact caaccaagtc attctgagaa tagtgtatgc ggcgaccgag   18360
ttgctcttgc ccggcgtcaa tacgggataa taccgcgcca catagcagaa ctttaaaagt   18420
gctcatcatt ggaaaacgtt cttcggggcg aaaactctca aggatcttac cgctgttgag   18480
atccagttcg atgtaaccca ctcgtgcacc caactgatct tcagcatctt ttactttcac   18540
cagcgtttct gggtgagcaa aaacaggaag gcaaaatgcc gcaaaaaagg gaataagggc   18600
gacacggaaa tgttgaatac tcatactctt cctttttcaa tattattgaa gcatttatca   18660
gggttattgt ctcatgagcg gatacatatt tgaatgtatt tagaaaaata aacaaatagg   18720
ggttccgcgc acatttcccc gaaaagtgcc acctgaaatt gtaaacgtta atattttgtt   18780
aaaattcgcg ttaaattttt gttaaatcag ctcattttt aaccaatagg ccgaaatcgg   18840
caaaatccct tataaatcaa aagaatagac cgagataggg ttgagtgttg ttccagtttg   18900
gaacaagagt ccactattaa agaacgtgga ctccaacgtc aaagggcgaa aaaccgtcta   18960
tcagggcgat ggcccactac gtgaaccatc accctaatca agttttttgg ggtcgaggtg   19020
```
ccgtaaagca ctaaatcgga accctaaagg gagcccccga tttagagctt gacggggaaa 19080
gccggcgaac gtggcgagaa aggaagggaa gaaagcgaaa ggagcgggcg ctagggcgct 19140
ggcaagtgta gcggtcacgc tgcgcgtaac caccacaccc gccgcgctta atgcgccgct 19200
acagggcgcg tcccattcgc cattcaggct gcgcaactgt tgggaagggc gatcggtgcg 19260
ggcctcttcg ctattacgcc agccaccgcg gtggcggccg ctaatacgac tcactatagg 19320
gccaactttg tttggtctga tgagtccgtg aggacgaaac ccggagtccc gggtc 19375

<210> SEQ ID NO 9
<211> LENGTH: 20251
<212> TYPE: DNA
<213> ORGANISM: Artificial Sequence
<220> FEATURE:
<223> OTHER INFORMATION: pTM-MV-M1&M2
<220> FEATURE:
<221> NAME/KEY: misc_RNA
<222> LOCATION: (1)..(17178)
<223> OTHER INFORMATION: MV-M1&M2_antigenome
<220> FEATURE:
<221> NAME/KEY: misc_feature
<222> LOCATION: (3378)..(4253)
<223> OTHER INFORMATION: ATU2
<220> FEATURE:
<221> NAME/KEY: misc_feature
<222> LOCATION: (3444)..(3449)
<223> OTHER INFORMATION: BsiWI restriction site
<220> FEATURE:
<221> NAME/KEY: misc_feature
<222> LOCATION: (3453)..(4214)
<223> OTHER INFORMATION: ORF for M1 consensus protein : M1opt
<220> FEATURE:
<221> NAME/KEY: misc_feature
<222> LOCATION: (4218)..(4223)
<223> OTHER INFORMATION: BssHII restriction site
<220> FEATURE:
<221> NAME/KEY: misc_feature
<222> LOCATION: (10052)..(10459)
<223> OTHER INFORMATION: ATU3
<220> FEATURE:
<221> NAME/KEY: misc_feature
<222> LOCATION: (10122)..(10127)
<223> OTHER INFORMATION: BsiWI restriction site
<220> FEATURE:
<221> NAME/KEY: misc_feature
<222> LOCATION: (10131)..(10427)
<223> OTHER INFORMATION: ORF for M2 consensus protein : M2opt
<220> FEATURE:
<221> NAME/KEY: misc_feature
<222> LOCATION: (10428)..(10433)
<223> OTHER INFORMATION: BssHII restriction site
<220> FEATURE:
<221> NAME/KEY: misc_feature
<222> LOCATION: (17179)..(20251)
<223> OTHER INFORMATION: plasmid_backbone

<400> SEQUENCE: 9
accaaacaaa gttgggtaag gatagttcaa tcaatgatca tcttctagtg cacttaggat 60
tcaagatcct attatcaggg acaagagcag gattagggat atccgagatg gccacacttt 120
taaggagctt agcattgttc aaaagaaaca aggacaaacc acccattaca tcaggatccg 180
gtggagccat cagaggaatc aaacacatta ttatagtacc aatccctgga gattcctcaa 240
ttaccactcg atccagactt ctggaccggt tggtgaggtt aattggaaac ccggatgtga 300
gcgggcccaa actaacaggg gcactaatag gtatattatc cttatttgtg gagtctccag 360
gtcaattgat tcagaggatc accgatgacc ctgacgttag cataaggctg ttagaggttg 420
tccagagtga ccagtcacaa tctggcctta ccttcgcatc aagaggtacc aacatggagg 480

| | |
|---|---|
| atgaggcgga ccaatacttt tcacatgatg atccaattag tagtgatcaa tccaggttcg | 540 |
| gatggttcgg gaacaaggaa atctcagata ttgaagtgca agaccctgag ggattcaaca | 600 |
| tgattctggg taccatccta gcccaaattt gggtcttgct cgcaaaggcg gttacggccc | 660 |
| cagacacggc agctgattcg gagctaagaa ggtggataaa gtacacccaa caaagaaggg | 720 |
| tagttggtga atttagattg gagagaaaat ggttggatgt ggtgaggaac aggattgccg | 780 |
| aggacctctc cttacgccga ttcatggtcg ctctaatcct ggatatcaag agaacacccg | 840 |
| gaaacaaacc caggattgct gaaatgatat gtgacattga tacatatatc gtagaggcag | 900 |
| gattagccag ttttatcctg actattaagt ttgggataga aactatgtat cctgctcttg | 960 |
| gactgcatga atttgctggt gagttatcca cacttgagtc cttgatgaac ctttaccagc | 1020 |
| aaatggggga aactgcaccc tacatggtaa tcctggagaa ctcaattcag aacaagttca | 1080 |
| gtgcaggatc ataccctctg ctctggagct atgccatggg agtaggagtg aacttgaaa | 1140 |
| actccatggg aggtttgaac tttggccgat cttactttga tccagcatat tttagattag | 1200 |
| ggcaagagat ggtaaggagg tcagctgaa aggtcagttc cacattggca tctgaactcg | 1260 |
| gtatcactgc cgaggatgca aggcttgttt cagagattgc aatgcatact actgaggaca | 1320 |
| agatcagtag agcggttgga cccagacaag cccaagtatc atttctacac ggtgatcaaa | 1380 |
| gtgagaatga gctaccgaga ttgggggca aggaagatag gagggtcaaa cagagtcgag | 1440 |
| gagaagccag ggagagctac agagaaaccg ggcccagcag agcaagtgat gcgagagctg | 1500 |
| cccatcttcc aaccggcaca cccctagaca ttgacactgc aacggagtcc agccaagatc | 1560 |
| cgcaggacag tcgaaggtca gctgacgccc tgcttaggct gcaagccatg gcaggaatct | 1620 |
| cggaagaaca aggctcagac acggacaccc ctatagtgta caatgacaga aatcttctag | 1680 |
| actaggtgcg agaggccgag ggccagaaca acatccgcct accatccatc attgttataa | 1740 |
| aaaacttagg aaccaggtcc acacagccgc cagcccatca accatccact cccacgattg | 1800 |
| gagccaatgg cagaagagca ggcacgccat gtcaaaaacg gactggaatg catccgggct | 1860 |
| ctcaaggccg agcccatcgg ctcactggcc atcgaggaag ctatggcagc atggtcagaa | 1920 |
| atatcagaca cccaggaca ggagcgagcc acctgcaggg aagagaaggc aggcagttcg | 1980 |
| ggtctcagca aaccatgcct ctcagcaatt ggatcaactg aaggcggtgc acctcgcatc | 2040 |
| cgcggtcagg gacctggaga gagcgatgac gacgctgaaa cttgggaat cccccaaga | 2100 |
| aatctccagg catcaagcac tgggttacag tgttattacg tttatgatca cagcggtgaa | 2160 |
| gcggttaagg gaatccaaga tgctgactct atcatggttc aatcaggcct tgatggtgat | 2220 |
| agcaccctct caggaggaga caatgaatct gaaaacagcg atgtggatat tggcgaacct | 2280 |
| gataccgagg gatatgctat cactgaccgg ggatctgctc ccatctctat ggggttcagg | 2340 |
| gcttctgatg ttgaaactgc agaaggaggg gagatccacg agctcctgag actccaatcc | 2400 |
| agaggcaaca actttccgaa gcttgggaaa actctcaatg ttcctccgcc cccgaccccc | 2460 |
| ggtagggcca gcacttccgg gacacccatt aaaaagggca cagacgcgag attagcctca | 2520 |
| tttggaacgg agatcgcgtc tttattgaca ggtggtgcaa cccaatgtgc tcgaaagtca | 2580 |
| ccctcggaac catcagggcc aggtgcacct gcggggaatg tccccgagtg tgtgagcaat | 2640 |
| gccgcactga tacaggagtg gacacccgaa tctggtacca caatctcccc gagatcccag | 2700 |
| aataatgaag aagggggaga ctattatgat gatgagctgt tctctgatgt ccaagatatt | 2760 |
| aaaacagcct tggccaaaat acacgaggat aatcagaaga taatctccaa gctagaatca | 2820 |
| ctgctgttat tgaagggaga agttgagtca attaagaagc agatcaacag gcaaaatatc | 2880 |

```
agcatatcca ccctggaagg acacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt ttgttcctga caccggccct    3180
gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagcct accctccatc attgttataa aaacttagg aaccaggtcc    3420 acacagccgc cagcccatca acgcgtacga ccatgagcct gctgaccgag gtggaaacct    3480
acgtgctgag catcatcccc agcggccctc tgaaggccga gatcgctcag cggctggaag    3540
atgtgttcgc cggcaagaac accgacctgg aagccctgat ggaatggctg aaaacccggc    3600
ccatcctgag ccccctgacc aagggcatcc tgggcttcgt gttcaccctg accgtgccct    3660
ctgagagagg cctgcagcgg agaagattcg tgcagaacgc cctgaacggc aacgcgacc    3720 ccaacaacat ggaccgggcc gtgaagctgt accggaagct gaagagagag atcaccttcc    3780
acggcgccaa agagatcgcc ctgagctact ctgctggcgc cctggcctct tgcatgggcc    3840
tgatctacaa ccggatgggc gccgtgacaa cagaggtggc ctttggcctc gtgtgcgcca    3900
catgcgagca gatcgccgac agccagcacc ggtcccacag acagatggtc accaccacca    3960 acccctgat ccggcacgag aacagaatgg tgctggcctc caccaccgcc aaggccatgg    4020
aacagatggc cggcagctct gagcaggccg ccgaagctat ggaagtggcc tctcaggccc    4080
ggcagatggt gcaggccatg agagccatcg gcacccaccc tagcagcagc accggcctga    4140
aggacgacct gctggaaaat ctgcaagctt accagaaaag aatgggcgtg cagatgcagc    4200
ggtttaagta atgacgagcg cgcagcgctt agacgtctcg cgatcgatac tagtacaacc    4260
taaatccatt ataaaaaact taggagcaaa gtgattgcct cccaaggtcc acaatgacag    4320
agacctacga cttcgacaag tcggcatggg acatcaaagg gtcgatcgct ccgatacaac    4380
ccaccaccta cagtgatggc aggctggtgc cccaggtcag agtcatagat cctggtctag    4440
gcgacaggaa ggatgaatgc tttatgtaca tgtttctgct gggggttgtt gaggacagcg    4500
attccctagg gcctccaatc gggcgagcat ttgggttcct gcccttaggt gttggcagat    4560
ccacagcaaa gcccgaaaaa ctcctcaaag aggccactga gcttgacata gttgttagac    4620
gtacagcagg gctcaatgaa aaactggtgt tctacaacaa cacccactaa actctcctca    4680 cacctggag aaaggtccta acaacaggga gtgtcttcaa cgcaaaccaa gtgtgcaatg    4740
cggttaatct gataccgctc gataccccgc agaggttccg tgttgtttat atgagcatca    4800
cccgtctttc ggataacggg tattacaccg ttcctagaag aatgctggaa ttcagatcgg    4860
tcaatgcagt ggccttcaac ctgctggtga cccttaggat tgacaaggcg ataggccctg    4920
ggaagatcat cgacaataca gagcaacttc ctgaggcaac attttatgtc cacatcggga    4980
acttcaggag aaagaagagt gaagtctact ctgccgatta ttgcaaaatg aaaatcgaaa    5040
agatgggcct ggttttttgca cttggtggga taggggcac cagtcttcac attagaagca    5100
caggcaaaat gagcaagact ctccatgcac aactcgggtt caagaagacc ttatgttacc    5160
cgctgatgga tatcaatgaa gaccttaatc gattactctg gaggagcaga tgcaagatag    5220
```

```
taagaatcca ggcagttttg cagccatcag ttcctcaaga attccgcatt tacgacgacg    5280
tgatcataaa tgatgaccaa ggactattca aagttctgta gaccgtagtg cccagcaatg    5340
cccgaaaacg accccctca caatgacagc cagaaggccc ggacaaaaaa gcccctccg    5400 aaagactcca cggaccaagc gagaggccag ccagcagccg acggcaagcg cgaacaccag    5460
gcggccccag cacagaacag ccctgacaca aggccaccac cagccacccc aatctgcatc    5520
ctcctcgtgg gaccccgag gaccaacccc caaggctgcc cccgatccaa accaccaacc    5580
gcatccccac caccccggg aaagaaaccc ccagcaattg gaaggcccct ccccctcttc    5640
ctcaacacaa gaactccaca accgaaccgc acaagcgacc gaggtgaccc aaccgcaggc    5700
atccgactcc ctagacagat cctctctccc cggcaaacta aacaaaactt agggccaagg    5760
aacatacaca cccaacagaa cccagacccc ggcccacggc gccgcgcccc caaccccga    5820 caaccagagg gagccccaa ccaatcccgc cggctccccc ggtgcccaca ggcagggaca    5880 ccaaccccg aacagaccca gcacccaacc atcgacaatc caagacgggg gggccccccc    5940 aaaaaaggc cccaggggc cgacagccag caccgcgagg aagcccaccc accccacaca    6000
cgaccacggc aaccaaacca gaacccagac cacctgggc caccagctcc cagactcggc    6060
catcaccccg cagaaaggaa aggccacaac ccgcgcaccc cagccccgat ccggcgggga    6120
gccacccaac ccgaaccagc acccaagagc gatccccgaa ggaccccga accgcaaagg    6180 acatcagtat cccacagcct ctccaagtcc cccggtctcc tcctcttctc gaagggacca    6240
aaagatcaat ccaccacacc cgacgacact caactcccca cccctaaagg agacaccggg    6300
aatcccagaa tcaagactca tccaatgtcc atcatgggtc tcaaggtgaa cgtctctgcc    6360
atattcatgg cagtactgtt aactctccaa acacccaccg gtcaaatcca ttggggcaat    6420
ctctctaaga taggggtggt aggaatagga agtgcaagct acaaagttat gactcgttcc    6480
agccatcaat cattagtcat aaaattaatg cccaatataa ctctcctcaa taactgcacg    6540
agggtagaga ttgcagaata caggagacta ctgagaacga ttttggaacc aattagagat    6600
gcacttaatg caatgaccca gaatataaga ccggttcaga gtgtagcttc aagtaggaga    6660
cacaagagat ttgcgggagt agtcctggca ggtgcggccc taggcgttgc cacagctgct    6720
cagataacag ccggcattgc acttcaccag tccatgctga actctcaagc catcgacaat    6780
ctgagagcga gcctggaaac tactaatcag gcaattgaga caatcagaca agcagggcag    6840
gagatgatat tggctgttca gggtgtccaa gactacatca ataatgagct gataccgtct    6900
atgaaccaac tatcttgtga tttaatcggc cagaagctcg gctcaaatt gctcagatac    6960 tatacagaaa tcctgtcatt atttggcccc agtttacggg accccatatc tgcggagata    7020
tctatccagg ctttgagcta tgcgcttgga ggagacatca ataaggtgtt agaaaagctc    7080
ggatacagtg gaggtgattt actgggcatc ttagagagcg gaggaataaa ggcccggata    7140
actcacgtcg acacagagtc ctacttcatt gtcctcagta tagcctatcc gacgctgtcc    7200
gagattaagg gggtgattgt ccaccggcta gagggggtct cgtacaacat aggctctcaa    7260
gagtggtata ccactgtgcc caagtatgtt gcaacccaag ggtaccttat ctcgaatttt    7320
gatgagtcat cgtgtactt catgccagag gggactgtgt gcagccaaaa tgccttgtac    7380
ccgatgagtc ctctgctcca agaatgcctc cgggggtaca ccaagtcctg tgctcgtaca    7440
ctcgtatccg ggtcttttgg gaaccggttc attttatcac aagggaacct aatagccaat    7500
tgtgcatcaa tcctttgcaa gtgttacaca acaggaacga tcattaatca agaccctgac    7560
aagatcctaa catacattgc tgccgatcac tgcccggtag tcgaggtgaa cggcgtgacc    7620
```

```
atccaagtcg ggagcaggag gtatccagac gctgtgtact tgcacagaat tgacctcggt   7680
cctcccatat cattggagag gttggacgta gggacaaatc tggggaatgc aattgctaag   7740
ttggaggatg ccaaggaatt gttggagtca tcggaccaga tattgaggag tatgaaaggt   7800
ttatcgagca ctagcatagt ctacatcctg attgcagtgt gtcttggagg gttgataggg   7860
atccccgctt taatatgttg ctgcaggggg cgttgtaaca aaaagggaga caagttggt    7920 atgtcaagac caggcctaaa gcctgatctt acgggaacat caaaatccta tgtaaggtcg   7980
ctctgatcct ctacaactct tgaaacacaa atgtcccaca agtctcctct tcgtcatcaa   8040
gcaaccaccg cacccagcat caagcccacc tgaaattatc tccggcttcc ctctggccga   8100
acaatatcgg tagttaatca aaacttaggg tgcaagatca tccacaatgt caccacaacg   8160
agaccggata aatgccttct acaaagataa ccccccatccc aagggaagta ggatagtcat  8220
taacagagaa catcttatga ttgatagacc ttatgttttg ctggctgttc tgtttgtcat   8280
gtttctgagc ttgatcgggt tgctagccat tgcaggcatt agacttcatc gggcagccat   8340
ctacaccgca gagatccata aaagcctcag caccaatcta gatgtaacta actcaatcga   8400
gcatcaggtc aaggacgtgc tgacaccact cttcaaaatc atcggtgatg aagtgggcct   8460
gaggacacct cagagattca ctgacctagt gaaattaatc tctgacaaga ttaaattcct   8520
taatccggat agggagtacg acttcagaga tctcacttgg tgtatcaacc cgccagagag   8580
aatcaaattg gattatgatc aatactgtgc agatgtggct gctgaagagc tcatgaatgc   8640
attggtgaac tcaactctac tggagaccag aacaaccaat cagttcctag ctgtctcaaa   8700
gggaaactgc tcagggccca ctacaatcag aggtcaattc tcaaacatgt cgctgtccct   8760
gttagacttg tatttaggtc gaggttacaa tgtgtcatct atagtcacta tgacatccca   8820
gggaatgtat gggggaactt acctagtgga aaagcctaat ctgagcagca aaggtcaga    8880 gttgtcacaa ctgagcatgt accgagtgtt tgaagtaggt gttatcagaa atccgggttt   8940
gggggctccg gtgttccata tgacaaacta tcttgagcaa ccagtcagta atgatctcag   9000
caactgtatg gtggctttgg gggagctcaa actcgcagcc ctttgtcacg ggaagattc    9060 tatcacaatt ccctatcagg gatcagggaa aggtgtcagc ttccagctcg tcaagctagg   9120
tgtctggaaa tccccaaccg acatgcaatc ctgggtcccc ttatcaacgg atgatccagt   9180
gatagacagg ctttacctct catctcacag aggtgttatc gctgacaatc aagcaaaatg   9240
ggctgtcccg acaacacgaa cagatgacaa gttgcgaatg gagacatgct ccaacaggc   9300 gtgtaagggt aaaatccaag cactctgcga gaatcccgag tgggcaccat gaaggataa    9360 caggattcct tcatacgggg tcttgtctgt tgatctgagt ctgacagttg agcttaaaat   9420
caaaattgct tcgggattcg ggccattgat cacacacggt tcaggatgg acctatacaa    9480 atccaaccac aacaatgtgt attggctgac tatcccgcca atgaagaacc tagccttagg   9540
tgtaatcaac acattggagt ggataccgag attcaaggtt agtccctacc tcttcactgt   9600
cccaattaag gaagcaggcg aagactgcca tgccccaaca tacctacctg cggaggtgga   9660
tggtgatgtc aaactcagtt ccaatctggt gattctacct ggtcaagatc tccaatatgt   9720
tttggcaacc tacgatactt ccaggggttga acatgctgtg gttttattcg tttacagccc  9780
aagccgctca ttttcttact tttatccttt taggttgcct ataaaggggg tccccatcga   9840 attcaagtg gaatgcttca catgggacca aaaactctgg tgccgtcact tctgtgtgct    9900
tgcggactca gaatctggtg gacatatcac tcactctggg atggtgggca tgggagtcag   9960
```

```
ctgcacagtc acccgggaag atggaaccaa tcgcagatag ggctgctagt gaaccaatca   10020
catgatgtca cccagacatc aggcataccc actagtctac cctccatcat tgttataaaa   10080
aacttaggaa ccaggtccac acagccgcca gcccatcaac gcgtacgacc atgagcctgc   10140
tgaccgaggt ggaaaccccc atcagaaacg agtggggctg ccggtgcaac gacagcagcg   10200
atcctctggt ggtggccgcc agcatcatcg gcatcctgca cctgatcctg tggattctgg   10260
accggctgtt cttcaagtgc atctacagac tgttcaagca cggcctgaag agaggcccca   10320
gcacagaagg cgtgcccgag agcatgcggg aagagtaccg gaaagaacag cagaacgccg   10380
tggacgccga cgacagccac ttcgtgtcca tcgagctgga atgataagcg cgcagcgctt   10440
agacgtctcg cgatcgatgc tagtgtgaaa tagacatcag aattaagaaa aacgtagggt   10500
ccaagtggtt ccccgttatg gactcgctat ctgtcaacca gatcttatac cctgaagttc   10560
acctagatag cccgatagtt accaataaga tagtagccat cctggagtat gctcgagtcc   10620
ctcacgctta cagcctggag gaccctacac tgtgtcagaa catcaagcac cgcctaaaaa   10680
acggattttc caaccaaatg attataaaca atgtggaagt tgggaatgtc atcaagtcca   10740
agcttaggag ttatccggcc cactctcata ttccatatcc aaattgtaat caggatttat   10800
ttaacataga agacaaagag tcaacgagga agatccgtga actcctcaaa aaggggaatt   10860
cgctgtactc caaagtcagt gataaggttt tccaatgctt aagggacact aactcacggc   10920
ttggcctagg ctccgaattg agggaggaca tcaaggagaa agttattaac ttgggagttt   10980
acatgcacag ctcccagtgg tttgagccct ttctgttttg gtttacagtc aagactgaga   11040
tgaggtcagt gattaaatca caaacccata cttgccatag gaggagacac acacctgtat   11100
tcttcactgg tagttcagtt gagttgctaa tctctcgtga ccttgttgct ataatcagta   11160
aagagtctca acatgtatat tacctgacat ttgaactggt tttgatgtat tgtgatgtca   11220
tagaggggag gttaatgaca gagaccgcta tgactattga tgctaggtat acagagcttc   11280
taggaagagt cagatacatg tggaaactga tagatggttt cttccctgca ctcgggaatc   11340
caacttatca aattgtagcc atgctggagc ctctttcact tgcttacctg cagctgaggg   11400
atataacagt agaactcaga ggtgcttttc cttaaccactg ctttactgaa atacatgatg   11460
ttcttgacca aaacgggttt tctgatgaag gtacttatca tgagttaact gaagctctag   11520
attacatttt cataactgat gacatacatc tgacagggga gattttctca ttttcagaa    11580 gtttcggcca ccccagactt gaagcagtaa cggctgctga aaatgttagg aaatacatga   11640
atcagcctaa agtcattgtg tatgagactc tgatgaaagg tcatgccata ttttgtggaa   11700
tcataatcaa cggctatcgt gacaggcacg gaggcagttg gccaccgctg accctccccc   11760
tgcatgctgc agacacaatc cggaatgctc aagcttcagg tgaagggtta acacatgagc   11820
agtgcgttga taactggaaa tcttttgctg gagtgaaatt tggctgcttt atgcctctta   11880
gcctggatag tgatctgaca atgtacctaa aggacaaggc acttgctgct ctccaaaggg   11940
aatgggattc agtttacccg aaagagttcc tgcgttacga ccctcccaag ggaaccgggt   12000
cacggaggct tgtagatgtt ttccttaatg attcgagctt tgacccatat gatgtgataa   12060
tgtatgttgt aagtgagct tacctccatg accctgagtt caacctgtct tacagcctga   12120
aagaaaagga gatcaaggaa acaggtagac ttttttgctaa aatgacttac aaaatgaggg   12180
catgccaagt gattgctgaa aatctaatct caaacgggat tggcaaatat tttaaggaca   12240
atgggatggc caaggatgag cacgatttga ctaaggcact ccacactcta gctgtctcag   12300
gagtccccaa agatctcaaa gaaagtcaca gggggggggcc agtcttaaaa acctactccc   12360
```

```
gaagcccagt ccacacaagt accaggaacg tgagagcagc aaaagggttt atagggttcc   12420
ctcaagtaat tcggcaggac caagacactg atcatccgga gaatatgaa gcttacgaga    12480 cagtcagtgc atttatcacg actgatctca agaagtactg ccttaattgg agatatgaga   12540
ccatcagctt gtttgcacag aggctaaatg agatttacgg attgccctca tttttccagt   12600
ggctgcataa gaggcttgag acctctgtcc tgtatgtaag tgaccctcat tgccccccg    12660 accttgacgc ccatatcccg ttatataaag tccccaatga tcaaatcttc attaagtacc   12720
ctatgggagg tatagaaggg tattgtcaga agctgtggac catcagcacc attccctatc   12780
tatacctggc tgcttatgag agcggagtaa ggattgcttc gttagtgcaa ggggacaatc    12840
agaccatagc cgtaacaaaa agggtaccca gcacatggcc ctacaacctt aagaaacggg   12900
aagctgctag agtaactaga gattactttg taattcttag gcaaaggcta catgatattg    12960
gccatcacct caaggcaaat gagacaattg tttcatcaca ttttttgtc tattcaaaag    13020 gaatatatta tgatgggcta cttgtgtccc aatcactcaa gagcatcgca agatgtgtat   13080
tctggtcaga gactatagtt gatgaaacaa gggcagcatg cagtaatatt gctacaacaa   13140
tggctaaaag catcgagaga ggttatgacc gttaccttgc atattccctg aacgtcctaa    13200
aagtgataca gcaaattctg atctctcttg gcttcacaat caattcaacc atgacccggg   13260
atgtagtcat accctcctc acaaacaacg acctcttaat aaggatggca ctgttgcccg    13320
ctcctattgg ggggatgaat tatctgaata tgagcaggct gtttgtcaga aacatcggtg    13380
atccagtaac atcatcaatt gctgatctca agagaatgat tctcgcctca ctaatgcctg    13440
aagagaccct ccatcaagta atgacacaac aaccggggga ctcttcattc ctagactggg    13500
ctagcgaccc ttactcagca aatcttgtat gtgtccagag catcactaga ctcctcaaga   13560
acataactgc aaggtttgtc ctgatccata gtccaaaccc aatgttaaaa ggattattcc   13620
atgatgacag taaagaagag gacgagggac tggcggcatt cctcatggac aggcatatta   13680
tagtacctag ggcagctcat gaaatcctgg atcatagtgt cacaggggca agagagtcta   13740
ttgcaggcat gctggatacc acaaaaggct tgattcgagc cagcatgagg aagggggggt    13800
taacctctcg agtgataacc agattgtcca attatgacta tgaacaattc agagcaggga    13860
tggtgctatt gacaggaaga aagagaaatg tcctcattga caaagagtca tgttcagtgc    13920
agctggcgag agctctaaga agccatatgt gggcgaggct agctcgagga cggcctattt    13980
acggccttga ggtccctgat gtactagaat ctatgcgagg ccaccttatt cggcgtcatg    14040
agacatgtgt catctgcgag tgtggatcag tcaactacgg atggttttt gtcccctcgg    14100 gttgccaact ggatgatatt gacaaggaaa catcatcctt gagagtccca tatattggtt    14160
ctaccactga tgagagaaca gacatgaagc ttgccttcgt aagagcccca agtcgatcct    14220
tgcgatctgc tgttagaata gcaacagtgt actcatgggc ttacggtgat gatgatagct    14280
cttggaacga agcctggttg ttggctaggc aaagggccaa tgtgagcctg gaggagctaa   14340
gggtgatcac tcccatctca acttcgacta atttagcgca taggttgagg gatcgtagca   14400
ctcaagtgaa atactcaggt acatcccttg tccgagtggc gaggtatacc acaatctcca   14460
acgacaatct ctcatttgtc atatcagata gaaggttga tactaacttt atataccaac   14520
aaggaatgct tctaggggttg ggtgttttag aaacattgtt tcgactcgag aaagataccg   14580
gatcatctaa cacggtatta catcttcacg tcgaaacaga ttgttgcgtg atcccgatga   14640
tagatcatcc caggatacc agctcccgca agctagagct gagggcagag ctatgtacca    14700
```

```
acccattgat atatgataat gcacctttaa ttgacagaga tgcaacaagg ctatacaccc    14760
agagccatag gaggcacctt gtggaatttg ttacatggtc cacacccaa ctatatcaca     14820 ttttagctaa gtccacagca ctatctatga ttgacctggt aacaaaattt gagaaggacc    14880
atatgaatga aatttcagct ctcatagggg atgacgatat caatagtttc ataactgagt    14940
ttctgctcat agagccaaga ttattcacta tctacttggg ccagtgtgcg gccatcaatt    15000
gggcatttga tgtacattat catagaccat cagggaaata tcagatgggg gagctgttgt    15060
catcgttcct ttctagaatg agcaaaggag tgtttaaggt gcttgtcaat gctctaagcc    15120
acccaaagat ctacaagaaa ttctggcatt gtggtattat agagcctatc catggtcctt    15180
cacttgatgc tcaaaacttg cacacaactg tgtgcaacat ggtttacaca tgctatatga    15240
cctacctcga cctgttgttg aatgaagagt tagaagagtt cacatttctc ttgtgtgaaa    15300
gcgacgagga tgtagtaccg gacagattcg acaacatcca ggcaaaacac ttatgtgttc    15360
tggcagattt gtactgtcaa ccagggacct gcccaccaat tcgaggtcta agaccggtag    15420
agaaatgtgc agttctaacc gaccatatca aggcagaggc tatgttatct ccagcaggat    15480
cttcgtggaa cataaatcca attattgtag accattactc atgctctctg acttatctcc    15540
ggcgaggatc gatcaaacag ataagattga gagttgatcc aggattcatt ttcgacgccc    15600
tcgctgaggt aaatgtcagt cagccaaaga tcggcagcaa caacatctca aatatgagca    15660
tcaaggcttt cagaccccca cacgatgatg ttgcaaaatt gctcaaagat atcaacacaa    15720
gcaagcacaa tcttcccatt tcagggggca atctcgccaa ttatgaaatc catgctttcc    15780
gcagaatcgg gttgaactca tctgcttgct acaaagctgt tgagatatca acattaatta    15840
ggagatgcct tgagccaggg gaggacggct tgttcttggg tgagggatcg ggttctatgt    15900
tgatcactta taaagagata cttaaactaa acaagtgctt ctataatagt ggggtttccg    15960
ccaattctag atctggtcaa agggaattag caccctatcc ctccgaagtt ggccttgtcg    16020
aacacagaat gggagtaggt aatattgtca aagtgctctt taacgggagg cccgaagtca    16080
cgtgggtagg cagtgtagat tgcttcaatt tcatagttag taatatccct acctctagtg    16140
tggggtttat ccattcagat atagagacct tgcctgacaa agatactata gagaagctag    16200
aggaattggc agccatctta tcgatggctc tgctcctggg caaaatagga tcaatactgg    16260
tgattaagct tatgccttc agcggggatt ttgttcaggg atttataagt tatgtagggt     16320
ctcattatag agaagtgaac cttgtatacc ctagatacag caacttcatc tctactgaat    16380
cttatttggt tatgacagat ctcaaggcta accggctaat gaatcctgaa aagattaagc    16440
agcagataat tgaatcatct gtgaggactt cacctggact tataggtcac atcctatcca    16500
ttaagcaact aagctgcata caagcaattg tgggagacgc agttagtaga ggtgatatca    16560
atcctactct gaaaaaactt acacctatag agcaggtgct gatcaattgc gggttggcaa    16620
ttaacggacc taagctgtgc aaagaattga tccaccatga tgttgcctca gggcaagatg    16680
gattgcttaa ttctatactc atcctctaca gggagttggc aagattcaaa gacaaccaaa    16740
gaagtcaaca agggatgttc cacgcttacc ccgtattggt aagtagcagg caacgagaac    16800
ttatatctag gatcaccgc aaattctggg ggcacattct tctttactcc gggaacaaaa     16860
agttgataaa taagtttatc cagaatctca gtccggcta tctgatacta gacttacacc     16920
agaatatctt cgttaagaat ctatccaagt cagagaaaca gattattatg acgggggtt     16980 tgaaacgtga gtgggttttt aaggtaacag tcaaggagac caaagaatgg tataagttag    17040
tcggatacag tgccctgatt aaggactaat tggttgaact ccggaaccct aatcctgccc    17100
```

```
taggtggtta ggcattattt gcaatatatt aaagaaaact ttgaaaatac gaagtttcta   17160
ttcccagctt tgtctggtgg ccggcatggt cccagcctcc tcgctggcgc cggctgggca   17220
acattccgag gggaccgtcc cctcggtaat ggcgaatggg acgcggccga tccggctgct   17280
aacaaagccc gaaaggaagc tgagttggct gctgccaccg ctgagcaata actagcataa   17340
ccccttgggg cctctaaacg ggtcttgagg ggttttttgc tgaaaggagg aactatatcc   17400
ggatgcggcc gcgggcccta tggtacccag cttttgttcc ctttagtgag ggttaattcc   17460
gagcttggcg taatcatggt catagctgtt tcctgtgtga aattgttatc cgctcacaat   17520
tccacacaac ataggagccg gaagcataaa gtgtaaagcc tggggtgcct aatgagtgag   17580
gtaactcaca ttaattgcgt tgcgctcact gcccgctttc cagtcgggaa acctgtcgtg   17640
ccagctgcat taatgaatcg gccaacgcgc ggggagaggc ggtttgcgta ttgggcgctc   17700
ttccgcttcc tcgctcactg actcgctgcg ctcggtcgtt cggctgcggc gagcggtatc   17760
agctcactca aaggcggtaa tacggttatc cacagaatca ggggataacg caggaaagaa   17820
catgtgagca aaaggccagc aaaaggccag gaaccgtaaa aaggccgcgt tgctggcgtt   17880
tttccatagg ctcggccccc ctgacgagca tcacaaaaat cgacgctcaa gtcagaggtg   17940
gcgaaacccg acaggactat aaagatacca ggcgttcccc cctggaagct ccctcgtgcg   18000
ctctcctgtt ccgaccctgc cgcttaccgg atacctgtcc gcctttctcc cttcgggaag   18060
cgtggcgctt tctcaatgct cacgctgtag gtatctcagt tcggtgtagg tcgttcgctc   18120
caagctgggc tgtgtgcacg aaccccccgt tcagcccgac cgctgcgcct tatccggtaa   18180
ctatcgtctt gagtccaacc cggtaagaca cgacttatcg ccactggcag cagccactgg   18240
taacaggatt agcagagcga ggtatgtagg cggtgctaca gagttcttga agtggtggcc   18300
taactacggc tacactagaa ggacagtatt tggtatctgc gctctgctga agccagttac   18360
cttcggaaaa agagttggta gctcttgatc cggcaaacaa accaccgctg gtagcggtgg   18420
tttttttgtt tgcaagcagc agattacgcg cagaaaaaaa ggatctcaag aagatccttt   18480
gatcttttct acggggtctg acgctcagtg gaacgaaaac tcacgttaag ggattttggt   18540
catgagatta tcaaaaagga tcttcaccta gatcctttta aattaaaaat gaagttttaa   18600
atcaatctaa agtatatatg agtaaacttg gtctgacagt taccaatgct taatcagtga   18660
ggcacctatc tcagcgatct gtctatttcg ttcatccata gttgcctgac tgcccgtcgt   18720
gtagataact acgatacggg agggcttacc atctggcccc agtgctgcaa tgataccgcg   18780
agacccacgc tcaccggctc cagatttatc agcaataaac cagccagccg gaagggccga   18840
gcgcagaagt ggtcctgcaa ctttatccgc ctccatccag tctattaatt gttgccggga   18900
agctagagta agtagttcgc cagttaatag tttgcgcaac gttgttgcca ttgctacagg   18960
catcgtggtg tcacgctcgt cgtttggtat ggcttcattc agctccggtt cccaacgatc   19020
aaggcgagtt acatgatccc ccatgttgtg aaaaaaagcg gttagctcct tcggtcctcc   19080
gatcgttgtc agaagtaagt tggccgcagt gttatcactc atgcttatgg cagcactgca   19140
taattctctt actgtcatgc catccgtaag atgcttttct gtgactggtg agtactcaac   19200
caagtcattc tgagaatagt gtatgcggcg accgagttgc tcttgcccgg cgtcaatacg   19260
ggataatacc gcgccacata gcagaacttt aaaagtgctc atcattggaa aacgttcttc   19320
ggggcgaaaa ctctcaagga tcttaccgct gttgagatcc agttcgatgt aacccactcg   19380
tgcacccaac tgatcttcag catcttttac tttcaccagc gtttctgggt gagcaaaaac   19440
```

-continued

```
aggaaggcaa aatgccgcaa aaaagggaat aagggcgaca cggaaatgtt gaatactcat  19500
actcttcctt tttcaatatt attgaagcat ttatcagggt tattgtctca tgagcggata  19560
catatttgaa tgtatttaga aaaataaaca aataggggtt ccgcgcacat ttccccgaaa  19620
agtgccacct gaaattgtaa acgttaatat tttgttaaaa ttcgcgttaa atttttgtta  19680
aatcagctca ttttttaacc aataggccga aatcggcaaa atcccttata aatcaaaaga  19740
atagaccgag atagggttga gtgttgttcc agtttggaac aagagtccac tattaaagaa  19800
cgtggactcc aacgtcaaag ggcgaaaaac cgtctatcag ggcgatggcc cactacgtga  19860
accatcaccc taatcaagtt ttttggggtc gaggtgccgt aaagcactaa atcggaaccc  19920
taaagggagc ccccgattta gagcttgacg gggaaagccg gcgaacgtgg cgagaaagga  19980
agggaagaaa gcgaaaggag cgggcgctag ggcgctggca agtgtagcgg tcacgctgcg  20040
cgtaaccacc acacccgccg cgcttaatgc gccgctacag ggcgcgtccc attcgccatt  20100
caggctgcgc aactgttggg aagggcgatc ggtgcgggcc tcttcgctat tacgccagcc  20160
accgcggtgg cggccgctaa tacgactcac tatagggcca actttgtttg gtctgatgag  20220
tccgtgagga cgaaacccgg agtcccgggt c                                 20251
```

<210> SEQ ID NO 10
<211> LENGTH: 20989
<212> TYPE: DNA
<213> ORGANISM: Artificial Sequence
<220> FEATURE:
<223> OTHER INFORMATION: pTM-MV-NPflu&M2
<220> FEATURE:
<221> NAME/KEY: misc_RNA
<222> LOCATION: (1)..(17916)
<223> OTHER INFORMATION: MV-NPflu&M2_antigenome
<220> FEATURE:
<221> NAME/KEY: misc_feature
<222> LOCATION: (3378)..(4991)
<223> OTHER INFORMATION: ATU2
<220> FEATURE:
<221> NAME/KEY: misc_feature
<222> LOCATION: (3444)..(3449)
<223> OTHER INFORMATION: BsiWI restriction site
<220> FEATURE:
<221> NAME/KEY: misc_feature
<222> LOCATION: (3456)..(4955)
<223> OTHER INFORMATION: ORF for NPflu consensus protein : NPflu
<220> FEATURE:
<221> NAME/KEY: misc_feature
<222> LOCATION: (4956)..(4961)
<223> OTHER INFORMATION: BssHII restriction site
<220> FEATURE:
<221> NAME/KEY: misc_feature
<222> LOCATION: (10790)..(11197)
<223> OTHER INFORMATION: ATU3
<220> FEATURE:
<221> NAME/KEY: misc_feature
<222> LOCATION: (10860)..(10865)
<223> OTHER INFORMATION: BsiWI restriction site
<220> FEATURE:
<221> NAME/KEY: misc_feature
<222> LOCATION: (10869)..(11165)
<223> OTHER INFORMATION: ORF for M2 consensus protein : M2opt
<220> FEATURE:
<221> NAME/KEY: misc_feature
<222> LOCATION: (11166)..(11171)
<223> OTHER INFORMATION: BssHII restriction site
<220> FEATURE:
<221> NAME/KEY: misc_feature
<222> LOCATION: (17917)..(20989)
<223> OTHER INFORMATION: plasmid_backbone

<400> SEQUENCE: 10

```
accaaacaaa gttgggtaag gatagttcaa tcaatgatca tcttctagtg cacttaggat     60
```

```
tcaagatcct attatcaggg acaagagcag gattagggat atccgagatg cccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtgaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caagaagggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg aacttgaaa    1140 actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc aacggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag ggccagaaca acatccgcct accatccatc attgttataa   1740
aaaacttagg aaccaggtcc acacagccgc cagcccatca accatccact cccacgattg   1800
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat cccccaaga    2100 aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
```

```
agaggcaaca actttccgaa gcttgggaaa actctcaatg ttcctccgcc cccggacccc    2460
ggtagggcca gcacttccgg gacacccatt aaaaagggca cagacgcgag attagcctca    2520
tttggaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aagggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg cacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt tgttcctga caccggccct    3180 gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagcct acctccatc attgttataa aaacttagg aaccaggtcc    3420 acacagccgc cagcccatca acgcgtacgg ccaccatggc ctctcagggc accaagagaa    3480
gctacgagca gatggaaacc gacgcgagc ggcagaacgc caccgagatt agagccagcg    3540
tgggcagaat gatcggcggc atcggccggt tctacatcca gatgtgcacc gagctgaagc    3600
tgagcgacta cgagggccgg ctgatccaga acagcctgac catcgagcgg atggtgctga    3660
gcgccttcga cgagcggcgg aacaagtacc tggaagaaca ccccagcgcc ggcaaggacc    3720
ccaagaaaac aggcggccct atctacgacg gggtggacgg caagtggatg cgcgagctgg    3780
tgctgtacga caaagaggaa atccggcgga tctggcggca ggccaacaat ggcgaagatg    3840
ccacagccgg cctgacccac atcatgatct ggcacagcaa cctgaacgac gccacctacc    3900
agcggaccag agcactcgtg cggacaggca tggaccccag aatgtgcagc ctgatgcagg    3960
gcagcaccct gccagaagaa tctggcgctg ctggcgcagc tgtgaagggc gtgggaacca    4020
tggtcatgga actgatcagg atgatcaagc ggggaatcaa cgaccggaac ttttggagag    4080
gcgagaacgg cagaaagacc cgcagcgcct acgagaggat gtgcaatatc ctgaagggca    4140
agttccagac agccgcccag cgggccatga tggatcaagt gcgcgagagc agaaaccccg    4200
gcaacgccga gatcgaggac ctgatcttcc tggccagaag cgccctgatc ctgagggct    4260 ctgtggccca caagagctgt ctgcctgcct gcgtgtacgg acctgccgtg ccagcggct    4320 acgacttcga gaagagggc tacagcctcg tgggcatcga cccattcaag ctgctgcaga    4380
actcccaggt gtacagcctg atccggccca acgagaaccc cgcccacaag tctcagctcg    4440
tgtggatggc ctgtcacagc gccgccttcg aggatctgag agtgtccagc ttcatccggg    4500
gcacaaaggt gtcccccaga ggcaagctga gcaccagagg cgtgcagatc gccagcaacg    4560
agaatatgga caacatgggc agctccaccc tggaactgcg gagccggtat tgggccatca    4620
gaaccagaag cggcggcaac accaaccagc agagagcctc tgccggacag atcagcgtgc    4680
agcccacctt tagcgtgcag agaaacctgc ccttcgagaa ggccacaatc atggccgcct    4740
tcaccggcaa taccgagggc agaaccagcg acatgcgggc cgagatcatc agaatgatgg    4800
```

-continued

```
aaagcgccaa gcccgaggaa gtgtcattcc agggcagggg cgtgttcgag ctgtccgacg    4860
agaaagccac caacccatc gtgcccagct tcgacatgag caacgagggc agctacttct     4920
tcggcgacaa cgccgaagag tacgacaact gataagcgcg cagcgcttag acgtctcgcg    4980
atcgatacta gtacaaccta aatccattat aaaaaactta ggagcaaagt gattgcctcc    5040
caaggtccac aatgacagag acctacgact tcgacaagtc ggcatgggac atcaaagggt    5100
cgatcgctcc gatacaaccc accacctaca gtgatggcag gctggtgccc caggtcagag    5160
tcatagatcc tggtctaggc gacaggaagg atgaatgctt tatgtacatg tttctgctgg    5220
gggttgttga ggacagcgat tccctagggc ctccaatcgg gcgagcattt gggttcctgc    5280
ccttaggtgt tggcagatcc acagcaaagc ccgaaaaact cctcaaagag gccactgagc    5340
ttgacatagt tgttagacgt acagcagggc tcaatgaaaa actggtgttc tacaacaaca    5400
ccccactaac tctcctcaca ccttggagaa aggtcctaac aacagggagt gtcttcaacg    5460
caaaccaagt gtgcaatgcg gttaatctga taccgctcga taccccgcag aggttccgtg    5520
ttgtttatat gagcatcacc cgtctttcgg ataacgggta ttacaccgtt cctagaagaa    5580
tgctggaatt cagatcggtc aatgcagtgg ccttcaacct gctggtgacc cttaggattg    5640
acaaggcgat aggccctggg aagatcatcg acaatacaga gcaacttcct gaggcaacat    5700
ttatggtcca catcgggaac ttcaggagaa agaagagtga agtctactct gccgattatt    5760
gcaaaatgaa aatcgaaaag atgggcctgg tttttgcact tggtgggata gggggcacca    5820
gtcttcacat tagaagcaca ggcaaaatga gcaagactct ccatgcacaa ctcgggttca    5880
agaagacctt atgttacccg ctgatggata tcaatgaaga ccttaatcga ttactctgga    5940
ggagcagatg caagatagta agaatccagg cagttttgca gccatcagtt cctcaagaat    6000
tccgcattta cgacgacgtg atcataaatg atgaccaagg actattcaaa gttctgtaga    6060
ccgtagtgcc cagcaatgcc cgaaaacgac cccctcaca atgacagcca gaaggcccgg     6120
acaaaaaagc cccctccgaa agactccacg gaccaagcga gaggccagcc agcagccgac    6180
ggcaagcgcg aacaccaggc ggccccagca cagaacagcc ctgacacaag gccaccacca    6240 gccacccaa tctgcatcct cctcgtggga ccccgagga ccaaccccca aggctgcccc      6300
cgatccaaac caccaaccgc atccccacca ccccgggaa agaaaccccc agcaattgga     6360
aggcccctcc ccctcttcct caacacaaga actccacaac cgaaccgcac aagcgaccga    6420
ggtgacccaa ccgcaggcat ccgactccct agacagatcc tctctccccg gcaaactaaa    6480
caaaacttag ggcaaggaa catacacacc caacagaacc cagaccccgg cccacggcgc     6540
cgcgccccca accccgaca accagaggga gccccaacc aatcccgccg gctccccgg      6600 tgcccacagg cagggacacc aaccccgaa cagacccagc acccaaccat cgacaatcca    6660
agacgggggg gccccccaa aaaaaggccc ccaggggccg acagccagca ccgcgaggaa    6720
gcccacccac cccacacacg accacggcaa ccaaaccaga acccagacca ccctgggcca   6780
ccagctccca gactcggcca tcaccccgca gaaaggaaag gccacaaccc gcgcacccca    6840
gccccgatcc ggcggggagc cacccaaccc gaaccagcac ccaagagcga tccccgaagg   6900 accccgaac cgcaaaggac atcagtatcc cacagcctct ccaagtcccc cggtctcctc    6960
ctcttctcga agggaccaaa agatcaatcc accacacccg acgacactca actccccacc    7020
cctaaaggag acaccgggaa tcccagaatc aagactcatc caatgtccat catgggtctc    7080
aaggtgaacg tctctgccat attcatggca gtactgttaa ctctccaaac acccaccggt    7140
```

```
caaatccatt ggggcaatct ctctaagata ggggtggtag gaataggaag tgcaagctac    7200
aaagttatga ctcgttccag ccatcaatca ttagtcataa aattaatgcc caatataact    7260
ctcctcaata actgcacgag ggtagagatt gcagaataca ggagactact gagaacagtt    7320
ttggaaccaa ttagagatgc acttaatgca atgacccaga atataagacc ggttcagagt    7380
gtagcttcaa gtaggagaca caagagattt gcgggagtag tcctggcagg tgcggcccta    7440
ggcgttgcca cagctgctca gataacagcc ggcattgcac ttcaccagtc catgctgaac    7500
tctcaagcca tcgacaatct gagagcgagc ctggaaacta ctaatcaggc aattgagaca    7560
atcagacaag cagggcagga gatgatattg gctgttcagg gtgtccaaga ctacatcaat    7620
aatgagctga taccgtctat gaaccaacta tcttgtgatt taatcggcca gaagctcggg    7680
ctcaaattgc tcagatacta tacagaaatc ctgtcattat ttggccccag tttacgggac    7740
cccatatctg cggagatatc tatccaggct ttgagctatg cgcttggagg agacatcaat    7800
aaggtgttag aaaagctcgg atacagtgga ggtgatttac tgggcatctt agagagcgga    7860
ggaataaagg cccggataac tcacgtcgac acagagtcct acttcattgt cctcagtata    7920
gcctatccga cgctgtccga gattaagggg gtgattgtcc accggctaga ggggtctcg    7980 tacaacatag gctctcaaga gtggtatacc actgtgccca gtatgttgc aacccaaggg    8040 taccttatct cgaattttga tgagtcatcg tgtactttca tgccagaggg gactgtgtgc    8100
agccaaaatg ccttgtaccc cgatgagtcct ctgctccaag aatgcctccg ggggtacacc    8160
aagtcctgtg ctcgtacact cgtatccggg tcttttggga accggttcat tttatcacaa    8220
gggaacctaa tagccaattg tgcatcaatc ctttgcaagt gttacacaac aggaacgatc    8280
attaatcaag accctgacaa gatcctaaca tacattgctg ccgatcactg cccggtagtc    8340
gaggtgaacg gcgtgaccat ccaagtcggg agcaggagg atccagacgc tgtgtacttg    8400
cacagaattg acctcggtcc tcccatatca ttggagaggt tggacgtagg gacaaatctg    8460
gggaatgcaa ttgctaagtt ggaggatgcc aaggaattgt tggagtcatc ggaccagata    8520
ttgaggagta tgaaaggttt atcgagcact agcatagtct acatcctgat gcagtgtgt    8580 cttggagggt tgatagggat ccccgcttta atatgttgct gcaggggggcg ttgtaacaaa    8640 aagggagaac aagttggtat gtcaagacca ggcctaaagc ctgatcttac gggaacatca    8700
aaatcctatg taaggtcgct ctgatcctct acaactcttg aaacacaaat gtcccacaag    8760
tctcctcttc gtcatcaagc aaccaccgca cccagcatca agcccacctg aaattatctc    8820
cggcttccct ctggccgaac aatatcggta gttaatcaaa acttagggtg caagatcatc    8880
cacaatgtca ccacaacgag accggataaa tgccttctac aaagataacc cccatcccaa    8940
gggaagtagg atagtcatta acagagaaca tcttatgatt gatagacctt atgttttgct    9000
ggctgttctg tttgtcatgt ttctgagctt gatcggggttg ctagccattg caggcattag    9060
acttcatcgg gcagccatct acaccgcaga gatcctataaa agcctcagca ccaatctaga    9120
tgtaactaac tcaatcgagc atcaggtcaa ggacgtgctg acaccactct tcaaaatcat    9180
cggtgatgaa gtgggcctga ggacacctca gagattcact gacctagtga aattaatctc    9240
tgacaagatt aaattcctta atccggatag ggagtacgac ttcagagatc tcacttggtg    9300
tatcaacccg ccagagagaa tcaaattgga ttatgatcaa tactgtgcag atgtggctgc    9360
tgaagagctc atgaatgcat tggtgaactc aactctactg gagaccagaa caaccaatca    9420
gttcctagct gtctcaaagg gaaactgctc agggcccact acaatcagag gtcaattctc    9480
aaacatgtcg ctgtccctgt tagacttgta tttaggtcga ggttacaatg tgtcatctat    9540
```

```
agtcactatg acatcccagg gaatgtatgg gggaacttac ctagtggaaa agcctaatct    9600
gagcagcaaa aggtcagagt tgtcacaact gagcatgtac cgagtgtttg aagtaggtgt    9660
tatcagaaat ccgggtttgg gggctccggt gttccatatg acaaactatc ttgagcaacc    9720
agtcagtaat gatctcagca actgtatggt ggctttgggg gagctcaaac tcgcagccct    9780
ttgtcacggg gaagattcta tcacaattcc ctatcaggga tcagggaaag gtgtcagctt    9840
ccagctcgtc aagctaggtg tctggaaatc cccaaccgac atgcaatcct gggtccectt    9900
atcaacggat gatccagtga tagacaggct ttacctctca tctcacagag gtgttatcgc    9960
tgacaatcaa gcaaaatggg ctgtcccgac aacacgaaca gatgacaagt tgcgaatgga   10020
gacatgcttc caacaggcgt gtaagggtaa aatccaagca ctctgcgaga atcccgagtg   10080
ggcaccattg aaggataaca ggattccttc atacgggggtc ttgtctgttg atctgagtct   10140
gacagttgag cttaaaatca aaattgcttc gggattcggg ccattgatca cacacggttc   10200
agggatggac ctatacaaat ccaaccacaa caatgtgtat tggctgacta tcccgccaat   10260
gaagaaccta gccttaggtg taatcaacac attggagtgg ataccgagat tcaaggttag   10320
tccctacctc ttcactgtcc caattaagga agcaggcgaa gactgccatg ccccaacata   10380
cctacctgcg gaggtggatg gtgatgtcaa actcagttcc aatctggtga ttctacctgg   10440
tcaagatctc caatatgttt tggcaaccta cgatacttcc agggttgaac atgctgtggt   10500
ttattacgtt tacagcccaa gccgctcatt ttcttacttt tatccttta ggttgcctat   10560
aaaggggtc cccatcgaat tacaagtgga atgcttcaca tgggaccaaa aactctggtg   10620
ccgtcacttc tgtgtgcttg cggactcaga atctggtgga catatcactc actctgggat   10680
ggtgggcatg ggagtcagct gcacagtcac ccgggaagat ggaaccaatc gcagataggg   10740
ctgctagtga accaatcaca tgatgtcacc cagacatcag gcatacccac tagtctaccc   10800
tccatcattg ttataaaaaa cttaggaacc aggtccacac agccgccagc ccatcaacgc   10860
gtacgaccat gagcctgctg accgaggtgg aaacccccat cagaaacgag tggggctgcc   10920
ggtgcaacga cagcagcgat cctctggtgg tggccgccag catcatcggc atcctgcacc   10980
tgatcctgtg gattctggac cggctgttct tcaagtgcat ctacagactg ttcaagcacg   11040
gcctgaagag aggcccccagc acagaaggcg tgcccgagag catgcgggaa gagtaccgga   11100
aagaacagca gaacgccgtg gacgccgacg acagccactt cgtgtccatc gagctggaat   11160
gataagcgcg cagcgcttag acgtctcgcg atcgatgcta gtgtgaaata gacatcagaa   11220
ttaagaaaaa cgtagggtcc aagtggttcc ccgttatgga ctcgctatct gtcaaccaga   11280
tcttataccc tgaagttcac ctagatagcc cgatagttac caataagata gtagccatcc   11340
tggagtatgc tcgagtccct cacgcttaca gcctggagga ccctacactg tgtcagaaca   11400
tcaagcaccg cctaaaaaac ggatttccca ccaaatgat tataaacaat gtggaagttg   11460
ggaatgtcat caagtccaag cttaggagtt atccggccca ctctcatatt ccatatccaa   11520
attgtaatca ggatttattt aacatagaag acaaagagtc aacgaggaag atccgtgaac   11580
tcctcaaaaa ggggaattcg ctgtactcca aagtcagtga taaggttttc caatgcttaa   11640
gggacactaa ctcacggctt ggcctaggct ccgaattgag ggaggacatc aaggagaaag   11700
ttattaactt gggagtttac atgcacagct cccagtggtt tgagcccttt ctgttttggt   11760
ttacagtcaa gactgagatg aggtcagtga ttaaatcaca aacccatact tgccataggga   11820
ggagacacac acctgtattc ttcactggta gttcagttga gttgctaatc tctcgtgacc   11880
```

```
ttgttgctat aatcagtaaa gagtctcaac atgtatatta cctgacattt gaactggttt    11940
tgatgtattg tgatgtcata gaggggaggt taatgacaga gaccgctatg actattgatg    12000
ctaggtatac agagcttcta ggaagagtca gatacatgtg gaaactgata gatggtttct    12060
tccctgcact cggaatccaa acttatcaaa ttgtagccat gctggagcct ctttcacttg    12120
cttacctgca gctgagggat ataacagtag aactcagagg tgctttcctt aaccactgct    12180
ttactgaaat acatgatgtt cttgaccaaa acgggttttc tgatgaaggt acttatcatg    12240
agttaactga agctctagat tacattttca taactgatga catacatctg acaggggaga    12300
ttttctcatt tttcagaagt ttcggccacc ccagacttga agcagtaacg gctgctgaaa    12360
atgttaggaa atacatgaat cagcctaaag tcattgtgta tgagactctg atgaaaggtc    12420
atgccatatt ttgtggaatc ataatcaacg gctatcgtga caggcacgga ggcagttggc    12480
caccgctgac cctcccccctg catgctgcag acacaatccg gaatgctcaa gcttcaggtg    12540
aagggttaac acatgagcag tgcgttgata actggaaatc ttttgctgga gtgaaatttg    12600
gctgctttat gcctcttagc ctggatagtg atctgacaat gtacctaaag gacaaggcac    12660
ttgctgctct ccaaagggaa tgggattcag tttacccgaa agagttcctg cgttacgacc    12720
ctcccaaggg aaccgggtca cggaggcttg tagatgtttt ccttaatgat tcgagctttg    12780
acccatatga tgtgataatg tatgttgtaa gtggagctta cctccatgac cctgagttca    12840
acctgtctta cagcctgaaa gaaaaggaga tcaaggaaac aggtagactt tttgctaaaa    12900
tgacttacaa aatgagggca tgccaagtga ttgctgaaaa tctaatctca aacgggattg    12960
gcaaatattt taaggacaat gggatggcca aggatgagca cgatttgact aaggcactcc    13020
acactctagc tgtctcagga gtccccaaag atctcaaaga aagtcacagg ggggggccag    13080
tcttaaaaac ctactcccga agcccagtcc acacaagtac caggaacgtg agagcagcaa    13140
aagggtttat agggttccct caagtaattc ggcaggacca agacactgat catccggaga    13200
atatggaagc ttacgagaca gtcagtgcat ttatcacgac tgatctcaag aagtactgcc    13260
ttaattggag atatgagacc atcagcttgt ttgcacagag gctaaatgag atttacggat    13320
tgccctcatt tttccagtgg ctgcataaga ggcttgagac ctctgtcctg tatgtaagtg    13380
accctcattg cccccccgac cttgacgccc atatcccgtt atataaagtc cccaatgatc    13440
aaatcttcat taagtacccct atgggaggta tagaagggta ttgtcagaag ctgtggacca    13500
tcagcaccat tccctatcta tacctggctg cttatgagag cggagtaagg attgcttcgt    13560
tagtgcaagg ggacaatcag accatagccg taacaaaaag ggtacccagc acatggccct    13620
acaaccttaa gaaacgggaa gctgctagag taactagaga ttactttgta attcttaggc    13680
aaaggctaca tgatattggc catcacctca aggcaaatga gacaattgtt tcatcacatt    13740
tttttgtcta ttcaaaagga atatattatg atgggctact tgtgtcccaa tcactcaaga    13800
gcatcgcaag atgtgtattc tggtcagaga ctatagttga tgaaacaagg gcagcatgca    13860
gtaatattgc tacaacaatg gctaaaagca tcgagagagg ttatgaccgt taccttgcat    13920
attccctgaa cgtcctaaaa gtgatacagc aaattctgat ctctcttggc ttcacaatca    13980
attcaaccat gacccgggat gtagtcatac ccctcctcac aaacaacgac ctcttaataa    14040
ggatggcact gttgcccgct cctattgggg ggatgaatta tctgaatatg agcaggctgt    14100
ttgtcagaaa catcggtgat ccagtaacat catcaattgc tgatctcaag agaatgattc    14160
tcgcctcact aatgccctgaa gagaccctcc atcaagtaat gacacaacaa ccggggggact    14220 cttcattcct agactgggct agcgaccctt actcagcaaa tcttgtatgt gtccagagca    14280
```

```
tcactagact cctcaagaac ataactgcaa ggtttgtcct gatccatagt ccaaacccaa   14340
tgttaaaagg attattccat gatgacagta aagaagagga cgagggactg gcggcattcc   14400
tcatggacag gcatattata gtacctaggg cagctcatga aatcctggat catagtgtca   14460
caggggcaag agagtctatt gcaggcatgc tggataccac aaaaggcttg attcgagcca   14520
gcatgaggaa ggggggggtta acctctcgag tgataaccag attgtccaat tatgactatg   14580
aacaattcag agcagggatg gtgctattga caggaagaaa gagaaatgtc ctcattgaca   14640
aagagtcatg ttcagtgcag ctggcgagag ctctaagaag ccatatgtgg gcgaggctag   14700
ctcgaggacg gcctatttac ggccttgagg tccctgatgt actagaatct atgcgaggcc   14760
accttattcg gcgtcatgag acatgtgtca tctgcgagtg tggatcagtc aactacggat   14820
ggttttttgt cccctcgggt tgccaactgg atgatattga caaggaaaca tcatccttga   14880
gagtcccata tattggttct accactgatg agagaacaga catgaagctt gccttcgtaa   14940
gagccccaag tcgatccttg cgatctgctg ttagaatagc aacagtgtac tcatgggctt   15000
acggtgatga tgatagctct tggaacgaag cctggttgtt ggctaggcaa agggccaatg   15060
tgagcctgga ggagctaagg gtgatcactc ccatctcaac ttcgactaat ttagcgcata   15120
ggttgaggga tcgtagcact caagtgaaat actcaggtac atcccttgtc cgagtggcga   15180
ggtataccac aatctccaac gacaatctct catttgtcat atcagataag aaggttgata   15240
ctaactttat ataccaacaa ggaatgcttc tagggttggg tgttttagaa acattgtttc   15300
gactcgagaa agataccgga tcatctaaca cggtattaca tcttcacgtc gaaacagatt   15360
gttgcgtgat cccgatgata gatcatccca ggatacccag ctcccgcaag ctagagctga   15420
gggcagagct atgtaccaac ccattgatat atgataatgc acctttaatt gacagagatg   15480
caacaaggct atacacccag agccatagga ggcaccttgt ggaatttgtt acatggtcca   15540 cacccccaact atatcacatt ttagctaagt ccacagcact atctatgatt gacctggtaa   15600
caaaatttga gaaggaccat atgaatgaaa tttcagctct cataggggat gacgatatca   15660
atagtttcat aactgagttt ctgctcatag agccaagatt attcactatc tacttgggcc   15720
agtgtgcggc catcaattgg gcatttgatg tacattatca tagaccatca gggaaatatc   15780
agatgggtga gctgttgtca tcgttccttt ctagaatgag caaaggagtg tttaaggtgc   15840
ttgtcaatgc tctaagccac ccaaagatct acaagaaatt ctggcattgt ggtattatag   15900
agcctatcca tggtccttca cttgatgctc aaaacttgca cacaactgtg tgcaacatgg   15960
tttacacatg ctatatgacc tacctcgacc tgttgttgaa tgaagagtta gaagagttca   16020
catttctctt gtgtgaaagc gacgaggatg tagtaccgga cagattcgac aacatccagg   16080
caaaacactt atgtgttctg gcagatttgt actgtcaacc agggacctgc ccaccaattc   16140
gaggtctaag accggtagag aaatgtgcag ttctaaccga ccatatcaag gcagaggcta   16200
tgttatctcc agcaggatct tcgtggaaca taaatccaat tattgtagac cattactcat   16260
gctctctgac ttatctccgg cgaggatcga tcaaacagat aagattgaga gttgatccag   16320
gattcatttt cgacgccctc gctgaggtaa atgtcagtca gccaaagatc ggcagcaaca   16380
acatctcaaa tatgagcatc aaggcttca gaccccaca cgatgatgtt gcaaaattgc   16440
tcaaagatat caacacaagc aagcacaatc ttcccatttc aggggcaat ctcgccaatt   16500 atgaaatcca tgctttccgc agaatcgggt tgaactcatc tgcttgctac aaagctgttg   16560
agatatcaac attaattagg agatgccttg agccagggga ggacggcttg ttcttgggtg   16620
```

-continued

```
agggatcggg ttctatgttg atcacttata aagagatact taaactaaac aagtgcttct    16680
ataatagtgg ggtttccgcc aattctagat ctggtcaaag ggaattagca ccctatccct    16740
ccgaagttgg ccttgtcgaa cacagaatgg gagtaggtaa tattgtcaaa gtgctcttta    16800
acgggaggcc cgaagtcacg tgggtaggca gtgtagattg cttcaatttc atagttagta    16860
atatccctac ctctagtgtg gggtttatcc attcagatat agagaccttg cctgacaaag    16920
atactataga gaagctagag gaattggcag ccatcttatc gatggctctg ctcctgggca    16980
aaataggatc aatactggtg attaagctta tgcctttcag cggggatttt gttcagggat    17040
ttataagtta tgtagggtct cattatagag aagtgaacct tgtataccct agatacagca    17100
acttcatctc tactgaatct tatttggtta tgacagatct caaggctaac cggctaatga    17160
atcctgaaaa gattaagcag cagataattg aatcatctgt gaggacttca cctggactta    17220
taggtcacat cctatccatt aagcaactaa gctgcataca agcaattgtg ggagacgcag    17280
ttagtagagg tgatatcaat cctactctga aaaacttac acctatagag caggtgctga    17340
tcaattgcgg gttggcaatt aacggaccta agctgtgcaa agaattgatc caccatgatg    17400
ttgcctcagg gcaagatgga ttgcttaatt ctatactcat cctctacagg gagttggcaa    17460
gattcaaaga caaccaaaga agtcaacaag ggatgttcca cgcttacccc gtattggtaa    17520
gtagcaggca acgagaactt atatctagga tcacccgcaa attctggggg cacattcttc    17580
tttactccgg gaacaaaaag ttgataaata agtttatcca gaatctcaag tccggctatc    17640
tgatactaga cttacaccag aatatcttcg ttaagaatct atccaagtca gagaaacaga    17700
ttattatgac gggggggtttg aaacgtgagt gggtttttaa ggtaacagtc aaggagacca    17760
aagaatggta taagttagtc ggatacagtg ccctgattaa ggactaattg gttgaactcc    17820
ggaaccctaa tcctgcccta ggtggttagg cattatttgc aatatattaa agaaaacttt    17880
gaaaatacga agtttctatt cccagctttg tctggtggcc ggcatggtcc cagcctcctc    17940
gctgcgcccg ctgggcaac attccgaggg gaccgtcccc tcggtaatgg cgaatgggac    18000
gcggccgatc cggctgctaa caaagcccga aggaagctg agttggctgc tgccaccgct    18060
gagcaataac tagcataacc ccttgggggcc tctaaacggg tcttgagggg tttttttgctg    18120 aaaggaggaa ctatatccgg atgcggccgc gggccctatg gtacccagct tttgttccct    18180
ttagtgaggt ttaattccga gcttggcgta atcatggtca tagctgtttc ctgtgtgaaa    18240
ttgttatccg ctcacaattc cacacaacat aggagccgga agcataaagt gtaaagcctg    18300
gggtgcctaa tgagtgaggt aactcacatt aattgcgttg cgctcactgc ccgctttcca    18360
gtcgggaaac ctgtcgtgcc agctgcatta atgaatcggc caacgcgcgg ggagaggcgg    18420
tttgcgtatt gggcgctctt ccgcttcctc gctcactgac tcgctgcgct cggtcgttcg    18480
gctgcggcga gcggtatcag ctcactcaaa ggcggtaata cggttatcca cagaatcagg    18540
ggataacgca ggaaagaaca tgtgagcaaa aggccagcaa aaggccagga accgtaaaaa    18600
ggccgcgttg ctggcgtttt tccataggct cggccccct gacgagcatc acaaaaatcg    18660
acgctcaagt cagaggtggc gaaacccgac aggactataa agataccagg cgttccccccc    18720 tggaagctcc ctcgtgcgct ctcctgttcc gaccctgccg cttaccggat acctgtccgc    18780
ctttctccct tcgggaagcg tggcgctttc tcaatgctca cgctgtaggt atctcagttc    18840
ggtgtaggtc gttcgctcca agctgggctg tgtgcacgaa ccccccgttc agcccgaccg    18900
ctgcgcctta tccggtaact atcgtcttga gtccaacccg gtaagacacg acttatcgcc    18960
actggcagca gccactggta acaggattag cagagcgagg tatgtaggcg gtgctacaga    19020
```

```
gttcttgaag tggtggccta actacggcta cactagaagg acagtatttg gtatctgcgc   19080
tctgctgaag ccagttacct tcggaaaaag agttggtagc tcttgatccg gcaaacaaac   19140
caccgctggt agcggtggtt ttttttgtttg caagcagcag attacgcgca gaaaaaaagg   19200
atctcaagaa gatcctttga tcttttctac ggggtctgac gctcagtgga acgaaaactc   19260
acgttaaggg attttggtca tgagattatc aaaaaggatc ttcacctaga tccttttaaa   19320
ttaaaaatga agttttaaat caatctaaag tatatatgag taaacttggt ctgacagtta   19380
ccaatgctta atcagtgagg cacctatctc agcgatctgt ctatttcgtt catccatagt   19440
tgcctgactg cccgtcgtgt agataactac gatacgggag gcttaccat ctggccccag    19500
tgctgcaatg ataccgcgag acccacgctc accggctcca gatttatcag caataaacca   19560
gccagccgga agggccgagc gcagaagtgg tcctgcaact ttatccgcct ccatccagtc   19620
tattaattgt tgccgggaag ctagagtaag tagttcgcca gttaatagtt tgcgcaacgt   19680
tgttgccatt gctacaggca tcgtggtgtc acgctcgtcg tttggtatgg cttcattcag   19740
ctccggttcc caacgatcaa ggcgagttac atgatccccc atgttgtgaa aaaagcggt    19800
tagctccttc ggtcctccga tcgttgtcag aagtaagttg gccgcagtgt tatcactcat   19860
gcttatggca gcactgcata attctcttac tgtcatgcca tccgtaagat gcttttctgt   19920
gactggtgag tactcaacca agtcattctg agaatagtgt atgcggcgac cgagttgctc   19980
ttgcccggcg tcaatacggg ataataccgc gccacatagc agaactttaa aagtgctcat   20040
cattggaaaa cgttcttcgg ggcgaaaact ctcaaggatc ttaccgctgt tgagatccag   20100
ttcgatgtaa cccactcgtg cacccaactg atcttcagca tcttttactt tcaccagcgt   20160
ttctgggtga gcaaaaacag gaaggcaaaa tgccgcaaaa aagggaataa gggcgacacg   20220
gaaatgttga atactcatac tcttcctttt tcaatattat tgaagcattt atcagggtta   20280
ttgtctcatg agcggataca tatttgaatg tatttagaaa aataaacaaa tagggggttcc   20340
gcgcacattt ccccgaaaag tgccacctga aattgtaaac gttaatattt tgttaaaatt   20400
cgcgttaaat ttttgttaaa tcagctcatt ttttaaccaa taggccgaaa tcggcaaaat   20460
cccttataaa tcaaaagaat agaccgagat agggttgagt gttgttccag tttggaacaa   20520
gagtccacta ttaaagaacg tggactccaa cgtcaaaggg cgaaaaaccg tctatcaggg   20580
cgatggccca ctacgtgaac catcacccta atcaagtttt tggggtcga ggtgccgtaa    20640
agcactaaat cggaacccta agggagcccc cgatttaga gcttgacggg gaaagccggc    20700
gaacgtggcg agaaaggaag ggaagaaagc gaaaggagcg ggcgctaggg cgctggcaag   20760
tgtagcggtc acgctgcgcg taaccaccac acccgccgcg cttaatgcgc cgctacaggg   20820
cgcgtcccat tcgccattca ggctgcgcaa ctgttgggaa gggcgatcgg tgcgggcctc   20880
ttcgctatta cgccagccac cgcggtggcg gccgctaata cgactcacta tagggccaac   20940
tttgtttggt ctgatgagtc cgtgaggacg aaacccggag tccgggtc               20989
```

```
<210> SEQ ID NO 11
<211> LENGTH: 20581
<212> TYPE: DNA
<213> ORGANISM: Artificial Sequence
<220> FEATURE:
<223> OTHER INFORMATION: pTM-MV-ATU2-NPflu
<220> FEATURE:
<221> NAME/KEY: misc_RNA
<222> LOCATION: (1)..(17508)
<223> OTHER INFORMATION: MV-ATU2-NPflu_antigenome
<220> FEATURE:
```

```
<221> NAME/KEY: misc_feature
<222> LOCATION: (3378)..(4991)
<223> OTHER INFORMATION: ATU2
<220> FEATURE:
<221> NAME/KEY: misc_feature
<222> LOCATION: (3444)..(3449)
<223> OTHER INFORMATION: BsiWI restriction site
<220> FEATURE:
<221> NAME/KEY: misc_feature
<222> LOCATION: (3456)..(4955)
<223> OTHER INFORMATION: ORF for NPflu consensus protein : NPflu
<220> FEATURE:
<221> NAME/KEY: misc_feature
<222> LOCATION: (4956)..(4961)
<223> OTHER INFORMATION: BssHII restriction site
<220> FEATURE:
<221> NAME/KEY: misc_feature
<222> LOCATION: (17509)..(20581)
<223> OTHER INFORMATION: plasmid_backbone

<400> SEQUENCE: 11
accaaacaaa gttgggtaag gatagttcaa tcaatgatca tcttctagtg cacttaggat     60
tcaagatcct attatcaggg acaagagcag gattagggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtgaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc aacggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag ggccagaaca acatccgcct accatccatc attgttataa   1740
```

```
aaaacttagg aaccaggtcc acacagccgc cagcccatca accatccact cccacgattg   1800
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa cttgggaat ccccccaaga    2100 aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccgaccccc   2460
ggtagggcca gcacttccgg gacacccatt aaaaagggca cagacgcgag attagcctca   2520 tttgaacgg agatcgcgtc tttattgaca ggtggtgcaa cccaatgtgc tcgaaagtca    2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctgaaagg cacctctca agcatcatga tcgccattcc tggacttggg    2940
aaggatccca acgaccccac tgcagatgtc gaaatcaatc ccgacttgaa acccatcata   3000
ggcagagatt caggccgagc actggccgaa gttctcaaga acccgttgc cagccgacaa    3060 ctccaaggaa tgacaaatgg acggaccagt tccagaggac agctgctgaa ggaatttcag   3120
ctaaagccga tcgggaaaaa gatgagctca gccgtcgggt tgttcctga caccggccct    3180 gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagcct accctccatc attgttataa aaaacttagg aaccaggtcc   3420
acacagccgc cagcccatca acgcgtacgg ccaccatggc ctctcagggc accaagagaa   3480
gctacgagca gatggaaacc gacggcgagc ggcagaacgc caccgagatt agagccagcg   3540
tgggcagaat gatcggcggc atcggccggt tctacatcca gatgtgcacc gagctgaagc   3600
tgagcgacta cgagggccgg ctgatccaga acagcctgac catcgagcgg atggtgctga   3660
gcgccttcga cgacgcggg aacaagtacc tggaagaaca ccccagcgcc ggcaaggacc    3720
ccaagaaaac aggcggccct atctacagac gggtggacgg caagtggatg cgcgagctgg   3780
tgctgtacga caaagaggaa atccggcgga tctggcggca ggccaacaat ggcgaagatg   3840
ccacagccgg cctgacccac atcatgatct ggcacagcaa cctgaacgac gccacctacc   3900
agcggaccag agcactcgtg cggacaggca tggacccag aatgtgcagc ctgatgcagg    3960 gcagcacccct gcccagaaga tctggcgctg ctggcgcagc tgtgaagggc gtgggaacca   4020
tggtcatgga actgatcagg atgatcaagc ggggaatcaa cgaccggaac ttttggagag   4080
```

-continued

```
gcgagaacgg cagaaagacc cgcagcgcct acgagaggat gtgcaatatc ctgaagggca    4140
agttccagac agccgcccag cgggccatga tggatcaagt gcgcgagagc agaaaccccg    4200
gcaacgccga gatcgaggac ctgatcttcc tggccagaag cgccctgatc ctgaggggct    4260
ctgtggccca agagctgtgt ctgcctgcct gcgtgtacgg acctgccgtg ccagcggct    4320 acgacttcga gaaagagggc tacagcctcg tgggcatcga cccattcaag ctgctgcaga    4380
actcccaggt gtacagcctg atccggccca cgagaaccc cgcccacaag tctcagctcg    4440
tgtggatggc ctgtcacagc gccgccttcg aggatctgag agtgtccagc ttcatccggg    4500
gcacaaaggt gtcccccaga ggcaagctga gcaccagagg cgtgcagatc gccagcaacg    4560
agaatatgga caacatgggc agctccaccc tggaactgcg gagccggtat tgggccatca    4620
gaaccagaag cggcggcaac accaaccagc agagagcctc tgccggacag atcagcgtgc    4680
agcccacctt tagcgtgcag agaaacctgc ccttcgagaa ggccacaatc atggccgcct    4740
tcaccggcaa taccgagggc agaaccagcg acatgcgggc cgagatcatc agaatgatgg    4800
aaagcgccaa gcccgaggaa gtgtcattcc agggcagggg cgtgttcgag ctgtccgacg    4860
agaaagccac caaccccatc gtgcccagct tcgacatgag caacgagggc agctacttct    4920
tcggcgacaa cgccgaagag tacgacaact gataagcgcg cagcgcttag acgtctcgcg    4980
atcgatacta gtacaaccta aatccattat aaaaaactta ggagcaaagt gattgcctcc    5040
caaggtccac aatgacagag acctacgact tcgacaagtc ggcatgggac atcaaagggt    5100
cgatcgctcc gatacaaccc accacctaca gtgatggcag gctggtgccc caggtcagag    5160
tcatagatcc tggtctaggc gacaggaagg atgaatgctt tatgtacatg tttctgctgg    5220
gggttgttga ggacagcgat tccctagggc ctccaatcgg gcgagcattt gggttcctgc    5280
ccttaggtgt tggcagatcc acagcaaagc ccgaaaaact cctcaaagag gccactgagc    5340
ttgacatagt tgttagacgt acagcagggc tcaatgaaaa actggtgttc tacaacaaca    5400
ccccactaac tctcctcaca ccttggagaa aggtcctaac aacagggagt gtcttcaacg    5460
caaaccaagt gtgcaatgcg gttaatctga taccgctcga taccccgcag aggttccgtg    5520
ttgtttatat gagcatcacc cgtctttcgg ataacgggta ttacaccgtt cctagaagaa    5580
tgctggaatt cagatcggtc aatgcagtgg ccttcaacct gctggtgacc cttaggattg    5640
acaaggcgat aggccctggg aagatcatcg acaatacaga gcaacttcct gaggcaacat    5700
ttatggtcca catcgggaac ttcaggagaa agaagagtga agtctactct gccgattatt    5760
gcaaaatgaa aatcgaaaag atgggcctgg ttttttgcact tggtgggata gggggcacca    5820
gtcttcacat tagaagcaca ggcaaaatga gcaagactct ccatgcacaa ctcgggttca    5880
agaagacctt atgttacccg ctgatggata tcaatgaaga ccttaatcga ttactctgga    5940
ggagcagatg caagatagta agaatccagg cagttttgca gccatcagtt cctcaagaat    6000
tccgcattta cgacgacgtg atcataaatg atgaccaagg actattcaaa gttctgtaga    6060
ccgtagtgcc cagcaatgcc cgaaaacgac ccccctcaca atgacagcca gaaggcccgg    6120
acaaaaaagc cccctccgaa agactccacg gaccaagcga gaggccagcc agcagccgac    6180
ggcaagcgcg aacaccaggc ggccccagca cagaacagcc ctgacacaag ccaccacca    6240 gccaccccaa tctgcatcct cctcgtggga ccccgagga ccaaccccca aggctgcccc    6300
cgatccaaac caccaccgc atccccacca ccccgggaa agaaacccc agcaattgga    6360 aggcccctcc ccctcttcct caacacaaga actccacaac cgaaccgcac aagcgaccga    6420
ggtgacccaa ccgcaggcat ccgactccct agacagatcc tctctccccg gcaaactaaa    6480
```

```
caaaacttag ggccaaggaa catacacacc aacagaacc cagacccgg cccacggcgc   6540 cgcgccccca accccgaca accagaggga gcccccaacc aatcccgccg gctccccgg   6600 tgcccacagg cagggacacc aaccccgaa cagacccagc acccaaccat cgacaatcca   6660
agacgggggg gcccccccaa aaaaggccc ccaggggccg acagccagca ccgcgaggaa   6720
gcccacccac cccacacacg accacggcaa ccaaaccaga acccagacca ccctgggcca   6780
ccagctccca gactcggcca tcaccccgca gaaaggaaag gccacaaccc gcgcacccca   6840
gccccgatcc ggcggggagc cacccaaccc gaaccagcac ccaagagcga tccccgaagg   6900 accccccgaac cgcaaaggac atcagtatcc cacagcctct ccaagtcccc cggtctcctc   6960
ctcttctcga agggaccaaa agatcaatcc accacacccg acgacactca actccccacc   7020
cctaaaggag acaccgggaa tcccagaatc aagactcatc caatgtccat catgggtctc   7080
aaggtgaacg tctctgccat attcatggca gtactgttaa ctctccaaac acccaccggt   7140
caaatccatt ggggcaatct ctctaagata ggggtggtag gaataggaag tgcaagctac   7200
aaagttatga ctcgttccag ccatcaatca ttagtcataa aattaatgcc caatataact   7260
ctcctcaata actgcacgag ggtagagatt gcagaataca ggagactact gagaacagtt   7320
ttggaaccaa ttagagatgc acttaatgca atgacccaga atataagacc ggttcagagt   7380
gtagcttcaa gtaggagaca caagagattt gcgggagtag tcctggcagg tgcggcccta   7440
ggcgttgcca cagctgctca gataacagcc ggcattgcac ttcaccagtc catgctgaac   7500
tctcaagcca tcgacaatct gagagcgagc ctggaaacta ctaatcaggc aattgagaca   7560
atcagacaag cagggcagga gatgatattg gctgttcagg gtgtccaaga ctacatcaat   7620
aatgagctga taccgtctat gaaccaacta tcttgtgatt taatcggcca gaagctcggg   7680
ctcaaattgc tcagatacta tacagaaatc ctgtcattat ttggccccag tttacgggac   7740
cccatatctg cggagatatc tatccaggct ttgagctatg cgcttggagg agacatcaat   7800
aaggtgttag aaaagctcgg atacagtgga ggtgatttac tgggcatctt agagagcgga   7860
ggaataaagg cccggataac tcacgtcgac acagagtcct acttcattgt cctcagtata   7920
gcctatccga cgctgtccga gattaagggg gtgattgtcc accggctaga gggggtctcg   7980
tacaacatag gctctcaaga gtggtatacc actgtgccca gtatgttgc aacccaaggg   8040 taccttatct cgaattttga tgagtcatcg tgtactttca tgccagaggg gactgtgtgc   8100
agccaaaatg ccttgtaccc gatgagtcct ctgctccaag aatgcctccg ggggtacacc   8160
aagtcctgtg ctcgtacact cgtatccggg tcttttggga accggttcat tttatcacaa   8220
gggaacctaa tagccaattg tgcatcaatc ctttgcaagt gttacacaac aggaacgatc   8280
attaatcaag accctgacaa gatcctaaca tacattgctg ccgatcactg cccggtagtc   8340
gaggtgaacg gcgtgaccat ccaagtcggg agcaggaggt atccagacgc tgtgtacttg   8400
cacagaattg acctcggtcc tcccatatca ttggagaggt tggacgtagg acaaatctg   8460 gggaatgcaa ttgctaagtt ggaggatgcc aaggaattgt tggagtcatc ggaccagata   8520
ttgaggagta tgaaaggttt atcgagcact agcatagtct acatcctgat tgcagtgtgt   8580
cttggagggt tgatagggat ccccgcttta atatgttgct gcaggggcg ttgtaacaaa   8640 aagggagaac aagttggtat gtcaagacca ggcctaaagc ctgatcttac gggaacatca   8700
aaatcctatg taaggtcgct ctgatcctct acaactcttg aaacacaaat gtcccacaag   8760
tctcctcttc gtcatcaagc aaccaccgca cccagcatca agcccacctg aaattatctc   8820
```

```
cggcttccct ctggccgaac aatatcggta gttaatcaaa acttagggtg caagatcatc   8880
cacaatgtca ccacaacgag accggataaa tgccttctac aaagataacc cccatcccaa   8940
gggaagtagg atagtcatta acagagaaca tcttatgatt gatagacctt atgttttgct   9000
ggctgttctg tttgtcatgt ttctgagctt gatcgggttg ctagccattg caggcattag   9060
acttcatcgg gcagccatct acaccgcaga gatccataaa agcctcagca ccaatctaga   9120
tgtaactaac tcaatcgagc atcaggtcaa ggacgtgctg acaccactct tcaaaatcat   9180
cggtgatgaa gtgggcctga ggacacctca gagattcact gacctagtga aattaatctc   9240
tgacaagatt aaattcctta atccggatag ggagtacgac ttcagagatc tcacttggtg   9300
tatcaacccg ccagagagaa tcaaattgga ttatgatcaa tactgtgcag atgtggctgc   9360
tgaagagctc atgaatgcat tggtgaactc aactctactg gagaccagaa caaccaatca   9420
gttcctagct gtctcaaagg gaaactgctc agggcccact acaatcagag gtcaattctc   9480
aaacatgtcg ctgtccctgt tagacttgta tttaggtcga ggttacaatg tgtcatctat   9540
agtcactatg acatcccagg gaatgtatgg gggaacttac ctagtggaaa agcctaatct   9600
gagcagcaaa aggtcagagt tgtcacaact gagcatgtac cgagtgtttg aagtaggtgt   9660
tatcagaaat ccgggtttgg gggctccggt gttccatatg acaaactatc ttgagcaacc   9720
agtcagtaat gatctcagca actgtatggt ggctttgggg gagctcaaac tcgcagccct   9780
ttgtcacggg gaagattcta tcacaattcc ctatcaggga tcaggaaaag tgtcagctt   9840 ccagctcgtc aagctaggtg tctggaaatc cccaaccgac atgcaatcct gggtcccctt   9900
atcaacggat gatccagtga tagacaggct ttacctctca tctcacagag gtgttatcgc   9960
tgacaatcaa gcaaaatggg ctgtcccgac aacacgaaca gatgacaagt gcgaatgga   10020 gacatgcttc caacaggcgt gtaagggtaa aatccaagca ctctgcgaga tcccgagtg   10080 ggcaccattg aaggataaca ggattccttc atacgggtc ttgtctgttg atctgagtct   10140
gacagttgag cttaaaatca aaattgcttc gggattcggg ccattgatca cacacggttc   10200
agggatggac ctatacaaat ccaaccacaa caatgtgtat tggctgacta tcccgccaat   10260
gaagaaccta gccttaggtg taatcaacac attggagtgg ataccgagat tcaaggttag   10320
tccctacctc ttcactgtcc caattaagga agcaggcgaa gactgccatg ccccaacata   10380
cctacctgcg gaggtggatg gtgatgtcaa actcagttcc aatctggtga ttctacctgg   10440
tcaagatctc caatatgttt tggcaaccta cgatacttcc agggttgaac atgctgtggt   10500
ttattacgtt tacagcccaa gccgctcatt ttcttacttt tatccttta ggttgcctat   10560 aaaggggtc cccatcgaat acaagtggga atgcttcaca tgggaccaaa aactctggtg   10620
ccgtcacttc tgtgtgcttg cggactcaga atctggtgga catatcactc actctgggat   10680
ggtgggcatg ggagtcagct gcacagtcac ccgggaagat ggaaccaatc gcagataggg   10740
ctgctagtga accaatcaca tgatgtcacc cagacatcag gcatacccac tagtgtgaaa   10800
tagacatcag aattaagaaa aacgtagggt ccaagtggtt ccccgttatg gactcgctat   10860
ctgtcaacca gatcttatac cctgaagttc acctagatag cccgatagtt accaataaga   10920
tagtagccat cctggagtat gctcgagtcc ctcacgctta cagcctggag gaccctacac   10980
tgtgtcagaa catcaagcac cgcctaaaaa acggattttc caaccaaatg attataaaca   11040
atgtggaagt tgggaatgtc atcaagtcca agcttaggag ttatccggcc cactctcata   11100
ttccatatcc aaattgtaat caggatttat ttaacataga agacaaagag tcaacgagga   11160
agatccgtga actcctcaaa aaggggaatt cgctgtactc caaagtcagt gataaggttt   11220
```

```
tccaatgctt aagggacact aactcacggc ttggcctagg ctccgaattg agggaggaca    11280
tcaaggagaa agttattaac ttgggagttt acatgcacag ctcccagtgg tttgagccct    11340
ttctgttttg gtttacagtc aagactgaga tgaggtcagt gattaaatca caaacccata    11400
cttgccatag gaggagacac acacctgtat tcttcactgg tagttcagtt gagttgctaa    11460
tctctcgtga ccttgttgct ataatcagta aagagtctca acatgtatat acctgacat    11520 ttgaactggt tttgatgtat tgtgatgtca tagaggggag gttaatgaca gagaccgcta    11580
tgactattga tgctaggtat acagagcttc taggaagagt cagatacatg tggaaactga    11640
tagatggttt cttccctgca ctcgggaatc caacttatca aattgtagcc atgctggagc    11700
ctctttcact tgcttacctg cagctgaggg atataacagt agaactcaga ggtgctttcc    11760
ttaaccactg ctttactgaa atacatgatg ttcttgacca aaacgggttt tctgatgaag    11820
gtacttatca tgagttaact gaagctctag attacatttt cataactgat gacatacatc    11880
tgacagggga gattttctca tttttcagaa gtttcggcca ccccagactt gaagcagtaa    11940
cggctgctga aaatgttagg aaatacatga atcagcctaa agtcattgtg tatgagactc    12000
tgatgaaagg tcatgccata ttttgtggaa tcataatcaa cggctatcgt gacaggcacg    12060
gaggcagttg gccaccgctg accctccccc tgcatgctgc agacacaatc cggaatgctc    12120
aagcttcagg tgaagggtta acacatgagc agtgcgttga taactggaaa tcttttgctg    12180
gagtgaaatt tggctgcttt atgcctctta gcctggatag tgatctgaca atgtacctaa    12240
aggacaaggc acttgctgct ctccaaaggg aatgggattc agtttacccg aaagagttcc    12300
tgcgttacga ccctcccaag ggaaccgggt cacggaggct tgtagatgtt ttccttaatg    12360
attcgagctt tgaccatat gatgtgataa tgtatgttgt aagtggagct tacctccatg    12420
accctgagtt caacctgtct tacagcctga agaaaagga gatcaaggaa acaggtagac    12480
tttttgctaa aatgacttac aaaatgaggg catgccaagt gattgctgaa atctaatct    12540 caaacgggat tggcaaatat tttaaggaca atgggatggc caaggatgag cacgatttga    12600
ctaaggcact ccacactcta gctgtctcag gagtccccaa agatctcaaa gaaagtcaca    12660 gggggggggcc agtcttaaaa acctactccc gaagcccagt ccacacaagt accaggaacg    12720
tgagagcagc aaaagggttt atagggttcc ctcaagtaat tcggcaggac caagacactg    12780
atcatccgga gaatatggaa gcttacgaga cagtcagtgc atttatcacg actgatctca    12840
agaagtactg ccttaattgg agatatgaga ccatcagctt gtttgcacag aggctaaatg    12900
agatttacgg attgccctca ttttttccagt ggctgcataa gaggcttgag acctctgtcc    12960
tgtatgtaag tgaccctcat tgcccccccg accttgacgc ccatatcccg ttatataaag    13020
tccccaatga tcaaatcttc attaagtacc ctatgggagg tatagaaggg tattgtcaga    13080
agctgtggac catcagcacc attccctatc tatacctggc tgcttatgag agcggagtaa    13140
ggattgcttc gttagtgcaa ggggacaatc agaccatagc cgtaacaaaa agggtaccca    13200
gcacatggcc ctacaacctt aagaaacggg aagctgctag agtaactaga gattactttg    13260
taattcttag gcaaaggcta catgatattg ccatcacct caaggcaaat gagacaattg    13320
tttcatcaca ttttttttgtc tattcaaaag gaatatatta tgatgggcta cttgtgtccc    13380
aatcactcaa gagcatcgca agatgtgtat tctggtcaga gactatagtt gatgaaacaa    13440
gggcagcatg cagtaatatt gctacaacaa tggctaaaag catcgagaga ggttatgacc    13500
gttaccttgc atattccctg aacgtcctaa aagtgataca gcaaattctg atctctcttg    13560
```

```
gcttcacaat caattcaacc atgacccggg atgtagtcat acccctcctc acaaacaacg   13620
acctcttaat aaggatggca ctgttgcccg ctcctattgg ggggatgaat tatctgaata   13680
tgagcaggct gtttgtcaga acatcggtg atccagtaac atcatcaatt gctgatctca    13740
agagaatgat tctcgcctca ctaatgcctg aagagaccct ccatcaagta atgacacaac   13800
aaccggggga ctcttcattc ctagactggg ctagcgaccc ttactcagca aatcttgtat   13860
gtgtccagag catcactaga ctcctcaaga acataactgc aaggtttgtc ctgatccata   13920
gtccaaaccc aatgttaaaa ggattattcc atgatgacag taaagaagag gacgagggac   13980
tggcggcatt cctcatggac aggcatatta tagtacctag ggcagctcat gaaatcctgg   14040
atcatagtgt cacaggggca agagagtcta ttgcaggcat gctggatacc acaaaaggct   14100
tgattcgagc cagcatgagg aagggggggt taacctctcg agtgataacc agattgtcca   14160
attatgacta tgaacaattc agagcaggga tggtgctatt gacaggaaga aagagaaatg   14220
tcctcattga caaagagtca tgttcagtgc agctggcgag agctctaaga agccatatgt   14280
gggcgaggct agctcgagga cggcctattt acggccttga ggtccctgat gtactagaat   14340
ctatgcgagg ccaccttatt cggcgtcatg agacatgtgt catctgcgag tgtggatcag   14400
tcaactacgg atggttttt gtcccctcgg gttgccaact ggatgatatt gacaaggaaa    14460
catcatcctt gagagtccca tatattggtt ctaccactga tgagagaaca gacatgaagc   14520
ttgccttcgt aagagcccca agtcgatcct tgcgatctgc tgttagaata gcaacagtgt   14580
actcatgggc ttacggtgat gatgatagct cttggaacga agcctggttg ttggctaggc   14640
aaagggccaa tgtgagcctg gaggagctaa gggtgatcac tcccatctca acttcgacta   14700
atttagcgca taggttgagg gatcgtagca ctcaagtgaa atactcaggt acatcccttg   14760
tccgagtggc gaggtatacc acaatctcca acgacaatct ctcatttgtc atatcagata   14820
agaaggttga tactaacttt atataccaac aaggaatgct tctagggttg ggtgttttag   14880
aaacattgtt tcgactcgag aaagataccg gatcatctaa cacggtatta catcttcacg   14940
tcgaaacaga ttgttgcgtg atcccgatga tagatcatcc caggatacccc agctcccgca   15000 agctagagct gagggcagag ctatgtacca acccattgat atatgataat gcaccttaa    15060 ttgacagaga tgcaacaagg ctatacaccc agagccatag gaggcacctt gtggaatttg   15120
ttacatggtc cacaccccaa ctatatcaca ttttagctaa gtccacagca ctatctatga   15180
ttgacctggt aacaaaattt gagaaggacc atatgaatga aatttcagct ctcataggg    15240 atgacgatat caatagtttc ataactgagt ttctgctcat agagccaaga ttattcacta   15300
tctacttggg ccagtgtgcg gccatcaatt gggcatttga tgtacattat catagaccat   15360
cagggaaata tcagatgggt gagctgttgt catcgttcct ttctagaatg agcaaaggag   15420
tgtttaaggt gcttgtcaat gctctaagcc acccaaagat ctacaagaaa ttctggcatt   15480
gtggtattat agagcctatc catggtcctt cacttgatgc tcaaaacttg cacacaactg   15540
tgtgcaacat ggtttacaca tgctatatga cctacctcga cctgttgttg aatgaagagt   15600
tagaagagtt cacatttctc ttgtgtgaaa gcgacgagga tgtagtaccg gacagattcg   15660
acaacatcca ggcaaacac ttatgtgttc tggcagattt gtactgtcaa ccagggacct    15720
gcccaccaat tcgaggtcta agaccggtag agaaatgtgc agttctaacc gaccatatca   15780
aggcagaggc tatgttatct ccagcaggat cttcgtggaa cataaatcca attattgtag   15840
accattactc atgctctctg acttatctcc ggcgaggatc gatcaaacag ataagattga   15900
gagttgatcc aggattcatt ttcgacgccc tcgctgaggt aaatgtcagt cagccaaaga   15960
```

```
tcggcagcaa caacatctca aatatgagca tcaaggcttt cagaccccca cacgatgatg   16020
ttgcaaaatt gctcaaagat atcaacacaa gcaagcacaa tcttcccatt tcagggggca   16080
atctcgccaa ttatgaaatc catgctttcc gcagaatcgg gttgaactca tctgcttgct   16140
acaaagctgt tgagatatca acattaatta ggagatgcct tgagccaggg gaggacggct   16200
tgttcttggg tgagggatcg ggttctatgt tgatcactta taaagagata cttaaactaa   16260
acaagtgctt ctataatagt gggtttccg ccaattctag atctggtcaa agggaattag    16320
caccctatcc ctccgaagtt ggccttgtcg aacacagaat gggagtaggt aatattgtca   16380
aagtgctctt taacgggagg cccgaagtca cgtgggtagg cagtgtagat tgcttcaatt   16440
tcatagttag taatatccct acctctagtg tggggtttat ccattcagat atagagacct   16500
tgcctgacaa agatactata gagaagctag aggaattggc agccatctta tcgatggctc   16560
tgctcctggg caaaatagga tcaatactgg tgattaagct tatgcctttc agcggggatt   16620
ttgttcaggg atttataagt tatgtagggt ctcattatag agaagtgaac cttgtatacc   16680
ctagatacag caacttcatc tctactgaat cttatttggt tatgacagat ctcaaggcta   16740
accggctaat gaatcctgaa aagattaagc agcagataat tgaatcatct gtgaggactt   16800
cacctggact tataggtcac atcctatcca ttaagcaact aagctgcata caagcaattg   16860
tgggagacgc agttagtaga ggtgatatca atcctactct gaaaaaactt acacctatag   16920
agcaggtgct gatcaattgc gggttggcaa ttaacggacc taagctgtgc aaagaattga   16980
tccaccatga tgttgcctca gggcaagatg gattgcttaa ttctatactc atcctctaca   17040
gggagttggc aagattcaaa gacaaccaaa gaagtcaaca agggatgttc cacgcttacc   17100
ccgtattggt aagtagcagg caacgagaac ttatatctag gatcacccgc aaattctggg   17160
ggcacattct tctttactcc gggaacaaaa agttgataaa taagtttatc cagaatctca   17220
agtccggcta tctgatacta gacttacacc agaatatctt cgttaagaat ctatccaagt   17280
cagagaaaca gattattatg acgggggtt tgaaacgtga gtgggttttt aaggtaacag    17340
tcaaggagac caaagaatgg tataagttag tcggatacag tgccctgatt aaggactaat   17400
tggttgaact ccggaacccT aatcctgccc taggtggtta ggcattattt gcaatatatt   17460
aaagaaaact ttgaaaatac gaagtttcta ttcccagctt tgtctggtgg ccggcatggt   17520
cccagcctcc tcgctggcgc cggctgggca acattccgag gggaccgtcc cctcggtaat   17580
ggcgaatggg acgcggccga tccggctgct aacaaagccc gaaaggaagc tgagttggct   17640
gctgccaccg ctgagcaata actagcataa ccccttgggg cctctaaacg ggtcttgagg   17700
ggttttttgc tgaaaggagg aactatatcc ggatgcggcc gcgggcccta tggtacccag   17760
cttttgttcc ctttagtgag ggttaattcc gagcttggcg taatcatggt catagctgtt   17820
tcctgtgtga aattgttatc cgctcacaat tccacacaac ataggagccg aagcataaa    17880 gtgtaaagcc tggggtgcct aatgagtgag taactcaca ttaattgcgt tgcgctcact    17940
gcccgctttc cagtcgggaa acctgtcgtg ccagctgcat taatgaatcg ccaacgcgc    18000 ggggagaggc ggtttgcgta ttgggcgctc ttccgcttcc tcgctcactg actcgctgcg   18060
ctcggtcgtt cggctgcggc gagcggtatc agctcactca aaggcggtaa tacgttatc    18120 cacagaatca ggggataacg caggaaagaa catgtgagca aaaggccagc aaaaggccag   18180
gaaccgtaaa aaggccgcgt tgctggcgtt tttccatagg ctcggccccc ctgacgagca   18240
tcacaaaaat cgacgctcaa gtcagaggtg gcgaaacccg acaggactat aaagatacca   18300
```

```
ggcgttcccc cctggaagct ccctcgtgcg ctctcctgtt ccgaccctgc cgcttaccgg   18360
atacctgtcc gcctttctcc cttcgggaag cgtggcgctt tctcaatgct cacgctgtag   18420
gtatctcagt tcggtgtagg tcgttcgctc caagctgggc tgtgtgcacg aaccccccgt   18480
tcagcccgac cgctgcgcct tatccggtaa ctatcgtctt gagtccaacc cggtaagaca   18540
cgacttatcg ccactggcag cagccactgg taacaggatt agcagagcga ggtatgtagg   18600
cggtgctaca gagttcttga agtggtggcc taactacggc tacactagaa ggacagtatt   18660
tggtatctgc gctctgctga agccagttac cttcggaaaa agagttggta gctcttgatc   18720
cggcaaacaa accaccgctg gtagcggtgg ttttttttgtt tgcaagcagc agattacgcg   18780
cagaaaaaaa ggatctcaag aagatccttt gatcttttct acggggtctg acgctcagtg   18840
gaacgaaaac tcacgttaag ggattttggt catgagatta caaaaagga tcttcaccta   18900
gatcctttta aattaaaaat gaagttttaa atcaatctaa agtatatatg agtaaacttg   18960
gtctgacagt taccaatgct taatcagtga ggcacctatc tcagcgatct gtctatttcg   19020
ttcatccata gttgcctgac tgcccgtcgt gtagataact acgatacggg agggcttacc   19080
atctggcccc agtgctgcaa tgataccgcg agacccacgc tcaccggctc cagatttatc   19140
agcaataaac cagccagccg aagggccga gcgcagaagt ggtcctgcaa ctttatccgc   19200
ctccatccag tctattaatt gttgccggga agctagagta agtagttcgc cagttaatag   19260
tttgcgcaac gttgttgcca ttgctacagg catcgtggtg tcacgctcgt cgtttggtat   19320
ggcttcattc agctccggtt cccaacgatc aaggcgagtt acatgatccc ccatgttgtg   19380
aaaaaaagcg gttagctcct tcggtcctcc gatcgttgtc agaagtaagt tggccgcagt   19440
gttatcactc atgcttatgg cagcactgca taattctctt actgtcatgc catccgtaag   19500
atgcttttct gtgactggtg agtactcaac caagtcattc tgagaatagt gtatgcggcg   19560
accgagttgc tcttgcccgg cgtcaatacg ggataatacc gcgccacata gcagaacttt   19620
aaaagtgctc atcattggaa aacgttcttc ggggcgaaaa ctctcaagga tcttaccgct   19680
gttgagatcc agttcgatgt aacccactcg tgcacccaac tgatcttcag catctttta   19740
tttcaccagc gtttctgggt gagcaaaaac aggaaggcaa aatgccgcaa aaaagggaat   19800
aagggcgaca cggaaatgtt gaatactcat actcttcctt tttcaatatt attgaagcat   19860
ttatcagggt tattgtctca tgagcggata catatttgaa tgtatttaga aaaataaaca   19920
aataggggtt ccgcgcacat ttccccgaaa agtgccacct gaaattgtaa acgttaatat   19980
tttgttaaaa ttcgcgttaa attttttgtta aatcagctca ttttttaacc aataggccga   20040
aatcggcaaa atcccttata aatcaaaaga atagaccgag atagggttga gtgttgttcc   20100
agtttggaac aagagtccac tattaaagaa cgtggactcc aacgtcaaag ggcgaaaaac   20160
cgtctatcag ggcgatggcc cactacgtga accatcaccc taatcaagtt ttttggggtc   20220
gaggtgccgt aaagcactaa atcggaaccc taaagggagc ccccgattta gagcttgacg   20280
gggaaagccg gcgaacgtgg cgagaaagga agggaagaaa gcgaaaggag cgggcgctag   20340
ggcgctggca agtgtagcgg tcacgctgcg cgtaaccacc acacccgccg cgcttaatgc   20400
gccgctacag ggcgcgtccc attcgccatt caggctgcgc aactgttggg aagggcgatc   20460
ggtgcgggcc tcttcgctat tacgccagcc accgcggtgg cggccgctaa tacgactcac   20520
tatagggcca actttgtttg gtctgatgag tccgtgagga cgaaacccgg agtcccgggt   20580
c                                                                   20581
```

<210> SEQ ID NO 12
<211> LENGTH: 20905
<212> TYPE: DNA
<213> ORGANISM: Artificial Sequence
<220> FEATURE:
<223> OTHER INFORMATION: pTM-MV-ATU2-N-3xM2e
<220> FEATURE:
<221> NAME/KEY: misc_RNA
<222> LOCATION: (1)..(17832)
<223> OTHER INFORMATION: MV-ATU2-N-3xM2e_antigenome
<220> FEATURE:
<221> NAME/KEY: misc_feature
<222> LOCATION: (3378)..(5315)
<223> OTHER INFORMATION: ATU2
<220> FEATURE:
<221> NAME/KEY: misc_feature
<222> LOCATION: (3444)..(3449)
<223> OTHER INFORMATION: BsiWI restriction site
<220> FEATURE:
<221> NAME/KEY: misc_feature
<222> LOCATION: (3453)..(5276)
<223> OTHER INFORMATION: ORF for N-3xM2e fusion protein : N-3xM2e_ORF
<220> FEATURE:
<221> NAME/KEY: misc_feature
<222> LOCATION: (5280)..(5285)
<223> OTHER INFORMATION: BssHII restriction site
<220> FEATURE:
<221> NAME/KEY: misc_feature
<222> LOCATION: (17833)..(20905)
<223> OTHER INFORMATION: plasmid_backbone

<400> SEQUENCE: 12
accaaacaaa gttgggtaag gatagttcaa tcaatgatca tcttctagtg cacttaggat 60
tcaagatcct attatcaggg acaagagcag gattagggat atccgagatg gccacacttt 120
taaggagctt agcattgttc aaaagaaaca aggacaaacc acccattaca tcaggatccg 180
gtggagccat cagaggaatc aaacacatta ttatagtacc aatccctgga gattcctcaa 240
ttaccactcg atccagactt ctggaccggt tggtgaggtt aattggaaac ccggatgtga 300
gcgggcccaa actaacaggg gcactaatag gtatattatc cttatttgtg gagtctccag 360
gtcaattgat tcagaggatc accgatgacc ctgacgttag cataaggctg ttagaggttg 420
tccagagtga ccagtcacaa tctggcctta ccttcgcatc aagaggtacc aacatggagg 480
atgaggcgga ccaatacttt tcacatgatg atccaattag tagtgatcaa tccaggttcg 540
gatggttcgg gaacaaggaa atctcagata ttgaagtgca agaccctgag ggattcaaca 600
tgattctggg taccatccta gcccaaattt gggtcttgct cgcaaaggcg gttacggccc 660
cagacacggc agctgattcg gagctaagaa ggtggataaa gtacacccaa caaagaaggg 720
tagttggtga atttagattg gagagaaaat ggttggatgt ggtgaggaac aggattgccg 780
aggacctctc cttacgccga ttcatggtcg ctctaatcct ggatatcaag agaacacccg 840
gaaacaaacc caggattgct gaaatgatat gtgacattga tacatatatc gtagaggcag 900
gattagccag ttttatcctg actattaagt ttgggataga aactatgtat cctgctcttg 960
gactgcatga atttgctggt gagttatcca cacttgagtc cttgatgaac ctttaccagc 1020
aaatggggga aactgcaccc tacatggtaa tcctggagaa ctcaattcag aacaagttca 1080
gtgcaggatc ataccctctg ctctggagct atgccatggg agtaggagtg gaacttgaaa 1140
actccatggg aggtttgaac tttggccgat cttactttga tccagcatat tttagattag 1200
ggcaagagat ggtaaggagg tcagctggaa aggtcagttc cacattggca tctgaactcg 1260
gtatcactgc cgaggatgca aggcttgttt cagagattgc aatgcatact actgaggaca 1320
agatcagtag agcggttgga cccagacaag cccaagtatc atttctacac ggtgatcaaa 1380

```
gtgagaatga gctaccgaga ttggggggca aggaagatag gagggtcaaa cagagtcgag    1440
gagaagccag ggagagctac agagaaaccg ggcccagcag agcaagtgat gcgagagctg    1500
cccatcttcc aaccggcaca cccctagaca ttgacactgc aacggagtcc agccaagatc    1560
cgcaggacag tcgaaggtca gctgacgccc tgcttaggct gcaagccatg gcaggaatct    1620
cggaagaaca aggctcagac acggacaccc ctatagtgta caatgacaga aatcttctag    1680
actaggtgcg agaggccgag ggccagaaca acatccgcct accatccatc attgttataa    1740
aaaacttagg aaccaggtcc acacagccgc cagcccatca accatccact cccacgattg    1800
gagccaatgg cagaagagca ggcacgccat gtcaaaaacg gactggaatg catccgggct    1860
ctcaaggccg agcccatcgg ctcactggcc atcgaggaag ctatggcagc atggtcagaa    1920
atatcagaca acccaggaca ggagcgagcc acctgcaggg aagagaaggc aggcagttcg    1980
ggtctcagca aaccatgcct ctcagcaatt ggatcaactg aaggcggtgc acctcgcatc    2040
cgcggtcagg gacctggaga gagcgatgac gacgctgaaa ctttgggaat cccccaaga    2100 aatctccagg catcaagcac tgggttacag tgttattacg tttatgatca cagcggtgaa    2160
gcggttaagg gaatccaaga tgctgactct atcatggttc aatcaggcct tgatggtgat    2220
agcaccctct caggaggaga caatgaatct gaaaacagcg atgtggatat tggcgaacct    2280
gataccgagg gatatgctat cactgaccgg ggatctgctc ccatctctat ggggttcagg    2340
gcttctgatg ttgaaactgc agaaggaggg gagatccacg agctcctgag actccaatcc    2400
agaggcaaca actttccgaa gcttgggaaa actctcaatg ttcctccgcc cccggacccc    2460
ggtagggcca gcacttccgg gacacccatt aaaaagggca cagacgcgag attagcctca    2520
tttggaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aagggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg cacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt ttgttcctga caccggccct    3180
gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc aacccccatg    3360
ccagtcgacc caactagcct accctccatc attgttataa aaaacttagg aaccaggtcc    3420
acacagccgc cagcccatca acgcgtacgg agatggccac acttttaagg agcttagcat    3480
tgttcaaaag aaacaaggac aaaccaccca ttacatcagg atccggtgga gccatcagag    3540
gaatcaaaca cattattata gtaccaatcc ctggagattc ctcaattacc actcgatcca    3600
gacttctgga ccggttggtg aggttaattg gaaacccgga tgtgagcggg cccaaactaa    3660
caggggcact aataggtata ttatccttat ttgtggagtc tccaggtcaa ttgattcaga    3720
ggatcaccga tgaccctgac gttagcataa ggctgttaga ggttgtccag agtgaccagt    3780
```

| | | |
|---|---|---|
| cacaatctgg ccttaccttc gcatcaagag gtaccaacat ggaggatgag gcggaccaat | 3840 |
| acttttcaca tgatgatcca attagtagtg atcaatccag gttcggatgg ttcgggaaca | 3900 |
| aggaaatctc agatattgaa gtgcaagacc ctgagggatt caacatgatt ctgggtacca | 3960 |
| tcctagccca aatttgggtc ttgctcgcaa aggcggttac ggcccagac acggcagctg | 4020 |
| attcggagct aagaaggtgg ataaagtaca cccaacaaag aagggtagtt ggtgaattta | 4080 |
| gattggagag aaaatggttg gatgtggtga ggaacaggat tgccgaggac ctctccttac | 4140 |
| gccgattcat ggtcgctcta atcctggata tcaagagaac acccggaaac aaacccagga | 4200 |
| ttgctgaaat gatatgtgac attgatacat atatcgtaga ggcaggatta gccagtttta | 4260 |
| tcctgactat taagtttggg atagaaacta tgtatcctgc tcttggactg catgaatttg | 4320 |
| ctggtgagtt atccacactt gagtccttga tgaacccttta ccagcaaatg ggggaaactg | 4380 |
| caccctacat ggtaatcctg gagaactcaa ttcagaacaa gttcagtgca ggatcatacc | 4440 |
| ctctgctctg gagctatgcc atgggagtag gagtggaact tgaaaactcc atgggaggtt | 4500 |
| tgaactttgg ccgatcttac tttgatccag catattttag attagggcaa gagatggtaa | 4560 |
| ggaggtcagc tggaaaggtc agttccacat tggcatctga actcggtatc actgccgagg | 4620 |
| atgcaaggct tgtttcagag attgcaatgc atactactga ggacaagatc agtagagcgg | 4680 |
| ttggacccag acaagcccaa gtatcatttc tacacggtga tcaaagtgag aatgagctac | 4740 |
| cgagattggg gggcaaggaa gataggaggg tcaaacagag tcgaggagaa gccagggaga | 4800 |
| gctacagaga aaccgggccc agcagagcaa gtgatgcgag agctgcccat cttccaaccg | 4860 |
| gcacacccct agacattgac actgcaacgg agtccagcca agatccgcag acagtcgaa | 4920 |
| ggtcagctga cgccctgctt aggctgcaag ccatggcagg aatctcggaa gaacaaggct | 4980 |
| cagacacgga caccctata gtgtacaatg acagaaatct tctagactcc ggaggatctg | 5040 |
| gcggctctct gctgaccgag gtggaaaccc ccatcagaaa cgagtggggc tgccggtgca | 5100 |
| acgacagctc tgatggcggc ggaagcctgc tgacagaagt ggaaacacct attcggaatg | 5160 |
| agtggggatg cagatgcaat gactccagca cggcggagg cagtctgctg actgaagtgg | 5220 |
| aaaccccaat tcgcaacgaa tggggatgtc gctgtaacga tagcagcgac tgataacgag | 5280 |
| cgcgcagcgc ttagacgtct cgcgatcgat actagtacaa cctaaatcca ttataaaaa | 5340 |
| cttaggagca aagtgattgc ctcccaaggt ccacaatgac agagacctac gacttcgaca | 5400 |
| agtcggcatg ggacatcaaa gggtcgatcg ctccgataca acccaccacc tacagtgatg | 5460 |
| gcaggctggt gccccaggtc agagtcatag atcctggtct aggcgacagg aaggatgaat | 5520 |
| gctttatgta catgtttctg ctggggggttg ttgaggacag cgattcccta gggcctccaa | 5580 |
| tcgggcgagc atttggggttc ctgccccttag gtgttggcag atccacagca aagcccgaaa | 5640 |
| aactcctcaa agaggccact gagcttgaca tagttgttag acgtacagca gggctcaatg | 5700 |
| aaaaactggt gttctacaac aacacccac taactctcct cacaccttgg agaaaggtcc | 5760 |
| taacaacagg gagtgtcttc aacgcaaacc aagtgtgcaa tgcggttaat ctgataccgc | 5820 |
| tcgataccc gcagaggttc cgtgttgttt atatgagcat cacccgtctt tcggataacg | 5880 |
| ggtattacac cgttcctaga agaatgctgg aattcagatc ggtcaatgca gtggccttca | 5940 |
| acctgctggt gacccttagg attgacaagg cgataggccc tgggaagatc atcgacaata | 6000 |
| cagagcaact tcctgaggca acattttatgg tccacatcgg gaacttcagg agaaagaaga | 6060 |
| gtgaagtcta ctctgccgat tattgcaaaa tgaaaatcga aagatgggc ctggttttg | 6120 |

```
cacttggtgg ataggggc accagtcttc acattagaag cacaggcaaa atgagcaaga      6180
ctctccatgc acaactcggg ttcaagaaga ccttatgtta cccgctgatg gatatcaatg    6240
aagaccttaa tcgattactc tggaggagca gatgcaagat agtaagaatc caggcagttt    6300
tgcagccatc agttcctcaa gaattccgca tttacgacga cgtgatcata aatgatgacc    6360
aaggactatt caaagttctg tagaccgtag tgcccagcaa tgcccgaaaa cgaccccct     6420 cacaatgaca gccagaaggc ccggacaaaa aagcccctc cgaaagactc cacgaccaa      6480 gcgagaggcc agccagcagc cgacggcaag cgcgaacacc aggcggcccc agcacagaac    6540
agccctgaca caaggccacc accagccacc ccaatctgca tcctcctcgt gggaccccg     6600 aggaccaacc cccaaggctg ccccgatcc aaaccaccaa ccgcatcccc accaccccg      6660 ggaaagaaac ccccagcaat tggaaggccc ctccccctct tcctcaacac aagaactcca    6720
caaccgaacc gcacaagcga ccgaggtgac ccaaccgcag gcatccgact ccctagacag    6780
atcctctctc cccggcaaac taaacaaaac ttagggccaa ggaacataca cacccaacag    6840
aacccagacc ccggccacg gcgccgcgcc cccaacccc gacaaccaga gggagccccc     6900
aaccaatccc gccggctccc ccggtgccca caggcaggga caccaacccc cgaacagacc    6960
cagcacccaa ccatcgacaa tccaagacgg gggggccccc ccaaaaaaag gccccaggg    7020 gccgacagcc agcaccgcga ggaagcccac ccaccccaca cacgaccacg gcaaccaaac    7080
cagaacccag accaccctgg gccaccagct cccagactcg gccatcaccc cgcagaaagg    7140
aaaggccaca acccgcgcac ccagcccccg atccggcggg gagccaccca acccgaacca    7200
gcacccaaga gcgatccccg aaggacccc gaaccgcaaa ggacatcagt atcccacagc    7260
ctctccaagt cccccggtct cctcctcttc tcgaagggac caaaagatca atccaccaca    7320
cccgacgaca ctcaactccc caccctaaa ggagacaccg ggaatcccag aatcaagact    7380
catccaatgt ccatcatggg tctcaaggtg aacgtctctg ccatattcat ggcagtactg    7440
ttaactctcc aaacacccac cggtcaaatc cattggggca atctctctaa gatagggtg    7500 gtaggaatag gaagtgcaag ctacaaagtt atgactcgtt ccagccatca atcattagtc    7560
ataaaattaa tgcccaatat aactctcctc aataactgca cgagggtaga gattgcagaa    7620
tacaggagac tactgagaac agttttggaa ccaattagag atgcacttaa tgcaatgacc    7680
cagaatataa gaccggttca gagtgtagct tcaagtagga gacacaagag atttgcggga    7740
gtagtcctgg caggtgcggc cctaggcgtt gccacagctg ctcagataac agccggcatt    7800
gcacttcacc agtccatgct gaactctcaa gccatcgaca atctgagagc gagcctggaa    7860
actactaatc aggcaattga gacaatcaga caagcagggc aggagatgat attggctgtt    7920
cagggtgtcc aagactacat caataatgag ctgataccgt ctatgaacca actatcttgt    7980
gatttaatcg gccagaagct cgggctcaaa ttgctcagat actatacaga aatcctgtca    8040
ttatttggcc ccagtttacg ggaccccata tctgcggaga tatctatcca ggctttgagc    8100
tatgcgcttg gaggagacat caataaggtg ttagaaaagc tcggatacag tggaggtgat    8160
ttactgggca tcttagagag cggaggaata aaggcccgga taactcacgt cgacacagag    8220
tcctacttca ttgtcctcag tatagcctat ccgacgctgt ccgagattaa ggggtgatt    8280 gtccaccggc tagaggggt ctcgtacaac ataggctctc aagagtggta taccactgtg    8340
cccaagtatg ttgcaaccca agggtaccttt atctcgaatt ttgatgagtc atcgtgtact    8400
ttcatgccag aggggactgt gtgcagccaa aatgccttgt acccgatgag tcctctgctc    8460
caagaatgcc tccgggggta caccaagtcc tgtgctcgta cactcgtatc cgggtctttt    8520
```

```
gggaaccggt tcattttatc acaagggaac ctaatagcca attgtgcatc aatcctttgc    8580
aagtgttaca caacaggaac gatcattaat caagaccctg acaagatcct aacatacatt    8640
gctgccgatc actgcccggt agtcgaggtg aacggcgtga ccatccaagt cgggagcagg    8700
aggtatccag acgctgtgta cttgcacaga attgacctcg gtcctcccat atcattggag    8760
aggttggacg tagggacaaa tctggggaat gcaattgcta agttggagga tgccaaggaa    8820
ttgttggagt catcggacca gatattgagg agtatgaaag gtttatcgag cactagcata    8880
gtctacatcc tgattgcagt gtgtcttgga gggttgatag ggatccccgc tttaatatgt    8940
tgctgcaggg ggcgttgtaa caaaagggga gaacaagttg gtatgtcaag accaggccta    9000
aagcctgatc ttacgggaac atcaaaatcc tatgtaaggt cgctctgatc ctctacaact    9060
cttgaaacac aaatgtccca caagtctcct cttcgtcatc aagcaaccac cgcacccagc    9120
atcaagccca cctgaaatta tctccggctt ccctctggcc gaacaatatc ggtagttaat    9180
caaaacttag ggtgcaagat catccacaat gtcaccacaa cgagaccgga taaatgcctt    9240
ctacaaagat aaccccccatc ccaagggaag taggatagtc attaacagag aacatcttat    9300
gattgataga cctatgtttt tgctggctgt tctgttttgtc atgtttctga gcttgatcgg    9360
gttgctagcc attgcaggca ttagacttca tcgggcagcc atctacaccg cagagatcca    9420
taaaagcctc agcaccaatc tagatgtaac taactcaatc gagcatcagg tcaaggacgt    9480
gctgacacca ctcttcaaaa tcatcggtga tgaagtgggc ctgaggacac ctcagagatt    9540
cactgaccta gtgaaattaa tctctgacaa gattaaattc cttaatccgg atagggagta    9600
cgacttcaga gatctcactt ggtgtatcaa cccgccagag agaatcaaat tggattatga    9660
tcaatactgt gcagatgtgg ctgctgaaga gctcatgaat gcattggtga actcaactct    9720
actggagacc agaacaacca atcagttcct agctgtctca aagggaaact gctcagggcc    9780
cactacaatc agaggtcaat tctcaaacat gtcgctgtcc ctgttagact tgtatttagg    9840
tcgaggttac aatgtgtcat ctatagtcac tatgacatcc cagggaatgt atgggggaac    9900
ttacctagtg gaaaagccta atctgagcag caaaaggtca gagttgtcac aactgagcat    9960
gtaccgagtg tttgaagtag gtgttatcag aaatccgggt ttgggggctc cggtgttcca    10020
tatgacaaac tatcttgagc aaccagtcag taatgatctc agcaactgta tggtggcttt    10080
gggggagctc aaactcgcag cccttttgtca cggggaagat tctatcacaa ttccctatca    10140
gggatcaggg aaaggtgtca gcttccagct cgtcaagcta ggtgtctgga atccccaac    10200 cgacatgcaa tcctgggtcc ccttatcaac ggatgatcca gtgatagaca ggctttacct    10260
ctcatctcac agaggtgtta tcgctgacaa tcaagcaaaa tgggctgtcc cgacaacacg    10320
aacagatgac aagttgcgaa tggagacatg cttccaacag gcgtgtaagg gtaaaatcca    10380
agcactctgc gagaatcccg agtgggcacc attgaaggat aacaggattc cttcatacgg    10440
ggtcttgtct gttgatctga gtctgacagt tgagcttaaa atcaaaattg cttcgggatt    10500
cgggccattg atcacacacg gttcagggat ggacctatac aaatccaacc acaacaatgt    10560
gtattggctg actatcccgc caatgaagaa cctagcctta ggtgtaatca acacattgga    10620 gtggatacccg agattcaagg ttagtcccta cctcttcact gtcccaatta aggaagcagg    10680
cgaagactgc catgccccaa catacctacc tgcggaggtg gatggtgatg tcaaactcag    10740
ttccaatctg gtgattctac ctggtcaaga tctccaatat gttttggcaa cctacgatac    10800
ttccagggtt gaacatgctg tggtttatta cgtttacagc ccaagccgct cattttctta    10860
```

```
cttttatcct tttaggttgc ctataaaggg ggtccccatc gaattacaag tggaatgctt    10920
cacatgggac caaaaactct ggtgccgtca cttctgtgtg cttgcggact cagaatctgg    10980
tggacatatc actcactctg ggatggtggg catgggagtc agctgcacag tcacccggga    11040
agatggaacc aatcgcagat agggctgcta gtgaaccaat cacatgatgt cacccagaca    11100
tcaggcatac ccactagtgt gaaatagaca tcagaattaa gaaaaacgta gggtccaagt    11160
ggttccccgt tatggactcg ctatctgtca accagatctt atacccctgaa gttcacctag    11220 atagcccgat agttaccaat aagatagtag ccatcctgga gtatgctcga gtccctcacg    11280
cttacagcct ggaggaccct acactgtgtc agaacatcaa gcaccgccta aaaaacggat    11340
tttccaacca aatgattata aacaatgtgg aagttgggaa tgtcatcaag tccaagctta    11400
ggagttatcc ggcccactct catattccat atccaaattg taatcaggat ttatttaaca    11460
tagaagacaa agagtcaacg aggaagatcc gtgaactcct caaaaagggg aattcgctgt    11520
actccaaagt cagtgataag gttttccaat gcttaaggga cactaactca cggcttggcc    11580
taggctccga attgagggag gacatcaagg agaaagttat taacttggga gtttacatgc    11640
acagctccca gtggtttgag ccctttctgt tttggtttac agtcaagact gagatgaggt    11700
cagtgattaa atcacaaacc catacttgcc ataggaggag acacacacct gtattcttca    11760
ctggtagttc agttgagttg ctaatctctc gtgaccttgt tgctataatc agtaaagagt    11820
ctcaacatgt atattacctg acatttgaac tggttttgat gtattgtgat gtcatagagg    11880
ggaggttaat gacagagacc gctatgacta ttgatgctag gtatacagag cttctaggaa    11940
gagtcagata catgtggaaa ctgatagatg gtttcttccc tgcactcggg aatccaactt    12000
atcaaattgt agccatgctg gagcctcttt cacttgctta cctgcagctg agggatataa    12060
cagtagaact cagaggtgct ttccttaacc actgctttac tgaaatacat gatgttcttg    12120
accaaaacgg gttttctgat gaaggtactt atcatgagtt aactgaagct ctagattaca    12180
ttttcataac tgatgacata catctgacag gggagatttt ctcatttttc agaagtttcg    12240 gccacccccag acttgaagca gtaacggctg ctgaaaatgt taggaaatac atgaatcagc    12300
ctaaagtcat tgtgtatgag actctgatga aaggtcatgc catattttgt ggaatcataa    12360
tcaacggcta tcgtgacagg cacggaggca gttggccacc gctgaccctc cccctgcatg    12420
ctgcagacac aatccggaat gctcaagctt caggtgaagg gttaacacat gagcagtgcg    12480
ttgataactg gaaatctttt gctggagtga aatttggctg ctttatgcct cttagcctgg    12540
atagtgatct gacaatgtac ctaaaggaca aggcacttgc tgctctccaa agggaatggg    12600
attcagttta cccgaaagag ttcctgcgtt acgaccctcc caagggaacc gggtcacgga    12660
ggcttgtaga tgtttttcctt aatgattcga gctttgaccc atatgatgtg ataatgtatg    12720
ttgtaagtgg agcttacctc catgaccctg agttcaacct gtcttacagc ctgaaagaaa    12780
aggagatcaa ggaaacaggt agacttttttg ctaaaatgac ttacaaaatg agggcatgcc    12840
aagtgattgc tgaaaatcta atctcaaacg ggattggcaa atattttaag gacaatggga    12900
tggccaagga tgagcacgat ttgactaagg cactccacac tctagctgtc tcaggagtcc    12960
ccaaagatct caaagaaagt cacaggggggg ggccagtctt aaaaacctac tcccgaagcc    13020
cagtccacac aagtaccagg aacgtgagag cagcaaaagg gtttataggg ttccctcaag    13080
taattcggca ggaccaagac actgatcatc cggagaatat ggaagcttac gagacagtca    13140
gtgcatttat cacgactgat ctcaagaagt actgccttaa ttggagatat gagaccatca    13200
gcttgtttgc acagaggcta aatgagattt acggattgcc ctcatttttc cagtggctgc    13260
```

-continued

```
ataagaggct tgagacctct gtcctgtatg taagtgaccc tcattgcccc ccgaccttg    13320
acgcccatat cccgttatat aaagtcccca atgatcaaat cttcattaag taccctatgg   13380
gaggtataga agggtattgt cagaagctgt ggaccatcag caccattccc tatctatacc   13440
tggctgctta tgagagcgga gtaaggattg cttcgttagt gcaaggggac aatcagacca   13500
tagccgtaac aaaaagggta cccagcacat ggccctacaa ccttaagaaa cgggaagctg   13560
ctagagtaac tagagattac tttgtaattc ttaggcaaag gctacatgat attggccatc   13620
acctcaaggc aaatgagaca attgtttcat cacatttttt tgtctattca aaaggaatat   13680
attatgatgg gctacttgtg tcccaatcac tcaagagcat cgcaagatgt gtattctggt   13740
cagagactat agttgatgaa acaagggcag catgcagtaa tattgctaca acaatggcta   13800
aaagcatcga gagaggttat gaccgttacc ttgcatattc cctgaacgtc ctaaaagtga   13860
tacagcaaat tctgatctct cttggcttca caatcaattc aaccatgacc cgggatgtag   13920
tcatacccct cctcacaaac aacgacctct taataaggat ggcactgttg cccgctccta   13980
ttgggggat gaattatctg aatatgagca ggctgtttgt cagaaacatc ggtgatccag    14040
taacatcatc aattgctgat ctcaagagaa tgattctcgc ctcactaatg cctgaagaga   14100
ccctccatca agtaatgaca caacaaccgg gggactcttc attcctagac tgggctagcg   14160
acccttactc agcaaatctt gtatgtgtcc agagcatcac tagactcctc aagaacataa   14220
ctgcaaggtt tgtcctgatc catagtccaa acccaatgtt aaaaggatta ttccatgatg   14280
acagtaaaga agaggacgag ggactggcgg cattcctcat ggacaggcat attatagtac   14340
ctagggcagc tcatgaaatc ctggatcata gtgtcacagg ggcaagagag tctattgcag   14400
gcatgctgga taccacaaaa ggcttgattc gagccagcat gaggaagggg gggttaacct   14460
ctcgagtgat aaccagattg tccaattatg actatgaaca attcagagca gggatggtgc   14520
tattgacagg aagaaagaga aatgtcctca ttgacaaaga gtcatgttca gtgcagctgg   14580
cgagagctct aagaagccat atgtgggcga ggctagctcg aggacggcct atttacggcc   14640
ttgaggtccc tgatgtacta gaatctatgc gaggccacct tattcggcgt catgagacat   14700
gtgtcatctg cgagtgtgga tcagtcaact acgatggtt ttttgtcccc tcgggttgcc    14760
aactggatga tattgacaag gaaacatcat ccttgagagt cccatatatt ggttctacca   14820
ctgatgagag aacagacatg aagcttgcct tcgtaagagc cccaagtcga tccttgcgat   14880
ctgctgttag aatagcaaca gtgtactcat gggcttacgg tgatgatgat agctcttgga   14940
acgaagcctg gttgttggct aggcaaaggg ccaatgtgag cctggaggag ctaagggtga   15000
tcactcccat ctcaacttcg actaatttag cgcataggtt gagggatcgt agcactcaag   15060
tgaaatactc aggtacatcc cttgtccgag tggcgaggta taccacaatc tccaacgaca   15120
atctctcatt tgtcatatca gataagaagg ttgatactaa ctttatatac caacaaggaa   15180
tgcttctagg gttgggtgtt ttagaaacat tgtttcgact cgagaaagat accggatcat   15240
ctaacacggt attacatctt cacgtcgaaa cagattgttg cgtgatcccg atgatagatc   15300
atcccaggat acccagctcc cgcaagctag agctgagggc agagctatgt accaacccat   15360
tgatatatga taatgcacct ttaattgaca gagatgcaac aaggctatac acccagagcc   15420
ataggaggca ccttgtggaa tttgttacat ggtccacacc ccaactatat cacatttag    15480
ctaagtccac agcactatct atgattgacc tggtaacaaa atttgagaag gaccatatga   15540
atgaaatttc agctctcata ggggatgacg atatcaatag tttcataact gagtttctgc   15600
```

```
tcatagagcc aagattattc actatctact tgggccagtg tgcggccatc aattgggcat    15660
ttgatgtaca ttatcataga ccatcaggga aatatcagat gggtgagctg ttgtcatcgt    15720
tcctttctag aatgagcaaa ggagtgttta aggtgcttgt caatgctcta agccacccaa    15780
agatctacaa gaaattctgg cattgtggta ttatagagcc tatccatggt ccttcacttg    15840
atgctcaaaa cttgcacaca actgtgtgca acatggttta cacatgctat atgacctacc    15900
tcgacctgtt gttgaatgaa gagttagaag agttcacatt tctcttgtgt gaaagcgacg    15960
aggatgtagt accggacaga ttcgacaaca tccaggcaaa acacttatgt gttctggcag    16020
atttgtactg tcaaccaggg acctgcccac caattcgagg tctaagaccg gtagagaaat    16080
gtgcagttct aaccgaccat atcaaggcag aggctatgtt atctccagca ggatcttcgt    16140
ggaacataaa tccaattatt gtagaccatt actcatgctc tctgacttat ctccggcgag    16200
gatcgatcaa acagataaga ttgagagttg atccaggatt cattttcgac gccctcgctg    16260
aggtaaatgt cagtcagcca agatcggca gcaacaacat ctcaaatatg agcatcaagg    16320
ctttcagacc cccacacgat gatgttgcaa aattgctcaa agatatcaac acaagcaagc    16380
acaatcttcc catttcaggg ggcaatctcg ccaattatga aatccatgct ttccgcagaa    16440
tcgggttgaa ctcatctgct tgctacaaag ctgttgagat atcaacatta attaggagat    16500
gccttgagcc aggggaggac ggcttgttct tgggtgaggg atcgggttct atgttgatca    16560
cttataaaga gatacttaaa ctaaacaagt gcttctataa tagtggggtt tccgccaatt    16620
ctagatctgg tcaaagggaa ttagcaccct atccctccga agttggcctt gtcgaacaca    16680
gaatgggagt aggtaatatt gtcaaagtgc tctttaacgg gaggcccgaa gtcacgtggg    16740
taggcagtgt agattgcttc aatttcatag ttagtaatat ccctacctct agtgtggggt    16800
ttatccattc agatatagag accttgcctg acaaagatac tatagagaag ctagaggaat    16860
tggcagccat cttatcgatg gctctgctcc tgggcaaaat aggatcaata ctggtgatta    16920
agcttatgcc tttcagcggg gattttgttc agggatttat aagttatgta gggtctcatt    16980
atagagaagt gaaccttgta taccctagat acagcaactt catctctact gaatcttatt    17040
tggttatgac agatctcaag gctaaccggc taatgaatcc tgaaaagatt aagcagcaga    17100
taattgaatc atctgtgagg acttcacctg gacttatagg tcacatccta tccattaagc    17160
aactaagctg catacaagca attgtgggag acgcagttag tagaggtgat atcaatccta    17220
ctctgaaaaa acttacacct atagagcagg tgctgatcaa ttgcgggttg gcaattaacg    17280
gacctaagct gtgcaaagaa ttgatccacc atgatgttgc ctcagggcaa gatggattgc    17340
ttaattctat actcatcctc tacagggagt tggcaagatt caaagacaac caaagaagtc    17400 aacagggat gttccacgct taccccgtat tggtaagtag caggcaacga gaacttatat    17460
ctaggatcac ccgcaaattc tgggggcaca ttcttctttta ctccgggaac aaaaagttga    17520
taaataagtt tatccagaat ctcaagtccg gctatctgat actagactta caccagaata    17580
tcttcgttaa gaatctatcc aagtcagaga acagattat tatgacgggg ggtttgaaac    17640
gtgagtgggt tttaaggta acagtcaagg agaccaaaga atggtataag ttagtcggat    17700
acagtgccct gattaaggac taattggttg aactccggaa ccctaatcct gcctaggtg    17760 gttaggcatt atttgcaata tattaaagaa aactttgaaa atacgaagtt tctattccca    17820
gctttgtctg gtggccggca tggtcccagc ctcctcgctg gcgccggctg ggcaacattc    17880 cgagggggacc gtccctcgg taatggcgaa tgggacgcgg ccgatccggc tgctaacaaa    17940
gcccgaaagg aagctgagtt ggctgctgcc accgctgagc aataactagc ataacccctt    18000
```

```
ggggcctcta aacgggtctt gaggggtttt ttgctgaaag gaggaactat atccggatgc   18060
ggccgcgggc cctatggtac ccagcttttg ttccctttag tgagggttaa ttccgagctt   18120
ggcgtaatca tggtcatagc tgtttcctgt gtgaaattgt tatccgctca caattccaca   18180
caacatagga gccggaagca taaagtgtaa agcctgggt gcctaatgag tgaggtaact    18240
cacattaatt gcgttgcgct cactgcccgc tttccagtcg ggaaacctgt cgtgccagct   18300
gcattaatga atcggccaac gcgcggggag aggcggtttg cgtattgggc gctcttccgc   18360
ttcctcgctc actgactcgc tgcgctcggt cgttcggctg cggcgagcgg tatcagctca   18420
ctcaaaggcg gtaatacggt tatccacaga atcaggggat aacgcaggaa agaacatgtg   18480
agcaaaaggc cagcaaaagg ccaggaaccg taaaaaggcc gcgttgctgg cgttttttcca  18540 taggctcggc cccctgacg agcatcacaa aaatcgacgc tcaagtcaga ggtggcgaaa    18600
cccgacagga ctataaagat accaggcgtt ccccctgga agctccctcg tgcgctctcc    18660
tgttccgacc ctgccgctta ccggatacct gtccgccttt ctcccttcgg gaagcgtggc   18720
gctttctcaa tgctcacgct gtaggtatct cagttcggtg taggtcgttc gctccaagct   18780
gggctgtgtg cacgaacccc ccgttcagcc cgaccgctgc gccttatccg gtaactatcg   18840
tcttgagtcc aacccggtaa gacacgactt atcgccactg gcagcagcca ctggtaacag   18900
gattagcaga gcgaggtatg taggcggtgc tacagagttc ttgaagtggt ggcctaacta   18960
cggctacact agaaggacag tatttggtat ctgcgctctg ctgaagccag ttaccttcgg   19020
aaaaagagtt ggtagctctt gatccggcaa acaaaccacc gctggtagcg gtggtttttt   19080
tgtttgcaag cagcagatta cgcgcagaaa aaaaggatct caagaagatc ctttgatctt   19140
ttctacgggg tctgacgctc agtggaacga aaactcacgt taagggattt tggtcatgag   19200
attatcaaaa aggatcttca cctagatcct tttaaattaa aaatgaagtt ttaaatcaat   19260
ctaaagtata tatgagtaaa cttggtctga cagttaccaa tgcttaatca gtgaggcacc   19320
tatctcagcg atctgtctat ttcgttcatc catagttgcc tgactgcccg tcgtgtagat   19380
aactacgata cgggagggct taccatctgg ccccagtgct gcaatgatac cgcgagaccc   19440
acgctcaccg gctccagatt tatcagcaat aaaccagcca gccggaaggg ccgagcgcag   19500
aagtggtcct gcaactttat ccgcctccat ccagtctatt aattgttgcc gggaagctag   19560
agtaagtagt tcgccagtta atagtttgcg caacgttgtt gccattgcta caggcatcgt   19620
ggtgtcacgc tcgtcgtttg gtatggcttc attcagctcc ggttcccaac gatcaaggcg   19680
agttacatga tcccccatgt tgtgaaaaaa agcggttagc tccttcggtc ctccgatcgt   19740
tgtcagaagt aagttggccg cagtgttatc actcatgctt atggcagcac tgcataattc   19800
tcttactgtc atgccatccg taagatgctt ttctgtgact ggtgagtact caaccaagtc   19860
attctgagaa tagtgtatgc ggcgaccgag ttgctcttgc ccggcgtcaa tacgggataa   19920
taccgcgcca catagcagaa ctttaaaagt gctcatcatt ggaaaacgtt cttcggggcg   19980
aaaactctca aggatcttac cgctgttgag atccagttcg atgtaaccca ctcgtgcacc   20040
caactgatct tcagcatctt ttactttcac cagcgtttct gggtgagcaa aaacaggaag   20100
gcaaaatgcc gcaaaaaagg gaataagggc gacacggaaa tgttgaatac tcatactctt   20160 ccttttttcaa tattattgaa gcatttatca gggttattgt ctcatgagcg gatacatatt   20220
tgaatgtatt tagaaaaata aacaaatagg ggttccgcgc acatttcccc gaaaagtgcc   20280
acctgaaatt gtaaacgtta atattttgtt aaaattcgcg ttaaattttt gttaaatcag   20340
```

```
ctcatttttt aaccaatagg ccgaaatcgg caaaatccct tataaatcaa aagaatagac  20400
cgagataggg ttgagtgttg ttccagtttg gaacaagagt ccactattaa agaacgtgga  20460
ctccaacgtc aaagggcgaa aaaccgtcta tcagggcgat ggcccactac gtgaaccatc  20520
accctaatca agttttttgg ggtcgaggtg ccgtaaagca ctaaatcgga accctaaagg  20580
gagcccccga tttagagctt gacggggaaa gccggcgaac gtggcgagaa aggaagggaa  20640
gaaagcgaaa ggagcgggcg ctagggcgct ggcaagtgta gcggtcacgc tgcgcgtaac  20700
caccacaccc gccgcgctta atgcgccgct acagggcgcg tcccattcgc cattcaggct  20760
gcgcaactgt tgggaagggc gatcggtgcg ggcctcttcg ctattacgcc agccaccgcg  20820
gtggcggccg ctaatacgac tcactatagg gccaactttg tttggtctga tgagtccgtg  20880
aggacgaaac ccggagtccc gggtc                                        20905
```
<210> SEQ ID NO 13
<211> LENGTH: 20827
<212> TYPE: DNA
<213> ORGANISM: Artificial Sequence
<220> FEATURE:
<223> OTHER INFORMATION: pTM-MV-ATU2-NPflu-3xM2e
<220> FEATURE:
<221> NAME/KEY: misc_RNA
<222> LOCATION: (1)..(17754)
<223> OTHER INFORMATION: MV-ATU2-NPflu-3xM2e_antigenome
<220> FEATURE:
<221> NAME/KEY: misc_feature
<222> LOCATION: (3378)..(5237)
<223> OTHER INFORMATION: ATU2
<220> FEATURE:
<221> NAME/KEY: misc_feature
<222> LOCATION: (3444)..(3449)
<223> OTHER INFORMATION: BsiWI restriction site
<220> FEATURE:
<221> NAME/KEY: misc_feature
<222> LOCATION: (3456)..(4949)
<223> OTHER INFORMATION: NPflu consensus polypeptide
<220> FEATURE:
<221> NAME/KEY: misc_feature
<222> LOCATION: (3456)..(5198)
<223> OTHER INFORMATION: ORF for NPflu-3xM2e fusion protein : NPflu-3xM2e_ORF
<220> FEATURE:
<221> NAME/KEY: misc_feature
<222> LOCATION: (4950)..(4967)
<223> OTHER INFORMATION: linker (SGG)2
<220> FEATURE:
<221> NAME/KEY: misc_feature
<222> LOCATION: (4968)..(5036)
<223> OTHER INFORMATION: M2e consensus polypeptide
<220> FEATURE:
<221> NAME/KEY: misc_feature
<222> LOCATION: (5046)..(5114)
<223> OTHER INFORMATION: M2e consensus polypeptide
<220> FEATURE:
<221> NAME/KEY: misc_feature
<222> LOCATION: (5124)..(5192)
<223> OTHER INFORMATION: M2e consensus polypeptide
<220> FEATURE:
<221> NAME/KEY: misc_feature
<222> LOCATION: (5202)..(5207)
<223> OTHER INFORMATION: BssHII restriction site
<220> FEATURE:
<221> NAME/KEY: misc_feature
<222> LOCATION: (17755)..(20827)
<223> OTHER INFORMATION: plasmid_backbone

<400> SEQUENCE: 13

```
accaaacaaa gttgggtaag gatagttcaa tcaatgatca tcttctagtg cacttaggat     60
tcaagatcct attatcaggg acaagagcag gattagggat atccgagatg gccacacttt    120
```

```
taaggagctt agcattgttc aaaagaaaca aggacaaacc acccattaca tcaggatccg      180
gtggagccat cagaggaatc aaacacatta ttatagtacc aatccctgga gattcctcaa      240
ttaccactcg atccagactt ctggaccggt tggtgaggtt aattggaaac ccggatgtga      300
gcgggcccaa actaacaggg gcactaatag gtatattatc cttatttgtg gagtctccag      360
gtcaattgat tcagaggatc accgatgacc ctgacgttag cataaggctg ttagaggttg      420
tccagagtga ccagtcacaa tctggcctta ccttcgcatc aagaggtacc aacatggagg      480
atgaggcgga ccaatacttt tcacatgatg atccaattag tagtgatcaa tccaggttcg      540
gatggttcgg gaacaaggaa atctcagata ttgaagtgca agaccctgag ggattcaaca      600
tgattctggg taccatccta gcccaaattt gggtcttgct cgcaaaggcg gttacggccc      660
cagacacggc agctgattcg gagctaagaa ggtggataaa gtacacccaa caaagaaggg      720
tagttggtga atttagattg gagagaaaat ggttggatgt ggtgaggaac aggattgccg      780
aggacctctc cttacgccga ttcatggtcg ctctaatcct ggatatcaag gaacacccg       840 gaaacaaacc caggattgct gaaatgatat gtgacattga tacatatatc gtagaggcag      900
gattagccag ttttatcctg actattaagt ttgggataga aactatgtat cctgctcttg      960
gactgcatga atttgctggt gagttatcca cacttgagtc cttgatgaac ctttaccagc     1020
aaatggggga aactgcaccc tacatggtaa tcctggagaa ctcaattcag aacaagttca     1080
gtgcaggatc atacctctg ctctggagct atgccatggg agtaggagtg aacttgaaa       1140 actccatggg aggtttgaac tttggccgat cttactttga tccagcatat tttagattag     1200
ggcaagagat ggtaaggagg tcagctggaa aggtcagttc cacattggca tctgaactcg     1260
gtatcactgc cgaggatgca aggcttgttt cagagattgc aatgcatact actgaggaca     1320
agatcagtag agcggttgga cccagacaag cccaagtatc atttctacac ggtgatcaaa     1380
gtgagaatga gctaccgaga ttgggggggca aggaagatag gagggtcaaa cagagtcgag     1440
gagaagccag ggagagctac agagaaaccg ggcccagcag agcaagtgat gcgagagctg     1500
cccatcttcc aaccggcaca cccctagaca ttgacactgc aacggagtcc agccaagatc     1560
cgcaggacag tcgaaggtca gctgacgccc tgcttaggct gcaagccatg gcaggaatct     1620
cggaagaaca aggctcagac acggacaccc ctatagtgta caatgacaga aatcttctag     1680
actaggtgcg agaggccgag ggccagaaca acatccgcct accatccatc attgttataa     1740
aaaacttagg aaccaggtcc acacagccgc cagcccatca accatccact cccacgattg     1800
gagccaatgg cagaagagca ggcacgccat gtcaaaaacg gactgaaatg catccgggct     1860
ctcaaggccg agcccatcgg ctcactggcc atcgaggaag ctatggcagc atggtcagaa     1920
atatcagaca acccaggaca ggagcgagcc acctgcaggg aagagaaggc aggcagttcg     1980
ggtctcagca aaccatgcct ctcagcaatt ggatcaactg aaggcggtgc acctcgcatc     2040
cgcggtcagg gacctggaga gagcgatgac gacgctgaaa cttggggaat ccccccaaga     2100
aatctccagg catcaagcac tgggttacag tgttattacg tttatgatca cagcggtgaa     2160
gcggttaagg gaatccaaga tgctgactct atcatggttc aatcaggcct tgatggtgat     2220
agcaccctct caggaggaga caatgaatct gaaaacagcg atgtggatat tggcgaacct     2280
gataccgagg gatatgctat cactgaccgg ggatctgctc ccatctctat ggggttcagg     2340
gcttctgatg ttgaaactgc agaaggaggg gagatccacg agctcctgag actccaatcc     2400
agaggcaaca actttccgaa gcttgggaaa actctcaatg ttcctccgcc cccggacccc     2460
ggtagggcca gcacttccgg gacacccatt aaaaagggca cagacgcgag attagcctca     2520
```

```
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aaggggagaa ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga acccgttgc cagccgacaa    3060 ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagcct accctccatc attgttataa aaaacttagg aaccaggtcc   3420
acacagccgc cagcccatca acgcgtacgg ccaccatggc ctctcagggc accaagagaa   3480
gctacgagca gatggaaacc gacggcgagc ggcagaacgc caccgagatt agagccagcg   3540
tgggcagaat gatcggcggc atcggccggt tctacatcca gatgtgcacc gagctgaagc   3600
tgagcgacta cgagggccgg ctgatccaga acagcctgac catcgagcgg atggtgctga   3660
gcgccttcga cgagcggcgg aacaagtacc tggaagaaca ccccagcgcc ggcaaggacc   3720
ccaagaaaac aggcggccct atctacagac gggtggacgg caagtggatg cgcgagctgg   3780
tgctgtacga caaagaggaa atccggcgga tctggcggca ggccaacaat ggcgaagatg   3840
ccacagccgg cctgacccac atcatgatct ggcacagcaa cctgaacgac gccacctacc   3900
agcggaccag agcactcgtg cggacaggca tggacccag aatgtgcagc ctgatgcagg    3960
gcagcaccct gcccagaaga tctggcgctg ctggcgcagc tgtgaagggc gtgggaacca   4020
tggtcatgga actgatcagg atgatcaagc ggggaatcaa cgaccggaac ttttggagag   4080
gcgagaacgg cagaaagacc cgcagcgcct acgagaggat gtgcaatatc ctgaagggca   4140
agttccagac agccgcccag cgggccatga tggatcaagt gcgcgagagc agaaaccccg   4200
gcaacgccga gatcgaggac ctgatcttcc tggccagaag cgccctgatc ctgagggct    4260 ctgtggccca aagagctgt ctgcctgcct gcgtgtacgg acctgccgtg gccagcggct    4320
acgacttcga gaaagagggc tacagcctcg tgggcatcga cccattcaag ctgctgcaga   4380
actcccaggt gtacagcctg atccggccca cgagaaccc cgcccacaag tctcagctcg    4440
tgtggatggc ctgtcacagc gccgccttcg aggatctgag agtgtccagc ttcatccggg   4500
gcacaaaggt gtcccccaga ggcaagctga gcaccagagg cgtgcagatc gccagcaacg   4560
agaatatgga caacatgggc agctccaccc tggaactgcg gagccggtat tgggccatca   4620
gaaccagaag cggcggcaac accaaccagc agagagcctc tgccgacag atcagcgtgc    4680 agcccacctt tagcgtgcag agaaacctgc ccttcgagaa ggccacaatc atggccgcct   4740
tcaccggcaa taccgagggc agaaccacgc acatgcgggc cgagatcatc agaatgatgg   4800
aaagcgccaa gcccgaggaa gtgtcattcc agggcagggg cgtgttcgag ctgtccgacg   4860
```

```
agaaagccac caacccatc gtgcccagct tcgacatgag caacgagggc agctacttct    4920
tcggcgacaa cgccgaagag tacgacaact ccggaggatc tggcggctct ctgctgaccg    4980
aggtggaaac ccccatcaga aacgagtggg gctgccggtg caacgacagc tctgatggcg    5040
gcggaagcct gctgacagaa gtggaaacac ctattcggaa tgagtgggga tgcagatgca    5100
atgactccag cgacggcgga ggcagtctgc tgactgaagt ggaaacccca attcgcaacg    5160
aatggggatg tcgctgtaac gatagcagcg actgataacg agcgcgcagc gcttagacgt    5220
ctcgcgatcg atactagtac aacctaaatc cattataaaa aacttaggag caaagtgatt    5280
gcctcccaag gtccacaatg acagagacct acgacttcga caagtcggca tgggacatca    5340
aagggtcgat cgctccgata caacccacca cctacagtga tggcaggctg gtgccccagg    5400
tcagagtcat agatcctggt ctaggcgaca ggaaggatga atgctttatg tacatgtttc    5460
tgctgggggt tgttgaggac agcgattccc tagggcctcc aatcgggcga gcatttgggt    5520
tcctgccctt aggtgttggc agatccacag caaagcccga aaaactcctc aaagaggcca    5580
ctgagcttga catagttgtt agacgtacag cagggctcaa tgaaaaactg gtgttctaca    5640
acaacacccc actaactctc ctcacacctt ggagaaaggt cctaacaaca gggagtgtct    5700
tcaacgcaaa ccagtgtgc aatgcggtta atctgatacc gctcgatacc ccgcagaggt    5760
tccgtgttgt ttatatgagc atcacccgtc tttcggataa cgggtattac accgttccta    5820
gaagaatgct ggaattcaga tcggtcaatg cagtggcctt caacctgctg gtgacccttat    5880
ggattgacaa ggcgataggc cctgggaaga tcatcgacaa tacagagcaa cttcctgagg    5940
caacatttat ggtccacatc gggaacttca ggagaaagaa gagtgaagtc tactctgccg    6000
attattgcaa aatgaaaatc gaaaagatgg gcctggtttt tgcacttggt gggatagggg    6060
gcaccagtct tcacattaga agcacaggca aaatgagcaa gactctccat gcacaactcg    6120
ggttcaagaa gaccttatgt tacccgctga tggatatcaa tgaagacctt aatcgattac    6180
tctggaggag cagatgcaag atagtaagaa tccaggcagt tttgcagcca tcagttcctc    6240
aagaattccg catttacgac gacgtgatca taaatgatga ccaaggacta ttcaaagttc    6300
tgtagaccgt agtgcccagc aatgcccgaa aacgaccccc ctcacaatga cagccagaag    6360
gcccggacaa aaaagccccc tccgaaagac tccacggacc aagcgagagg ccagccagca    6420
gccgacggca agcgcgaaca ccaggcggcc ccagcacaga acagccctga cacaaggcca    6480
ccaccagcca ccccaatctg catcctcctc gtgggacccc cgaggaccaa ccccaaggc    6540
tgccccgat ccaaaccacc aaccgcatcc ccaccacccc cgggaaagaa acccccagca    6600
attggaaggc ccctccccct cttcctcaac acaagaactc cacaaccgaa ccgcacaagc    6660
gaccgaggtg acccaaccgc aggcatccga ctccctagac agatcctctc tccccggcaa    6720
actaaacaaa acttagggcc aaggaacata cacacccaac agaacccaga ccccggccca    6780
cggcgccgcg ccccaaccc ccgacaacca gagggagccc caaccaatc ccgccggctc    6840
cccccggtgcc cacaggcagg acaccaacc cccgaacaga cccagcaccc aaccatcgac    6900
aatccaagac ggggggcccc cccaaaaaa aggcccccag gggccgacag ccagcaccgc    6960
gaggaagccc acccacccca cacacgacca cggcaaccaa accagaaccc agaccaccct    7020
gggccaccag ctcccagact cggccatcac cccgcagaaa ggaaaggcca aacccgcgc    7080
accccagccc cgatccggcg gggagccacc caacccgaac cagcacccaa gagcgatccc    7140
cgaaggaccc ccgaaccgca aaggacatca gtatcccaca gcctctccaa gtccccggtt    7200
ctcctcctct tctcgaaggg accaaaagat caatccacca cacccgacga cactcaactc    7260
```

```
cccacccta   aaggagacac   cgggaatccc   agaatcaaga   ctcatccaat   gtccatcatg   7320
ggtctcaagg   tgaacgtctc   tgccatattc   atggcagtac   tgttaactct   ccaaacaccc   7380
accggtcaaa   tccattgggg   caatctctct   aagatagggg   tggtaggaat   aggaagtgca   7440
agctacaaag   ttatgactcg   ttccagccat   caatcattag   tcataaaatt   aatgcccaat   7500
ataactctcc   tcaataactg   cacgagggta   gagattgcag   aatacaggag   actactgaga   7560
acagttttgg   aaccaattag   agatgcactt   aatgcaatga   cccagaatat   aagaccggtt   7620
cagagtgtag   cttcaagtag   gagacacaag   agatttgcgg   gagtagtcct   ggcaggtgcg   7680
gccctaggcg   ttgccacagc   tgctcagata   acagccggca   ttgcacttca   ccagtccatg   7740
ctgaactctc   aagccatcga   caatctgaga   gcgagcctgg   aaactactaa   tcaggcaatt   7800
gagacaatca   gacaagcagg   gcaggagatg   atattggctg   ttcagggtgt   ccaagactac   7860
atcaataatg   agctgatacc   gtctatgaac   caactatctt   gtgatttaat   cggccagaag   7920
ctcgggctca   aattgctcag   atactataca   gaaatcctgt   cattatttgg   ccccagttta   7980
cgggaccca   tatctgcgga   gatatctatc   caggctttga   gctatgcgct   tggaggagac   8040
atcaataagg   tgttagaaaa   gctcggatac   agtggaggtg   atttactggg   catcttagag   8100
agcggaggaa   taaaggcccg   gataactcac   gtcgacacag   agtcctactt   cattgtcctc   8160
agtatagcct   atccgacgct   gtccgagatt   aaggggtga   ttgtccaccg   gctagagggg   8220
gtctcgtaca   acataggctc   tcaagagtgg   tataccactg   tgcccaagta   tgttgcaacc   8280
caagggtacc   ttatctcgaa   ttttgatgag   tcatcgtgta   ctttcatgcc   agaggggact   8340
gtgtgcagcc   aaaatgcctt   gtacccgatg   agtcctctgc   tccaagaatg   cctccggggg   8400
tacaccaagt   cctgtgctcg   tacactcgta   tccgggtctt   ttgggaaccg   gttcattta   8460
tcacaaggga   acctaatagc   caattgtgca   tcaatccttt   gcaagtgtta   cacaacagga   8520
acgatcatta   atcaagaccc   tgacaagatc   ctaacataca   ttgctgccga   tcactgcccg   8580
gtagtcgagg   tgaacggcgt   gaccatccaa   gtcgggagca   ggaggtatcc   agacgctgtg   8640
tacttgcaca   gaattgacct   cggtcctccc   atatcattgg   agaggttgga   cgtagggaca   8700
aatctgggga   atgcaattgc   taagttggag   gatgccaagg   aattgttgga   gtcatcggac   8760
cagatattga   ggagtatgaa   aggtttatcg   agcactagca   tagtctacat   cctgattgca   8820
gtgtgtcttg   gagggttgat   agggatcccc   gctttaatat   gttgctgcag   ggggcgttgt   8880
aacaaaaagg   gagaacaagt   tggtatgtca   agaccaggcc   taaagcctga   tcttacggga   8940
acatcaaaat   cctatgtaag   gtcgctctga   tcctctacaa   ctcttgaaac   acaaatgtcc   9000
cacaagtctc   ctcttcgtca   tcaagcaacc   accgcaccca   gcatcaagcc   cacctgaaat   9060
tatctccggc   ttccctctgg   ccgaacaata   tcggtagtta   atcaaaactt   agggtgcaag   9120
atcatccaca   atgtcaccac   aacgagaccg   gataaatgcc   ttctacaaag   ataaccccca   9180
tcccaaggga   agtaggatag   tcattaacag   agaacatctt   atgattgata   gaccttatgt   9240
tttgctggct   gttctgtttg   tcatgtttct   gagcttgatc   gggttgctag   ccattgcagg   9300
cattagactt   catcgggcag   ccatctacac   cgcagagatc   cataaaagcc   tcagcaccaa   9360
tctagatgta   actaactcaa   tcgagcatca   ggtcaaggac   gtgctgacac   cactcttcaa   9420
aatcatcggt   gatgaagtgg   gcctgaggac   acctcagaga   ttcactgacc   tagtgaaatt   9480
aatctctgac   aagattaaat   tccttaatcc   ggataggggag   tacgacttca   gagatctcac   9540
ttggtgtatc   aacccgccag   agagaatcaa   attggattat   gatcaatact   gtgcagatgt   9600
```

-continued

```
ggctgctgaa gagctcatga atgcattggt gaactcaact ctactggaga ccagaacaac   9660
caatcagttc ctagctgtct caaagggaaa ctgctcaggg cccactacaa tcagaggtca   9720
attctcaaac atgtcgctgt ccctgttaga cttgtattta ggtcgaggtt acaatgtgtc   9780
atctatagtc actatgacat cccagggaat gtatggggga acttacctag tggaaaagcc   9840
taatctgagc agcaaaaggt cagagttgtc acaactgagc atgtaccgag tgtttgaagt   9900
aggtgttatc agaaatccgg gtttgggggc tccggtgttc catatgacaa actatcttga   9960
gcaaccagtc agtaatgatc tcagcaactg tatggtggct ttgggggagc tcaaactcgc  10020
agccctttgt cacggggaag attctatcac aattccctat cagggatcag ggaaaggtgt  10080
cagcttccag ctcgtcaagc taggtgtctg gaaatcccca accgacatgc aatcctgggt  10140
ccccttatca acggatgatc cagtgataga caggctttac ctctcatctc acagaggtgt  10200
tatcgctgac aatcaagcaa aatgggctgt cccgacaaca cgaacagatg acaagttgcg  10260
aatggagaca tgcttccaac aggcgtgtaa gggtaaaatc caagcactct gcgagaatcc  10320
cgagtgggca ccattgaagg ataacaggat tccttcatac ggggtcttgt ctgttgatct  10380
gagtctgaca gttgagctta aaatcaaaat tgcttcggga ttcgggccat tgatcacaca  10440
cggttcaggg atggacctat acaaatccaa ccacaacaat gtgtattggc tgactatccc  10500
gccaatgaag aacctagcct taggtgtaat caacacattg gagtggatac cgagattcaa  10560
ggttagtccc tacctcttca ctgtcccaat taaggaagca ggcgaagact gccatgcccc  10620
aacataccta cctgcggagg tggatggtga tgtcaaactc agttccaatc tggtgattct  10680
acctggtcaa gatctccaat atgttttggc aacctacgat acttccaggg ttgaacatgc  10740
tgtggtttat tacgtttaca gcccaagccg ctcatttttct tactttttatc cttttaggtt  10800 gcctataaag ggggtcccca tcgaattaca agtggaatgc ttcacatggg accaaaaact  10860
ctggtgccgt cacttctgtg tgcttgcgga ctcagaatct ggtggacata tcactcactc  10920
tgggatggtg ggcatgggag tcagctgcac agtcacccgg gaagatggaa ccaatcgcag  10980
atagggctgc tagtgaacca atcacatgat gtcacccaga catcaggcat acccactagt  11040
gtgaaataga catcagaatt aagaaaaacg tagggtccaa gtggttcccc gttatggact  11100
cgctatctgt caaccagatc ttatacctg aagttcacct agatagcccg atagttacca   11160
ataagatagt agccatcctg gagtatgctc gagtccctca cgcttacagc ctggaggacc  11220
ctacactgtg tcagaacatc aagcaccgcc taaaaacgg attttccaac caaatgatta  11280
taaacaatgt ggaagttggg aatgtcatca gtccaagct taggagttat ccggcccact   11340
ctcatattcc atatccaaat tgtaatcagg atttattaa catagaagac aaagagtcaa   11400
cgaggaagat ccgtgaactc ctcaaaaagg ggaattcgct gtactccaaa gtcagtgata  11460
aggttttcca atgcttaagg gacactaact cacggcttgg cctaggctcc gaattgaggg  11520
aggacatcaa ggagaaagtt attaacttgg gagtttacat gcacagctcc cagtggtttg  11580
agcccttcct gttttggttt acagtcaaga ctgagatgag gtcagtgatt aaatcacaaa  11640
cccatacttg ccataggagg agacacacac ctgtattctt cactggtagt tcagttgagt  11700
tgctaatctc tcgtgacctt gttgctataa tcagtaaaga gtctcaacat gtatattacc  11760
tgacatttga actggttttg atgtattgtg atgtcataga ggggaggtta atgacagaga  11820
ccgctatgac tattgatgct aggtatacag agcttctagg aagagtcaga tacatgtgga  11880
aactgataga tggtttcttc cctgcactcg ggaatccaac ttatcaaatt gtagccatgc  11940
tggagcctct ttcacttgct tacctgcagc tgagggatat aacagtagaa ctcagaggtg  12000
```

```
ctttccttaa ccactgcttt actgaaatac atgatgttct tgaccaaaac gggttttctg    12060
atgaaggtac ttatcatgag ttaactgaag ctctagatta catttcata actgatgaca    12120 tacatctgac aggggagatt ttctcatttt tcagaagttt cggccacccc agacttgaag    12180
cagtaacggc tgctgaaaat gttaggaaat acatgaatca gcctaaagtc attgtgtatg    12240
agactctgat gaaaggtcat gccatatttt gtggaatcat aatcaacggc tatcgtgaca    12300
ggcacggagg cagttggcca ccgctgaccc tccccctgca tgctgcagac acaatccgga    12360
atgctcaagc ttcaggtgaa gggttaacac atgagcagtg cgttgataac tggaaatctt    12420
ttgctggagt gaaatttggc tgcttttatgc ctcttagcct ggatagtgat ctgacaatgt    12480
acctaaagga caaggcactt gctgctctcc aaagggaatg ggattcagtt acccgaaag    12540 agttcctgcg ttcgacccct cccaagggaa ccgggtcacg gaggcttgta gatgttttcc    12600
ttaatgattc gagctttgac ccatatgatg tgataatgta tgttgtaagt ggagcttacc    12660
tccatgaccc tgagttcaac ctgtcttaca gcctgaaaga aaaggagatc aaggaaacag    12720
gtagactttt tgctaaaatg acttacaaaa tgagggcatg ccaagtgatt gctgaaaatc    12780
taatctcaaa cggattggc aaatatttta aggacaatgg gatggccaag gatgagcacg    12840
atttgactaa ggcactccac actctagctg tctcaggagt ccccaaagat ctcaaagaaa    12900
gtcacagggg ggggccagtc ttaaaaacct actcccgaag cccagtccac acaagtacca    12960
ggaacgtgag agcagcaaaa gggtttatag ggttccctca agtaattcgg caggaccaag    13020
acactgatca tccggagaat atggaagctt acgagacagt cagtgcattt atcacgactg    13080
atctcaagaa gtactgcctt aattggagat atgagaccat cagcttgttt gcacagaggc    13140
taaatgagat ttacggattg ccctcatttt tccagtggct gcataagagg cttgagacct    13200
ctgtcctgta tgtaagtgac cctcattgcc cccccgacct tgacgcccat atcccgttat    13260
ataaagtccc caatgatcaa atcttcatta agtaccctat gggaggtata gaagggtatt    13320
gtcagaagct gtggaccatc agcaccattc cctatctata cctggctgct tatgagagcg    13380
gagtaaggat tgcttcgtta gtgcaagggg acaatcagac catagccgta acaaaagggg    13440
tacccagcac atggccctac aaccttaaga acgggaagc tgctagagta actagagatt    13500
actttgtaat tcttaggcaa aggctacatg atattggcca tcacctcaag gcaaatgaga    13560
caattgtttc atcacatttt tttgtctatt caaaaggaat atattatgat gggctacttg    13620
tgtcccaatc actcaagagc atcgcaagat gtgtattctg gtcagagact atagttgatg    13680
aaacaagggc agcatgcagt aatattgcta caacaatggc taaaagcatc gagagaggtt    13740
atgaccgtta ccttgcatat tccctgaacg tcctaaaagt gatacagcaa attctgatct    13800
ctcttggctt cacaatcaat tcaaccatga cccgggatga gtcataccc ctcctcacaa    13860 acaacgacct cttaataagg atggcactgt tgcccgctcc tattgggggg atgaattatc    13920
tgaatatgag caggctgttt gtcagaaaca tcggtgatcc agtaacatca tcaattgctg    13980
atctcaagag aatgattctc gcctcactaa tgcctgaaga ccctccat caagtaatga    14040 cacaacaacc gggggactct tcattcctag actgggctag cgaccttac tcagcaaatc    14100 ttgtatgtgt ccagagcatc actagactcc tcaagaacat aactgcaagg tttgtcctga    14160
tccatagtcc aaacccaatg ttaaaaggat tattccatga tgacagtaaa gaagaggacg    14220
agggactggc ggcattcctc atggacaggc atattatagt acctagggca gctcatgaaa    14280
tcctggatca tagtgtcaca ggggcaagag agtctattgc aggcatgctg gataccacaa    14340
```

```
aaggcttgat tcgagccagc atgaggaagg gggggttaac ctctcgagtg ataaccagat  14400
tgtccaatta tgactatgaa caattcagag cagggatggt gctattgaca ggaagaaaga  14460
gaaatgtcct cattgacaaa gagtcatgtt cagtgcagct ggcgagagct ctaagaagcc  14520
atatgtgggc gaggctagct cgaggacggc ctatttacgg ccttgaggtc cctgatgtac  14580
tagaatctat gcgaggccac cttattcggc gtcatgagac atgtgtcatc tgcgagtgtg  14640
gatcagtcaa ctacggatgg ttttttgtcc cctcgggttg ccaactggat gatattgaca  14700
aggaaacatc atccttgaga gtcccatata ttggttctac cactgatgag agaacagaca  14760
tgaagcttgc cttcgtaaga gccccaagtc gatccttgcg atctgctgtt agaatagcaa  14820
cagtgtactc atgggcttac ggtgatgatg atagctcttg aacgaagcc tggttgttgg   14880
ctaggcaaag ggccaatgtg agcctggagg agctaagggt gatcactccc atctcaactt  14940
cgactaattt agcgcatagg ttgagggatc gtagcactca agtgaaatac tcaggtacat  15000
cccttgtccg agtggcgagg tataccacaa tctccaacga caatctctca tttgtcatat  15060
cagataagaa ggttgatact aactttatat accaacaagg aatgcttcta gggttgggtg  15120
ttttagaaac attgtttcga ctcgagaaag ataccggatc atctaacacg gtattacatc  15180
ttcacgtcga aacagattgt tgcgtgatcc cgatgataga tcatcccagg atacccagct  15240
cccgcaagct agagctgagg gcagagctat gtaccaaccc attgatatat gataatgcac  15300
cttttaattga cagagatgca acaaggctat acacccagag ccataggagg caccttgtgg  15360
aatttgttac atggtccaca ccccaactat atcacatttt agctaagtcc acagcactat  15420
ctatgattga cctggtaaca aaatttgaga aggaccatat gaatgaaatt tcagctctca  15480
taggggatga cgatatcaat agtttcataa ctgagtttct gctcatagag ccaagattat  15540
tcactatcta cttgggccag tgtgcggcca tcaattgggc atttgatgta cattatcata  15600
gaccatcagg gaaatatcag atgggtgagc tgttgtcatc gttcctttct agaatgagca  15660
aaggagtgtt taaggtgctt gtcaatgctc taagccaccc aaagatctac aagaaattct  15720
ggcattgtgg tattatagag cctatccatg gtccttcact tgatgctcaa aacttgcaca  15780
caactgtgtg caacatggtt tacacatgct atatgaccta cctcgacctg ttgttgaatg  15840
aagagttaga agagttcaca tttctcttgt gtgaaagcga cgaggatgta gtaccggaca  15900
gattcgacaa catccaggca aaacactat gtgttctggc agatttgtac tgtcaaccag    15960
ggacctgccc accaattcga ggtctaagac cggtagagaa atgtgcagtt ctaaccgacc  16020
atatcaaggc agaggctatg ttatctccag caggatcttc gtggaacata atccaatta   16080
ttgtagacca ttactcatgc tctctgactt atctccggcg aggatcgatc aaacagataa  16140
gattgagagt tgatccagga ttcatttcg acgccctcgc tgaggtaaat gtcagtcagc    16200
caaagatcgg cagcaacaac atctcaaata tgagcatcaa ggctttcaga cccccacacg  16260
atgatgttgc aaaattgctc aaagatatca acacaagcaa gcacaatctt cccatttcag  16320
ggggcaatct cgccaattat gaaatccatg ctttccgcag aatcgggttg aactcatctg  16380
cttgctacaa agctgttgag atatcaacat taattaggag atgccttgag ccaggggagg  16440
acggcttgtt cttgggtgag ggatcggtt ctatgttgat cacttataaa gagatactta   16500
aactaaacaa gtgcttctat aatagtgggg tttccgccaa ttctagatct ggtcaaaggg  16560
aattagcacc ctatccctcc gaagttggcc ttgtcgaaca cagaatggga gtaggtaata  16620
ttgtcaaagt gctcttaac gggaggcccg aagtcacgtg gtaggcagt gtagattgct     16680
tcaatttcat agttagtaat atccctacct ctagtgtggg gtttatccat tcagatatag  16740
```

```
agaccttgcc tgacaaagat actatagaga agctagagga attggcagcc atcttatcga    16800
tggctctgct cctgggcaaa ataggatcaa tactggtgat taagcttatg cctttcagcg    16860
gggattttgt tcagggattt ataagttatg tagggtctca ttatagagaa gtgaaccttg    16920
tatacectag atacagcaac ttcatctcta ctgaatctta tttggttatg acagatctca    16980
aggctaaccg gctaatgaat cctgaaaaga ttaagcagca gataattgaa tcatctgtga    17040
ggacttcacc tggacttata ggtcacatcc tatccattaa gcaactaagc tgcatacaag    17100
caattgtggg agacgcagtt agtagaggtg atatcaatcc tactctgaaa aaacttacac    17160
ctatagagca ggtgctgatc aattgcgggt tggcaattaa cggacctaag ctgtgcaaag    17220
aattgatcca ccatgatgtt gcctcagggc aagatggatt gcttaattct atactcatcc    17280
tctacaggga gttggcaaga ttcaaagaca accaaagaag tcaacaaggg atgttccacg    17340
cttaccccgt attggtaagt agcaggcaac gagaacttat atctaggatc acccgcaaat    17400
tctgggggca cattcttctt tactccggga acaaaaagtt gataaataag tttatccaga    17460
atctcaagtc cggctatctg atactagact tacaccagaa tatcttcgtt aagaatctat    17520
ccaagtcaga gaaacagatt attatgacgg ggggtttgaa acgtgagtgg gtttttaagg    17580
taacagtcaa ggagaccaaa gaatggtata agttagtcgg atacagtgcc ctgattaagg    17640
actaattggt tgaactccgg aaccctaatc ctgccctagg tggttaggca ttatttgcaa    17700
tatattaaag aaaactttga aaatacgaag tttctattcc cagctttgtc tggtggccgg    17760
catggtccca gcctcctcgc tggcgccggc tgggcaacat tccgagggga ccgtcccctc    17820
ggtaatggcg aatgggacgc ggccgatccg gctgctaaca aagcccgaaa ggaagctgag    17880
ttggctgctg ccaccgctga gcaataacta gcataacccc ttggggcctc taaacgggtc    17940
ttgaggggtt ttttgctgaa aggaggaact atatccggat gcggccgcgg gccctatggt    18000
acccagcttt tgttcccttt agtgagggtt aattccgagc ttggcgtaat catggtcata    18060
gctgtttcct gtgtgaaatt gttatccgct cacaattcca cacaacatag gagccggaag    18120
cataaagtgt aaagcctggg gtgcctaatg agtgaggtaa ctcacattaa ttgcgttgcg    18180
ctcactgccc gctttccagt cgggaaacct gtcgtgccag ctgcattaat gaatcggcca    18240
acgcgcgggg agaggcggtt tgcgtattgg gcgctcttcc gcttcctcgc tcactgactc    18300
gctgcgctcg tcgttcggc tgcggcgagc ggtatcagct cactcaaagg cggtaatacg    18360
gttatccaca gaatcagggg ataacgcagg aaagaacatg tgagcaaaag gccagcaaaa    18420
ggccaggaac cgtaaaaagg ccgcgttgct ggcgtttttc cataggctcg ccccccctga    18480
cgagcatcac aaaaatcgac gctcaagtca gaggtggcga aacccgacag gactataaag    18540
ataccaggcg ttccccctg gaagctccct cgtgcgctct cctgttccga ccctgccgct    18600
taccggatac ctgtccgcct ttctcccttc gggaagcgtg gcgctttctc aatgctcacg    18660
ctgtaggtat ctcagttcgg tgtaggtcgt tcgctccaag ctgggctgtg tgcacgaacc    18720
ccccgttcag cccgaccgct gcgccttatc cggtaactat cgtcttgagt ccaacccggt    18780
aagacacgac ttatcgccac tggcagcagc cactggtaac aggattagca gagcgaggta    18840
tgtaggcggt gctacagagt tcttgaagtg gtggcctaac tacggctaca ctagaaggac    18900
agtatttggt atctgcgctc tgctgaagcc agttaccttc ggaaaaagag ttggtagctc    18960
ttgatccggc aaacaaacca ccgctggtag cggtggtttt tttgtttgca agcagcagat    19020
tacgcgcaga aaaaaaggat ctcaagaaga tcctttgatc ttttctacgg ggtctgacgc    19080
```

```
tcagtggaac gaaaactcac gttaagggat tttggtcatg agattatcaa aaaggatctt    19140
cacctagatc cttttaaatt aaaaatgaag ttttaaatca atctaaagta tatatgagta    19200
aacttggtct gacagttacc aatgcttaat cagtgaggca cctatctcag cgatctgtct    19260
atttcgttca tccatagttg cctgactgcc cgtcgtgtag ataactacga tacgggaggg    19320
cttaccatct ggccccagtg ctgcaatgat accgcgagac ccacgctcac cggctccaga    19380
tttatcagca ataaccagc cagccggaag ggccgagcgc agaagtggtc ctgcaacttt    19440
atccgcctcc atccagtcta ttaattgttg ccgggaagct agagtaagta gttcgccagt    19500
taatagtttg cgcaacgttg ttgccattgc tacaggcatc gtggtgtcac gctcgtcgtt    19560
tggtatggct tcattcagct ccggttccca acgatcaagg cgagttacat gatccccat    19620 gttgtgaaaa aaagcggtta gctccttcgg tcctccgatc gttgtcagaa gtaagttggc    19680
cgcagtgtta tcactcatgc ttatggcagc actgcataat tctcttactg tcatgccatc    19740
cgtaagatgc ttttctgtga ctggtgagta ctcaaccaag tcattctgag aatagtgtat    19800
gcggcgaccg agttgctctt gcccggcgtc aatacgggat aataccgcgc cacatagcag    19860
aactttaaaa gtgctcatca ttggaaaacg ttcttcgggg cgaaaactct caaggatctt    19920
accgctgttg agatccagtt cgatgtaacc cactcgtgca cccaactgat cttcagcatc    19980
ttttactttc accagcgttt ctgggtgagc aaaaacagga aggcaaaatg ccgcaaaaaa    20040
gggaataagg gcgacacgga aatgttgaat actcatactc ttccttttc aatattattg    20100 aagcatttat cagggttatt gtctcatgag cggatacata tttgaatgta tttagaaaaa    20160
taaacaaata ggggttccgc gcacatttcc ccgaaaagtg ccacctgaaa ttgtaaacgt    20220
taatattttg ttaaaattcg cgttaaattt ttgttaaatc agctcatttt ttaaccaata    20280
ggccgaaatc ggcaaaatcc cttataaatc aaaagaatag accgagatag ggttgagtgt    20340
tgttccagtt tggaacaaga gtccactatt aaagaacgtg gactccaacg tcaaagggcg    20400
aaaaaccgtc tatcagggcg atggcccact acgtgaacca tcaccctaat caagttttt    20460 ggggtcgagg tgccgtaaag cactaaatcg gaaccctaaa gggagccccc gatttagagc    20520
ttgacgggga agccggcga acgtggcgag aaaggaaggg aagaaagcga aggagcggg    20580 cgctagggcg ctggcaagtg tagcggtcac gctgcgcgta accaccacac ccgccgcgct    20640
taatgcgccg ctacagggcg cgtcccattc gccattcagg ctgcgcaact gttgggaagg    20700
gcgatcggtg cgggcctctt cgctattacg ccagccaccg cggtggcggc cgctaatacg    20760
actcactata gggccaactt tgtttggtct gatgagtccg tgaggacgaa acccggagtc    20820
ccgggtc                                                             20827
```

<210> SEQ ID NO 14  
<211> LENGTH: 19843  
<212> TYPE: DNA  
<213> ORGANISM: Artificial Sequence  
<220> FEATURE:  
<223> OTHER INFORMATION: pTM-MVSchw-ATU1  
<220> FEATURE:  
<221> NAME/KEY: misc_RNA  
<222> LOCATION: (1)..(16770)  
<223> OTHER INFORMATION: MVSchw-ATU1-eGFP_antigenome  
<220> FEATURE:  
<221> NAME/KEY: misc_feature  
<222> LOCATION: (53)..(928)  
<223> OTHER INFORMATION: ATU1  
<220> FEATURE:  
<221> NAME/KEY: misc_feature  
<222> LOCATION: (111)..(116)  
<223> OTHER INFORMATION: BsiWI restriction site

```
<220> FEATURE:
<221> NAME/KEY: misc_feature
<222> LOCATION: (117)..(836)
<223> OTHER INFORMATION: ORF for eGFP : eGFP_ORF
<220> FEATURE:
<221> NAME/KEY: misc_feature
<222> LOCATION: (837)..(842)
<223> OTHER INFORMATION: BssHII restriction site
<220> FEATURE:
<221> NAME/KEY: misc_feature
<222> LOCATION: (16771)..(19843)
<223> OTHER INFORMATION: plasmid_backbone

<400> SEQUENCE: 14
```

| | | | | | |
|---|---|---|---|---|---|
| accaaacaaa | gttgggtaag | gatagttcaa | tcaatgatca | tcttctagtg | cacttaggat | 60 |
| tcaagatcct | attatcaggg | acaagagcag | gattagggat | atccgagacg | cgtacgatgg | 120 |
| tgagcaaggg | cgaggagctg | ttcaccgggg | tggtgcccat | cctggtcgag | ctggacggcg | 180 |
| acgtaaacgg | ccacaagttc | agcgtgtccg | gcgagggcga | gggcgatgcc | acctacggca | 240 |
| agctgaccct | gaagttcatc | tgcaccaccg | gcaagctgcc | cgtgccctgg | cccaccctcg | 300 |
| tgaccaccct | gacctacggc | gtgcagtgct | tcagccgcta | ccccgaccac | atgaagcagc | 360 |
| acgacttctt | caagtccgcc | atgcccgaag | gctacgtcca | ggagcgcacc | atcttcttca | 420 |
| aggacgacgg | caactacaag | acccgcgccg | aggtgaagtt | cgagggcgac | accctggtga | 480 |
| accgcatcga | gctgaagggc | atcgacttca | aggaggacgg | caacatcctg | ggcacaagc | 540 |
| tggagtacaa | ctacaacagc | cacaacgtct | atatcatggc | cgacaagcag | aagaacggca | 600 |
| tcaaggtgaa | cttcaagatc | cgccacaaca | tcgaggacgg | cagcgtgcag | ctcgccgacc | 660 |
| actaccagca | gaacaccccc | atcggcgacg | gccccgtgct | gctgcccgac | aaccactacc | 720 |
| tgagcaccca | gtccgccctg | agcaaagacc | ccaacgagaa | gcgcgatcac | atggtcctgc | 780 |
| tggagttcgt | gaccgccgcc | gggatcactc | tcggcatgga | cgagctgtac | aagtaggcgc | 840 |
| gcagcgctta | gacgtctcgc | gatcgattag | tgcgagaggc | cgaggccag | aacaacatcc | 900 |
| gcctaccatc | catcattgtt | ataaaaaact | taggattcaa | gatcctatta | tcagggacaa | 960 |
| gagcaggatt | agggatatcc | gagatggcca | cacttttaag | gagcttagca | ttgttcaaaa | 1020 |
| gaaacaagga | caaaccaccc | attacatcag | gatccggtgg | agccatcaga | ggaatcaaac | 1080 |
| acattattat | agtaccaatc | cctggagatt | cctcaattac | cactcgatcc | agacttctgg | 1140 |
| accggttggt | gaggttaatt | ggaaacccgg | atgtgagcgg | gcccaaacta | acaggggcac | 1200 |
| taataggtat | attatccta | tttgtggagt | ctccaggtca | attgattcag | aggatcaccg | 1260 |
| atgaccctga | cgttagcata | aggctgttag | aggttgtcca | gagtgaccag | tcacaatctg | 1320 |
| gccttacctt | cgcatcaaga | ggtaccaaca | tggaggatga | ggcggaccaa | tacttttcac | 1380 |
| atgatgatcc | aattagtagt | gatcaatcca | ggttcggatg | gttcgggaac | aaggaaatct | 1440 |
| cagatattga | agtgcaagac | cctgagggat | tcaacatgat | tctgggtacc | atcctagccc | 1500 |
| aaattgggt | cttgctcgca | aaggcggtta | cggccccaga | cacggcagct | gattcggagc | 1560 |
| taagaaggtg | gataaagtac | acccaacaaa | gaagggtagt | tggtgaattt | agattggaga | 1620 |
| gaaaatggtt | ggatgtggtg | aggaacagga | ttgccgagga | cctctcctta | cgccgattca | 1680 |
| tggtcgctct | aatcctggat | atcaagagaa | caccggaaa | caaacccagg | attgctgaaa | 1740 |
| tgatatgtga | cattgataca | tatatcgtag | aggcaggatt | agccagtttt | atcctgacta | 1800 |
| ttaagtttgg | gatagaaact | atgtatcctg | ctcttggact | gcatgaattt | gctggtgagt | 1860 |
| tatccacact | tgagtccttg | atgaacccttt | accagcaaat | gggggaaact | gcaccctaca | 1920 |

```
tggtaatcct ggagaactca attcagaaca agttcagtgc aggatcatac cctctgctct   1980
ggagctatgc catgggagta ggagtggaac ttgaaaactc catgggaggt ttgaactttg   2040
gccgatctta ctttgatcca gcatatttta gattagggca agagatggta aggaggtcag   2100
ctggaaaggt cagttccaca ttggcatctg aactcggtat cactgccgag gatgcaaggc   2160
ttgtttcaga gattgcaatg catactactg aggacaagat cagtagagcg gttggaccca   2220
gacaagccca agtatcattt ctacacggtg atcaaagtga aatgagcta ccgagattgg    2280 ggggcaagga agataggagg gtcaaacaga gtcgaggaga agccagggag agctacagag   2340
aaaccgggcc cagcagagca agtgatgcga gagctgccca tcttccaacc ggcacacccc   2400
tagacattga cactgcaacg gagtccagcc aagatccgca ggacagtcga aggtcagctg   2460
acgccctgct taggctgcaa gccatggcag gaatctcgga agaacaaggc tcagacacgg   2520
acacccctat agtgtacaat gacagaaatc ttctagacta ggtgcgagag gccgagggcc   2580
agaacaacat ccgcctacca tccatcattg ttataaaaaa cttaggaacc aggtccacac   2640
agccgccagc ccatcaacca tccactccca cgattggagc caatggcaga agagcaggca   2700
cgccatgtca aaacggact ggaatgcatc cgggctctca aggccgagcc catcggctca    2760
ctggccatcg aggaagctat ggcagcatgg tcagaaatat cagacaaccc aggacaggag   2820
cgagccacct gcagggaaga aaggcaggc agttcgggtc tcagcaaacc atgcctctca    2880
gcaattggat caactgaagg cggtgcacct cgcatccgcg gtcagggacc tggagagagc   2940
gatgacgacg ctgaaacttt gggaatcccc ccaagaaatc tccaggcatc aagcactggg   3000
ttacagtgtt attacgttta tgatcacagc ggtgaagcgg ttaagggaat ccaagatgct   3060
gactctatca tggttcaatc aggccttgat ggtgatagca ccctctcagg aggagacaat   3120
gaatctgaaa acagcgatgt ggatattggc gaacctgata ccgagggata tgctatcact   3180
gaccggggat ctgctcccat ctctatgggg ttcagggctt ctgatgttga aactgcagaa   3240
ggaggggaga tccacgagct cctgagactc caatccagag caacaacttt ccgaagctt    3300 gggaaaactc tcaatgttcc tccgcccccg gaccccggta gggccagcac ttccgggaca   3360
cccattaaaa agggcacaga cgcgagatta gcctcatttg aacgagat cgcgtcttta     3420 ttgacaggtg gtgcaaccca atgtgctcga aagtcaccct cggaaccatc agggccaggt   3480
gcacctgcgg ggaatgtccc cgagtgtgtg agcaatgccg cactgataca ggagtggaca   3540
cccgaatctg gtaccacaat ctccccgaga tcccagaata atgaagaagg gggagactat   3600
tatgatgatg agctgttctc tgatgtccaa gatattaaaa cagccttggc caaaatacac   3660
gaggataatc agaagataat ctccaagcta gaatcactgc tgttattgaa gggagaagtt   3720
gagtcaatta agaagcagat caacaggcaa aatatcagca tatccaccct ggaaggacac   3780
ctctcaagca tcatgatcgc cattcctgga cttgggaagg atcccaacga ccccactgca   3840
gatgtcgaaa tcaatcccga cttgaaaccc atcataggca gagattcagg ccgagcactg   3900
gccgaagttc tcaagaaacc cgttgccagc cgacaactcc aaggaatgac aaatggacgg   3960
accagttcca gaggacagct gctgaaggaa tttcagctaa agccgatcgg aaaaagatg    4020 agctcagccg tcgggtttgt tcctgacacc ggccctgcat cacgcagtgt aatccgctcc   4080 attataaaaat ccagccggct agaggaggat cggaagcgtt acctgatgac tctccttgat   4140
gatatcaaag gagccaatga tcttgccaag ttccaccaga tgctgatgaa gataataatg   4200
aagtagctac agctcaactt acctgccaac cccatgccag tcgacccaac tagtacaacc   4260
taaatccatt ataaaaaact taggagcaaa gtgattgcct cccaaggtcc acaatgacag   4320
```

```
agacctacga cttcgacaag tcggcatggg acatcaaagg gtcgatcgct ccgatacaac    4380
ccaccaccta cagtgatggc aggctggtgc cccaggtcag agtcatagat cctggtctag    4440
gcgacaggaa ggatgaatgc tttatgtaca tgtttctgct gggggttgtt gaggacagcg    4500
attccctagg gcctccaatc gggcgagcat ttgggttcct gcccttaggt gttggcagat    4560
ccacagcaaa gcccgaaaaa ctcctcaaag aggccactga gcttgacata gttgttagac    4620
gtacagcagg gctcaatgaa aaactggtgt tctacaacaa cacccactaa actctcctca    4680
caccttggag aaaggtccta acaacaggga gtgtcttcaa cgcaaaccaa gtgtgcaatg    4740
cggttaatct gataccgctc gatacccgc agaggttccg tgttgtttat atgagcatca     4800
cccgtctttc ggataacggg tattacaccg ttcctagaag aatgctggaa ttcagatcgg    4860
tcaatgcagt ggccttcaac ctgctggtga cccttaggat tgacaaggcg ataggccctg    4920
ggaagatcat cgacaataca gagcaacttc ctgaggcaac atttatggtc cacatcggga    4980
acttcaggag aaagaagagt gaagtctact ctgccgatta ttgcaaaatg aaaatcgaaa    5040
agatgggcct ggttttttgca cttggtggga tagggggcac cagtcttcac attagaagca   5100
caggcaaaat gagcaagact ctccatgcac aactcgggtt caagaagacc ttatgttacc    5160
cgctgatgga tatcaatgaa gaccttaatc gattactctg gaggagcaga tgcaagatag    5220
taagaatcca ggcagttttg cagccatcag ttcctcaaga attccgcatt tacgacgacg    5280
tgatcataaa tgatgaccaa ggactattca aagttctgta gaccgtagtg cccagcaatg    5340
cccgaaaacg accccctca caatgacagc cagaaggccc ggacaaaaaa gcccctccg     5400 aaagactcca cggaccaagc gagaggccag ccagcagccg acggcaagcg cgaacaccag    5460
gcggccccag cacagaacag ccctgacaca aggccaccac cagccacccc aatctgcatc    5520
ctcctcgtgg gaccccgag gaccaacccc caaggctgcc cccgatccaa accaccaacc     5580
gcatccccac caccccggg aaagaaaccc ccagcaattg gaaggcccct ccccctcttc     5640
ctcaacacaa gaactccaca accgaaccgc acaagcgacc gaggtgaccc aaccgcaggc    5700
atccgactcc ctagacagat cctctctccc cggcaaacta acaaaaactt agggccaagg    5760
aacatacaca cccaacagaa cccagacccc ggccacggc gccgcgcccc caaccccga      5820 caaccagagg gagcccccaa ccaatcccgc cggctccccc ggtgcccaca ggcagggaca    5880
ccaacccccg aacagaccca gcacccaacc atcgacaatc caagacgggg gggccccccc    5940
aaaaaaaggc cccaggggc cgacagccag caccgcgagg aagcccaccc accccacaca     6000
cgaccacggc aaccaaacca gaaccagac caccctgggc caccagctcc cagactcggc     6060
catcaccccg cagaaaggaa aggccacaac ccgcgcaccc cagccccgat ccggcgggga    6120
gccacccaac ccgaaccagc acccaagagc gatccccgaa ggaccccga accgcaaagg     6180 acatcagtat cccacagcct ctccaagtcc cccggtctcc tcctcttctc gaagggacca    6240
aaagatcaat ccaccacacc cgacgacact caactcccca cccctaaagg agacaccggg    6300
aatcccagaa tcaagactca tccaatgtcc atcatgggtc tcaaggtgaa cgtctctgcc    6360
atattcatgg cagtactgtt aactctccaa acacccaccg gtcaaatcca ttggggcaat    6420
ctctctaaga taggggtggt aggaatagga agtgcaagct acaaagttat gactcgttcc    6480
agccatcaat cattagtcat aaaattaatg cccaatataa ctctcctcaa taactgcacg    6540
agggtagaga ttgcagaata caggagacta ctgagaacag ttttggaacc aattagagat    6600
gcacttaatg caatgaccca gaatataaga ccggttcaga gtgtagcttc aagtaggaga    6660
```

```
cacaagagat tgcgggagt agtcctggca ggtgcggccc taggcgttgc cacagctgct    6720
cagataacag ccggcattgc acttcaccag tccatgctga actctcaagc catcgacaat    6780
ctgagagcga gcctggaaac tactaatcag gcaattgaga caatcagaca agcagggcag    6840
gagatgatat tggctgttca gggtgtccaa gactacatca ataatgagct gataccgtct    6900
atgaaccaac tatcttgtga tttaatcggc cagaagctcg ggctcaaatt gctcagatac    6960
tatacagaaa tcctgtcatt atttggcccc agtttacggg accccatatc tgcggagata    7020
tctatccagg ctttgagcta tgcgcttgga ggagacatca ataaggtgtt agaaaagctc    7080
ggatacagtg gaggtgattt actgggcatc ttagagagcg gaggaataaa ggcccggata    7140
actcacgtcg acacagagtc ctacttcatt gtcctcagta tagcctatcc gacgctgtcc    7200
gagattaagg gggtgattgt ccaccggcta gaggggtct cgtacaacat aggctctcaa    7260
gagtggtata ccactgtgcc caagtatgtt gcaacccaag ggtaccttat ctcgaatttt    7320
gatgagtcat cgtgtacttt catgccagag gggactgtgt gcagccaaaa tgccttgtac    7380
ccgatgagtc ctctgctcca agaatgcctc cgggggtaca ccaagtcctg tgctcgtaca    7440
ctcgtatccg ggtctttggg gaaccggttc attttatcac aagggaacct aatagccaat    7500
tgtgcatcaa tcctttgcaa gtgttacaca acaggaacga tcattaatca agaccctgac    7560
aagatcctaa catacattgc tgccgatcac tgcccggtag tcgaggtgaa cggcgtgacc    7620
atccaagtcg ggagcaggag gtatccgac gctgtgtact tgcacagaat tgacctcggt    7680
cctcccatat cattggagag gttggacgta gggacaaatc tggggaatgc aattgctaag    7740
ttggaggatg ccaaggaatt gttggagtca tcggaccaga tattgaggag tatgaaaggt    7800
ttatcgagca ctagcatagt ctacatcctg attgcagtgt gtcttggagg gttgataggg    7860
atccccgctt taatatgttg ctgcaggggg cgttgtaaca aaaagggaga acaagttggt    7920
atgtcaagac caggcctaaa gcctgatctt acgggaacat caaaatccta tgtaaggtcg    7980
ctctgatcct ctacaactct tgaaacacaa atgtcccaca agtctcctct tcgtcatcaa    8040
gcaaccaccg cacccagcat caagcccacc tgaaattatc tccggcttcc ctctggccga    8100
acaatatcgg tagttaatca aaacttaggg tgcaagatca tccacaatgt caccacaacg    8160
agaccggata aatgccttct acaaagataa ccccccatccc aagggaagta ggatagtcat    8220
taacagagaa catcttatga ttgatagacc ttatgttttg ctggctgttc tgtttgtcat    8280
gtttctgagc ttgatcgggt tgctagccat tgcaggcatt agacttcatc gggcagccat    8340
ctacaccgca gagatccata aaagcctcag caccaatcta gatgtaacta actcaatcga    8400
gcatcaggtc aaggacgtgc tgacaccact cttcaaaatc atcggtgatg aagtgggcct    8460
gaggacacct cagagattca ctgacctagt gaaattaatc tctgacaaga ttaaattcct    8520
taatccggat agggagtacg acttcagaga tctcacttgg tgtatcaacc cgccagagag    8580
aatcaaattg gattatgatc aatactgtgc agatgtggct gctgaagagc tcatgaatgc    8640
attggtgaac tcaactctac tggagaccag aacaaccaat cagttcctag ctgtctcaaa    8700
gggaaactgc tcagggccca ctacaatcag aggtcaattc tcaaacatgt cgctgtccct    8760
gttagacttg tatttaggtc gaggttacaa tgtgtcatct atagtcacta tgacatccca    8820
gggaatgtat gggggaactt acctagtgga aaagcctaat ctgagcagca aaggtcaga    8880 gttgtcacaa ctgagcatgt accgagtgtt tgaagtaggt gttatcagaa atccgggttt    8940 ggggggctccg gtgttccata tgacaaaacta tcttgagcaa ccagtcagta atgatctcag    9000
caactgtatg gtggctttgg gggagctcaa actcgcagcc ctttgtcacg gggaagattc    9060
```

```
tatcacaatt ccctatcagg gatcagggaa aggtgtcagc ttccagctcg tcaagctagg    9120
tgtctggaaa tccccaaccg acatgcaatc ctgggtcccc ttatcaacgg atgatccagt    9180
gatagacagg ctttacctct catctcacag aggtgttatc gctgacaatc aagcaaaatg    9240
ggctgtcccg acaacacgaa cagatgacaa gttgcgaatg gagacatgct tccaacaggc    9300
gtgtaagggt aaaatccaag cactctgcga gaatcccgag tgggcaccat tgaaggataa    9360
caggattcct tcatacgggg tcttgtctgt tgatctgagt ctgacagttg agcttaaaat    9420
caaaattgct tcgggattcg ggccattgat cacacacggt tcagggatgg acctatacaa    9480
atccaaccac aacaatgtgt attggctgac tatcccgcca atgaagaacc tagccttagg    9540
tgtaatcaac acattggagt ggataccgag attcaaggtt agtccctacc tcttcactgt    9600
cccaattaag gaagcaggcg aagactgcca tgccccaaca tacctacctg cggaggtgga    9660
tggtgatgtc aaactcagtt ccaatctggt gattctacct ggtcaagatc tccaatatgt    9720
tttggcaacc tacgatactt ccaggggttga acatgctgtg gtttattacg tttacagccc    9780
aagccgctca ttttcttact tttatccttt taggttgcct ataaaggggg tccccatcga    9840
attacaagtg gaatgcttca catgggacca aaaactctgg tgccgtcact tctgtgtgct    9900
tgcggactca gaatctggtg gacatatcac tcactctggg atggtgggca tgggagtcag    9960
ctgcacagtc acccgggaag atggaaccaa tcgcagatag ggctgctagt gaaccaatca   10020
catgatgtca cccagacatc aggcataccc actagtgtga aatagacatc agaattaaga   10080
aaaacgtagg gtccaagtgg ttccccgtta tggactcgct atctgtcaac cagatcttat   10140
accctgaagt tcacctagat agcccgatag ttaccaataa gatagtagcc atcctggagt   10200
atgctcgagt ccctcacgct tacagcctgg aggaccctac actgtgtcag aacatcaagc   10260
accgcctaaa aaacggattt tccaaccaaa tgattataaa caatgtggaa gttgggaatg   10320
tcatcaagtc caagcttagg agttatccgg cccactctca tattccatat ccaaattgta   10380
atcaggattt atttaacata gaagacaaag agtcaacgag gaagatccgt gaactcctca   10440
aaaaggggaa ttcgctgtac tccaaagtca gtgataaggt ttttccaatgc ttaagggaca   10500 ctaactcacg gcttggccta ggctccgaat tgagggagga catcaaggag aaagttatta   10560
acttgggagt ttacatgcac agctcccagt ggtttgagcc cttttctgttt tggtttacag   10620 tcaagactga gatgaggtca gtgattaaat cacaaaccca tacttgccat aggaggagac   10680
acacacctgt attcttcact ggtagttcag ttgagttgct aatctctcgt gaccttgttg   10740
ctataatcag taaagagtct caacatgtat attacctgac atttgaactg gttttgatgt   10800
attgtgatgt catagagggg aggttaatga cagagaccgc tatgactatt gatgctaggt   10860
atacagagct tctaggaaga gtcagataca tgtggaaact gatagatggt ttcttccctg   10920
cactcgggaa tccaacttat caaattgtag ccatgctgga gcctctttca cttgcttacc   10980
tgcagctgag ggatataaca gtagaactca gaggtgcttt ccttaaccac tgctttactg   11040
aaatacatga tgttcttgac caaaacgggt tttctgatga aggtacttat catgagttaa   11100
ctgaagctct agattacatt ttcataactg atgacataca tctgacaggg gagattttct   11160 cattttttcag aagtttcggc cacccccgac ttgaagcagt aacggctgct gaaaatgtta   11220
ggaaatacat gaatcagcct aaagtcattg tgtatgagac tctgatgaaa ggtcatgcca   11280 tatttttgtgg aatcataatc aacggctatc gtgacaggca cggaggcagt tggccaccgc   11340 tgacccctccc cctgcatgct gcagacacaa tccggaatgc tcaagcttca ggtgaagggt   11400
```

```
taacacatga gcagtgcgtt gataactgga aatcttttgc tggagtgaaa tttggctgct   11460
ttatgcctct tagcctggat agtgatctga caatgtacct aaaggacaag gcacttgctg   11520
ctctccaaag ggaatgggat tcagtttacc cgaaagagtt cctgcgttac gaccctccca   11580
agggaaccgg gtcacggagg cttgtagatg ttttccttaa tgattcgagc tttgacccat   11640
atgatgtgat aatgtatgtt gtaagtggag cttacctcca tgaccctgag ttcaacctgt   11700
cttacagcct gaaagaaaag gagatcaagg aaacaggtag acttttttgct aaaatgactt   11760 acaaaatgag ggcatgccaa gtgattgctg aaaatctaat ctcaaacggg attggcaaat   11820
attttaagga caatgggatg gccaaggatg agcacgattt gactaaggca ctccacactc   11880
tagctgtctc aggagtcccc aaagatctca agaaagtca caggggggggg ccagtcttaa   11940 aaacctactc ccgaagccca gtccacacaa gtaccaggaa cgtgagagca gcaaaagggt   12000 ttataggggtt ccctcaagta attcggcagg accaagacac tgatcatccg gagaatatgg   12060
aagcttacga gacagtcagt gcatttatca cgactgatct caagaagtac tgccttaatt   12120
ggagatatga gaccatcagc ttgtttgcac agaggctaaa tgagatttac ggattgccct   12180
catttttcca gtggctgcat aagaggcttg agacctctgt cctgtatgta agtgaccctc   12240 attgccccc cgaccttgac gcccatatcc cgttatataa agtccccaat gatcaaatct   12300
tcattaagta ccctatggga ggtatagaag ggtattgtca gaagctgtgg accatcagca   12360
ccattcccta tctatacctg gctgcttatg agagcggagt aaggattgct tcgttagtgc   12420
aaggggacaa tcagaccata gccgtaacaa aagggtacc cagcacatgg ccctacaacc   12480
ttaagaaacg ggaagctgct agagtaacta gagattactt tgtaattctt aggcaaaggc   12540
tacatgatat tggccatcac ctcaaggcaa atgagacaat tgtttcatca cattttttg   12600 tctattcaaa aggaatatat tatgatgggc tacttgtgtc ccaatcactc aagagcatcg   12660
caagatgtgt attctggtca gagactatag ttgatgaaac aagggcagca tgcagtaata   12720
ttgctacaac aatggctaaa agcatcgaga gaggttatga ccgttacctt gcatattccc   12780
tgaacgtcct aaaagtgata cagcaaattc tgatctctct tggcttcaca atcaattcaa   12840
ccatgacccg ggatgtagtc ataccctcc tcacaaacaa cgacctctta ataaggatgg   12900
cactgttgcc cgctcctatt gggggggatga attatctgaa tatgagcagg ctgttgtgca   12960
gaaacatcgg tgatccagta acatcatcaa ttgctgatct caagaaatg attctcgcct   13020 cactaatgcc tgaagagacc ctccatcaag taatgacaca acaaccgggg gactcttcat   13080
tcctagactg ggctagcgac ccttactcag caaatcttgt atgtgtccag agcatcacta   13140
gactcctcaa gaacataact gcaaggtttg tcctgatcca tagtccaaac ccaatgttaa   13200
aaggattatt ccatgatgac agtaaagaag gaggacgaggg actggcggca ttcctcatgg   13260
acaggcatat tatagtacct agggcagctc atgaaatcct ggatcatagt gtcacaggggg   13320 caagagagtc tattgcaggc atgctggata ccacaaaagg cttgattcga ccagcatga   13380 ggaagggggg gttaacctct cgagtgataa ccagattgtc caattatgac tatgaacaat   13440
tcagagcagg gatggtgcta ttgacaggaa gaaagagaaa tgtcctcatt gacaaagagt   13500
catgttcagt gcagctggcg agagctctaa gaagccatat gtgggcgagg ctagctcgag   13560
gacggcctat ttacggcctt gaggtccctg atgtactaga atctatgcga ggccaccttta   13620 ttcggcgtca tgagacatgt gtcatctgcg agtgtggatc agtcaactac ggatggttttt   13680 tgtccccctc gggttgccaa ctggatgata ttgacaagga aacatcatcc ttgagagtcc   13740
catatattgg ttctaccact gatgagagaa cagacatgaa gcttgccttc gtaagagccc   13800
```

```
caagtcgatc cttgcgatct gctgttagaa tagcaacagt gtactcatgg gcttacggtg    13860
atgatgatag ctcttggaac gaagcctggt tgttggctag gcaaagggcc aatgtgagcc    13920
tggaggagct aagggtgatc actcccatct caacttcgac taatttagcg cataggttga    13980
gggatcgtag cactcaagtg aaatactcag gtacatccct tgtccgagtg gcgaggtata    14040
ccacaatctc caacgacaat ctctcatttg tcatatcaga taagaaggtt gatactaact    14100
ttatatacca acaaggaatg cttctagggt tgggtgtttt agaaacattg tttcgactcg    14160
agaaagatac cggatcatct aacacggtat tacatcttca cgtcgaaaca gattgttgcg    14220
tgatcccgat gatagatcat cccaggatac ccagctcccg caagctagag ctgagggcag    14280
agctatgtac caacccattg atatatgata atgcaccttt aattgacaga gatgcaacaa    14340
ggctatacac ccagagccat aggaggcacc ttgtggaatt tgttacatgg tccacacccc    14400
aactatatca cattttagct aagtccacag cactatctat gattgacctg gtaacaaaat    14460
ttgagaagga ccatatgaat gaaatttcag ctctcatagg ggatgacgat atcaatagtt    14520
tcataactga gtttctgctc atagagccaa gattattcac tatctacttg ggccagtgtg    14580
cggccatcaa ttgggcattt gatgtacatt atcatagacc atcagggaaa tatcagatgg    14640
gtgagctgtt gtcatcgttc cttctagaa tgagcaaagg agtgtttaag gtgcttgtca    14700
atgctctaag ccacccaaag atctacaaga aattctggca ttgtggtatt atagagccta    14760
tccatggtcc ttcacttgat gctcaaaact tgcacacaac tgtgtgcaac atggtttaca    14820
catgctatat gacctacctc gacctgttgt tgaatgaaga gttagaagag ttcacatttc    14880
tcttgtgtga aagcgacgag gatgtagtac cggacagatt cgacaacatc caggcaaaac    14940
acttatgtgt tctggcagat ttgtactgtc aaccagggac ctgcccacca attcgaggtc    15000
taagaccggt agagaaatgt gcagttctaa ccgaccatat caaggcagag gctatgttat    15060
ctccagcagg atcttcgtgg aacataaatc caattattgt agaccattac tcatgctctc    15120
tgacttatct ccggcgagga tcgatcaaac agataagatt gagagttgat ccaggattca    15180
ttttcgacgc cctcgctgag gtaaatgtca gtcagccaaa gatcggcagc aacaacatct    15240
caaatatgag catcaaggct ttcagacccc cacacgatga tgttgcaaaa ttgctcaaag    15300
atatcaacac aagcaagcac aatcttccca tttcagggg caatctcgcc aattatgaaa    15360
tccatgcttt ccgcagaatc gggttgaact catctgcttg ctacaaagct gttgagatat    15420
caacattaat taggagatgc cttgagccag gggaggacgg cttgttcttg ggtgagggat    15480
cgggttctat gttgatcact tataaagaga tacttaaact aaacaagtgc ttctataata    15540
gtggggtttc cgccaattct agatctggtc aaagggaatt agcaccctat ccctccgaag    15600
ttggccttgt cgaacacaga atgggagtag gtaatattgt caaagtgctc tttaacggga    15660
ggcccgaagt cacgtgggta ggcagtgtag attgcttcaa tttcatagtt agtaatatcc    15720
ctacctctag tgtgggtttt atccattcag atatagagac cttgcctgac aaagatacta    15780
tagagaagct agaggaattg gcagccatct tatcgatggc tctgctcctg gcaaaatag    15840
gatcaatact ggtgattaag cttatgcctt tcagcgggga ttttgttcag ggatttataa    15900
gttatgtagg gtctcattat agagaagtga accttgtata ccctagatac agcaacttca    15960
tctctactga atcttatttg gttatgacag atctcaaggc taaccggcta atgaatcctg    16020
aaaagattaa gcagcagata attgaatcat ctgtgaggac ttcacctgga cttataggtc    16080
acatcctatc cattaagcaa ctaagctgca tacaagcaat tgtgggagac gcagttagta    16140
```

```
gaggtgatat caatcctact ctgaaaaaac ttacacctat agagcaggtg ctgatcaatt    16200
gcgggttggc aattaacgga cctaagctgt gcaaagaatt gatccaccat gatgttgcct    16260
cagggcaaga tggattgctt aattctatac tcatcctcta cagggagttg gcaagattca    16320
aagacaacca aagaagtcaa caagggatgt tccacgctta ccccgtattg gtaagtagca    16380
ggcaacgaga acttatatct aggatcaccc gcaaattctg ggggcacatt cttctttact    16440
ccgggaacaa aaagttgata aataagttta tccagaatct caagtccggc tatctgatac    16500
tagacttaca ccagaatatc ttcgttaaga atctatccaa gtcagagaaa cagattatta    16560
tgacgggggg tttgaaacgt gagtgggttt taaggtaac agtcaaggag accaaagaat    16620
ggtataagtt agtcggatac agtgccctga ttaaggacta attggttgaa ctccggaacc    16680
ctaatcctgc cctaggtggt taggcattat ttgcaatata ttaaagaaaa ctttgaaaat    16740
acgaagtttc tattcccagc tttgtctggt ggccggcatg gtcccagcct cctcgctggc    16800
gccggctggg caacattccg aggggaccgt cccctcggta atggcgaatg ggacgcggcc    16860
gatccggctg ctaacaaagc ccgaaaggaa gctgagttgg ctgctgccac cgctgagcaa    16920
taactagcat aaccccttgg ggcctctaaa cgggtcttga ggggtttttt gctgaaagga    16980
ggaactatat ccgatgcgg ccgcgggccc tatggtaccc agcttttgtt cccttagtg    17040 agggttaatt ccgagcttgg cgtaatcatg gtcatagctg tttcctgtgt gaaattgtta    17100
tccgctcaca attccacaca acataggagc cggaagcata aagtgtaaag cctggggtgc    17160
ctaatgagtg aggtaactca cattaattgc gttgcgctca ctgcccgctt tccagtcggg    17220
aaacctgtcg tgccagctgc attaatgaat cggccaacgc gcgggagag gcggtttgcg    17280 tattgggcgc tcttccgctt cctcgctcac tgactcgctg cgctcggtcg ttcggctgcg    17340
gcgagcggta tcagctcact caaaggcggt aatacggtta tccacagaat caggggataa    17400
cgcaggaaag aacatgtgag caaaaggcca gcaaaaggcc aggaaccgta aaaaggccgc    17460
gttgctggcg ttttttccata ggctcggccc ccctgacgag catcacaaaa atcgacgctc    17520
aagtcagagg tggcgaaacc cgacaggact ataaagatac caggcgttcc ccctggaag    17580 ctccctcgtg cgctctcctg ttccgaccct gccgcttacc ggatacctgt ccgcctttct    17640
cccttcggga agcgtggcgc tttctcaatg ctcacgctgt aggtatctca gttcggtgta    17700
ggtcgttcgc tccaagctgg gctgtgtgca cgaacccccc gttcagcccg accgctgcgc    17760
cttatccggt aactatcgtc ttgagtccaa cccggtaaga cacgacttat cgccactggc    17820
agcagccact ggtaacagga ttagcagagc gaggtatgta ggcggtgcta cagagttctt    17880
gaagtggtgg cctaactacg gctacactag aaggacagta tttggtatct gcgctctgct    17940
gaagccagtt accttcggaa aaagagttgg tagctcttga tccggcaaac aaaccaccgc    18000
tggtagcggt ggttttttg tttgcaagca gcagattacg cgcagaaaaa aaggatctca    18060
agaagatcct ttgatctttt ctacggggtc tgacgctcag tggaacgaaa actcacgtta    18120
agggattttg gtcatgagat tatcaaaaag gatcttcacc tagatccttt taaattaaaa    18180
atgaagtttt aaatcaatct aaagtatata tgagtaaact tggtctgaca gttaccaatg    18240
cttaatcagt gaggcaccta tctcagcgat ctgtctattt cgttcatcca tagttgcctg    18300
actgcccgtc gtgtagataa ctacgatacg ggagggctta ccatctggcc ccagtgctgc    18360
aatgataccg cgagacccac gctcaccggc tccagattta tcagcaataa accagccagc    18420
cggaagggcc gagcgcagaa gtggtcctgc aactttatcc gcctccatcc agtctattaa    18480
ttgttgccgg gaagctagag taagtagttc gccagttaat agtttgcgca acgttgttgc    18540
```

```
cattgctaca ggcatcgtgg tgtcacgctc gtcgtttggt atggcttcat tcagctccgg    18600
ttcccaacga tcaaggcgag ttacatgatc ccccatgttg tgaaaaaaag cggttagctc    18660
cttcggtcct ccgatcgttg tcagaagtaa gttggccgca gtgttatcac tcatgcttat    18720
ggcagcactg cataattctc ttactgtcat gccatccgta agatgctttt ctgtgactgg    18780
tgagtactca accaagtcat tctgagaata gtgtatgcgg cgaccgagtt gctcttgccc    18840
ggcgtcaata cgggataata ccgcgccaca tagcagaact ttaaaagtgc tcatcattgg    18900
aaaacgttct cggggcgaaa actctcaag  gatcttaccg ctgttgagat ccagttcgat    18960
gtaacccact cgtgcaccca actgatcttc agcatctttt actttcacca gcgtttctgg    19020
gtgagcaaaa acaggaaggc aaaatgccgc aaaaaaggga ataagggcga cacggaaatg    19080
ttgaatactc atactcttcc tttttcaata ttattgaagc atttatcagg gttattgtct    19140
catgagcgga tacatatttg aatgtattta gaaaaataaa caaataggggttccgcgcac    19200 atttccccga aaagtgccac ctgaaattgt aaacgttaat attttgttaa aattcgcgtt    19260
aaatttttgt taaatcagct cattttttaa ccataggcc gaaatcggca aaatccctta    19320
taaatcaaaa gaatagaccg agatagggtt gagtgttgtt ccagtttgga acaagagtcc    19380
actattaaag aacgtggact ccaacgtcaa agggcgaaaa accgtctatc agggcgatgg    19440
cccactacgt gaaccatcac cctaatcaag ttttttgggg tcgaggtgcc gtaaagcact    19500
aaatcggaac cctaaaggga gcccccgatt tagagcttga cggggaaagc cggcgaacgt    19560
ggcgagaaag gaagggaaga aagcgaaagg agcgggcgct agggcgctgg caagtgtagc    19620
ggtcacgctg cgcgtaacca ccacacccgc cgcgcttaat gcgccgctac agggcgcgtc    19680
ccattcgcca ttcaggctgc gcaactgttg gaagggcga tcggtgcggg cctcttcgct    19740
attacgccag ccaccgcggt ggcggccgct aatacgactc actatagggc caactttgtt    19800
tggtctgatg agtccgtgag gacgaaaccc ggagtcccgg gtc                     19843

<210> SEQ ID NO 15
<211> LENGTH: 19795
<212> TYPE: DNA
<213> ORGANISM: Artificial Sequence
<220> FEATURE:
<223> OTHER INFORMATION: pTM-MVSchw-ATU2
<220> FEATURE:
<221> NAME/KEY: misc_RNA
<222> LOCATION: (1)..(16722)
<223> OTHER INFORMATION: MVSchw-ATU2-eGFP_antigenome
<220> FEATURE:
<221> NAME/KEY: misc_feature
<222> LOCATION: (3378)..(4205)
<223> OTHER INFORMATION: ATU2
<220> FEATURE:
<221> NAME/KEY: misc_feature
<222> LOCATION: (3444)..(3449)
<223> OTHER INFORMATION: BsiWI restriction site
<220> FEATURE:
<221> NAME/KEY: misc_feature
<222> LOCATION: (3450)..(4169)
<223> OTHER INFORMATION: ORF for eGFP : eGFP_ORF
<220> FEATURE:
<221> NAME/KEY: misc_feature
<222> LOCATION: (4170)..(4175)
<223> OTHER INFORMATION: BssHII restriction site
<220> FEATURE:
<221> NAME/KEY: misc_feature
<222> LOCATION: (16723)..(19795)
<223> OTHER INFORMATION:

| | |
|---|---|
| accaaacaaa gttgggtaag gatagttcaa tcaatgatca tcttctagtg cacttaggat | 60 |
| tcaagatcct attatcaggg acaagagcag gattagggat atccgagatg gccacacttt | 120 |
| taaggagctt agcattgttc aaaagaaaca aggacaaacc acccattaca tcaggatccg | 180 |
| gtggagccat cagaggaatc aaacacatta ttatagtacc aatccctgga gattcctcaa | 240 |
| ttaccactcg atccagactt ctggaccggt tggtgaggtt aattggaaac ccggatgtga | 300 |
| gcgggcccaa actaacaggg gcactaatag gtatattatc cttatttgtg gagtctccag | 360 |
| gtcaattgat tcagaggatc accgatgacc ctgacgttag cataaggctg ttagaggttg | 420 |
| tccagagtga ccagtcacaa tctggcctta ccttcgcatc aagaggtacc aacatggagg | 480 |
| atgaggcgga ccaatacttt tcacatgatg atccaattag tagtgatcaa tccaggttcg | 540 |
| gatggttcgg gaacaaggaa atctcagata ttgaagtgca agaccctgag ggattcaaca | 600 |
| tgattctggg taccatccta gcccaaattt gggtcttgct cgcaaaggcg gttacggccc | 660 |
| cagacacggc agctgattcg gagctaagaa ggtggataaa gtacacccaa caaagaaggg | 720 |
| tagttggtga atttagattg gagagaaaat ggttggatgt ggtgaggaac aggattgccg | 780 |
| aggacctctc cttacgccga ttcatggtcg ctctaatcct ggatatcaag gaacacccg | 840 |
| gaaacaaacc caggattgct gaaatgatat gtgacattga tacatatatc gtagaggcag | 900 |
| gattagccag ttttatcctg actattaagt ttgggataga aactatgtat cctgctcttg | 960 |
| gactgcatga atttgctggt gagttatcca cacttgagtc cttgatgaac ctttaccagc | 1020 |
| aaatggggga aactgcaccc tacatggtaa tcctggagaa ctcaattcag aacaagttca | 1080 |
| gtgcaggatc atacctctg ctctggagct atgccatggg agtaggagtg gaacttgaaa | 1140 |
| actccatggg aggtttgaac tttggccgat cttactttga tccagcatat tttagattag | 1200 |
| ggcaagagat ggtaaggagg tcagctggaa aggtcagttc cacattggca tctgaactcg | 1260 |
| gtatcactgc cgaggatgca aggcttgttt cagagattgc aatgcatact actgaggaca | 1320 |
| agatcagtag agcggttgga cccagacaag cccaagtatc atttctacac ggtgatcaaa | 1380 |
| gtgagaatga gctaccgaga ttggggggca aggaagatag gagggtcaaa cagagtcgag | 1440 |
| gagaagccag ggagagctac agagaaaccg ggcccagcag agcaagtgat gcgagagctg | 1500 |
| cccatcttcc aaccggcaca cccctagaca ttgacactgc aacggagtcc agccaagatc | 1560 |
| cgcaggacag tcgaaggtca gctgacgccc tgcttaggct gcaagccatg gcaggaatct | 1620 |
| cggaagaaca aggctcagac acggacaccc ctatagtgta caatgacaga aatcttctag | 1680 |
| actaggtgcg agaggccgag ggccagaaca acatccgcct accatccatc attgttataa | 1740 |
| aaaacttagg aaccaggtcc acacagccgc cagcccatca accatccact cccacgattg | 1800 |
| gagccaatgg cagaagagca ggcacgccat gtcaaaaacg gactggaatg catccgggct | 1860 |
| ctcaaggccg agcccatcgg ctcactggcc atcgaggaag ctatggcagc atggtcagaa | 1920 |
| atatcagaca acccaggaca ggagcgagcc acctgcaggg aagagaaggc aggcagttcg | 1980 |
| ggtctcagca accatgcct ctcagcaatt ggatcaactg aaggcggtgc acctcgcatc | 2040 |
| cgcggtcagg gacctggaga gagcgatgac gacgctgaaa cttgggaat cccccaaga | 2100 |
| aatctccagg catcaagcac tgggttacag tgttattacg tttatgatca cagcggtgaa | 2160 |
| gcggttaagg gaatccaaga tgctgactct atcatggttc aatcaggcct tgatggtgat | 2220 |
| agcaccctct caggaggaga caatgaatct gaaaacagcg atgtggatat ggcgaacct | 2280 |
| gataccgagg atatgctat cactgaccgg ggatctgctc ccatctctat ggggttcagg | 2340 |
| gcttctgatg ttgaaactgc agaaggaggg gagatccacg agctcctgag actccaatcc | 2400 |

```
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagcct accctccatc attgttataa aaaacttagg aaccaggtcc   3420
acacagccgc cagcccatca acgcgtacga tggtgagcaa gggcgaggag ctgttcaccg   3480
gggtggtgcc catcctggtc gagctggacg gcgacgtaaa cggccacaag ttcagcgtgt   3540
ccggcgaggg cgagggcgat gccacctacg gcaagctgac cctgaagttc atctgcacca   3600
ccggcaagct gcccgtgccc tggcccaccc tcgtgaccac cctgacctac ggcgtgcagt   3660
gcttcagccg ctaccccgac cacatgaagc agcacgactt cttcaagtcc gccatgcccg   3720
aaggctacgt ccaggagcgc accatcttct tcaaggacga cggcaactac aagacccgcg   3780
ccgaggtgaa gttcgagggc gacacccctg tgaaccgcat cgagctgaag ggcatcgact   3840
tcaaggagga cggcaacatc ctggggcaca agctggagta caactacaac agccacaacg   3900
tctatatcat ggccgacaag cagaagaacg gcatcaaggt gaacttcaag atccgccaca   3960
acatcgagga cggcagcgtg cagctcgccg accactacca gcagaacacc cccatcggcg   4020
acggccccgt gctgctgccc gacaaccact acctgagcac ccagtccgcc ctgagcaaag   4080
accccaacga gaagcgcgat cacatggtcc tgctggagtt cgtgaccgcc gcgggatcaa   4140
ctctcggcat ggacgagctg tacaagtagg cgcgcagcgc ttagacgtct cgcgatcgat   4200
actagtacaa cctaaatcca ttataaaaaa cttaggagca aagtgattgc ctcccaaggt   4260
ccacaatgac agagacctac gacttcgaca gtcggcatgg gacatcaaa gggtcgatcg   4320
ctccgataca acccaccacc tacagtgatg gcaggctggt gccccaggtc agagtcatag   4380
atcctggtct aggcgacagg aaggatgaat gctttatgta catgtttctg ctgggggttg   4440
ttgaggacag cgattcccta gggcctccaa tcgggcgagc atttgggttc ctgcccttag   4500
gtgttggcag atccacagca aagcccgaaa aactcctcaa agaggccact gagcttgaca   4560
tagttgttag acgtacagca gggctcaatg aaaaactggt gttctacaac aacacccccac   4620
taactctcct cacaccttgg agaaaggtcc taacaacagg gagtgtcttc aacgcaaacc   4680
aagtgtgcaa tgcggttaat ctgataccgc tcgataccc gcagaggttc cgtgttgttt   4740
```

```
atatgagcat cacccgtctt tcggataacg ggtattacac cgttcctaga agaatgctgg    4800
aattcagatc ggtcaatgca gtggccttca acctgctggt gacccttagg attgacaagg    4860
cgataggccc tgggaagatc atcgacaata cagagcaact tcctgaggca acatttatgg    4920
tccacatcgg gaacttcagg agaaagaaga gtgaagtcta ctctgccgat tattgcaaaa    4980
tgaaaatcga aaagatgggc ctggtttttg cacttggtgg gatagggggc accagtcttc    5040
acattagaag cacaggcaaa atgagcaaga ctctccatgc acaactcggg ttcaagaaga    5100
ccttatgtta cccgctgatg gatatcaatg aagaccttaa tcgattactc tggaggagca    5160
gatgcaagat agtaagaatc caggcagttt tgcagccatc agttcctcaa gaattccgca    5220
tttacgacga cgtgatcata aatgatgacc aaggactatt caaagttctg tagaccgtag    5280
tgcccagcaa tgcccgaaaa cgacccccct cacaatgaca gccagaaggc ccggacaaaa    5340
aagccccctc cgaaagactc cacggaccaa gcgagaggcc agccagcagc cgacggcaag    5400
cgcgaacacc aggcggcccc agcacagaac agccctgaca caaggccacc accagccacc    5460
ccaatctgca tcctcctcgt gggaccccccg aggaccaacc cccaaggctg cccccgatcc    5520
aaaccaccaa ccgcatcccc accacccccg ggaaagaaac cccagcaat tggaaggccc    5580 ctccccctct tcctcaacac aagaactcca caaccgaacc gcacaagcga ccgaggtgac    5640
ccaaccgcag gcatccgact ccctagacag atcctctctc cccggcaaac taaacaaaac    5700
ttagggccaa ggaacataca cacccaacag aacccagacc ccggcccacg gcgccgcgcc    5760
cccaaccccc gacaaccaga gggagccccc aaccaatccc gccggctccc ccggtgccca    5820
caggcaggga caccaacccc cgaacagacc cagcacccaa ccatcgacaa tccaagacgg    5880
ggggcccccc ccaaaaaaag gcccccaggg gccgacagcc agcaccgcga ggaagcccac    5940
ccaccccaca cacgaccacg gcaaccaaac cagaacccag accaccctgg gccaccagct    6000
cccagactcg gccatcaccc cgcagaaagg aaaggccaca acccgcgcac cccagccccg    6060
atccggcggg gagccaccca acccgaacca gcacccaaga gcgatccccg aaggaccccc    6120
gaaccgcaaa ggacatcagt atcccacagc ctctccaagt ccccccggtct cctcctcttc    6180 tcgaagggac caaagatca atccaccaca cccgacgaca ctcaactccc cacccctaaa    6240
ggagacaccg ggaatcccag aatcaagact catccaatgt ccatcatggg tctcaaggtg    6300
aacgtctctg ccatattcat ggcagtactg ttaactctcc aaacacccac cggtcaaatc    6360
cattggggca atctctctaa gatagggtg gtaggaatag gaagtgcaag ctacaaagtt    6420
atgactcgtt ccagccatca atcattagtc ataaaattaa tgcccaatat aactctcctc    6480
aataactgca cgagggtaga gattgcagaa tacaggagac tactgagaac agttttggaa    6540
ccaattagag atgcacttaa tgcaatgacc cagaatataa gaccggttca gagtgtagct    6600
tcaagtagga gacacaagag atttgcggga gtagtcctgg caggtgcggc cctaggcgtt    6660
gccacagctg ctcagataac agccggcatt gcacttcacc agtccatgct gaactctcaa    6720
gccatcgaca atctgagagc gagcctggaa actactaatc aggcaattga gacaatcaga    6780
caagcagggc aggagatgat attggctgtt cagggtgtcc aagactacat caataatgag    6840
ctgataccgt ctatgaacca actatcttgt gatttaatcg gccagaagct cgggctcaaa    6900
ttgctcagat actatacaga aatcctgtca ttatttggcc ccagtttacg ggaccccata    6960
tctgcggaga tatctatcca ggctttgagc tatgcgcttg gaggagacat caataaggtg    7020
ttagaaaagc tcggatacag tggaggtgat ttactgggca tcttagagag cggaggaata    7080
aaggcccgga taactcacgt cgacacagag tcctacttca ttgtcctcag tatagcctat    7140
```

```
ccgacgctgt ccgagattaa gggggtgatt gtccaccggc tagaggggt  ctcgtacaac    7200
ataggctctc aagagtggta taccactgtg cccaagtatg ttgcaaccca agggtacctt    7260
atctcgaatt ttgatgagtc atcgtgtact ttcatgccag aggggactgt gtgcagccaa    7320
aatgccttgt acccgatgag tcctctgctc caagaatgcc tccggggta  caccaagtcc    7380
tgtgctcgta cactcgtatc cgggtctttt gggaaccggt tcattttatc acaagggaac    7440
ctaatagcca attgtgcatc aatcctttgc aagtgttaca caacaggaac gatcattaat    7500
caagaccctg acaagatcct aacatacatt gctgccgatc actgcccggt agtcgaggtg    7560
aacggcgtga ccatccaagt cgggagcagg aggtatccag acgctgtgta cttgcacaga    7620
attgacctcg gtcctcccat atcattggag aggttggacg tagggacaaa tctggggaat    7680
gcaattgcta agttggagga tgccaaggaa ttgttggagt catcggacca gatattgagg    7740
agtatgaaag gtttatcgag cactagcata gtctacatcc tgattgcagt gtgtcttgga    7800
gggttgatag ggatcccccgc tttaatatgt tgctgcaggg ggcgttgtaa caaaaaggga    7860
gaacaagttg gtatgtcaag accaggccta agcctgatc  ttacgggaac atcaaaatcc    7920
tatgtaaggt cgctctgatc ctctacaact cttgaaacac aaatgtccca caagtctcct    7980
cttcgtcatc aagcaaccac cgcacccagc atcaagccca cctgaaatta tctccggctt    8040
ccctctggcc gaacaatatc ggtagttaat caaaacttag ggtgcaagat catccacaat    8100
gtcaccacaa cgagaccgga taaatgcctt ctacaaagat aaccccccatc ccaagggaag    8160
taggatagtc attaacagag aacatcttat gattgataga ccttatgttt tgctggctgt    8220
tctgtttgtc atgtttctga gcttgatcgg gttgctagcc attgcaggca ttagacttca    8280
tcgggcagcc atctacaccg cagagatcca taaaagcctc agcaccaatc tagatgtaac    8340
taactcaatc gagcatcagg tcaaggacgt gctgacacca ctcttcaaaa tcatcggtga    8400
tgaagtgggc ctgaggacac ctcagagatt cactgaccta gtgaaattaa tctctgacaa    8460
gattaaattc cttaatccgg ataggagta  cgacttcaga gatctcactt ggtgtatcaa    8520
cccgccagag agaatcaaat tggattatga tcaatactgt gcagatgtgg ctgctgaaga    8580
gctcatgaat gcattggtga actcaactct actggagacc agaacaacca atcagttcct    8640
agctgtctca aagggaaact gctcaggacc cactacaatc agaggtcaat tctcaaacat    8700
gtcgctgtcc ctgttagact tgtatttagg tcgaggttac aatgtgtcat ctatagtcac    8760
tatgacatcc cagggaatgt atgggggaac ttacctagtg gaaaagccta atctgagcag    8820
caaaaggtca gagttgtcac aactgagcat gtaccgagtg tttgaagtag gtgttatcag    8880
aaatccgggt ttgggggctc cggtgttcca tatgacaaac tatcttgagc aaccagtcag    8940
taatgatctc agcaactgta tggtggcttt gggggagctc aaactcgcag ccctttgtca    9000
cggggaagat tctatcacaa ttccctatca gggatcaggg aaaggtgtca gcttccagct    9060
cgtcaagcta ggtgtctgga atccccaac  cgacatgcaa tcctgggtcc ccttatcaac    9120
ggatgatcca gtgatagaca ggctttacct ctcatctcac agaggtgtta tcgctgacaa    9180
tcaagcaaaa tgggctgtcc cgacaacacg aacagatgac aagttgcgaa tggagacatg    9240
cttccaacag cgcgtgtaagg gtaaaatcca agcactctgc gagaatcccg agtgggcacc    9300
attgaaggat aacaggattc cttcatacgg ggtcttgtct gttgatctga gtctgacagt    9360
tgagcttaaa atcaaaattg cttcgggatt cgggccattg atcacacacg gttcagggat    9420
ggacctatac aaatccaacc acaacaatgt gtattggctg actatcccgc caatgaagaa    9480
```

```
cctagcctta ggtgtaatca acacattgga gtggataccg agattcaagg ttagtccctA    9540
cctcttcact gtcccaatta aggaagcagg cgaagactgc catgcccaa catacctacc     9600
tgcggaggtg gatggtgatg tcaaactcag ttccaatctg gtgattctac ctggtcaaga    9660
tctccaatat gttttggcaa cctacgatac ttccagggtt gaacatgctg tggtttatta    9720
cgtttacagc ccaagccgct cattttctta cttttatcct tttaggttgc ctataaaggg    9780
ggtccccatc gaattacaag tggaatgctt cacatgggac caaaaactct ggtgccgtca    9840
cttctgtgtg cttgcggact cagaatctgg tggacatatc actcactctg ggatggtggg    9900
catgggagtc agctgcacag tcacccggga agatggaacc aatcgcagat agggctgcta    9960
gtgaaccaat cacatgatgt cacccagaca tcaggcatac ccactagtgt gaaatagaca   10020
tcagaattaa gaaaaacgta gggtccaagt ggttccccgt tatggactcg ctatctgtca   10080
accagatctt ataccctgaa gttcacctag atagcccgat agttaccaat aagatagtag   10140
ccatcctgga gtatgctcga gtccctcacg cttacagcct ggaggaccct acactgtgtc   10200
agaacatcaa gcaccgccta aaaacggat tttccaacca atgattata aacaatgtgg     10260
aagttgggaa tgtcatcaag tccaagctta ggagttatcc ggcccactct catattccat   10320
atccaaattg taatcaggat ttatttaaca tagaagacaa agagtcaacg aggaagatcc   10380
gtgaactcct caaaaggggg aattcgctgt actccaaagt cagtgataag gttttccaat   10440
gcttaaggga cactaactca cggcttggcc taggctccga attgagggag gacatcaagg   10500
agaaagttat taacttggga gtttacatgc acagctccca gtggtttgag ccctttctgt   10560
tttggtttac agtcaagact gagatgaggt cagtgattaa atcacaaacc catacttgcc   10620
ataggaggag acacacacct gtattcttca ctggtagttc agttgagttg ctaatctctc   10680
gtgaccttgt tgctataatc agtaaagagt ctcaacatgt atattacctg acatttgaac   10740
tggttttgat gtattgtgat gtcatagagg ggaggttaat gacagagacc gctatgacta   10800
ttgatgctag gtacagagag cttctaggaa gagtcagata catgtggaaa ctgatagatg   10860
gtttcttccc tgcactcggg aatccaactt atcaaattgt agccatgctg gagcctcttt   10920
cacttgctta cctgcagctg agggatataa cagtagaact cagaggtgct ttccttaacc   10980
actgctttac tgaaatacat gatgttcttg accaaaacgg gttttctgat gaaggtactt   11040
atcatgagtt aactgaagct ctagattaca ttttcataac tgatgacata catctgacag   11100
gggagatttt ctcattttc agaagtttcg gccacccag acttgaagca gtaacggctg     11160
ctgaaaatgt taggaaatac atgaatcagc ctaaagtcat tgtgtatgag actctgatga   11220
aaggtcatgc catattttgt ggaatcataa tcaacggcta tcgtgacagg cacggaggca   11280
gttggccacc gctgaccctc cccctgcatg ctgcagacac aatccggaat gctcaagctt   11340
caggtgaagg gttaacacat gagcagtgcg ttgataactg gaaatctttt gctggagtga   11400
aatttggctg ctttatgcct cttagcctgg atagtgatct gacaatgtac ctaaaggaca   11460
aggcacttgc tgctctccaa agggaatggg attcagttta cccgaaagag ttcctgcgtt   11520
acgaccctcc caagggaacc gggtcacgga ggcttgtaga tgttttcctt aatgattcga   11580
gctttgaccc atatgatgtg ataatgtatg ttgtaagtgg agcttacctc catgaccctg   11640
agttcaacct gtcttacagc ctgaaagaaa aggagatcaa ggaaacaggt agacttttttg   11700
ctaaaatgac ttacaaaatg agggcatgcc aagtgattgc tgaaaatcta atctcaaacg   11760
ggattggcaa atatttttaag gacaatggga tggccaagga tgagcacgat ttgactaagg   11820
cactccacac tctagctgtc tcaggagtcc ccaaagatct caaagaaagt cacagggggg   11880
```

```
ggccagtctt aaaaacctac tcccgaagcc cagtccacac aagtaccagg aacgtgagag    11940
cagcaaaagg gtttataggg ttccctcaag taattcggca ggaccaagac actgatcatc    12000
cggagaatat ggaagcttac gagacagtca gtgcatttat cacgactgat ctcaagaagt    12060
actgccttaa ttggagatat gagaccatca gcttgtttgc acagaggcta aatgagattt    12120
acggattgcc ctcattttc cagtggctgc ataagaggct tgagacctct gtcctgtatg     12180
taagtgaccc tcattgcccc cccgaccttg acgcccatat cccgttatat aaagtcccca    12240
atgatcaaat cttcattaag taccctatgg gaggtataga agggtattgt cagaagctgt    12300
ggaccatcag caccattccc tatctatacc tggctgctta tgagagcgga gtaaggattg    12360
cttcgttagt gcaaggggac aatcagacca tagccgtaac aaaaagggta cccagcacat    12420
ggccctacaa ccttaagaaa cgggaagctg ctagagtaac tagagattac tttgtaattc    12480
ttaggcaaag gctacatgat attggccatc acctcaaggc aaatgagaca attgtttcat    12540 cacattttt tgtctattca aaaggaatat attatgatgg gctacttgtg tcccaatcac    12600
tcaagagcat cgcaagatgt gtattctggt cagagactat agttgatgaa acaagggcag    12660
catgcagtaa tattgctaca acaatggcta aaagcatcga gagaggttat gaccgttacc    12720
ttgcatattc cctgaacgtc ctaaaagtga tacagcaaat tctgatctct cttggcttca    12780
caatcaattc aaccatgacc cgggatgtag tcatacccct cctcacaaac aacgacctct    12840
taataaggat ggcactgttg cccgctccta ttgggggat gaattatctg aatatgagca     12900
ggctgtttgt cagaaacatc ggtgatccag taacatcatc aattgctgat ctcaagagaa    12960
tgattctcgc ctcactaatg cctgaagaga ccctccatca agtaatgaca caacaaccgg    13020
gggactcttc attcctagac tgggctagcg acccttactc agcaaatctt gtatgtgtcc    13080
agagcatcac tagactcctc aagaacataa ctgcaaggtt tgtcctgatc catagtccaa    13140
acccaatgtt aaaaggatta ttccatgatg acagtaaaga agaggacgag ggactggcgg    13200
cattcctcat ggacaggcat attatagtac ctagggcagc tcatgaaatc ctggatcata    13260
gtgtcacagg ggcaagagag tctattgcag gcatgctgga taccacaaaa ggcttgattc    13320
gagccagcat gaggaagggg gggttaacct ctcgagtgat aaccagattg tccaattatg    13380
actatgaaca attcagagca gggatggtgc tattgacagg aagaaagaga aatgtcctca    13440
ttgacaaaga gtcatgttca gtgcagctgg cgagagctct aagaagccat atgtgggcga    13500
ggctagctcg aggacggcct atttacggcc ttgaggtccc tgatgtacta gaatctatgc    13560
gaggccacct tattcggcgt catgagacat gtgtcatctg cgagtgtgga tcagtcaact    13620
acggatggtt ttttgtcccc tcgggttgcc aactggatga tattgacaag gaaacatcat    13680
ccttgagagt cccatatatt ggttctacca ctgatgagag aacagacatg aagcttgcct    13740
tcgtaagagc cccaagtcga tccttgcgat ctgctgttag aatagcaaca gtgtactcat    13800
gggcttacgg tgatgatgat agctcttgga cgaagcctg gttgttggct aggcaaaggg     13860
ccaatgtgag cctggaggag ctaagggtga tcactcccat ctcaacttcg actaatttag    13920
cgcataggtt gagggatcgt agcactcaag tgaaatactc aggtacatcc cttgtccgag    13980
tggcgaggta taccacaatc tccaacgaca atctctcatt tgtcatatca gataagaagg    14040
ttgatactaa cttttatatac caacaaggaa tgcttctagg gttgggtgtt ttagaaacat    14100
tgtttcgact cgagaaagat accggatcat ctaacacggt attacatctt cacgtcgaaa    14160
cagattgttg cgtgatcccg atgatagatc atcccaggat acccagctcc cgcaagctag    14220
```

-continued

```
agctgagggc agagctatgt accaacccat tgatatatga taatgcacct ttaattgaca    14280
gagatgcaac aaggctatac acccagagcc ataggaggca ccttgtggaa tttgttacat    14340
ggtccacacc ccaactatat cacattttag ctaagtccac agcactatct atgattgacc    14400
tggtaacaaa atttgagaag gaccatatga atgaaatttc agctctcata ggggatgacg    14460
atatcaatag tttcataact gagtttctgc tcatagagcc aagattattc actatctact    14520
tgggccagtg tgcggccatc aattgggcat ttgatgtaca ttatcataga ccatcaggga    14580
aatatcagat gggtgagctg ttgtcatcgt tcctttctag aatgagcaaa ggagtgttta    14640
aggtgcttgt caatgctcta agccacccaa agatctacaa gaaattctgg cattgtggta    14700
ttatagagcc tatccatggt ccttcacttg atgctcaaaa cttgcacaca actgtgtgca    14760
acatggttta cacatgctat atgacctacc tcgacctgtt gttgaatgaa gagttagaag    14820
agttcacatt tctcttgtgt gaaagcgacg aggatgtagt accggacaga ttcgacaaca    14880
tccaggcaaa acacttatgt gttctggcag atttgtactg tcaaccaggg acctgcccac    14940
caattcgagg tctaagaccg gtagagaaat gtgcagttct aaccgaccat atcaaggcag    15000
aggctatgtt atctccagca ggatcttcgt ggaacataaa tccaattatt gtagaccatt    15060
actcatgctc tctgacttat ctccggcgag gatcgatcaa acagataaga ttgagagttg    15120
atccaggatt cattttcgac gccctcgctg aggtaaatgt cagtcagcca agatcggca     15180 gcaacaacat ctcaaatatg agcatcaagg ctttcagacc cccacacgat gatgttcaa     15240 aattgctcaa agatatcaac acaagcaagc acaatcttcc catttcaggg ggcaatctcg    15300
ccaattatga aatccatgct ttccgcagaa tcgggttgaa ctcatctgct tgctacaaag    15360
ctgttgagat atcaacatta attaggagat gccttgagcc aggggaggac ggcttgttct    15420
tgggtgaggg atcgggttct atgttgatca cttataaaga gatacttaaa ctaaacaagt    15480
gcttctataa tagtggggtt tccgccaatt ctagatctgg tcaaagggaa ttagcaccct    15540
atccctccga agttggcctt gtcgaacaca gaatgggagt aggtaatatt gtcaaagtgc    15600
tctttaacgg gaggcccgaa gtcacgtggg taggcagtgt agattgcttc aatttcatag    15660
ttagtaatat ccctacctct agtgtggggt ttatccattc agatatagag accttgcctg    15720
acaaagatac tatagagaag ctagaggaat tggcagccat cttatcgatg gctctgctcc    15780
tgggcaaaat aggatcaata ctggtgatta agcttatgcc tttcagcggg gattttgttc    15840
agggatttat aagttatgta gggtctcatt atagagaagt gaaccttgta taccctagat    15900
acagcaactt catctctact gaatcttatt tggttatgac agatctcaag gctaaccggc    15960
taatgaatcc tgaaaagatt aagcagcaga taattgaatc atctgtgagg acttcacctg    16020
gacttatagg tcacatccta tccattaagc aactaagctg catacaagca attgtgggag    16080
acgcagttag tagaggtgat atcaatccta ctctgaaaaa acttacacct atagagcagg    16140
tgctgatcaa ttgcgggttg gcaattaacg gacctaagct gtgcaaagaa ttgatccacc    16200
atgatgttgc ctcagggcaa gatggattgc ttaattctat actcatcctc tacagggagt    16260
tggcaagatt caaagacaac caaagaagtc aacaagggat gttccacgct taccccgtat    16320
tggtaagtag caggcaacga gaacttatat ctaggatcac ccgcaaattc tgggggcaca    16380
ttcttcttta ctccgggaac aaaaagttga taaataagtt tatccagaat ctcaagtccg    16440
gctatctgat actagactta caccagaata tcttcgttaa gaatctatcc aagtcagaga    16500
aacagattat tatgacgggg ggtttgaaac gtgagtgggt tttaaggta acagtcaagg    16560 agaccaaaga atggtataag ttagtcggat acagtgccct gattaaggac taattggttg    16620
```

```
aactccggaa ccctaatcct gccctaggtg gttaggcatt atttgcaata tattaaagaa  16680
aactttgaaa atacgaagtt tctattccca gctttgtctg gtggccggca tggtcccagc  16740
ctcctcgctg gcgccggctg ggcaacattc cgagggacc gtcccctcgg taatggcgaa  16800
tgggacgcgg ccgatccggc tgctaacaaa gcccgaaagg aagctgagtt ggctgctgcc  16860
accgctgagc aataactagc ataacccctt ggggcctcta aacgggtctt gaggggtttt  16920
ttgctgaaag gaggaactat atccggatgc ggccgcgggc cctatggtac ccagcttttg  16980 ttcccttag tgagggttaa ttccgagctt ggcgtaatca tggtcatagc tgtttcctgt  17040
gtgaaattgt tatccgctca caattccaca acataggaa gccggaagca taagtgtaa  17100 agcctgggt gcctaatgag tgaggtaact cacattaatt gcgttgcgct cactgcccgc  17160
tttccagtcg ggaaacctgt cgtgccagct gcattaatga atcggccaac gcgcggggag  17220
aggcggtttg cgtattgggc gctcttccgc ttcctcgctc actgactcgc tgcgctcggt  17280
cgttcggctg cggcgagcgg tatcagctca ctcaaaggcg gtaatacggt tatccacaga  17340
atcaggggat aacgcaggaa agaacatgtg agcaaaaggc cagcaaaagg ccaggaaccg  17400
taaaaaggcc gcgttgctgg cgtttttcca taggctcggc cccctgacg agcatcacaa  17460 aaatcgacgc tcaagtcaga ggtggcgaaa cccgacagga ctataaagat accaggcgtt  17520 ccccctgga agctccctcg tgcgctctcc tgttccgacc ctgccgctta ccggatacct  17580
gtccgccttt ctcccttcgg gaagcgtggc gctttctcaa tgctcacgct gtaggtatct  17640
cagttcggtg taggtcgttc gctccaagct gggctgtgtg cacgaacccc ccgttcagcc  17700
cgaccgctgc gccttatccg gtaactatcg tcttgagtcc aacccggtaa gacacgactt  17760
atcgccactg gcagcagcca ctggtaacag gattagcaga gcgaggtatg taggcggtgc  17820
tacagagttc ttgaagtggt ggcctaacta cggctacact agaaggacag tatttggtat  17880
ctgcgctctg ctgaagccag ttaccttcgg aaaaagagtt ggtagctctt gatccggcaa  17940
acaaaccacc gctggtagcg gtggtttttt tgtttgcaag cagcagatta cgcgcagaaa  18000
aaaaggatct caagaagatc ctttgatctt ttctacgggg tctgacgctc agtggaacga  18060
aaactcacgt taagggattt tggtcatgag attatcaaaa aggatcttca cctagatcct  18120
tttaaattaa aaatgaagtt ttaaatcaat ctaaagtata tatgagtaaa cttggtctga  18180
cagttaccaa tgcttaatca gtgaggcacc tatctcagcg atctgtctat ttcgttcatc  18240
catagttgcc tgactccccg tcgtgtagat aactacgata cgggagggct taccatctgg  18300
ccccagtgct gcaatgatac cgcgagaccc acgctcaccg gctccagatt tatcagcaat  18360
aaaccagcca gccggaaggg ccgagcgcag aagtggtcct gcaactttat ccgcctccat  18420
ccagtctatt aattgttgcc gggaagctag agtaagtagt tcgccagtta atagtttgcg  18480
caacgttgtt gccattgcta caggcatcgt ggtgtcacgc tcgtcgtttg gtatggcttc  18540
attcagctcc ggttcccaac gatcaaggcg agttacatga tcccccatgt tgtgaaaaaa  18600
agcggttagc tccttcggtc ctccgatcgt tgtcagaagt aagttggccg cagtgttatc  18660
actcatgctt atggcagcac tgcataattc tcttactgtc atgccatccg taagatgctt  18720
ttctgtgact ggtgagtact caaccaagtc attctgagaa tagtgtatgc ggcgaccgag  18780
ttgctcttgc ccggcgtcaa tacgggataa taccgcgcca catagcagaa ctttaaaagt  18840
gctcatcatt ggaaaacgtt cttcggggcg aaaactctca aggatcttac cgctgttgag  18900
atccagttcg atgtaaccca ctcgtgcacc caactgatct tcagcatctt ttactttcac  18960
```

```
cagcgtttct gggtgagcaa aaacaggaag gcaaaatgcc gcaaaaaagg gaataagggc   19020
gacacggaaa tgttgaatac tcatactctt cctttttcaa tattattgaa gcatttatca   19080
gggttattgt ctcatgagcg gatacatatt tgaatgtatt tagaaaaata aacaaatagg   19140
ggttccgcgc acatttcccc gaaaagtgcc acctgaaatt gtaaacgtta atattttgtt   19200
aaaattcgcg ttaaattttt gttaaatcag ctcattttt aaccaatagg ccgaaatcgg    19260
caaaatccct tataaatcaa agaatagac cgagataggg ttgagtgttg ttccagtttg    19320
gaacaagagt ccactattaa agaacgtgga ctccaacgtc aaagggcgaa aaaccgtcta   19380
tcagggcgat ggcccactac gtgaaccatc accctaatca agtttttgg ggtcgaggtg    19440 ccgtaaagca ctaaatcgga accctaaagg gagcccccga tttagagctt gacggggaaa   19500
gccggcgaac gtggcgagaa aggaagggaa gaaagcgaaa ggagcgggcg ctagggcgct   19560
ggcaagtgta gcggtcacgc tgcgcgtaac caccacaccc gccgcgctta atgcgccgct   19620
acagggcgcg tcccattcgc cattcaggct gcgcaactgt tgggaagggc gatcggtgcg   19680
ggcctcttcg ctattacgcc agccaccgcg gtggcggccg ctaatacgac tcactatagg   19740
gccaactttg tttggtctga tgagtccgtg aggacgaaac ccggagtccc gggtc        19795

<210> SEQ ID NO 16
<211> LENGTH: 19795
<212> TYPE: DNA
<213> ORGANISM: Artificial Sequence
<220> FEATURE:
<223> OTHER INFORMATION: pTM-MVSchw-ATU3
<220> FEATURE:
<221> NAME/KEY: misc_RNA
<222> LOCATION: (1)..(16722)
<223> OTHER INFORMATION: MVSchw-ATU3-eGFP_antigenome
<220> FEATURE:
<221> NAME/KEY: misc_feature
<222> LOCATION: (9176)..(10003)
<223> OTHER INFORMATION: ATU3
<220> FEATURE:
<221> NAME/KEY: misc_feature
<222> LOCATION: (9246)..(9251)
<223> OTHER INFORMATION: BsiWI restriction site
<220> FEATURE:
<221> NAME/KEY: misc_feature
<222> LOCATION: (9252)..(9971)
<223> OTHER INFORMATION: ORF for eGFP : eGFP_ORF
<220> FEATURE:
<221> NAME/KEY: misc_feature
<222> LOCATION: (9972)..(9977)
<223> OTHER INFORMATION: BssHII restriction site
<220> FEATURE:
<221> NAME/KEY: misc_feature
<222> LOCATION: (16723)..(19795)
<223> OTHER INFORMATION: plasmid_backbone

<400> SEQUENCE: 16
accaaacaaa gttgggtaag gatagttcaa tcaatgatca tcttctagtg cacttaggat      60
tcaagatcct attatcaggg acaagagcag gattagggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtgaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg   480
atgaggcgga ccaatacttt tcacatgatg atccaattag tagtgatcaa tccaggttcg    540
```

-continued

```
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg aacttgaaa    1140 actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggca aggaagatag gagggtcaaa cagagtcgag    1440
gagaagccag ggagagctac agagaaaccg ggcccagcag agcaagtgat gcgagagctg   1500
cccatcttcc aaccggcaca cccctagaca ttgacactgc aacggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag ggccagaaca acatccgcct accatccatc attgttataa   1740
aaaacttagg aaccaggtcc acacagccgc cagcccatca accatccact cccacgattg   1800
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca accatgcct ctcagcaatt ggatcaactg aaggcggtgc acctcgcatc    2040
cgcggtcagg gacctggaga gagcgatgac gacgctgaaa cttgggaat ccccccaaga    2100 aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aaggggagga ctattatgat gatgagctgt ctctctgatgt ccaagatatt   2760 aaaacagcct tggccaaaat acacgaggat aatcagaaga taatctccaa gctagaatca   2820
ctgctgttat tgaagggaga agttgagtca attaagaagc agatcaacag gcaaaatatc   2880
```

```
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagtac aacctaaatc cattataaaa aacttaggag caaagtgatt   3420
gcctcccaag gtccacaatg acagagacct acgacttcga caagtcggca tgggacatca   3480
aagggtcgat cgctccgata caacccacca cctacagtga tggcaggctg gtgccccagg   3540
tcagagtcat agatcctggt ctaggcgaca ggaaggatga atgctttatg tacatgtttc   3600
tgctgggggt tgttgaggac agcgattccc tagggcctcc aatcgggcga gcatttgggt   3660
tcctgccctt aggtgttggc agatccacag caaagcccga aaaactcctc aaagaggcca   3720
ctgagcttga catagttgtt agacgtacag cagggctcaa tgaaaaactg gtgttctaca   3780
acaacacccc actaactctc ctcacaccct tggagaaaggt cctaacaaca gggagtgtct   3840
tcaacgcaaa ccagtgtgc aatgcggtta atctgatacc gctcgatacc ccgcagaggt   3900
tccgtgttgt ttatatgagc atcacccgtc tttcggataa cgggtattac accgttccta   3960
gaagaatgct ggaattcaga tcggtcaatg cagtggcctt caacctgctg gtgacccttta   4020 ggattgacaa ggcgataggc cctgggaaga tcatcgacaa tacagagcaa cttcctgagg   4080 caacattttat ggtccacatc gggaacttca ggagaaagaa gagtgaagtc tactctgccg   4140
attattgcaa aatgaaaatc gaaagatgg gcctggtttt tgcacttggt gggatagggg   4200
gcaccagtct tcacattaga agcacaggca aaatgagcaa gactctccat gcacaactcg   4260
ggttcaagaa gaccttatgt taccccgctga tggatatcaa tgaagacctt aatcgattac   4320
tctggaggag cagatgcaag atagtaagaa tccaggcagt tttgcagcca tcagttcctc   4380
aagaattccg catttacgac gacgtgatca taaatgatga ccaaggacta ttcaaagttc   4440
tgtagaccgt agtgcccagc aatgcccgaa acgaccccc ctcacaatga cagccagaag   4500
gcccggacaa aaaagccccc tccgaaagac tccacggacc aagcgagagg ccagccagca   4560
gccgacggca agcgcgaaca ccaggcggcc ccagcacaga acagccctga cacaaggcca   4620
ccaccagcca ccccaatctg catcctcctc gtgggacccc cgaggaccaa cccccaaggc   4680 tgccccccgat ccaaaccacc aaccgcatcc ccaccaccc cgggaaagaa accccagca   4740 attggaaggc ccctccccct cttcctcaac acaagaactc cacaaccgaa ccgcacaagc   4800
gaccgaggtg acccaaccgc aggcatccga ctccctagac agatcctctc tcccggcaa   4860 actaaacaaa acttagggcc aaggaacata cacacccaac agaacccaga ccccggccca   4920
cggcgccgcg ccccaacccc ccgacaacca gagggagccc ccaaccaatc ccgccggctc   4980
ccccggtgcc cacaggcagg gacaccaacc cccgaacaga cccagcaccc aaccatcgac   5040
aatccaagac gggggggccc ccccaaaaaa aggcccccag gggccgacag ccagcaccgc   5100
gaggaagccc accccaccca cacacgacca cggcaaccaa accagaaccc agaccaccct   5160
gggccaccag ctcccagact cggccatcac cccgcagaaa ggaaaggcca aacccgcgc   5220 accccagccc cgatccggcg gggagccacc caacccgaac cagcacccaa gagcgatccc   5280
```

```
cgaaggaccc ccgaaccgca aaggacatca gtatcccaca gcctctccaa gtccccggt   5340 ctcctcctct tctcgaaggg accaaaagat caatccacca cacccgacga cactcaactc   5400
cccaccccta aaggagacac cgggaatccc agaatcaaga ctcatccaat gtccatcatg   5460
ggtctcaagg tgaacgtctc tgccatattc atggcagtac tgttaactct ccaaacaccc   5520
accggtcaaa tccattgggg caatctctct aagatagggg tggtaggaat aggaagtgca   5580
agctacaaag ttatgactcg ttccagccat caatcattag tcataaaatt aatgcccaat   5640
ataactctcc tcaataactg cacgagggta gagattgcag aatacaggag actactgaga   5700
acagttttgg aaccaattag agatgcactt aatgcaatga cccagaatat aagaccggtt   5760
cagagtgtag cttcaagtag gagacacaag agatttgcgg gagtagtcct ggcaggtgcg   5820
gccctaggcg ttgccacagc tgctcagata acagccggca ttgcacttca ccagtccatg   5880
ctgaactctc aagccatcga caatctgaga gcgagcctgg aaactactaa tcaggcaatt   5940
gagacaatca gacaagcagg gcaggagatg atattggctg ttcagggtgt ccaagactac   6000
atcaataatg agctgatacc gtctatgaac caactatctt gtgatttaat cggccagaag   6060
ctcgggctca aattgctcag atactataca gaaatcctgt cattatttgg ccccagttta   6120
cgggacccca tatctgcgga gatatctatc caggctttga gctatgcgct tggaggagac   6180
atcaataagg tgttagaaaa gctcggatac agtggaggtg atttactggg catcttagag   6240
agcggaggaa taaaggcccg gataactcac gtcgacacag agtcctactt cattgtcctc   6300
agtatagcct atccgacgct gtccgagatt aagggggtga ttgtccaccg gctagagggg   6360
gtctcgtaca acataggctc tcaagagtgg tataccactg tgcccaagta tgttcaacc   6420 caagggtacc ttatctcgaa ttttgatgag tcatcgtgta ctttcatgcc agaggggact   6480
gtgtgcagcc aaaatgcctt gtacccgatg agtcctctgc tccaagaatg cctccggggg   6540
tacaccaagt cctgtgctcg tacactcgta tccgggtctt ttgggaaccg gttcattttta   6600 tcacaaggga acctaatagc caattgtgca tcaatccttt gcaagtgtta cacaacagga   6660
acgatcatta atcaagaccc tgacaagatc ctaacataca ttgctgccga tcactgcccg   6720
gtagtcgagg tgaacggcgt gaccatccaa gtcgggagcg ggaggtatcc agacgctgtg   6780
tacttgcaca gaattgacct cggtcctccc atatcattgg agaggttgga cgtagggaca   6840
aatctgggga atgcaattgc taagttggag gatgccaagg aattgttgga gtcatcggac   6900
cagatattga ggagtatgaa aggtttatcg agcactagca tagtctacat cctgattgca   6960
gtgtgtcttg gagggttgat agggatcccc gctttaatat gttgctgcag ggggcgttgt   7020
aacaaaaagg gagaacaagt tggtatgtca agaccaggcc taaagcctga tcttacggga   7080
acatcaaaat cctatgtaag gtcgctctga tcctctacaa ctcttgaaac acaaatgtcc   7140
cacaagtctc ctcttcgtca tcaagcaacc accgcaccca gcatcaagcc cacctgaaat   7200
tatctccggc ttccctctgg ccgaacaata tcggtagtta atcaaaactt agggtgcaag   7260
atcatccaca atgtcaccac aacgagaccg gataaatgcc ttctacaaag ataaccccca   7320
tcccaaggga gtaggatag tcattaacag agaacatctt atgattgata gaccttatgt   7380
tttgctggct gttctgtttg tcatgttttct gagcttgatc gggttgctag ccattgcagg   7440
cattagactt catcgggcag ccatctacac cgcagagatc cataaaagcc tcagcaccaa   7500
tctagatgta actaactcaa tcgagcatca ggtcaaggac gtgctgacac cactcttcaa   7560
aatcatcggt gatgaagtgg gcctgaggac acctcagaga ttcactgacc tagtgaaatt   7620
```

```
aatctctgac aagattaaat tccttaatcc ggatagggag tacgacttca gagatctcac   7680
ttggtgtatc aacccgccag agagaatcaa attggattat gatcaatact gtgcagatgt   7740
ggctgctgaa gagctcatga atgcattggt gaactcaact ctactggaga ccagaacaac   7800
caatcagttc ctagctgtct caaagggaaa ctgctcaggg cccactacaa tcagaggtca   7860
attctcaaac atgtcgctgt ccctgttaga cttgtattta ggtcgaggtt acaatgtgtc   7920
atctatagtc actatgacat cccagggaat gtatggggga acttacctag tggaaaagcc   7980
taatctgagc agcaaaaggt cagagttgtc acaactgagc atgtaccgag tgtttgaagt   8040
aggtgttatc agaaatccgg gtttgggggc tccggtgttc catatgacaa actatcttga   8100
gcaaccagtc agtaatgatc tcagcaactg tatggtggct ttgggggagc tcaaactcgc   8160
agcccttttgt cacggggaag attctatcac aattccctat cagggatcag ggaaaggtgt   8220
cagcttccag ctcgtcaagc taggtgtctg gaaatcccca accgacatgc aatcctgggt   8280
cccccttatca acggatgatc cagtgataga caggctttac ctctcatctc acagaggtgt   8340
tatcgctgac aatcaagcaa aatgggctgt cccgacaaca cgaacagatg acaagttgcg   8400
aatggagaca tgcttccaac aggcgtgtaa gggtaaaatc caagcactct gcgagaatcc   8460
cgagtgggca ccattgaagg ataacaggat tccttcatac ggggtcttgt ctgttgatct   8520
gagtctgaca gttgagctta aaatcaaaat tgcttcggga ttcgggccat tgatcacaca   8580
cggttcaggg atggacctat acaaatccaa ccacaacaat gtgtattggc tgactatccc   8640
gccaatgaag aacctagcct taggtgtaat caacacattg gagtggatac cgagattcaa   8700
ggttagtccc tacctcttca ctgtcccaat taaggaagca ggcgaagact gccatgcccc   8760
aacatacccta cctgcggagg tggatggtga tgtcaaactc agttccaatc tggtgattct   8820
acctggtcaa gatctccaat atgttttggc aacctacgat acttccaggg ttgaacatgc   8880
tgtggtttat tacgtttaca gcccaagccg ctcatttcct tactttttatc cttttaggtt   8940
gcctataaag ggggtcccca tcgaattaca agtggaatgc ttcacatggg accaaaaact   9000
ctggtgccgt cacttctgtg tgcttgcgga ctcagaatct ggtggacata tcactcactc   9060
tgggatggtg ggcatgggag tcagctgcac agtcacccgg gaagatggaa ccaatcgcag   9120
atagggctgc tagtgaacca atcacatgat gtcacccaga catcaggcat acccactagt   9180
ctaccctcca tcattgttat aaaaaactta ggaaccaggt ccacacagcc gccagcccat   9240
caacgcgtac gatggtgagc aagggcgagg agctgttcac cggggtggtg cccatcctgg   9300
tcgagctgga cggcgacgta aacggccaca agttcagcgt gtccggcgag ggcgagggcg   9360
atgccaccta cggcaagctg accctgaagt tcatctgcac caccggcaag ctgcccgtgc   9420
cctggcccac cctcgtgacc accctgacct acggcgtgca gtgcttcagc cgctaccccg   9480
accacatgaa gcagcacgac ttcttcaagt ccgccatgcc cgaaggctac gtccaggagc   9540
gcaccatctt cttcaaggac gacggcaact acaagacccg cgccgaggtg aagttcgagg   9600
gcgacaccct ggtgaaccgc atcgagctga agggcatcga cttcaaggag gacggcaaca   9660
tcctggggca caagctggag tacaactaca acagccacaa cgtctatatc atggccgaca   9720
agcagaagaa cggcatcaag gtgaacttca agatccgcca caacatcgag gacggcagcg   9780
tgcagctcgc cgaccactac cagcagaaca cccccatcgg cgacggcccc gtgctgctgc   9840
ccgacaacca ctacctgagc acccagtccg ccctgagcaa agaccccaac gagaagcgcg   9900
atcacatggt cctgctggag ttcgtgaccg ccgccgggat cactctcggc atggacgagc   9960
tgtacaagta ggcgcgcagc gcttagacgt ctcgcgatcg atgctagtgt gaaatagaca  10020
```

```
tcagaattaa gaaaaacgta gggtccaagt ggttccccgt tatggactcg ctatctgtca   10080
accagatctt ataccctgaa gttcacctag atagcccgat agttaccaat aagatagtag   10140
ccatcctgga gtatgctcga gtccctcacg cttacagcct ggaggaccct acactgtgtc   10200
agaacatcaa gcaccgccta aaaaacggat tttccaacca atgattata aacaatgtgg    10260 aagttgggaa tgtcatcaag tccaagctta ggagttatcc ggcccactct catattccat   10320
atccaaattg taatcaggat ttatttaaca tagaagacaa agagtcaacg aggaagatcc   10380
gtgaactcct caaaaagggg aattcgctgt actccaaagt cagtgataag gttttccaat   10440
gcttaaggga cactaactca cggcttggcc taggctccga attgagggag acatcaagg    10500 agaaagttat taacttggga gtttacatgc acagctccca gtggtttgag ccctttctgt   10560
tttggtttac agtcaagact gagatgaggt cagtgattaa atcacaaacc catacttgcc   10620
ataggaggag acacacacct gtattcttca ctggtagttc agttgagttg ctaatctctc   10680
gtgaccttgt tgctataatc agtaaagagt ctcaacatgt atattacctg acatttgaac   10740
tggttttgat gtattgtgat gtcatagagg ggaggttaat gacagagacc gctatgacta   10800
ttgatgctag gtatacagag cttctaggaa gagtcagata catgtggaaa ctgatagatg   10860
gtttcttccc tgcactcggg aatccaactt atcaaattgt agccatgctg gagcctcttt   10920
cacttgctta cctgcagctg agggatataa cagtagaact cagaggtgct ttccttaacc   10980
actgctttac tgaaatacat gatgttcttg accaaaacgg gttttctgat gaaggtactt   11040
atcatgagtt aactgaagct ctagattaca ttttcataac tgatgacata catctgacag   11100
gggagatttt ctcattttc agaagtttcg gccacccag acttgaagca gtaacggctg     11160
ctgaaaatgt taggaaatac atgaatcagc ctaaagtcat tgtgtatgag actctgatga   11220
aaggtcatgc catattttgt ggaatcataa tcaacggcta tcgtgacagg cacggaggca   11280
gttggccacc gctgaccctc cccctgcatg ctgcagacac aatccggaat gctcaagctt   11340
caggtgaagg gttaacacat gagcagtgcg ttgataactg gaaatctttt gctggagtga   11400
aatttggctg ctttatgcct cttagcctgg atagtgatct gacaatgtac ctaaaggaca   11460
aggcacttgc tgctctccaa agggaatggg attcagttta cccgaaagag ttcctgcgtt   11520
acgaccctcc caagggaacc gggtcacgga ggcttgtaga tgttttcctt aatgattcga   11580
gctttgaccc atatgatgtg ataatgtatg ttgtaagtgg agcttacctc catgaccctg   11640
agttcaacct gtcttacagc ctgaaagaaa aggagatcaa ggaaacaggt agactttttg   11700
ctaaaatgac ttacaaaatg agggcatgcc aagtgattgc tgaaaatcta atctcaaacg   11760
ggattggcaa atattttaag gacaatggga tggccaagga tgagcacgat ttgactaagg   11820
cactccacac tctagctgtc tcaggagtcc ccaaagatct caaagaaagt cacgggggg    11880 ggccagtctt aaaaacctac tcccgaagcc cagtccacac aagtaccagg aacgtgagag   11940
cagcaaaagg gttataggg ttccctcaag taattcggca ggaccaagac actgatcatc     12000
cggagaatat ggaagcttac gagacagtca gtgcatttat cacgactgat ctcaagaagt   12060
actgccttaa ttggagatat gagaccatca gcttgttttgc acagaggcta aatgagattt   12120
acggattgcc ctcattttc cagtggctgc ataagaggct tgagacctct gtcctgtatg    12180
taagtgaccc tcattgcccc cccgaccttg acgcccatat cccgttatat aaagtcccca   12240
atgatcaaat cttcattaag tacccctatg gaggtataga agggtattgt cagaagctgt   12300
ggaccatcag caccattccc tatctatacc tggctgctta tgagagcgga gtaaggattg   12360
```

```
cttcgttagt gcaaggggac aatcagacca tagccgtaac aaaaagggta cccagcacat   12420
ggccctacaa ccttaagaaa cgggaagctg ctagagtaac tagagattac tttgtaattc   12480
ttaggcaaag gctacatgat attggccatc acctcaaggc aaatgagaca attgtttcat   12540
cacatttttt tgtctattca aaaggaatat attatgatgg ctacttgtg tcccaatcac    12600 tcaagagcat cgcaagatgt gtattctggt cagagactat agttgatgaa acaagggcag   12660
catgcagtaa tattgctaca acaatggcta aaagcatcga gagaggttat gaccgttacc   12720
ttgcatattc cctgaacgtc ctaaaagtga tacagcaaat tctgatctct cttggcttca   12780
caatcaattc aaccatgacc cgggatgtag tcatacccct cctcacaaac aacgacctct   12840
taataaggat ggcactgttg cccgctccta ttgggggat gaattatctg aatatgagca    12900
ggctgtttgt cagaaacatc ggtgatccag taacatcatc aattgctgat ctcaagagaa   12960
tgattctcgc ctcactaatg cctgaagaga ccctccatca agtaatgaca caacaaccgg   13020
gggactcttc attcctagac tgggctagcg acccttactc agcaaatctt gtatgtgtcc   13080
agagcatcac tagactcctc aagaacataa ctgcaaggtt tgtcctgatc catagtccaa   13140
acccaatgtt aaaaggatta ttccatgatg acagtaaaga agaggacgag ggactggcgg   13200
cattcctcat ggacaggcat attatagtac ctagggcagc tcatgaaatc ctggatcata   13260
gtgtcacagg ggcaagagag tctattgcag gcatgctgga taccacaaaa ggcttgattc   13320
gagccagcat gaggaagggg gggttaacct ctcgagtgat aaccagattg tccaattatg   13380
actatgaaca attcagagca gggatggtgc tattgacagg aagaaagaga aatgtcctca   13440
ttgacaaaga gtcatgttca gtgcagctgg cgagagctct aagaagccat atgtgggcga   13500
ggctagctcg aggacggcct atttacggcc ttgaggtccc tgatgtacta gaatctatgc   13560
gaggccacct tattcggcgt catgagacat gtgtcatctg cgagtgtgga tcagtcaact   13620
acggatggtt ttttgtcccc tcgggttgcc aactggatga tattgacaag gaaacatcat   13680
ccttgagagt cccatatatt ggttctacca ctgatgagag aacagacatg aagcttgcct   13740
tcgtaagagc cccaagtcga tccttgcgat ctgctgttag aatagcaaca gtgtactcat   13800
gggcttacgg tgatgatgat agctcttgga acgaagcctg gttgttggct aggcaaaggg   13860
ccaatgtgag cctggaggag ctaagggtga tcactcccat ctcaacttcg actaatttag   13920
cgcataggtt gagggatcgt agcactcaag tgaaatactc aggtacatcc cttgtccgag   13980
tggcgaggta taccacaatc tccaacgaca atctctcatt tgtcatatca gataagaagg   14040
ttgatactaa ctttatatac caacaaggaa tgcttctagg gttgggtgtt ttagaaacat   14100
tgtttcgact cgagaaagat accggatcat ctaacacggt attacatctt cacgtcgaaa   14160
cagattgttg cgtgatcccg atgatagatc atcccaggat acccagctcc cgcaagctag   14220
agctgagggc agagctatgt accaacccat tgatatatga taatgcacct ttaattgaca   14280
gagatgcaac aaggctatac acccagagcc ataggaggca ccttgtggaa tttgttacat   14340
ggtccacacc ccaactatat cacattttag ctaagtccac agcactatct atgattgacc   14400
tggtaacaaa atttgagaag gaccatatga atgaaatttc agctctcata ggggatgacg   14460
atatcaatag tttcataact gagtttctgc tcatagagcc aagattattc actatctact   14520
tgggccagtg tgcggccatc aattgggcat ttgatgtaca ttatcataga ccatcaggga   14580
aatatcagat gggtgagctg ttgtcatcgt tcctttctag aatgagcaaa ggagtgttta   14640
aggtgcttgt caatgctcta agccacccaa agatctacaa gaaattctgg cattgtggta   14700
ttatagagcc tatccatggt ccttcacttg atgctcaaaa cttgcacaca actgtgtgca   14760
```

```
acatggttta cacatgctat atgacctacc tcgacctgtt gttgaatgaa gagttagaag   14820
agttcacatt tctcttgtgt gaaagcgacg aggatgtagt accggacaga ttcgacaaca   14880
tccaggcaaa acacttatgt gttctggcag atttgtactg tcaaccaggg acctgcccac   14940
caattcgagg tctaagaccg gtagagaaat gtgcagttct aaccgaccat atcaaggcag   15000
aggctatgtt atctccagca ggatcttcgt ggaacataaa tccaattatt gtagaccatt   15060
actcatgctc tctgacttat ctccggcgag gatcgatcaa acagataaga ttgagagttg   15120
atccaggatt cattttcgac gccctcgctg aggtaaatgt cagtcagcca aagatcggca   15180
gcaacaacat ctcaaatatg agcatcaagg ctttcagacc cccacacgat gatgttgcaa   15240
aattgctcaa agatatcaac acaagcaagc acaatcttcc catttcaggg ggcaatctcg   15300
ccaattatga aatccatgct ttccgcagaa tcgggttgaa ctcatctgct tgctacaaag   15360
ctgttgagat atcaacatta attaggagat gccttgagcc aggggaggac ggcttgttct   15420
tgggtgaggg atcgggttct atgttgatca cttataaaga gatacttaaa ctaaacaagt   15480
gcttctataa tagtggggtt tccgccaatt ctagatctgg tcaaagggaa ttagcaccct   15540
atccctccga agttggcctt gtcgaacaca gaatgggagt aggtaatatt gtcaaagtgc   15600
tctttaacgg gaggcccgaa gtcacgtggg taggcagtgt agattgcttc aatttcatag   15660
ttagtaatat ccctacctct agtgtggggt ttatccattc agatatagag accttgcctg   15720
acaaagatac tatagagaag ctagaggaat tggcagccat cttatcgatg gctctgctcc   15780
tgggcaaaat aggatcaata ctggtgatta agcttatgcc tttcagcggg gattttgttc   15840
agggatttat aagttatgta gggtctcatt atagagaagt gaaccttgta taccctagat   15900
acagcaactt catctctact gaatcttatt tggttatgac agatctcaag gctaaccggc   15960
taatgaatcc tgaaaagatt aagcagcaga taattgaatc atctgtgagg acttcacctg   16020
gacttatagg tcacatccta tccattaagc aactaagctg catacaagca attgtgggag   16080
acgcagttag tagaggtgat atcaatccta ctctgaaaaa acttacacct atagagcagg   16140
tgctgatcaa ttgcgggttg gcaattaacg gacctaagct gtgcaaagaa ttgatccacc   16200
atgatgttgc ctcagggcaa gatggattgc ttaattctat actcatcctc tacagggagt   16260
tggcaagatt caaagacaac caaagaagtc aacagggat gttccacgct taccccgtat   16320
tggtaagtag caggcaacga gaacttatat ctaggatcac ccgcaaattc tgggggcaca   16380
ttcttcttta ctccgggaac aaaaagttga taaataagtt tatccagaat ctcaagtccg   16440
gctatctgat actagactta caccagaata tcttcgttaa gaatctatcc aagtcagaga   16500
aacagattat tatgacgggg ggtttgaaac gtgagtgggt ttttaaggta acagtcaagg   16560
agaccaaaga atggtataag ttagtcggat acagtgccct gattaaggac taattggttg   16620
aactccggaa ccctaatcct gccctaggtg gttaggcatt atttgcaata tattaaagaa   16680
aactttgaaa atacgaagtt tctattccca gctttgtctg gtggccggca tggtcccagc   16740
ctcctcgctg gcgccggctg gcaacattc cgaggggacc gtcccctcgg taatggcgaa   16800
tgggacgcgg ccgatccggc tgctaacaaa gcccgaaagg aagctgagtt ggctgctgcc   16860
accgctgagc aataactagc ataacccctt ggggcctcta acgggtctt gaggggtttt   16920
ttgctgaaag gaggaactat atccggatgc ggccgcgggc cctatggtac ccagcttttg   16980
ttccctttag tgagggttaa ttccgagctt ggcgtaatca tggtcatagc tgtttcctgt   17040
gtgaaattgt tatccgctca caattccaca caacatagga gccggaagca taaagtgtaa   17100
```

```
agcctggggt gcctaatgag tgaggtaact cacattaatt gcgttgcgct cactgcccgc   17160
tttccagtcg ggaaacctgt cgtgccagct gcattaatga atcggccaac gcgcggggag   17220
aggcggtttg cgtattgggc gctcttccgc ttcctcgctc actgactcgc tgcgctcggt   17280
cgttcggctg cggcgagcgg tatcagctca ctcaaaggcg gtaatacggt tatccacaga   17340 atcagggggat aacgcaggaa agaacatgtg agcaaaaggc cagcaaaagg ccaggaaccg   17400
taaaaaggcc gcgttgctgg cgtttttcca taggctcggc cccctgacg agcatcacaa   17460 aaatcgacgc tcaagtcaga ggtggcgaaa cccgacagga ctataaagat accaggcgtt   17520
ccccctggaa gctccctcg tgcgctctcc tgttccgacc ctgccgctta ccggatacct   17580
gtccgccttt ctcccttcgg aagcgtggc gctttctcaa tgctcacgct gtaggtatct   17640
cagttcggtg taggtcgttc gctccaagct gggctgtgtg cacgaacccc ccgttcagcc   17700
cgaccgctgc gccttatccg gtaactatcg tcttgagtcc aacccggtaa gacacgactt   17760
atcgccactg gcagcagcca ctggtaacag gattagcaga gcgaggtatg taggcggtgc   17820
tacagagttc ttgaagtggt ggcctaacta cggctacact agaaggacag tatttggtat   17880
ctgcgctctg ctgaagccag ttaccttcgg aaaaagagtt ggtagctctt gatccggcaa   17940
acaaaccacc gctggtagcg gtggtttttt tgtttgcaag cagcagatta cgcgcagaaa   18000
aaaaggatct caagaagatc ctttgatctt ttctacgggg tctgacgctc agtggaacga   18060
aaactcacgt taagggattt tggtcatgag attatcaaaa aggatcttca cctagatcct   18120
tttaaattaa aaatgaagtt ttaaatcaat ctaaagtata tatgagtaaa cttggtctga   18180
cagttaccaa tgcttaatca gtgaggcacc tatctcagcg atctgtctat ttcgttcatc   18240
catagttgcc tgactgcccg tcgtgtagat aactacgata cgggagggct taccatctgg   18300
ccccagtgct gcaatgatac cgcgagaccc acgctcaccg gctccagatt tatcagcaat   18360
aaaccagcca gccggaaggg ccgagcgcag aagtggtcct gcaactttat ccgcctccat   18420
ccagtctatt aattgttgcc gggaagctag agtaagtagt tcgccagtta atagtttgcg   18480
caacgttgtt gccattgcta caggcatcgt ggtgtcacgc tcgtcgtttg gtatggcttc   18540
attcagctcc ggttcccaac gatcaaggcg agttacatga tcccccatgt tgtgaaaaaa   18600
agcggttagc tccttcggtc ctccgatcgt tgtcagaagt aagttggccg cagtgttatc   18660
actcatgctt atggcagcac tgcataattc tcttactgtc atgccatccg taagatgctt   18720
ttctgtgact ggtgagtact caaccaagtc attctgagaa tagtgtatgc ggcgaccgag   18780
ttgctcttgc ccggcgtcaa tacgggataa taccgcgcca catagcagaa ctttaaaagt   18840
gctcatcatt ggaaaacgtt cttcggggcg aaaactctca aggatcttac cgctgttgag   18900
atccagttcg atgtaaccca ctcgtgcacc caactgatct tcagcatctt ttactttcac   18960
cagcgtttct gggtgagcaa aaacaggaag gcaaaatgcc gcaaaaaagg gaataagggc   19020
gacacggaaa tgttgaatac tcatactctt cctttttcaa tattattgaa gcatttatca   19080
gggttattgt ctcatgagcg gatacatatt tgaatgtatt tagaaaaata aacaaatagg   19140
ggttccgcgc acatttcccc gaaaagtgcc acctgaaatt gtaaacgtta atattttgtt   19200
aaaattcgcg ttaaattttt gttaaatcag ctcattttt aaccaatagg ccgaaatcgg   19260
caaaatccct tataaatcaa aagaatagac cgagataggg ttgagtgttg ttccagtttg   19320
gaacaagagt ccactattaa agaacgtgga ctccaacgtc aaagggcgaa aaaccgtcta   19380
tcagggcgat ggcccactac gtgaaccatc accctaatca agttttttgg ggtcgaggtg   19440
ccgtaaagca ctaaatcgga accctaaagg gagcccccga tttagagctt gacggggaaa   19500
```

```
gccggcgaac gtggcgagaa aggaagggaa gaaagcgaaa ggagcgggcg ctagggcgct      19560
ggcaagtgta gcggtcacgc tgcgcgtaac caccacaccc gccgcgctta atgcgccgct      19620
acagggcgcg tcccattcgc cattcaggct gcgcaactgt tgggaagggc gatcggtgcg      19680
ggcctcttcg ctattacgcc agccaccgcg gtggcggccg ctaatacgac tcactatagg      19740
gccaactttg tttggtctga tgagtccgtg aggacgaaac ccggagtccc gggtc          19795
```

```
<210> SEQ ID NO 17
<211> LENGTH: 336
<212> TYPE: DNA
<213> ORGANISM: Artificial Sequence
<220> FEATURE:
<223> OTHER INFORMATION: M2raw_synthetic_gene
<220> FEATURE:
<221> NAME/KEY: misc_feature
<222> LOCATION: (13)..(18)
<223> OTHER INFORMATION: BsiW1 restriction site
<220> FEATURE:
<221> NAME/KEY: misc_feature
<222> LOCATION: (22)..(318)
<223> OTHER INFORMATION: CDS - M2 consensus protein : M2raw_ORF
<220> FEATURE:
<221> NAME/KEY: misc_feature
<222> LOCATION: (319)..(324)
<223> OTHER INFORMATION: BssHII restriction site

<400> SEQUENCE: 17
```

```
gctagcggat cccgtacgac catgagcctt ctaaccgagg tcgaaacgcc tatcagaaac       60 gaatggggt gcagatgcaa cgattcaagt gaccctcttg ttgttgccgc gagtatcatt       120
gggatcttgc acttgatatt gtggattctt gatcgtcttt tcttcaaatg catctatcga      180
ctcttcaaac acggtctgaa aagaggacct tctacggaag gagtacctga gtctatgagg      240
gaagaatatc gaaaggaaca gcagaatgct gtggatgctg acgacagtca ttttgtcagc      300
atagagctgg agtgataagc gcgcctcgag gaattc                                336
```

```
<210> SEQ ID NO 18
<211> LENGTH: 336
<212> TYPE: DNA
<213> ORGANISM: Artificial Sequence
<220> FEATURE:
<223> OTHER INFORMATION: M2opt_synthetic_gene
<220> FEATURE:
<221> NAME/KEY: misc_feature
<222> LOCATION: (13)..(18)
<223> OTHER INFORMATION: BsiWI restriction site
<220> FEATURE:
<221> NAME/KEY: misc_feature
<222> LOCATION: (22)..(318)
<223> OTHER INFORMATION: CDS - M2 consensus protein : M2opt_ORF
<220> FEATURE:
<221> NAME/KEY: misc_feature
<222> LOCATION: (319)..(324)
<223> OTHER INFORMATION: BssHII restriction site

<400> SEQUENCE: 18
```

```
gctagcggat cccgtacgac catgagcctg ctgaccgagg tggaaacccc catcagaaac       60
gagtggggct gccggtgcaa cgacagcagc gatcctctgg tggtggccgc cagcatcatc      120
ggcatcctgc acctgatcct gtggattctg gaccggctgt tcttcaagtg catctacaga      180
ctgttcaagc acggcctgaa gagaggcccc agcacagaag gcgtgcccga gagcatgcgg      240
gaagagtacc ggaaagaaca gcagaacgcc gtggacgccg acgacagcca cttcgtgtcc      300
atcgagctgg aatgataagc gcgcctcgag gaattc                                336
```

<210> SEQ ID NO 19
<211> LENGTH: 97
<212> TYPE: PRT
<213> ORGANISM: Artificial Sequence
<220> FEATURE:
<223> OTHER INFORMATION: M2_consensus_protein

<400> SEQUENCE: 19

```
Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Leu Ile Leu Trp Ile Leu Asp Arg Leu Phe Phe
        35                  40                  45

Lys Cys Ile Tyr Arg Leu Phe Lys His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Asn Ala Val Asp Ala Asp Asp Ser His Phe Val Ser Ile Glu Leu
                85                  90                  95

Glu
```

<210> SEQ ID NO 20
<211> LENGTH: 69
<212> TYPE: DNA
<213> ORGANISM: Artificial Sequence
<220> FEATURE:
<223> OTHER INFORMATION: optimized_M2e_coding_sequence
<220> FEATURE:
<221> NAME/KEY: misc_feature
<222> LOCATION: (1)..(69)
<223> OTHER INFORMATION: M2e consensus polypeptide

<400> SEQUENCE: 20
tctctgctga ccgaggtgga aaccccatc agaaacgagt ggggctgccg gtgcaacgac    60
agctctgat                                                           69

<210> SEQ ID NO 21
<211> LENGTH: 23
<212> TYPE: PRT
<213> ORGANISM: Artificial Sequence
<220> FEATURE:
<223> OTHER INFORMATION: M2e_consensus_polypeptide

<400> SEQUENCE: 21

```
Ser Leu Leu Thr Glu Val Glu Thr Pro Ile Arg Asn Glu Trp Gly Cys
1               5                   10                  15

Arg Cys Asn Asp Ser Ser Asp
            20
```

<210> SEQ ID NO 22
<211> LENGTH: 804
<212> TYPE: DNA
<213> ORGANISM: Artificial Sequence
<220> FEATURE:
<223> OTHER INFORMATION: M1opt_synthetic_gene
<220> FEATURE:
<221> NAME/KEY: misc_feature
<222> LOCATION: (13)..(18)
<223> OTHER INFORMATION: M2e consensus polypeptide
<220> FEATURE:
<221> NAME/KEY: misc_feature
<222> LOCATION: (22)..(783)
<223> OTHER INFORMATION: CDS - M1 consensus protein : M1opt_ORF

```
<220> FEATURE:
<221> NAME/KEY: misc_feature
<222> LOCATION: (787)..(792)
<223> OTHER INFORMATION: BssHII restriction site

<400> SEQUENCE: 22
gctagcggat cccgtacgac catgagcctg ctgaccgagg tggaaaccta cgtgctgagc      60
atcatcccca gcggccctct gaaggccgag atcgctcagc ggctggaaga tgtgttcgcc     120
ggcaagaaca ccgacctgga agccctgatg gaatggctga aaacccggcc catcctgagc     180
cccctgacca agggcatcct gggcttcgtg ttcaccctga ccgtgccctc tgagagaggc     240
ctgcagcgga agattcgt gcagaacgcc ctgaacggca acggcgaccc caacaacatg      300
gaccgggccg tgaagctgta ccggaagctg aagagagaga tcaccttcca cggcgccaaa     360
gagatcgccc tgagctactc tgctggcgcc ctggcctctt gcatgggcct gatctacaac     420
cggatgggcg ccgtgacaac agaggtggcc tttggcctcg tgtgcgccac atgcgagcag     480
atcgccgaca gccagcaccg gtcccacaga cagatggtca ccaccaccaa ccccctgatc     540
cggcacgaga acagaatggt gctggcctcc accaccgcca aggccatgga acagatggcc     600
ggcagctctg agcaggccgc cgaagctatg gaagtggcct ctcaggcccg gcagatggtg     660
caggccatga gagccatcgg cacccaccct agcagcagca ccggcctgaa ggacgacctg     720
ctggaaaatc tgcaagctta ccagaaaaga atgggcgtgc agatgcagcg gtttaagtaa     780
tgacgagcgc gcctcgagga attc                                           804
```

```
<210> SEQ ID NO 23
<211> LENGTH: 252
<212> TYPE: PRT
<213> ORGANISM: Artificial Sequence
<220> FEATURE:
<223> OTHER INFORMATION: M1_consensus_protein

<400> SEQUENCE: 23
```

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met

```
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Ala Ile Gly Thr His Pro Ser
    210                 215                 220

Ser Ser Thr Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 24
<211> LENGTH: 1764
<212> TYPE: DNA
<213> ORGANISM: Artificial Sequence
<220> FEATURE:
<223> OTHER INFORMATION: NPflu-3xM2e_fusion_gene
<220> FEATURE:
<221> NAME/KEY: misc_feature
<222> LOCATION: (1)..(6)
<223> OTHER INFORMATION: BsiWI restriction site
<220> FEATURE:
<221> NAME/KEY: misc_feature
<222> LOCATION: (13)..(1755)
<223> OTHER INFORMATION: ORF for NPflu-3xM2e fusion protein :
      NPflu-3xM2e_ORF
<220> FEATURE:
<221> NAME/KEY: misc_feature
<222> LOCATION: (13)..(1506)
<223> OTHER INFORMATION: NPflu consensus polypeptide
<220> FEATURE:
<221> NAME/KEY: misc_feature
<222> LOCATION: (1507)..(1512)
<223> OTHER INFORMATION: BspE1 restriction site
<220> FEATURE:
<221> NAME/KEY: misc_feature
<222> LOCATION: (1507)..(1524)
<223> OTHER INFORMATION: linker (SGG)2
<220> FEATURE:
<221> NAME/KEY: misc_feature
<222> LOCATION: (1525)..(1593)
<223> OTHER INFORMATION: M2e consensus polypeptide
<220> FEATURE:
<221> NAME/KEY: misc_feature
<222> LOCATION: (1603)..(1671)
<223> OTHER INFORMATION: M2e consensus polypeptide
<220> FEATURE:
<221> NAME/KEY: misc_feature
<222> LOCATION: (1681)..(1749)
<223> OTHER INFORMATION: M2e consensus polypeptide
<220> FEATURE:
<221> NAME/KEY: misc_feature
<222> LOCATION: (1759)..(1764)
<223> OTHER INFORMATION: BssHII restriction site

<400> SEQUENCE: 24
cgtacggcca ccatggcctc tcagggcacc aagagaagct acgagcagat ggaaaccgac      60
ggcgagcggc agaacgccac cgagattaga gccagcgtgg gcagaatgat cggcggcatc     120
ggccggttct acatccagat gtgcaccgag ctgaagctga gcgactacga gggccggctg     180
atccagaaca gcctgaccat cgagcggatg gtgctgagcg ccttcgacga gcggcggaac     240
aagtacctgg aagaacaccc cagcgccggc aaggacccca agaaaacagg cggccctatc     300
tacagacggg tggacggcaa gtggatgcgc gagctggtgc tgtacgacaa agaggaaatc     360
cggcggatct ggcggcaggc caacaatggc gaagatgcca cagccggcct gacccacatc     420
atgatctggc acagcaacct gaacgacgcc acctaccagc ggaccagagc actcgtgcgg     480
acaggcatgg accccagaat gtgcagcctg atgcagggca gcaccctgcc cagaagatct     540
```

```
ggcgctgctg gcgcagctgt gaagggcgtg ggaaccatgg tcatggaact gatcaggatg      600
atcaagcggg gaatcaacga ccggaacttt tggagaggcg agaacggcag aaagacccgc      660
agcgcctacg agaggatgtg caatatcctg aagggcaagt tccagacagc cgcccagcgg      720
gccatgatgg atcaagtgcg cgagagcaga accccggca acgccgagat cgaggacctg       780
atcttcctgg ccagaagcgc cctgatcctg aggggctctg tggcccacaa gagctgtctg      840
cctgcctgcg tgtacggacc tgccgtggcc agcggctacg acttcgagaa agagggctac      900
agcctcgtgg gcatcgaccc attcaagctg ctgcagaact cccaggtgta cagcctgatc      960
cggcccaacg agaaccccgc ccacaagtct cagctcgtgt ggatggcctg tcacagcgcc      1020
gccttcgagg atctgagagt gtccagcttc atccggggca caaggtgtc ccccagaggc       1080 aagctgagca ccagaggcgt gcagatcgcc agcaacgaga atatggacaa catgggcagc      1140 tccacccctgg aactgcggag ccggtattgg gccatcagaa ccagaagcgg cggcaacacc     1200
aaccagcaga gagcctctgc cggacagatc agcgtgcagc ccacctttag cgtgcagaga      1260 aacctgcccct tcgagaaggc cacaatcatg gccgccttca ccgcaatac cgagggcaga     1320 accagcgaca tgcgggccga gatcatcaga atgatggaaa gcgccaagcc cgaggaagtg     1380
tcattccagg gcagggggcgt gttcgagctg tccgacgaga agccaccaa cccatcgtg      1440 cccagcttcg acatgagcaa cgagggcagc tacttcttcg gcgacaacgc cgaagagtac      1500
gacaactccg aggatctgg cggctctctg ctgaccgagg tggaaccc catcagaaac       1560 gagtggggct gccggtgcaa cgacagctct gatggcggcg aagcctgct gacagaagtg      1620 gaaacaccta ttcggaatga gtggggatgc agatgcaatg actccagcga cggcggaggc     1680
agtctgctga ctgaagtgga aaccccaatt cgcaacgaat ggggatgtcg ctgtaacgat      1740
agcagcgact gataacgagc gcgc                                             1764
```

<210> SEQ ID NO 25
<211> LENGTH: 579
<212> TYPE: PRT
<213> ORGANISM: Artificial Sequence
<220> FEATURE:
<223> OTHER INFORMATION: NPflu-3xM2e_fusion_protein

<400> SEQUENCE: 25

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
                20                  25                  30

Ile Gly Gly Ile Gly Arg Phe Tyr Ile Gln Met Cys Thr Glu Leu Lys
            35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Ile Met Ile Trp His Ser Asn Leu Asn
    130                 135                 140
```

```
Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
            165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
            195                 200                 205

Gly Glu Asn Gly Arg Lys Thr Arg Ser Ala Tyr Glu Arg Met Cys Asn
            210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
            245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
            275                 280                 285

Tyr Asp Phe Glu Lys Glu Gly Tyr Ser Leu Val Gly Ile Asp Pro Phe
            290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
            325                 330                 335

Ala Phe Glu Asp Leu Arg Val Ser Ser Phe Ile Arg Gly Thr Lys Val
            340                 345                 350

Ser Pro Arg Gly Lys Leu Ser Thr Arg Gly Val Gln Ile Ala Ser Asn
            355                 360                 365

Glu Asn Met Asp Asn Met Gly Ser Ser Thr Leu Glu Leu Arg Ser Arg
            370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
            405                 410                 415

Asn Leu Pro Phe Glu Lys Ala Thr Ile Met Ala Ala Phe Thr Gly Asn
            420                 425                 430

Thr Glu Gly Arg Thr Ser Asp Met Arg Ala Glu Ile Ile Arg Met Met
            435                 440                 445

Glu Ser Ala Lys Pro Glu Glu Val Ser Phe Gln Gly Arg Gly Val Phe
450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
            485                 490                 495

Asp Asn Ser Gly Gly Ser Gly Gly Ser Leu Leu Thr Glu Val Glu Thr
            500                 505                 510

Pro Ile Arg Asn Glu Trp Gly Cys Arg Cys Asn Asp Ser Ser Asp Gly
            515                 520                 525

Gly Gly Ser Leu Leu Thr Glu Val Glu Thr Pro Ile Arg Asn Glu Trp
            530                 535                 540

Gly Cys Arg Cys Asn Asp Ser Ser Asp Gly Gly Ser Leu Leu Thr
545                 550                 555                 560

Glu Val Glu Thr Pro Ile Arg Asn Glu Trp Gly Cys Arg Cys Asn Asp
```

Ser Ser Asp

<210> SEQ ID NO 26
<211> LENGTH: 1692
<212> TYPE: DNA
<213> ORGANISM: Artificial Sequence
<220> FEATURE:
<223> OTHER INFORMATION: N-1xM2e_(fusion_gene)
<220> FEATURE:
<221> NAME/KEY: misc_feature
<222> LOCATION: (4)..(9)
<223> OTHER INFORMATION: BsiWI restriction site
<220> FEATURE:
<221> NAME/KEY: misc_feature
<222> LOCATION: (13)..(1680)
<223> OTHER INFORMATION: ORF for N-1xM2e fusion protein : N-1xM2e_ORF
<220> FEATURE:
<221> NAME/KEY: misc_feature
<222> LOCATION: (13)..(1587)
<223> OTHER INFORMATION: N
<220> FEATURE:
<221> NAME/KEY: misc_feature
<222> LOCATION: (1588)..(1593)
<223> OTHER INFORMATION: BspEI restriction site
<220> FEATURE:
<221> NAME/KEY: misc_feature
<222> LOCATION: (1588)..(1605)
<223> OTHER INFORMATION: linker (SGG)2
<220> FEATURE:
<221> NAME/KEY: misc_feature
<222> LOCATION: (1606)..(1674)
<223> OTHER INFORMATION: M2e consensus polypeptide
<220> FEATURE:
<221> NAME/KEY: misc_feature
<222> LOCATION: (1684)..(1689)
<223> OTHER INFORMATION: BssHII restriction site

<400> SEQUENCE: 26
agtcgtacgg agatggccac acttttaagg agcttagcat tgttcaaaag aaacaaggac 60
aaaccaccca ttacatcagg atccggtgga gccatcagag gaatcaaaca cattattata 120
gtaccaatcc ctggagattc ctcaattacc actcgatcca gacttctgga ccggttggtg 180
aggttaattg gaaacccgga tgtgagcggg cccaaactaa caggggcact aataggtata 240
ttatccttat ttgtggagtc tccaggtcaa ttgattcaga ggatcaccga tgaccctgac 300
gttagcataa ggctgttaga ggttgtccag agtgaccagt cacaatctgg ccttaccttc 360
gcatcaagag gtaccaacat ggaggatgag gcggaccaat acttttcaca tgatgatcca 420
attagtagtg atcaatccag gttcggatgg ttcgggaaca aggaaatctc agatattgaa 480
gtgcaagacc ctgagggatt caacatgatt ctgggtacca tcctagccca aatttgggtc 540
ttgctcgcaa aggcggttac ggccccagac acggcagctg attcggagct aagaaggtgg 600
ataaagtaca cccaacaaag aagggtagtt ggtgaattta gattggagag aaaatggttg 660
gatgtggtga ggaacaggat tgccgaggac ctctccttac gccgattcat ggtcgctcta 720
atcctggata tcaagagaac acccggaaac aaacccagga ttgctgaaat gatatgtgac 780
attgatacat atatcgtaga ggcaggatta gccagtttta tcctgactat taagtttggg 840
atagaaacta tgtatcctgc tcttggactg catgaatttg ctggtgagtt atccacactt 900
gagtccttga tgaaccttta ccagcaaatg gggaaactg caccctacat ggtaatcctg 960
gagaactcaa ttcagaacaa gttcagtgca ggatcatacc ctctgctctg gagctatgcc 1020
atgggagtag gagtggaact tgaaaactcc atgggaggtt tgaactttgg ccgatcttac 1080
tttgatccag catattttag attagggcaa gagatggtaa ggaggtcagc tggaaaggtc 1140

```
agttccacat tggcatctga actcggtatc actgccgagg atgcaaggct tgtttcagag    1200
attgcaatgc atactactga ggacaagatc agtagagcgg ttggacccag acaagcccaa    1260
gtatcatttc tacacggtga tcaaagtgag aatgagctac cgagattggg gggcaaggaa    1320
gataggaggg tcaaacagag tcgaggagaa gccaggagaa gctacagaga aaccgggccc    1380
agcagagcaa gtgatgcgag agctgcccat cttccaaccg gcacacccct agacattgac    1440
actgcaacga gtccagcca agatccgcag gacagtcgaa ggtcagctga cgccctgctt    1500
aggctgcaag ccatggcagg aatctcggaa gaacaaggct cagacacgga cacccctata    1560
gtgtacaatg acagaaatct tctagactcc ggaggatctg gcggctctct gctgaccgag    1620
gtggaaaccc ccatcagaaa cgagtggggc tgccggtgca acgacagctc tgattgataa    1680
cgagcgcgca ac                                                        1692
```

<210> SEQ ID NO 27
<211> LENGTH: 2035
<212> TYPE: DNA
<213> ORGANISM: Artificial Sequence
<220> FEATURE:
<223> OTHER INFORMATION: N-3xM2e_(fusion_gene)
<220> FEATURE:
<221> NAME/KEY: misc_feature
<222> LOCATION: (4)..(9)
<223> OTHER INFORMATION: BsiWI restriction site
<220> FEATURE:
<221> NAME/KEY: misc_feature
<222> LOCATION: (13)..(1836)
<223> OTHER INFORMATION: ORF for N-3xM2e fusion protein : N-3xM2e_ORF
<220> FEATURE:
<221> NAME/KEY: misc_feature
<222> LOCATION: (13)..(1587)
<223> OTHER INFORMATION: N
<220> FEATURE:
<221> NAME/KEY: misc_feature
<222> LOCATION: (1588)..(1593)
<223> OTHER INFORMATION: BspEI restriction site
<220> FEATURE:
<221> NAME/KEY: misc_feature
<222> LOCATION: (1588)..(1605)
<223> OTHER INFORMATION: linker (SGG)2
<220> FEATURE:
<221> NAME/KEY: misc_feature
<222> LOCATION: (1606)..(1674)
<223> OTHER INFORMATION: M2e consensus polypeptide
<220> FEATURE:
<221> NAME/KEY: misc_feature
<222> LOCATION: (1684)..(1752)
<223> OTHER INFORMATION: M2e consensus polypeptide
<220> FEATURE:
<221> NAME/KEY: misc_feature
<222> LOCATION: (1762)..(1830)
<223> OTHER INFORMATION: M2e consensus polypeptide
<220> FEATURE:
<221> NAME/KEY: misc_feature
<222> LOCATION: (1840)..(1845)
<223> OTHER INFORMATION: BssHII restriction site

<400> SEQUENCE: 27

```
agtcgtacgg agatggccac acttttaagg agcttagcat tgttcaaaag aaacaaggac     60
aaaccaccca ttacatcagg atccggtgga gccatcagag gaatcaaaca cattattata    120
gtaccaatcc ctggagattc ctcaattacc actcgatcca gacttctgga ccggttggtg    180
aggttaattg gaaacccgga tgtgagcggg cccaaactaa caggggcact aataggtata    240
ttatccttat ttgtggagtc tccaggtcaa ttgattcaga ggatcaccga tgaccctgac    300
gttagcataa ggctgttaga ggttgtccag agtgaccagt cacaatctgg ccttaccttc    360
```

```
gcatcaagag gtaccaacat ggaggatgag gcggaccaat acttttcaca tgatgatcca    420
attagtagtg atcaatccag gttcggatgg ttcgggaaca aggaaatctc agatattgaa    480
gtgcaagacc ctgagggatt caacatgatt ctgggtacca tcctagccca aatttgggtc    540
ttgctcgcaa aggcggttac ggccccagac acggcagctg attcggagct aagaaggtgg    600
ataaagtaca cccaacaaag aagggtagtt ggtgaattta gattggagag aaaatggttg    660
gatgtggtga ggaacaggat tgccgaggac ctctccttac gccgattcat ggtcgctcta    720
atcctggata tcaagagaac acccggaaac aaacccagga ttgctgaaat gatatgtgac    780
attgatacat atatcgtaga ggcaggatta gccagtttta tcctgactat taagtttggg    840
atagaaacta tgtatcctgc tcttggactg catgaatttg ctggtgagtt atccacactt    900
gagtccttga tgaaccttta ccagcaaatg ggggaaactg caccctacat ggtaatcctg    960
gagaactcaa ttcagaacaa gttcagtgca ggatcatacc ctctgctctg gagctatgcc   1020
atgggagtag gagtggaact tgaaaactcc atgggaggtt tgaactttgg ccgatcttac   1080
tttgatccag catattttag attagggcaa gagatggtaa ggaggtcagc tggaaaggtc   1140
agttccacat tggcatctga actcggtatc actgccgagg atgcaaggct tgtttcagag   1200
attgcaatgc atactactga ggacaagatc agtagagcgg ttggacccag acaagcccaa   1260
gtatcatttc tacacggtga tcaaagtgag aatgagctac cgagattggg gggcaaggaa   1320
gataggaggg tcaaacagag tcgaggagaa gccaggggaga gctacagaga aaccgggccc   1380
agcagagcaa gtgatgcgag agctgcccat cttccaaccg gcacacccct agacattgac   1440
actgcaacga gtccagcca agatccgcag gacagtcgaa ggtcagctga cgccctgctt   1500
aggctgcaag ccatggcagg aatctcggaa gaacaaggct cagacacgga caccctata    1560
gtgtacaatg acagaaatct tctagactcc ggaggatctg gcggctctct gctgaccgag   1620
gtggaaaccc ccatcagaaa cgagtgggc tgccggtgca acgacagctc tgatggcggc    1680
ggaagcctgc tgacagaagt ggaaacacct attcggaatg agtggggatg cagatgcaat   1740
gactccagcg acggcggagg cagtctgctg actgaagtgg aaaccccaat tcgcaacgaa   1800
tggggatgtc gctgtaacga tagcagcgac tgataacgag cgcgcttcga agtgcgagag   1860
gccgagggcc agaacaacat ccgcctacca tccatcattg ttataaaaaa cttaggaacc   1920
aggtccacac agccgccagc ccatcaacca tccactccca cgattggagc caatggcaga   1980
agagcaggca cgccatgtca aaacggact ggaatgcatc cgggctctca aggcc          2035
```

<210> SEQ ID NO 28
<211> LENGTH: 554
<212> TYPE: PRT
<213> ORGANISM: Artificial Sequence
<220> FEATURE:
<223> OTHER INFORMATION: N-1xM2e_fusion_protein

<400> SEQUENCE: 28

Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Ar

-continued

```
                65                  70                  75                  80
Val Glu Ser Pro Gly Gln Leu Ile Gln Arg Ile Thr Asp Asp Pro Asp
                    85                  90                  95

Val Ser Ile Arg Leu Leu Glu Val Val Gln Ser Asp Gln Ser Gln Ser
                100                 105                 110

Gly Leu Thr Phe Ala Ser Arg Gly Thr Asn Met Glu Asp Glu Ala Asp
                115                 120                 125

Gln Tyr Phe Ser His Asp Asp Pro Ile Ser Ser Asp Gln Ser Arg Phe
            130                 135                 140

Gly Trp Phe Gly Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                    165                 170                 175

Leu Leu Ala Lys Ala Val Thr Ala Pro Asp Thr Ala Ala Asp Ser Glu
                180                 185                 190

Leu Arg Arg Trp Ile Lys Tyr Thr Gln Gln Arg Arg Val Val Gly Glu
            195                 200                 205

Phe Arg Leu Glu Arg Lys Trp Leu Asp Val Val Arg Asn Arg Ile Ala
210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                    245                 250                 255

Ile Asp Thr Tyr Ile Val Glu Ala Gly Leu Ala Ser Phe Ile Leu Thr
                260                 265                 270

Ile Lys Phe Gly Ile Glu Thr Met Tyr Pro Ala Leu Gly Leu His Glu
            275                 280                 285

Phe Ala Gly Glu Leu Ser Thr Leu Glu Ser Leu Met Asn Leu Tyr Gln
290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                    325                 330                 335

Met Gly Val Gly Val Glu Leu Glu Asn Ser Met Gly Gly Leu Asn Phe
                340                 345                 350

Gly Arg Ser Tyr Phe Asp Pro Ala Tyr Phe Arg Leu Gly Gln Glu Met
            355                 360                 365

Val Arg Arg Ser Ala Gly Lys Val Ser Ser Thr Leu Ala Ser Glu Leu
370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                    405                 410                 415

Val Ser Phe Leu His Gly Asp Gln Ser Glu Asn Glu Leu Pro Arg Leu
                420                 425                 430

Gly Gly Lys Glu Asp Arg Arg Val Lys Gln Ser Arg Gly Glu Ala Arg
            435                 440                 445

Glu Ser Tyr Arg Glu Thr Gly Pro Ser Arg Ala Ser Asp Ala Arg Ala
450                 455                 460

Ala His Leu Pro Thr Gly Thr Pro Leu Asp Ile Asp Thr Ala Thr Glu
465                 470                 475                 480

Ser Ser Gln Asp Pro Gln Asp Ser Arg Arg Ser Ala Asp Ala Leu Leu
                    485                 490                 495
```

```
Arg Leu Gln Ala Met Ala Gly Ile Ser Glu Glu Gln Gly Ser Asp Thr
                500                 505                 510

Asp Thr Pro Ile Val Tyr Asn Asp Arg Asn Leu Leu Asp Ser Gly Gly
                515                 520                 525

Ser Gly Gly Ser Leu Leu Thr Glu Val Glu Thr Pro Ile Arg Asn Glu
530                 535                 540

Trp Gly Cys Arg Cys Asn Asp Ser Ser Asp
545                 550

<210> SEQ ID NO 29
<211> LENGTH: 606
<212> TYPE: PRT
<213> ORGANISM: Artificial Sequence
<220> FEATURE:
<223> OTHER INFORMATION: N-3xM2e_fusion_protein

<400> SEQUENCE: 29

Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
                20                  25                  30

His Ile Ile Ile Val Pro Ile Pro Gly Asp Ser Ser Ile Thr Thr Arg
            35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
                100                 105                 110

Gly Leu Thr Phe Ala Ser Arg Gly Thr Asn Met Glu Asp Glu Ala Asp
            115                 120                 125

Gln Tyr Phe Ser His Asp Asp Pro Ile Ser Ser Asp Gln Ser Arg Phe
    130                 135                 140

Gly Trp Phe Gly Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
                180                 185                 190

Leu Arg Arg Trp Ile Lys Tyr Thr Gln Gln Arg Arg Val Val Gly Glu
            195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
                260                 265                 270

Ile Lys Phe Gly Ile Glu Thr Met Tyr Pro Ala Leu Gly Leu His Glu
            275                 280                 285

Phe Ala Gly Glu Leu Ser Thr Leu Glu Ser Leu Met Asn Leu Tyr Gln
    290                 295                 300
```

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
            325                 330                 335

Met Gly Val Gly Val Glu Leu Glu Asn Ser Met Gly Gly Leu Asn Phe
        340                 345                 350

Gly Arg Ser Tyr Phe Asp Pro Ala Tyr Phe Arg Leu Gly Gln Glu Met
    355                 360                 365

Val Arg Arg Ser Ala Gly Lys Val Ser Ser Thr Leu Ala Ser Glu Leu
370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
    450                 455                 460

Ala His Leu Pro Thr Gly Thr Pro Leu Asp Ile Asp Thr Ala Thr Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Ile Val Tyr Asn Asp Arg Asn Leu Leu Asp Ser Gly Gly
        515                 520                 525

Ser Gly Gly Ser Leu Leu Thr Glu Val Glu Thr Pro Ile Arg Asn Glu
530                 535                 540

Trp Gly Cys Arg Cys Asn Asp Ser Ser Asp Gly Gly Ser Leu Leu
545                 550                 555                 560

Thr Glu Val Glu Thr Pro Ile Arg Asn Glu Trp Gly Cys Arg Cys Asn
                565                 570                 575

Asp Ser Ser Asp Gly Gly Ser Leu Leu Thr Glu Val Glu Thr Pro
            580                 585                 590

Ile Arg Asn Glu Trp Gly Cys Arg Cys Asn Asp Ser Ser Asp
        595                 600                 605

<210> SEQ ID NO 30
<211> LENGTH: 1542
<212> TYPE: DNA
<213> ORGANISM: Artificial Sequence
<220> FEATURE:
<223> OTHER INFORMATION: NPflu_synthetic_gene
<220> FEATURE:
<221> NAME/KEY: misc_feature
<222> LOCATION: (13)..(18)
<223> OTHER INFORMATION: BsiWI restriction site
<220> FEATURE:
<221> NAME/KEY: misc_feature
<222> LOCATION: (25)..(1524)
<223> OTHER INFORMATION: ORF for NPflu consensus protein : NPflu_ORF
<220> FEATURE:
<221> NAME/KEY: misc_feature
<222> LOCATION: (1525)..(1530)
<223> OTHER INFORMATION: BssHII restriction site

<400> SEQUENCE: 30

-continued

```
gctagcggat cccgtacggc caccatggcc tctcagggca ccaagagaag ctacgagcag      60
atggaaaccg acggcgagcg gcagaacgcc accgagatta gagccagcgt gggcagaatg     120
atcggcggca tcggccggtt ctacatccag atgtgcaccg agctgaagct gagcgactac     180
gagggccggc tgatccagaa cagcctgacc atcgagcgga tggtgctgag cgccttcgac     240
gagcggcgga acaagtacct ggaagaacac cccagcgccg gcaaggaccc caagaaaaca     300
ggcggcccta tctacagacg gtggacggc aagtggatgc gcgagctggt gctgtacgac     360
aaagaggaaa tccggcggat ctggcggcag gccaacaatg gcgaagatgc cacagccggc     420
ctgacccaca tcatgatctg gcacagcaac ctgaacgacg ccacctacca gcggaccaga     480
gcactcgtgc ggacaggcat ggaccccaga atgtgcagcc tgatgcaggg cagcacccctg     540 cccagaagat ctggcgctgc tggcgcagct gtgaagggcg tgggaaccat ggtcatggaa     600
ctgatcagga tgatcaagcg gggaatcaac gaccggaact tttggagagg cgagaacggc     660
agaaagaccc gcagcgccta cgagaggatg tgcaatatcc tgaagggcaa gttccagaca     720
gccgcccagc gggccatgat ggatcaagtg cgcgagagca gaaaccccgg caacgccgag     780
atcgaggacc tgatcttcct ggccagaagc gccctgatcc tgaggggctc tgtggcccac     840
aagagctgtc tgcctgcctg cgtgtacgga cctgccgtgg ccagcggcta cgacttcgag     900
aaagagggct acagcctcgt gggcatcgac ccattcaagc tgctgcagaa ctcccaggtg     960
tacagcctga tccggcccaa cgagaacccc gcccacaagt ctcagctcgt gtggatggcc    1020
tgtcacagcg ccgccttcga ggatctgaga gtgtccagct tcatccgggg cacaaaggtg    1080
tcccccagag gcaagctgag caccagaggc gtgcagatcg ccagcaacga gaatatggac    1140
aacatgggca gctccaccct ggaactgcgg agccggtatt gggccatcag aaccagaagc    1200
ggcggcaaca ccaaccagca gagagcctct gccggacaga tcagcgtgca gcccacctt   1260 agcgtgcaga gaaaccctgcc cttcgagaag gccacaatca tggccgcctt caccggcaat    1320
accgagggca gaaccagcga catgcgggcc gagatcatca agatgatgga aagcgccaag    1380
cccgaggaag tgtcattcca gggcaggggc gtgttcgagc tgtccgacga gaaagccacc    1440
aaccccatcg tgcccagctt cgacatgagc aacgagggca gctacttctt cggcgacaac    1500
gccgaagagt acgacaactg ataagcgcgc ctcgaggaat tc                       1542
```

<210> SEQ ID NO 31
<211> LENGTH: 498
<212> TYPE: PRT
<213> ORGANISM: Artificial Sequence
<220> FEATURE:
<223> OTHER INFORMATION: NPflu_consensus_protein

<400> SEQUENCE: 31

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
```

```
                    85                  90                  95
Tyr Arg Arg Val Asp Gly Lys Trp Met Arg Glu Leu Val Leu Tyr Asp
                100                 105                 110

Lys Glu Glu Ile Arg Arg Ile Trp Arg Gln Ala Asn Asn Gly Glu Asp
                115                 120                 125

Ala Thr Ala Gly Leu Thr His Ile Met Ile Trp His Ser Asn Leu Asn
            130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190

Leu Ile Arg Met Ile Lys Arg Gly Ile Asn Asp Arg Asn Phe Trp Arg
                195                 200                 205

Gly Glu Asn Gly Arg Lys Thr Arg Ser Ala Tyr Glu Arg Met Cys Asn
                210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Val Tyr Gly Pro Ala Val Ala Ser Gly
                275                 280                 285

Tyr Asp Phe Glu Lys Glu Gly Tyr Ser Leu Val Gly Ile Asp Pro Phe
            290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Lys Val
                340                 345                 350

Ser Pro Arg Gly Lys Leu Ser Thr Arg Gly Val Gln Ile Ala Ser Asn
            355                 360                 365

Glu Asn Met Asp Asn Met Gly Ser Ser Thr Leu Glu Leu Arg Ser Arg
            370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Lys Ala Thr Ile Met Ala Ala Phe Thr Gly Asn
                420                 425                 430

Thr Glu Gly Arg Thr Ser Asp Met Arg Ala Glu Ile Ile Arg Met Met
            435                 440                 445

Glu Ser Ala Lys Pro Glu Glu Val Ser Phe Gln Gly Arg Gly Val Phe
            450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 32
<211> LENGTH: 23
<212> TYPE: PRT
<213> ORGANISM: Artificial Sequence
<220> FEATURE:
<223> OTHER INFORMATION: M2e consensus polypeptide for H1N1v

<400> SEQUENCE: 32

```
Ser Leu Leu Thr Glu Val Glu Thr Pro Thr Arg Ser Glu Trp Glu Cys
1               5                   10                  15

Arg Cys Ser Asp Ser Ser Asp
            20
```

<210> SEQ ID NO 33
<211> LENGTH: 30
<212> TYPE: DNA
<213> ORGANISM: Artificial Sequence
<220> FEATURE:
<223> OTHER INFORMATION: N-3xM2e forward primer

<400> SEQUENCE: 33
agtcgtacgg agatggccac acttttaagg 30

<210> SEQ ID NO 34
<211> LENGTH: 19
<212> TYPE: DNA
<213> ORGANISM: Artificial Sequence
<220> FEATURE:
<223> OTHER INFORMATION: N-3xM2e reverse primer

<400> SEQUENCE: 34
ggccttgaga gcccggatg 19

<210> SEQ ID NO 35
<211> LENGTH: 37
<212> TYPE: DNA
<213> ORGANISM: Artificial Sequence
<220> FEATURE:
<223> OTHER INFORMATION: N-1xM2e reverse primer

<400> SEQUENCE: 35
gttgcgcgct cgttatcaat cagagctgtc gttgcac 37

<210> SEQ ID NO 36
<211> LENGTH: 25
<212> TYPE: DNA
<213> ORGANISM: Artificial Sequence
<220> FEATURE:
<223> OTHER INFORMATION: NPflu forward primer

<400> SEQUENCE: 36
agtcgtacgg ccaccatggc ctctc 25

<210> SEQ ID NO 37
<211> LENGTH: 42
<212> TYPE: DNA
<213> ORGANISM: Artificial Sequence
<220> FEATURE:
<223> OTHER INFORMATION: NPflu reverse primer

<400> SEQUENCE: 37
tcggcgcgcg atcctccgga gttgtcgtac tcttcggcgt tg 42

<210> SEQ ID NO 38
<211> LENGTH: 6

```
<212> TYPE: PRT
<213> ORGANISM: Artificial Sequence
<220> FEATURE:
<223> OTHER INFORMATION: Linker

<400> SEQUENCE: 38

Ser Gly Gly Ser Gly Gly
1               5

<210> SEQ ID NO 39
<211> LENGTH: 24
<212> TYPE: PRT
<213> ORGANISM: Artificial Sequence
<220> FEATURE:
<223> OTHER INFORMATION: M2e_consensus_polypeptide modified for
      biotinylation

<400> SEQUENCE: 39

Ser Leu Leu Thr Glu Val Glu Thr Pro Ile Arg Asn Glu Trp Gly Cys
1               5                   10                  15

Arg Cys Asn Asp Ser Ser Asp Lys
            20

<210> SEQ ID NO 40
<211> LENGTH: 23
<212> TYPE: PRT
<213> ORGANISM: Artificial Sequence
<220> FEATURE:
<223> OTHER INFORMATION: M2e consensus polypeptide for H5N1

<400> SEQUENCE: 40

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 41
<211> LENGTH: 9
<212> TYPE: PRT
<213> ORGANISM: Artificial Sequence
<220> FEATURE:
<223> OTHER INFORMATION: Influenza A virus consensus peptide

<400> SEQUENCE: 41

Ala Ser Asn Glu Asn Met Asp Asn Met
1               5

<210> SEQ ID NO 42
<211> LENGTH: 9
<212> TYPE: PRT
<213> ORGANISM: Artificial Sequence
<220> FEATURE:
<223> OTHER INFORMATION: Influenza A virus consensus peptide

<400> SEQUENCE: 42

Ala Ser Asn Glu Asn Met Asp Thr Met
1               5

<210> SEQ ID NO 43
<211> LENGTH: 14
<212> TYPE: PRT
<213> ORGANISM: Artificial Sequence
<220> FEATURE:
<223> OTHER INFORMATION: Influenza A virus consensus peptide

<400> SEQUENCE: 43
```

```
Ala Leu Ile Leu Arg Gly Ser Val Ala His Lys Ser Cys Leu
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Measles virus peptide

<400> SEQUENCE: 44

Arg Ile Val Ile Asn Arg Glu His Leu
1               5

<210> SEQ ID NO 45
<211> LENGTH: 9
<212> TYPE: PRT
<213> ORGANISM: Artificial Sequence
<220> FEATURE:
<223> OTHER INFORMATION: Measles virus peptide

<400> SEQUENCE: 45

Ser Asn His Asn Asn Val Tyr Trp Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Measles virus peptide

<400> SEQUENCE: 46

Phe Gln Pro Gln Asn Gly Gln Phe Ile
1               5
```